US012325699B2

(12) United States Patent
Teng et al.

(10) Patent No.: US 12,325,699 B2
(45) Date of Patent: Jun. 10, 2025

(54) ANTIBACTERIAL COMPOUNDS

(71) Applicant: Blacksmith Medicines, Inc., San Diego, CA (US)

(72) Inventors: Min Teng, San Diego, CA (US); Baskar Nammalwar, San Diego, CA (US); Xiaoming Li, San Diego, CA (US); Christian Perez, San Diego, CA (US); Ian Yule, Abingdon (GB); Adele Faulkner, Abingdon (GB); Holly Atton, Abingdon (GB); Alastair Parkes, Abingdon (GB); Serge Convers-Reignier, Abingdon (GB); Michelle Southey, Abingdon (GB); David T. Puerta, San Diego, CA (US)

(73) Assignee: BLACKSMITH MEDICINES, INC., San Diego, CA (US)

( * ) Notice: Subject to any disclaimer, the term of this patent is extended or adjusted under 35 U.S.C. 154(b) by 92 days.

(21) Appl. No.: 17/836,255

(22) Filed: Jun. 9, 2022

(65) Prior Publication Data
US 2022/0324846 A1    Oct. 13, 2022

Related U.S. Application Data

(60) Division of application No. 17/205,750, filed on Mar. 18, 2021, now Pat. No. 11,407,740, which is a continuation of application No. PCT/US2019/052021, filed on Sep. 19, 2019.

(60) Provisional application No. 62/767,313, filed on Nov. 14, 2018, provisional application No. 62/734,173, filed on Sep. 20, 2018.

(51) Int. Cl.
| | | |
|---|---|---|
| *C07D 403/14* | (2006.01) | |
| *A61P 31/04* | (2006.01) | |
| *C07D 239/54* | (2006.01) | |
| *C07D 401/06* | (2006.01) | |
| *C07D 401/10* | (2006.01) | |
| *C07D 401/12* | (2006.01) | |
| *C07D 403/10* | (2006.01) | |
| *C07D 405/12* | (2006.01) | |
| *C07D 405/14* | (2006.01) | |
| *C07D 409/12* | (2006.01) | |
| *C07D 413/14* | (2006.01) | |
| *C07D 487/04* | (2006.01) | |
| *C07D 491/048* | (2006.01) | |
| *C07D 491/107* | (2006.01) | |

(52) U.S. Cl.
CPC ............ *C07D 403/14* (2013.01); *A61P 31/04* (2018.01); *C07D 239/54* (2013.01); *C07D 401/06* (2013.01); *C07D 401/10* (2013.01); *C07D 401/12* (2013.01); *C07D 403/10* (2013.01); *C07D 405/12* (2013.01); *C07D 405/14* (2013.01); *C07D 409/12* (2013.01); *C07D 413/14* (2013.01); *C07D 487/04* (2013.01); *C07D 491/048* (2013.01); *C07D 491/107* (2013.01)

(58) Field of Classification Search
CPC .. C07D 403/14; C07D 239/54; C07D 401/06; C07D 401/10; C07D 401/12; C07D 403/10; C07D 405/12; C07D 405/14; C07D 409/12; C07D 413/14; C07D 487/04; C07D 491/048; C07D 491/107; A61P 31/04
See application file for complete search history.

(56) References Cited

U.S. PATENT DOCUMENTS

| | | | |
|---|---|---|---|
| 5,543,534 A | 8/1996 | Vuligonda et al. | |
| 5,846,514 A | 12/1998 | Foster et al. | |
| 6,334,997 B1 | 1/2002 | Foster et al. | |
| 6,699,849 B1 | 3/2004 | Loftsson et al. | |
| 7,211,572 B2 | 5/2007 | Miyazaki et al. | |
| 7,579,486 B2 | 8/2009 | Puerta et al. | |
| 7,786,316 B2 | 8/2010 | Puerta et al. | |
| 9,145,381 B2 | 9/2015 | Fanelli et al. | |
| 10,130,714 B2 | 11/2018 | Wong et al. | |
| 10,414,735 B2 | 9/2019 | Teng et al. | |
| 10,611,747 B2 | 4/2020 | Teng et al. | |
| 10,875,832 B2 | 12/2020 | Teng et al. | |
| 11,021,471 B2 | 6/2021 | Teng et al. | |
| 11,407,740 B2 * | 8/2022 | Teng ................. | C07D 491/107 |
| 2003/0181472 A1 | 9/2003 | Clark et al. | |
| 2003/0190608 A1 | 10/2003 | Blackburn | |
| 2005/0009101 A1 | 1/2005 | Blackburn | |

(Continued)

FOREIGN PATENT DOCUMENTS

| | | |
|---|---|---|
| CN | 105777464 A | 7/2016 |
| CN | 110072844 A | 7/2019 |

(Continued)

OTHER PUBLICATIONS

Aytemir et al. Synthesis and Evaluation of Anticonvulsant and Antimicrobial Activities of 3-Hydroxy-6-methyl-2-substituted 4H-Pyran-4-one Derivatives. Archiv Der Pharmazie 337(5):281-288 (2004).

(Continued)

Primary Examiner — Erich A Leeser
(74) Attorney, Agent, or Firm — WILSON SONSINI GOODRICH & ROSATI

(57) ABSTRACT

Provided herein are heterocyclic derivative compounds and pharmaceutical compositions comprising said compounds that are useful for inhibiting the growth of gram-negative bacteria. Furthermore, the subject compounds and compositions are useful for the treatment of bacterial infection, such as urinary tract infection and the like.

18 Claims, No Drawings

(56) References Cited

U.S. PATENT DOCUMENTS

| | | | |
|---|---|---|---|
| 2007/0117848 | A1 | 5/2007 | Puerta et al. |
| 2007/0149556 | A1 | 6/2007 | Mikamiyama et al. |
| 2008/0317851 | A1 | 12/2008 | Appel et al. |
| 2012/0035255 | A1 | 2/2012 | Fanelli et al. |
| 2012/0041032 | A1 | 2/2012 | Puerta et al. |
| 2012/0329741 | A1 | 12/2012 | Oyelere et al. |
| 2014/0038990 | A1 | 2/2014 | Buschmann et al. |
| 2014/0079666 | A1 | 3/2014 | Webb et al. |
| 2015/0202208 | A1 | 7/2015 | Kiyama et al. |
| 2017/0088525 | A1 | 3/2017 | Fu et al. |
| 2017/0088532 | A1 | 3/2017 | Cohen et al. |
| 2017/0290918 | A1 | 10/2017 | Honda et al. |
| 2018/0327365 | A1 | 11/2018 | Teng et al. |
| 2019/0106398 | A1 | 4/2019 | Cohen et al. |
| 2020/0062789 | A1 | 2/2020 | Shoji et al. |
| 2020/0095236 | A1 | 3/2020 | Teng et al. |
| 2021/0078957 | A1 | 3/2021 | Teng et al. |
| 2021/0221796 | A1 | 7/2021 | Teng et al. |
| 2021/0309651 | A1 | 10/2021 | Teng et al. |
| 2021/0315902 | A1 | 10/2021 | Teng et al. |
| 2022/0081421 | A1 | 3/2022 | Teng et al. |
| 2023/0201214 | A1 | 6/2023 | Teng et al. |
| 2023/0382891 | A1 | 11/2023 | Teng et al. |
| 2024/0002373 | A1 | 1/2024 | Teng et al. |
| 2024/0270773 | A1 | 8/2024 | Teng |

FOREIGN PATENT DOCUMENTS

| | | |
|---|---|---|
| EP | 2181985 B1 | 10/2011 |
| WO | WO-9830205 A1 | 7/1998 |
| WO | WO-2004062601 A2 | 7/2004 |
| WO | WO-2005110399 A2 | 11/2005 |
| WO | WO-2006028523 A2 | 3/2006 |
| WO | WO-2008027466 A1 | 3/2008 |
| WO | WO-2008045668 A1 | 4/2008 |
| WO | WO-2008154642 A2 | 12/2008 |
| WO | WO-2010059838 A2 | 5/2010 |
| WO | WO-2010100475 A1 | 9/2010 |
| WO | WO-2012151567 A1 | 11/2012 |
| WO | WO-2012177638 A1 | 12/2012 |
| WO | WO-2013151923 A1 | 10/2013 |
| WO | WO-2014117090 A1 | 7/2014 |
| WO | WO-2014160649 A1 | 10/2014 |
| WO | WO-2015024010 A2 | 2/2015 |
| WO | WO-2015085238 A1 | 6/2015 |
| WO | WO-2015099107 A1 | 7/2015 |
| WO | WO-2017083431 A2 | 5/2017 |
| WO | WO-2017083434 A1 | 5/2017 |
| WO | WO-2018115421 A1 | 6/2018 |
| WO | WO-2018208985 A2 | 11/2018 |
| WO | WO-2018208987 A2 | 11/2018 |
| WO | WO-2018216822 A1 | 11/2018 |
| WO | WO-2019086452 A1 | 5/2019 |
| WO | WO-2019154412 A1 | 8/2019 |
| WO | WO-2020061375 A1 | 3/2020 |
| WO | WO-2020102572 A1 | 5/2020 |
| WO | WO-2021195258 A1 | 9/2021 |
| WO | WO-2021195260 A1 | 9/2021 |
| WO | WO-2022173756 A1 | 8/2022 |
| WO | WO-2022173758 A1 | 8/2022 |
| WO | WO-2023055686 A1 | 4/2023 |
| WO | WO-2024036170 A1 | 2/2024 |
| WO | WO-2024036176 A1 | 2/2024 |

OTHER PUBLICATIONS

Banker et al. Modern Pharmaceutics. 3rd ed. Marcel Dekker, New York. p. 596 (1996).
Berge et al. Pharmaceutical Salts. Journal of Pharmaceutical Sciences 66(1):1-19 (Jan. 1977).
Bingi et al. One-pot catalyst free synthesis of novel kojic acid tagged 2-aryl/alkyl substituted-4H-chromenes and evaluation of their antimicrobial and anti-biofilm activities. Bioorganic & Medicinal Chemistry Letters 25(9):1915-1919 (2015).
Bundgaard et al. Design of Prodrugs pp. 7-9, 21-24 (1985).
Di Francesco et al. Development of 2-t butyl-N-methyl pyrimidones as potent inhibitors of HIV integrase. Bioorg Med Chem Lett 18(8):2709-13 (2008).
Ding et al. Design, synthesis and biological evaluation of LpxC inhibitors with novel hydrophilic terminus. Chinese Chemical Letters 26(6):763-767 (2015).
Emami et al. Mannich bases of 7-piperazinylquinolones and kojic acid derivatives: Synthesis, in vitro antibacterial activity and in silico study. Ep J Med Chem 68:185-191 (2010).
Evans. Synthesis of radiolabeled compounds. J Radioanal Chem 64(1-2):9-32 (1981).
Garrett et al. The Art of Meeting Palladium Specifications in Active Pharmaceutical Ingredients Produced by Pd-Catalyzed Reactions. Adv. Synth. Catal. 346:889-900 (2004).
Guideline on the Specification Limits for Residues of Metal Catalysts. European Medicines Agency. Pre-authorization Evaluation of Medicines for Human Use, London (Jan. 2007) (pp. 1-32).
Hale et al. Exploring the UDP pocket of LpxC through amino acid analogs. Bioorg Med Chem Lett. 23:2362-2367 (2013).
Kabalka et al. The Synthesis of Radiolabeled Compounds via Organometallic Intermediates. Tetrahedron 45(21):6601-6621 (1989).
Krivonogov et al. Aminomethylation of pyrimidines. Russian Journal of Organic Chemistry 36(8):1219-1224 Chemical Abstracts CAS No. 345959-90-2P (2000).
Li et al. Design, synthesis and biological evaluation of 2-substituted 3-hydroxy-6-methyl-4H-pyran-4-one derivatives as Pseudomonas aeruginosa biofilm inhibitors. Eur J Med Chem 158:753-766 (2018).
Lin et al. Inhibition of LpxC protects mice from resistant Acinetobacter baumannii by modulating inflammation and enhancing phagocytosis. Mbio 3(5):pii:e00312-12 (2012).
Montgomery et al. Pyridone methylsulfone hydroxamate LpxC inhibitors for the treatment of serious gram-negative infections. J Med Chem 55:1662-1670 (2012).
PCT/US2016/061195 International Search Report and Written Opinion dated Jul. 31, 2017.
PCT/US2016/061198 International Search Report and Written Opinion dated Feb. 15, 2017.
PCT/US2018/031896 International Search Report and Written Opinion dated Nov. 7, 2018.
PCT/US2018/031898 International Search Report and Written Opinion dated Nov. 7, 2018.
PCT/US2019/051986 International Search Report and Written Opinion dated Jan. 3, 2020.
PCT/US2019/052021 International Search Report and Written Opinion dated Jan. 6, 2020.
PCT/US2019/061529 International Search Report and Written Opinion dated Mar. 13, 2020.
PCT/US2021/023948 International Search Report and Written Opinion dated Jun. 10, 2021.
PCT/US2021/023950 International Search Report and Witten Opinion dated Jul. 28, 2021.
Ravin. Chapter 76: Preformulation. Remington's Pharmaceutical Sciences, 17th ed., Mack Publishing Company, Easton, Pa. (pp. 1409-1423) (1985).
Storr et al., Vanadyl-thiazolidinedione combination agents for diabetes therapy. Bioconjugate Chemistry 14(1):212-221 (2003).
Us et al. 4H-Pyran-4-one derivatives:; leading molecule for preparation of compounds with antimycobacterial potential. Turkish Journal of Chemistry 30:803-812 (2009).
Us et al. Mannich base derivatives of 3-hydroxy-6-methyl-4H-pyran-4-one with antimicrobial activity. Turkish Journal of Chemistry 33:447-456 (2010).
Vaara: Antibiotic-supersusceptible mutants of Escherichia coli and Salmonella typhimurium. Antimicrob Agents Chemother. 37(11):2255-2260 (1993).
Wolff, (ed.), Burger's Medicinal Chemistry and Drug Discovery, Fifth Edition, vol. 1: Principles and Practice, San Diego, California, John Wiley & Sons, 1994, pp. 975-977. (4 pages).
Yan et al. Synthesis of hydroxypyrone- and hydroxythiopyrone-based matrix metalloproteinase inhibitors: Developing a structure-activity relationship. Bioorg. Med. Chem. Lett. 19(7):1970-1976 (2009).

(56) References Cited

OTHER PUBLICATIONS

Young et al.: Leakage of periplasmic enzymes from envA1 strains of *Escherichia coli*. J. Bacteriol.173(12):3609-3614 (1991).

Fathalla et al. Synthesis of new 2-thiouracil-5-sulphonamide derivatives with antibacterial and antifungal activity. Arch Farm Res 28(11):1205-1212 (2005).

PCT/US2022/015679 International Search Report and Written Opinion dated May 31, 2022.

PCT/US2022/015682 International Search Report and Written Opinion dated May 31, 2022.

PCT/US2022/044710 International Search Report and Written Opinion dated Jan. 16, 2023.

Ushiyama et al., Lead optimization of 2-hydroxymethyl imidazoles as non-hydroxamate LpxC inhibitors: Discovery of TP0586532. Bioorg Med Chem. 30:115964 (2021).

Wuts et al. Greene's Protective Groups in Organic Synthesis. 4th ed., Wiley & Sons (pp. 1-1082) (2007).

Barb et al. Mechanism and inhibition of LpxC: an essential zinc-dependent deacetylase of bacterial lipid A synthesis. Curr Pharm Biotechnol 9(1):9-15 (2008).

U.S. Appl. No. 18/173,207 Office Action dated Sep. 19, 2023.

BoltromeyUK. General Chemistry. Minsk, Higher School, p. 65 (2012).

\* cited by examiner

ANTIBACTERIAL COMPOUNDS

RELATED APPLICATIONS

This application is a division of application Ser. No. 17/205,750, filed Mar. 18, 2021, which is a continuation of International Application No. PCT/US2019/052021, filed Sep. 19, 2019, which claims the benefit of U.S. Provisional Patent Application No. 62/734,173 filed on Sep. 20, 2018, and U.S. Provisional Patent Application No. 62/767,313 filed on Nov. 14, 2018, each of which is herein incorporated by reference in its entirety.

GOVERNMENT SUPPORT

This invention was made with government support under IDSEP160030-03 awarded by the U.S. Department of Health & Human Services. The government has certain rights in the invention.

BACKGROUND

A need exists in the medicinal arts for the effective treatment of illness caused by bacterial infection.

BRIEF SUMMARY OF THE INVENTION

Provided herein are heterocyclic derivative compounds and pharmaceutical compositions comprising said compounds that are useful for inhibiting the growth of gram-negative bacteria. Furthermore, the subject compounds and compositions are useful for the treatment of bacterial infection, such as urinary tract infection and the like.

Provided herein is a compound, or a pharmaceutically acceptable salt, solvate, or prodrug thereof, having the structure of Formula (I):

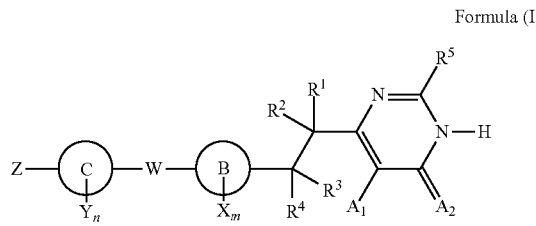

Formula (I)

wherein
n is 0-4;
m is 0-4;
$A_1$ is OH or SH;
$A_2$ is O or S;
$R^1$ and $R^2$ are each independently H or optionally substituted alkyl;
or $R^1$ and $R^2$ are taken together with the carbon to which they are attached to form $=C(R^{11})_2$, $=NR^{11}$, $=O$, or $=S$;
or $R^1$ and $R^2$ are taken together with the carbon to which they are attached to form an optionally substituted 3- to 6-membered carbocyclyl or optionally substituted 4- to 7-membered heterocyclyl containing 1 or 2 heteroatoms selected from O, N, and S;
$R^3$ is optionally substituted alky, optionally substituted carbocyclyl, optionally substituted carbocyclylalkyl, optionally substituted aryl, optionally substituted aralkyl, optionally substituted heteroaryl, optionally substituted heteroaralkyl, optionally substituted heterocyclyl, optionally substituted heterocyclyalkyl, optionally substituted ($C_0$-$C_4$ alkylene)-$COR^{11}$, optionally substituted ($C_0$-$C_4$ alkylene)-$CO_2R^{11}$, optionally substituted ($C_0$-$C_4$ alkylene)-$CON(R^{11})_2$, optionally substituted ($C_0$-$C_4$ alkylene)-CN, optionally substituted ($C_0$-$C_4$ alkylene)-$OR^{11}$, optionally substituted ($C_0$-$C_4$ alkylene)-$N(R^{11})$, optionally substituted ($C_0$-$C_4$ alkylene)-$N(R^{12})$—$COR^{11}$, optionally substituted ($C_0$-$C_4$ alkylene-$N(R^{12})$—$CO_2R^{11}$, optionally substituted ($C_0$-$C_4$ alkylene)-$N(R^{12})$—$CON(R^{11})_2$, optionally substituted ($C_0$-$C_4$ alkylene)-$N(R^{12})$—$SO_2N(R^{11})_2$, optionally substituted ($C_0$-$C_4$ alkylene)-O—$SO_2N(R^{11})_2$, optionally substituted ($C_0$-$C_4$ alkylene)-$N(R^{11})$—PO (optionally substituted $C_1$-$C_4$ alkyl)$_2$, optionally substituted ($C_1$-$C_4$ alkylene)-$SO_2R^{11}$, optionally substituted ($C_0$-$C_4$ alkylene)-$N(R^{12})$—$SO_2R^{11}$, optionally substituted ($C_0$-$C_4$ alkylene)-O—$SO_2^{11}$, optionally substituted ($C_0$-$C_4$ alkylene)-C($=N$—$OR^{11})(R^{11})$, or optionally substituted ($C_0$-$C_4$ alkylene)-$OP(=O)(OR^{11})_2$;
$R^4$ is H or optionally substituted alkyl;
or $R^3$ and $R^4$ are taken together with the carbon to which they are attached to form $=C(R^{11})_2$, $=NR^{11}$, $=O$, or $=S$;
or $R^3$ and $R^4$ are taken together with the carbon to which they are attached to form an optionally substituted 3- to 6-membered carbocyclyl or optionally substituted 4- to 7-membered heterocyclyl containing 1 or 2 heteroatoms selected from O, N, and S;
$R^5$ is H, halogen, optionally substituted alkyl, hydroxyl, alkoxyl, cyano, amino, or nitro;
Ring B is aryl, carbocyclyl, heteroaryl, or heterocyclyl;
W is a bond, —C≡C—, bicyclo[1.1.1]pentanylene, —C≡C—C≡C—, —CH=CH—, or —$CH_2CH_2$—;
Ring C is aryl, carbocyclyl, heteroaryl, or heterocyclyl;
each X and Y is independently H, optionally substituted alkyl, halo, fluoroalkyl, cyano, nitro, —$N(R^{13})_2$, or —$OR^{13}$;
or $R^3$ and one X are taken together with the intervening atoms to form an optionally substituted 5- to 7-membered carbocyclyl or optionally substituted 5- to 7-membered heterocyclyl containing 1 or 2 heteroatoms selected from O, N, and S;
Z is H, halo, nitro, or -L-G:
L is a bond or optionally substituted $C_1$-$C_4$ alkylene;
G is optionally substituted alkyl, optionally substituted alkenyl, optionally substituted alkynyl, optionally substituted carbocyclyl, optionally substituted aryl, optionally substituted heterocyclyl, optionally substituted heteroaryl, —CN, —$N(R^{13})$), —$OR^{13}$, —$COR^{13}$, —$CO_2R^{13}$, —$CON(R^{13})_2$, —$N(R^{14})$—$COR^{13}$, —$SO_2R^{13}$—, —$SO_2N(R^{13})_2$, —$N(R^{14})$—$SO_2R^{13}$, —$N(R^{14})$—$CON(R^{13})_2$, —$N(R^{14})$—$CO_2R^{13}$, —O—$CON(R^{13})_2$—, —$N(R^{14})$—$SO_2N(R^{13})_2$, —O—$SO_2N(R^{13})$, —$N(R^{14})$—$SO_2$—$OR^{13}$, or —C($=N$—$OR^{14})(R^{13})$;
each $R^{11}$ is independently H, optionally substituted allyl, optionally substituted alkenyl, optionally substituted alkynyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl;
or two $R^{11}$ on the same nitrogen atom are taken together with the nitrogen to which they are attached to form an optionally substituted N-heterocyclyl;

each $R^{12}$ is independently H, optionally substituted alkyl, optionally substituted carbocyclyl, optionally substituted carbocyclylalkyl, optionally substituted heterocyclyl, or optionally substituted heterocyclylalkyl;

each $R^{13}$ is H, optionally substituted alkyl, optionally substituted alkenyl, optionally substituted alkynyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl;

or two $R^{13}$ on the sane nitrogen atom are taken together with the nitrogen to which they are attached to form an optionally substituted N-heterocyclyl; and each $R^{14}$ is independently H, optionally substituted alkyl, optionally substituted carbocyclyl, optionally substituted carbocyclylalkyl, optionally substituted heterocyclyl, or optionally substituted heterocyclylalkyl.

In some embodiments provided herein, the compound of Formula (I) is a compound of Formula (II):

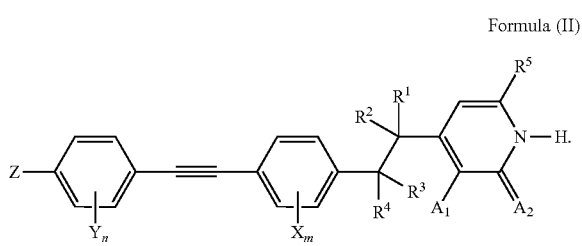

Formula (II)

In some embodiments provided herein, the compound of Formula (I) or Formula (II) is a compound of Formula (III):

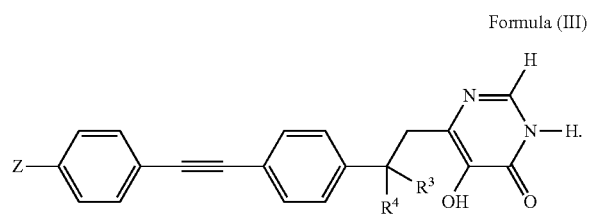

Formula (III)

In some embodiments provided herein, the compound of Formula (I) or Formula (II) or Formula (III) is a compound of Formula (IV):

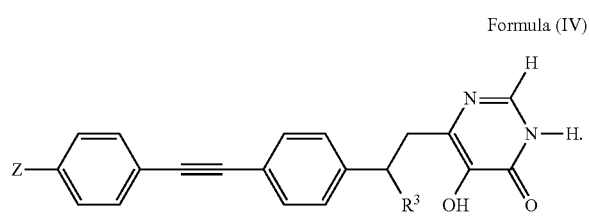

Formula (IV)

In some embodiments provided herein, the compound of Formula (I) or Formula (II) or Formula (III) is a compound of Formula (IVa):

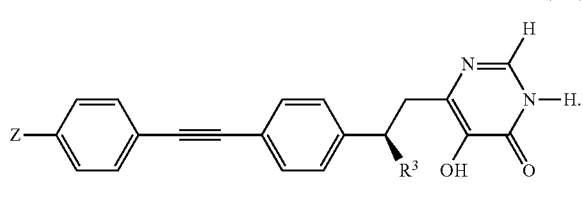

Formula (IVa)

In some embodiments provided herein, the compound of Formula (I) or Formula (II) or Formula (III) is a compound of Formula (IVb):

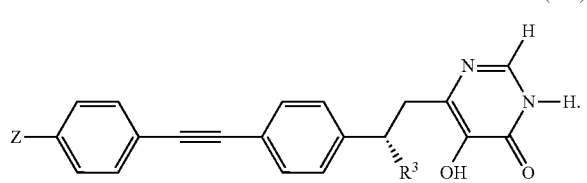

Formula (IVb)

Another aspect provides a pharmaceutical composition comprising a compound described herein, or a pharmaceutically acceptable salt, solvate, or prodrug thereof, and a pharmaceutically acceptable excipient.

In another aspect provided herein, is a method of treating a gram-negative bacterial infection in a patient in need thereof comprising administering to the patient a pharmaceutical composition comprising a compound described herein, or a pharmaceutically acceptable salt, solvate, or prodrug thereof, and a pharmaceutically acceptable excipient. In some embodiments provided herein, the gram-negative bacterial infection is selected from pneumonia, sepsis, cystic fibrosis, intra-abdominal infection, skin infection and urinary tract infection. In some embodiments provided herein, the gram-negative bacterial infection is selected from chronic urinary tract infection, complicated urinary tract infection, cystitis, pyelonephritis, urethritis, recurrent urinary tract infections, bladder infections, urethral infections and kidney infections.

In another aspect provided herein is a method of inhibiting UDP-{3-O—[(R)-3-hydroxymyristoyl]}-N-acetylglucosamine deacetylase enzyme comprising contacting the enzyme with a compound described herein.

In another aspect provided herein is a method for treating bacterial infection in a patient in need thereof comprising administering to the patient a composition comprising a compound described herein, or a pharmaceutically acceptable salt, solvate, or prodrug thereof, and a pharmaceutically acceptable excipient.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "an," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH$_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_5$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_{15}$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_2$-$C_5$ alkyl). In other embodiments, the alkyl group is selected from methyl, ethyl, 1-propyl (n-propyl), 1-methylethyl (iso-propyl), 1-butyl (n-butyl), n-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, amino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$), —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" or "alkoxyl" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^{11}$, —C(O)N(R$^a$)$_2$, —N(R$^a$)C(O)OR$^{11}$, —OC(O)—N(R$^a$)$_2$, —N(R$^a$)C(O)R$^a$, —N(R$^a$)S(O)$_t$R$^a$ (where t is 1 or 2), —S(O)—OR$^{11}$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR, —SR$^a$, —OC(O)—

$R^a$, —N($R^a$)$_2$, —C(O)$R^a$, —C(O)O$R^{11}$, —C(O)N($R^a$), —N($R^a$)C(O)O$R^{11}$, —OC(O)—N($R^{11}$)$_2$, —N($R^a$)C(O)$R^1$, —N($R^a$)S(O$R^a$ (where t is 1 or 2), —S(O)$_t$O$R^a$ (where t is 1 or 2), —S(O)$_t$$R^a$ (where is 1 or 2) and —S(O)N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_1$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —O$R^a$, —S$R^a$, —OC(O)—$R^a$, —N($R^a$)$_2$, —C(O)$R^a$, —C(O)O$R^{11}$, —C(O)N($R^a$), —N($R^a$)C(O)OR, —OC(O)—N($R^a$)$_2$—N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted With halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroacyl (optionally substituted width halogen, hydroxy, methoxy, or trifluoromethyl), or heteroarylalkyl (optionally substituted with halogen, hydroxy, methoxy, or trifluoromethyl).

"Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. In certain embodiments, an alkenylene comprises two to eight carbon atoms (e.g., $C_2$-$C_8$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e.g., $C_2$-$C_3$ alkenylene). In other embodiments, an alkenylene comprises five to eight carbon atoms (e.g. $C_5$-$C_8$ alkenylene). In other embodiments, an alkenylene comprises two to five carbon atoms (e, g $C_2$-$C_5$ alkenylene). In other embodiments, an alkenylene comprises three to five carbon atoms (e.g. $C_3$-$C_5$ alkenylene). Unless stated otherwise specifically in the specification, an alkenylene chain is optionally substituted by one or more of the following substituents: halo, cyano, nitro, oxo, thioxo, imino, oximo, trimethylsilanyl, —O$R^a$, —S$R^a$, —OC(O)—$R^a$, —N($R^a$)$_2$, —C(O)$R^a$, —C(O)O$R^a$, —C(O)N($R^a$), —N($R^a$)C(O)O$R^a$, —OC(O)—N($R^a$), —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_5$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atom (e.g., $C_2$ alkylene). In other embodiments, ala alkynylene comprises five to eight carbon atoms (e.g., $C_5$-$C_8$alkynylene). In other embodiments, an alkynylene comprises three to five carbon atoms (e.g., $C_3$-$C_5$alkynylene). Unless stated otherwise specifically in the specification, an alkynylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where 1 is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclyalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently, selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroaryloalkyl, —R$^b$—OR$^a$; —R$^b$—OC(O)—R$^a$, —R$^b$—OC(O)—OR$^{11}$, —R$^b$—OC(O)—N(R$^a$)$_2$, —R$^b$—N(R$^a$)$_2$, —R$^b$—C(O)R$^a$, —R$^b$—C(O)OR$^{11}$, —R$^b$—C(O)N(R$^a$)$_2$, —R$^b$—O—R$^b$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloakyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbomyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally, substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroaryalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical are optionally substituted as defined above.

"Carbocyclylalkynyl" refers to a radical of the formula —$R^c$-carbocyclyl where $R^c$ is an alkynylene chain as defined above. The alkynylene chain and the carbocyclyl radical are optionally substituted as defined above.

"Carbocyclyl alkoxy" refers to a radical bonded through an oxygen atom of the formula —O—$R^c$-carbocyclyl where $R^c$ is an alkylene chain as defined above. The alkylene chain and the carbocyclyl radical are optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

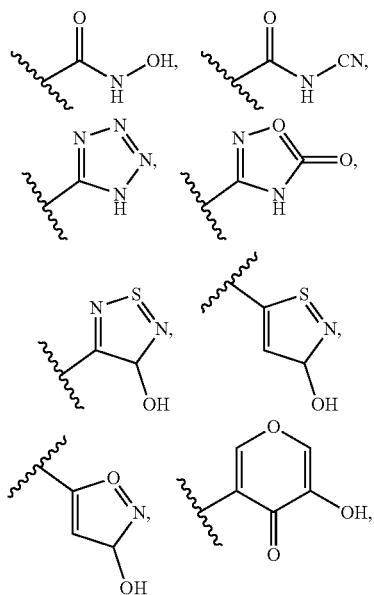

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused, bridged, or spirocyclic ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolidinyl, isothiazolidinyl, isoxazolidinyl, morpholinyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroaryl, —$R^b$—$OR^a$, —$R^b$—OC(O)—$R^a$, —$R^b$—OC(O)—$OR^a$, —$R^b$—OC(O)—N(R^a)_2$, $N(R^a)_2$, —$R^b$—C(O)OR^a$, —$R^b$—C(O)N(R^a)_2$, —$R^b$—O—$R^c(O)N(R^a)_2$, —$R^b$—N(R^a)(O)OR^a$, —$R^b$—N(R^a)C(O)R^a$, —$R^b$—N(R^a)S(O)_tR^a$ (where t is 1 or 2), —$R^b$—S(O)_tR^a$ (where t is 1 or 2), —$R^b$—S(O)_tOR^a$ (where t is 1 or 2) and —$R^b$—S(O)_tN(R^a)_2$ (where t is 1 or 2), where each $R^a$ is independently hydrogen, alkyl (optionally, substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), ail (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A ('-heterocyclyl radical is optionally substituted as described above for heterocycyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains acyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[dithiazolyl, benzothiadiazolyl, benzo[b][1,4]dioxepinyl, benzo[b][1,4] oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazol 1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h] quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo [3,2-c]pyridinyl, 5,6,7,8,9,10-hexahydrocycloocta[d]pyrimidinyl, 5,6,7,8,9,10-hexahydrocycloocta[d]pyridazinyl, 5,6, 7,8,9,10-hexahydrocycloocta[d]pyridinyl, isothiazolyl, indazolyl, indolyl, isoindolyl, indolinyl, isoindolinyl isoquinolyl, indolizinyl, isoxazolyl 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10, 10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl quinazolinyl, quinoxalinyl quinolinyl isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, tetrazolyl, triazinyl, thieno[2,3-d]pyrimidinyl, thieno[3,2-d] pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$; —$R^b$—OC(O)—$R^a$, —$R^b$—OC (O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroaryl alkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)— or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

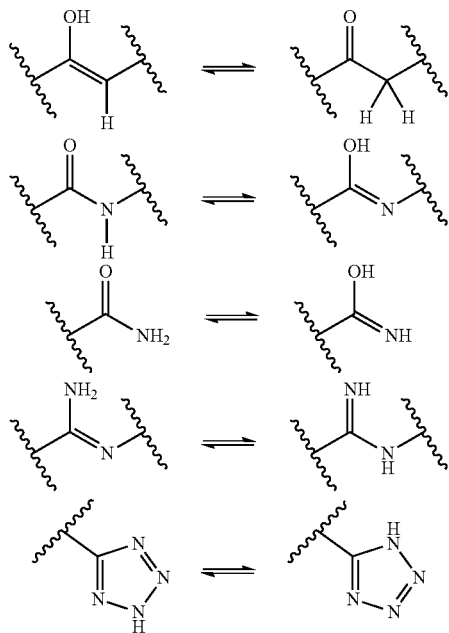

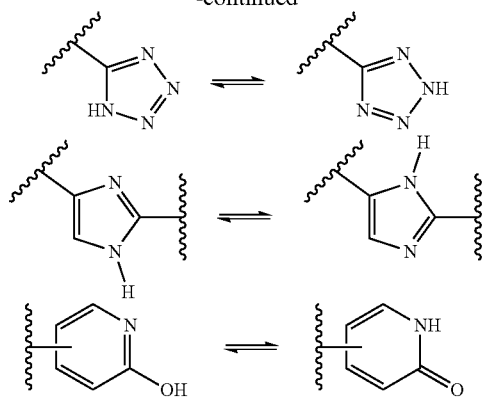

In some instances, the heterocyclic LpxC inhibitory compounds disclosed herein exist in tautomeric forms. The structures of said compounds are illustrated in the one tautomeric form for clarity. The alternative tautomeric forms are expressly included in this disclosure, such as, for example, the structures illustrated below.

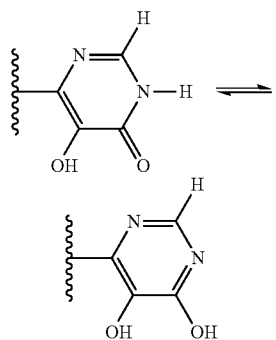

The compounds disclosed herein, in some embodiments, are used in different enriched isotopic forms, e.g., enriched in the content of $^2$H, $^3$H, $^{11}$C, $^{13}$C and/or $^{14}$C. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2$H), tritium ($^3$H), iodine-125 ($^{125}$I) or carbon-14 ($^{14}$C). Isotopic substitution with $^2$H, $^{11}$H, $^{13}$C, $^{14}$C, $^{15}$C, $^{12}$N, $^{13}$N, $^{15}$N, $^{16}$N, $^{18}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, $^{125}$I are all contemplated. All isotopic variations of the compounds of the present disclosure, whether radioactive or not, are encompassed within the scope of the present disclosure.

In certain embodiments, the compounds disclosed herein have some or all of the $^1$H atoms replaced with $^2$H atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6 (10)]2000, 110 pp; George W.; Varma, Rajender S. The Synthesis of Radiolabeled Compounds via. Organometallic Intermediates, Tetrahedron, 1989, 45(21), 6601-21; and Evans, E. Anthony. Synthesis of radiolabeled compounds, J. Radioanal. Chem., 1981, 64 (1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Deuterium-transfer reagents suitable for use in nucleophilic substitution reactions, such as iodomethane-d$_3$ (CD$_3$I), are readily available and may be employed to transfer a deuterium-substituted carbon atom under nucleophilic substitution reaction conditions to the reaction substrate. The use of CD$_3$I is illustrated, by way of example only, in the reaction schemes below.

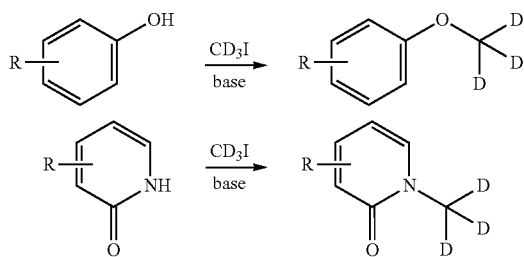

Deuterium-transfer reagents, such as lithium aluminum deuteride (LiAlD$_4$), are employed to transfer deuterium under reducing conditions to the reaction substrate. The use of LiAlD$_4$ is illustrated, by way of example only, in the reaction schemes below.

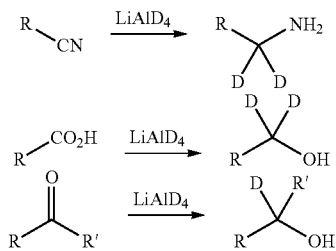

Deuterium gas and palladium catalyst are employed to reduce unsaturated carbon-carbon linkages and to perform a reductive substitution of aryl carbon-halogen bonds as illustrated, by way of example only, in the reaction schemes below.

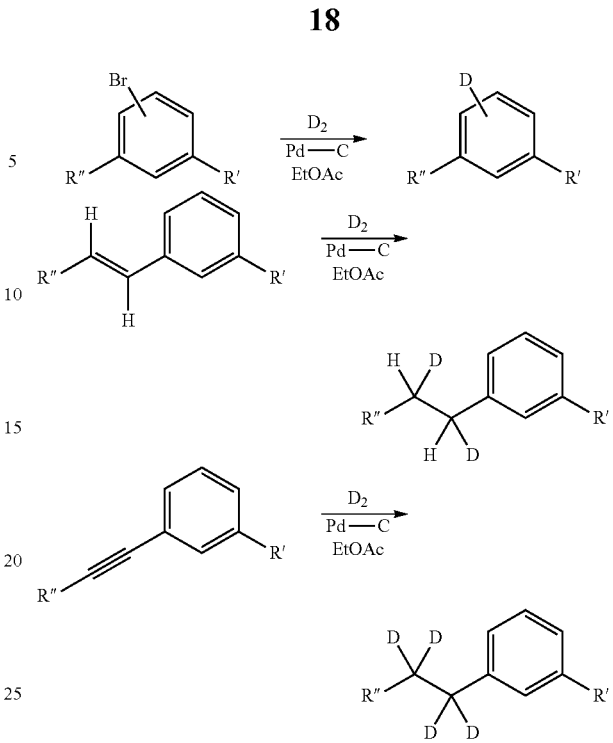

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1$H hydrogen atoms. In one embodiment, the level of deuterium incorporation is determined by synthetic methods in which a deuterated synthetic building block is used as a starting material.

In one embodiment, the compounds disclosed herein contain one or more boron atom, silicon atom, or any combination thereof. In some embodiments, one or more carbon atoms in the compound disclosed herein are replaced with a boron atom, a silicon atom, or any combination thereof.

In some embodiments, one or more carbon atoms in the compound disclosed herein are replaced with a boron atom. In some embodiments, one carbon atom in the compound disclosed herein is replaced with a boron atom. In some embodiments, two carbon atoms in the compound disclosed herein are replaced with two boron atoms. In some embodiments, three carbon atoms in the compound disclosed herein are replaced with three boron atoms. In some embodiments, tour carbon atoms in the compound disclosed herein are replaced with four boron atoms. In some embodiments, five carbon atoms in the compound disclosed herein are replaced with five boron atoms.

In some embodiments, one or more carbon atoms in the compound disclosed herein are replaced with a silicon atom. In some embodiments, one carbon atom in the compound disclosed herein is replaced with a silicon atom. In some embodiments, two carbon atoms in the compound disclosed herein are replaced with two silicon atoms. In some embodiments, three carbon atoms in the compound disclosed herein are replaced with three silicon atoms. In some embodiments, four carbon atoms in the compound disclosed herein are replaced with four silicon atoms. In some embodiments, five carbon atoms in the compound disclosed herein are replaced with five silicon atoms.

"Pharmaceutically acceptable salt" includes both acid and base addition salts. A pharmaceutically acceptable salt of any one of the heterocyclic LpxC inhibitory compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and di carboxylic acids, phenyl-substituted alkanoic acids, hydroxy, alkanoic acids, alkanedioic acids, aromatic acids, aliphatic and, aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, finales, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconate and galacturonates (e, for maniple, Berge S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design. of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

LpxC Inhibitory Compounds

Provided herein are heterocyclic LpxC inhibitory compounds and pharmaceutical compositions comprising said compounds. The subject compounds and compositions are useful for inhibiting UDP-{3-O—[(R)-3-hydroxymyristoyl]}-N-acetylglucosamine deacetylase (LpxC) and for the treatment of bacterial infection.

Also provided herein is a compound, or a pharmaceutically acceptable salt, solvate, or prodrug thereof, having the structure of Formula (I):

Formula (I)

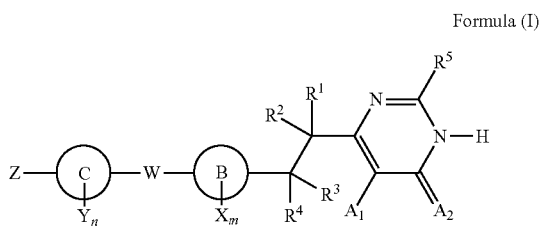

wherein,
n is 0-4;
m is 0-4;
$A_1$ is OH or SH;
$A_2$ is O or S;
$R^1$ and $R^2$ are each independently H or optionally substituted alkyl;
or $R^1$ and $R^2$ are taken together with the carbon to which they are attached to form $=C(R^{11})_2$, $=NR^{11}$, $=O$, or $=S$;
or $R^1$ and $R^2$ are taken together with the carbon to which they are attached to form an optionally substituted 3- to 6-membered carbocyclyl or optionally substituted 4- to 7-membered heterocyclyl containing 1 or 2 heteroatoms selected from O, N, and S;
$R^3$ is optionally substituted alkyl, optionally substituted carbocyclyl, optionally substituted carbocyclylalkyl, optionally substituted amyl, optionally substituted aralkyl, optionally substituted heteroaryl, optionally substituted heteroalkyl, optionally substituted heterocyclyl, optionally substituted heterocyclylalkyl, optionally substituted $(C_0-C_4$ alkylene$)$-$COR^{11}$, optionally substituted $(C_0-C_4$ alkylene$)$-$CO_2R^{11}$, optionally substituted $(C_0-C_4$ alkylene$)$-$CON(R^{11})_2$ optionally substituted $(C_0-C_4$ alkylene$)$-CN, optionally substituted $(C_0-C_4$ alkylene$)$-$OR^{11}$, optionally substituted $(C_0-C_4$ alkylene$)$-$N(R^{11})_2$; optionally substituted $(C_0-C_4$ alkylene$)$-$N(R^{12})$-$COR^{11}$, optionally substituted $(C_0-C_4$ alkylene$)$-$N(R^{12})$-$CO_2R^{11}$, optionally substituted $(C_0-C_4$ alkylene$)$-$N(R^{12})$-$CON(R^{11})_2$, optionally substituted $(C_0-C_4$ alkylene$)$-$N(R^{12})$-$SO_2N(R^{11})_2$, optionally substituted $(C_0-C_4$ alkylene$)$-O-$SO_2N(R^{11})_2$, optionally substituted $(C_0-C_4$ alkylene$)$-$N(R^{11})$-PO-(optionally substituted $C_1-C_4$ alkyl$)_2$, optionally substituted $(C_0-C_4$ alkylene$)$-$SO_2R^{11}$, optionally substituted $(C_0-C_4$ alkylene$)$-O-$SO_2R^{11}$, optionally substituted $(C_0-C_4$ alkylene$)$-$N(R^{12})$-$SO_2R^{11}$, optionally substituted $(C_0-C_4$ alkylene$)$-$C(=N$-$OR^{11})(R^{11})$, or optionally substituted $(C_0-C_4$ alkylene$)$-$OP(=O)(OR^{11})_2$; $R^4$ is H or optionally substituted alkyl;
or $R^3$ and $R^4$ are taken together with the carbon to which they are attached to form $=C(R^{11})_2$, $=NR^{11}$, $=O$, or $=S$,
or $R^3$ and $R^4$ are taken together with the carbon to which they are attached to form an optionally substituted 3- to 6-membered carbocyclyl or optionally substituted 4- to 7-membered heterocyclyl containing 1 or 2 heteroatoms selected from O, N, and S;
$R^5$ is H, halogen, optionally substituted alkyl, hydroxyl, alkoxyl, cyano, amino, or nitro;
Ring B is aryl, carbocyclyl, heteroaryl, or heterocyclyl:
W is a bond, $-C\equiv C-$, bicyclo[1.1.1]pentanylene, $-C\equiv C-C\equiv CH-$, $-CH=CH-$, or $-CH_2CH_2-$;
Ring C is aryl, carbocyclyl, heteroaryl, or heterocyclyl;

each X and Y is independently H, optionally substituted alkyl, halo, fluoroalkyl, cyano, nitro, $-N(R^{13})_2$, or $-OR^{13}$,
or $R^3$ and one X are taken together with the intervening atoms to form an optionally substituted 5- to 7-membered carbocyclyl or optionally substituted 5- to 7-membered heterocyclyl containing 1 or 2 heteroatoms selected from O, N, and S;
Z is 1-1, halo, nitro, or -L-G;
L is a bond or optionally substituted $C_1$-$C_4$ alkylene;
G is optionally substituted alkyl, optionally substituted alkenyl, optionally substituted alkynyl, optionally substituted carbocyclyl, optionally substituted aryl, optionally substituted heterocyclyl, optionally substituted heteroaryl, $-CN$, $-N(R^{13})_2$, $-OR^{13}$, $-COR^{13}$, $-CO_2R^{13}$, $-CON(R^{13})_2$, $-N(R^{14})$-$COR^{13}$, $-SO_2R^{13}$, $-SO_2N(R^{13})_2$, $-N(R^{14})$-$SO_2R^{13}$, $-N(R^{14})$-$CON(R^{13})_2$, $-N(R^{14})$-$CO_2R^{13}$, $-O$-$CON(R^{13})_2$-, $-N(R^{14})$-$SO_2N(R^{13})_2$, $-O$-$SO_2N(R^{13})_2$, $-N(R^{14})$-$SO_2$-$OR^{13}$, or $-C(=N$-$OR^{14})(R^{13})$;
each $R^{11}$ is independently H, optionally substituted alkyl, optionally substituted alkenyl, optionally substituted alkynyl, optionally substituted carbocyclyl, optionally substituted carbocyclylalkyl optionally substituted aryl, optionally substituted aralkyl, optionally substituted heterocyclyl, optionally substituted heterocyclylalkyl, optionally substituted heteroaryl, or optionally substituted heteroarylalkyl;
or two $R^{11}$ on the same nitrogen atom are taken together with the nitrogen to which they are attached to form an optionally substituted N-heterocyclyl;
each $R^{12}$ is independently H, optionally substituted alkyl, optionally substituted carbocyclyl, optionally substituted carbocyclylalkyl, optionally substituted heterocyclyl, or optionally substituted heterocyclylalkyl;
each $R^{13}$ is H, optionally substituted alkyl, optionally substituted alkenyl, optionally substituted alkynyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl;
or two $R^{13}$ on the same nitrogen atom are taken together with the nitrogen to which they are attached to form an optionally substituted N-heterocyclyl; and
each $R^{14}$ is independently H, optionally substituted alkyl, optionally substituted carbocyclyl, optionally substituted carbocyclylalkyl, optionally substituted heterocyclyl, or optionally substituted heterocyclylalkyl.

In some embodiments of a compound disclosed herein, or a pharmaceutically acceptable salt, solvate, or prodrug thereof, Ring B is monocyclic or bicyclic aryl, monocyclic or bicyclic heteroaryl containing 1 or 2 heteroatoms selected from O, N, and S, or monocyclic or bicyclic 5 to 12-membered heterocyclyl containing 1 to 3 heteroatoms selected from O, N, and S. In some embodiments of a compound disclosed herein, or a pharmaceutically acceptable salt, solvate, or prodrug thereof, Ring B is phenyl,

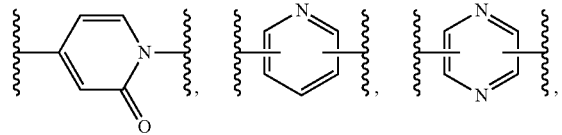

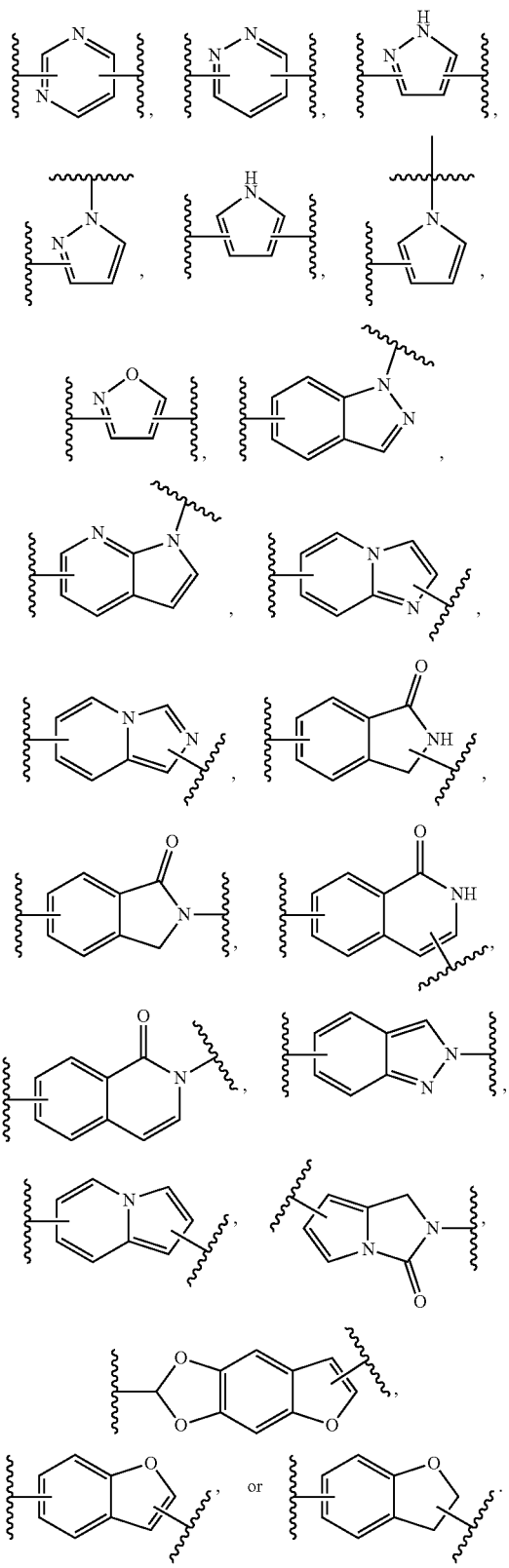

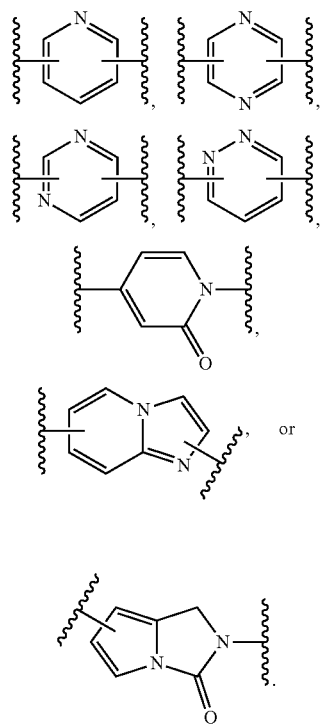

In some embodiments of a compound disclosed herein, or a pharmaceutically acceptable salt, solvate, or prodrug thereof, Ring B is phenyl. In some embodiments of a compound disclosed herein, or a pharmaceutically acceptable salt, solvate, or prodrug thereof, Ring B is carbocyclyl. In some embodiments of a compound disclosed herein, or a pharmaceutically acceptable salt, solvate, or prodrug thereof, Ring B is heteroaryl. In some embodiments of a compound disclosed herein, or a pharmaceutically acceptable salt, solvate, or prodrug thereof, Ring B is heterocyclyl. In some embodiments of a compound disclosed herein, or a pharmaceutically acceptable salt, solvate, or prodrug thereof, Ring B is

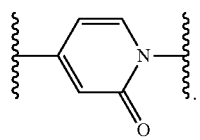 [SMILES: *c1ccn(*)c(=O)c1]

In some embodiments of a compound disclosed herein, or a pharmaceutically acceptable salt, solvate, or prodrug thereof, Ring B is

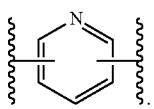

In some embodiments of a compound disclosed herein, or a pharmaceutically acceptable salt, solvate, or prodrug thereof, Ring B is phenyl, In some embodiments of a compound disclosed herein, or a pharmaceutically acceptable salt, solvate, or prodrug thereof, Ring B is

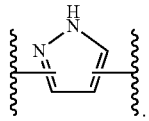

In some embodiments of a compound disclosed herein, or a pharmaceutically acceptable salt, solvate, or prodrug thereof, Ring B is

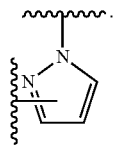

In some embodiments of a compound disclosed herein, or a pharmaceutically acceptable salt, solvate, or prodrug thereof, Ring B is

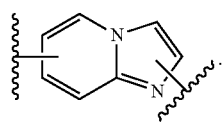

In some embodiments of a compound disclosed herein, or a pharmaceutically acceptable salt, solvate, or prodrug thereof. Ring B is

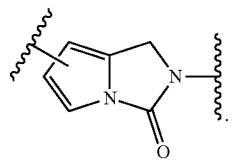

In some embodiments of a compound disclosed herein, or a pharmaceutically acceptable salt, solvate, or prodrug thereof, W is a bond. In some embodiments of a compound disclosed herein, or a pharmaceutically acceptable salt, solvate, or prodrug thereof, W is —C≡C—, bicyclo[1.1.1]pentanylene, —C≡C—C≡C—, —CH═CH—, or —CH$_2$CH$_2$—. In some embodiments of a compound disclosed herein, or a pharmaceutically acceptable salt, solvate, or prodrug thereof, W is —C≡C—, —C≡C—C≡C—, —CH═CH—, or —CH$_2$CH$_2$. In some embodiments of a compound disclosed herein, or a pharmaceutically acceptable salt, solvate, or prodrug thereof, W is —CH═CH—, —CH═CH—, or —CH$_2$CH$_2$—. In some embodiments of a compound disclosed herein, or a pharmaceutically acceptable salt, solvate, or prodrug thereof, W is —C≡C—. In some embodiments of a compound disclosed herein, or a pharmaceutically acceptable salt, solvate, or prodrug thereof, W is bicyclo[1.1.1]pentanylene. In some embodiments of a compound disclosed herein, or a pharmaceutically acceptable salt, solvate, or prodrug thereof, W is —C≡C—C≡C—. In some embodiments of a compound disclosed herein, or a pharmaceutically acceptable salt, solvate, or prodrug thereof, W is —CH═CH—. In some embodiments of a compound disclosed herein, or a pharmaceutically acceptable salt, solvate, or prodrug thereof, W is —CH$_2$CH$_2$—.

In some embodiments of a compound disclosed herein, or a pharmaceutically acceptable salt, solvate, or prodrug thereof, Ring C is monocyclic or bicyclic aryl, monocyclic or bicyclic 3- to 12-membered carbocyclyl, monocyclic or bicyclic heteroaryl containing 1 or 2 heteroatoms selected from O, N, and S, or monocyclic or bicyclic 5- to 12-membered heterocyclyl containing 1 to 3 heteroatoms selected from O, N, and S. In some embodiments of a compound disclosed herein, or a pharmaceutically acceptable salt, solvate, or prodrug thereof, Ring C is phenyl, monocyclic 3- to 6-membered carbocyclyl, or monocyclic or bicyclic heteroaryl containing 1 or 2 heteroatoms selected from O, N, and S. In some embodiments of a compound disclosed herein, or a pharmaceutically acceptable salt, solvate, or prodrug thereof, Ring C is phenyl, cyclohexyl,

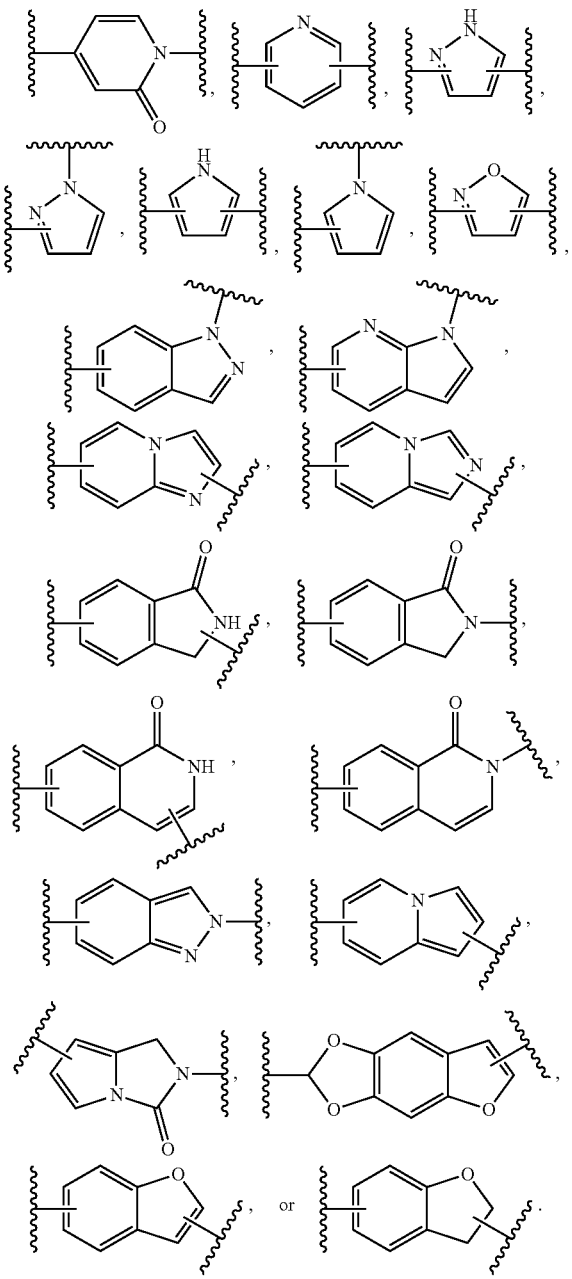

In some embodiments of a compound disclosed herein, or a pharmaceutically acceptable salt, solvate, or prodrug thereof, Ring C is phenyl, cyclohexyl,

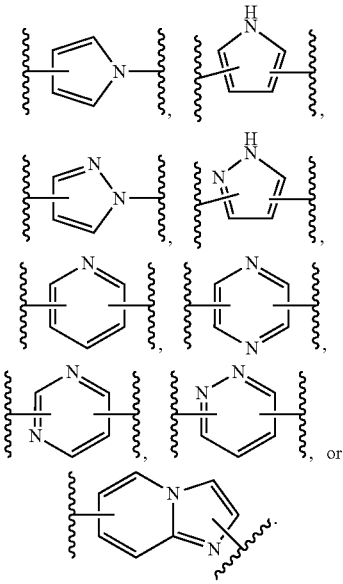

In some embodiments of a compound disclosed herein, or a pharmaceutically acceptable salt, solvate, or prodrug thereof, Ring C is phenyl. In some embodiments of a compound disclosed herein, or a pharmaceutically acceptable salt, solvate, or prodrug thereof, Ring C is carbocyclyl. In some embodiments of a compound disclosed herein, or a pharmaceutically acceptable salt, solvate, or prodrug thereof, Ring C is monocyclic cycloalkyl. In some embodiments of a compound disclosed herein, or a pharmaceutically acceptable salt, solvate, or prodrug thereof, Ring C is cyclohexane. In some embodiments of a compound disclosed herein, or a pharmaceutically acceptable salt, solvate, or prodrug thereof, Ring C is heteroaryl. In some embodiments of a compound disclosed herein, or a pharmaceutically acceptable salt, solvate, or prodrug thereof, Ring C is heterocyclyl. In some embodiments of a compound disclosed herein, or a pharmaceutically acceptable salt, solvate, or prodrug thereof, Ring C is monocyclic heterocyclyl. In some embodiments of a compound disclosed herein, or a pharmaceutically acceptable salt, solvate, or prodrug thereof, Ring C is piperidine. In some embodiments of a compound disclosed herein, or a pharmaceutically acceptable salt, solvate, or prodrug thereof, Ring C is piperazine. In some embodiments of a compound disclosed herein, or a pharmaceutically acceptable salt, solvate, or prodrug thereof, Ring C is

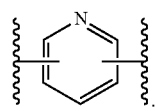

In some embodiments of a compound disclosed herein, or a pharmaceutically acceptable salt, solvate, or prodrug thereof, Ring C is

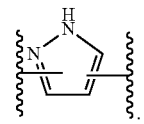

In some embodiments of a compound disclosed herein, or a pharmaceutically acceptable salt, solvate, or prodrug thereof, Ring C is

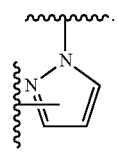

In some embodiments of a compound disclosed herein, or a pharmaceutically acceptable salt, solvate, or prodrug thereof, Ring C is

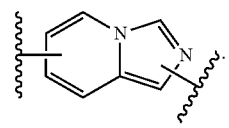

In some embodiments of a compound disclosed herein, or a pharmaceutically acceptable salt, solvate, or prodrug thereof, Ring C is

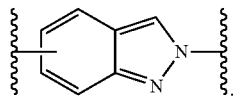

In some embodiments of a compound disclosed herein, or a pharmaceutically acceptable salt, solvate, or prodrug thereof, Ring C is

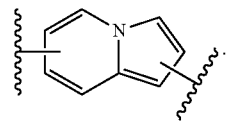

In some embodiments of a compound disclosed herein, or a pharmaceutically acceptable salt, solvate, or prodrug thereof, Ring B is phenyl; and Ring C is phenyl.

In some embodiments of a compound disclosed herein, or a pharmaceutically acceptable salt, solvate, or prodrug thereof, the compound of Formula (I) has the structure of Formula (II):

Formula (II)

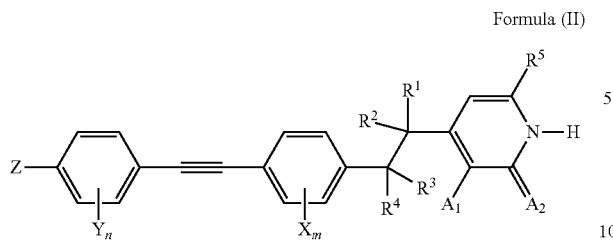

wherein,
n is 0-4;
m is 0-4;
$A_1$ is OH or SH;
$A_2$ is O or S;
$R^1$ and $R^2$ are each independently H or optionally substituted alkyl;
or $R^1$ and $R^2$ are taken together with the carbon to which they are attached to $=C(R^{11})_2$, $=NR^{11}$, $=O$, or $=S$;
or $R^1$ and $R^2$ are taken together with the carbon to which they are attached to form an optionally substituted 3- to 6-membered carbocyclyl or optionally substituted 4- to 7-membered heterocyclyl containing 1 or 2 heteroatoms selected from O, N, and S;
$R^3$ is optionally substituted alkyl, optionally substituted carbocyclyl, optionally substituted carbocyclylalkyl, optionally substituted aryl, optionally substituted aralkyl, optionally substituted heteroaryl, optionally substituted heteroaralkyl, optionally substituted heterocyclyl, optionally substituted heterocyclylalkyl, optionally substituted ($C_0$-$C_4$ alkylene)-$COR^{11}$, optionally substituted ($C_0$-$C_4$ alkylene)-$CO_2R^{11}$, optionally substituted ($C_0$-$C_4$ alkylene)-$CON(R^{11})_2$, optionally substituted ($C_0$-$C_4$ alkylene)-CN, optionally substituted ($C_0$-$C_4$ alkylene)-$OR^{11}$, optionally substituted ($C_0$-$C_4$ alkylene)-$N(R^{11})_2$, optionally substituted ($C_0$-$C_4$ alkylene)-$N(R^{12})$—$COR^{11}$, optionally substituted ($C_0$-$C_4$ alkylene)-$N(R^{12})$—$CO_2R^{11}$, optionally substituted ($C_0$-$C_4$ alkylene)-$N(R^{12})$—$CON(R^{11})_2$, optionally substituted ($C_0$-$C_4$ alkylene)-$N(R^{12})$—$SO_2N(R^{11})_2$, optionally substituted ($C_0$-$C_4$ alkylene)-O—$SO_2N(R^{11})_2$, optionally substituted ($C_0$-$C_4$ alkylene)-$N(R^{11})_2$, (optionally substituted $C_1$-$C_4$alkyl)$_2$, optionally substituted ($C_0$-$C_4$ alkylene)-$SO_2R^{11}$, optionally substituted ($C_0$-$C_4$ alkylene)-O—$SO_2R^{11}$, optionally substituted ($C_0$-$C_4$ alkylene)-$N(R^{12})$—$SO_2R^{11}$, optionally substituted ($C_0$-$C_4$ alkylene)-C(=N—$OR^{11}$)($R^{11}$), or optionally substituted ($C_0$-$C_4$ alkylene)-OP(=O)($OR^{11}$)$_2$;
$R^4$ is H or optionally substituted alkyl;
or $R^3$ and $R^4$ are taken together with the carbon to which they are attached to form $=C(R^{11})_2$, $=NR^{11}$, $=O$, or $=S$.
or $R^3$ and $R^4$ are taken together with the carbon to which they are attached to form an optionally substituted 3- to 6-membered carbocyclyl or optionally substituted 4- to 7-membered heterocyclyl containing 1 or 2 heteroatoms selected from O, N, and S;
$R^5$ is H, halogen, optionally substituted alkyl, hydroxyl, alkoxyl, cyano, amino, or nitro;
each X and Y is independently H, optionally substituted alkyl, halo, fluoroalkyl, cyano, nitro-$N(R^{13})_2$, or —$OR^{13}$;
or $R^3$ and one X are taken together with the intervening atoms to form an optionally substituted 5- to 7-membered carbocyclyl or optionally substituted 5- to 7-membered heterocyclyl containing 1 or 2 heteroatoms selected from O, N, and S;
Z is H, halo; nitro; or -L-G;
L is a bond or optionally substituted $C_1$-$C_4$ alkylene;
G is optionally substituted alkyl, optionally substituted alkenyl, optionally substituted alkynyl, optionally substituted carbocyclyl, optionally substituted aryl, optionally substituted heterocyclyl, optionally substituted heteroaryl, —CN, —$N(R^{13})_2$, —$OR^{13}$, —$COR^{13}$, —$CO_2R^{13}$, —$CON(R^{13})_2$, —$N(R^{14})$—$COR^{13}$, —$SO_2R^{13}$—, —$SO_2N(R^{13})_2$, —$N(R^{14})$—$SO_2R^{13}$, —$N(R^{14})$—$CON(R^{13})_2$, —$N(R^{14})$—$CO_2R^{13}$, —O—$CON(R^{13})_2$—, —$N(R^{14})$—$SO_2N(R^{13})_2$, —O—$SO_2N(R^{13})_2$, —$N(R^{14})$—$SO_2$—$OR^{13}$, or —C(=N—$OR^{14}$)($R^{13}$);
each $R^{11}$ is independently H, optionally substituted alkyl, optionally substituted alkenyl, optionally substituted alkynyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl;
or two $R^{11}$ on the same nitrogen atom are taken together with the nitrogen to Which they are attached to form an optionally substituted N-heterocyclyl;
each $R^{12}$ is independently H, optionally substituted alkyl, optionally substituted carbocyclyl, optionally substituted carbocyclylalkyl, optionally substituted heterocyclyl, or optionally substituted heterocyclylalkyl;
each $R^{13}$ is H, optionally substituted alkyl, optionally substituted alkenyl, optionally substituted alkynyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl;
or two $R^{13}$ on the same nitrogen atom are taken together with the nitrogen to which they are attached to form an optionally substituted N-heterocyclyl; and
each $R^{14}$ is independently H, optionally substituted alkyl, optionally substituted carbocyclyl, optionally substituted carbocyclyalkyl, optionally substituted heterocyclyl, or optionally substituted heterocyclylalkyl.

In some embodiments of a compound disclosed herein, or a pharmaceutically acceptable salt, solvate, or prodrug thereof, each X and Y is independently H, optionally substituted alkyl, halo, fluoroalkyl, cyano, or nitro. In some embodiments of a compound disclosed herein, or a pharmaceutically acceptable salt, solvate, or prodrug thereof, each X and Y is independently H, optionally substituted alkyl, halo, cyano, OH, or $NH_2$. In some embodiments of a compound disclosed herein, or a pharmaceutically acceptable salt, solvate, or prodrug thereof, each X and Y is independently H, optionally substituted alkyl, halo, or cyano. In some embodiments of a compound disclosed herein, or a pharmaceutically acceptable salt, solvate, or prodrug thereof, each X and Y is independently H, halo, or cyano. In some embodiments of a compound disclosed herein, or a pharmaceutically acceptable salt, solvate, or prodrug thereof, each X and Y is independently H, halo, cyano, OH, or $NH_2$. In some embodiments of a compound disclosed herein, or a pharmaceutically acceptable salt, solvate, or prodrug thereof, each X and Y is independently H or halo. In some embodiments of a compound disclosed herein, or a pharmaceutically acceptable salt, solvate, or prodrug thereof, each X and Y is independently H, halo, OH, or $NH_2$. In some embodiments of a compound disclosed herein, or a pharmaceutically acceptable salt, solvate, or prodrug thereof, each X and Y is independently H, F, or Cl. In some embodiments of a compound disclosed herein, or a pharmaceutically acceptable salt, solvate, or prodrug thereof, each X and Y is H.

In some embodiments of a compound disclosed herein, or a pharmaceutically acceptable salt, solvate, or prodrug thereof, each X is independently H, optionally substituted alkyl, halo, or cyano. In some embodiments of a compound disclosed herein, or a pharmaceutically acceptable salt, solvate, or prodrug thereof, each X is independently H, optionally substituted alkyl, halo, or cyano. In some embodiments of a compound disclosed herein, or a pharmaceutically acceptable salt, solvate, or prodrug thereof, each X is independently H, halo, or cyano. In some embodiments of a compound disclosed herein, or a pharmaceutically acceptable salt, solvate, or prodrug thereof, each X is independently H or halo. In some embodiments of a compound disclosed herein, or a pharmaceutically acceptable salt, solvate, or prodrug thereof, each X is independently H, F, or Cl. In some embodiments of a compound disclosed herein, or a pharmaceutically acceptable salt, solvate, or prodrug thereof, each X is H.

In some embodiments of a compound disclosed herein, or a pharmaceutically acceptable salt, solvate, or prodrug thereof, each Y is independently H, optionally substituted alkyl, halo, or cyano. In some embodiments of a compound disclosed herein, or a pharmaceutically acceptable salt, solvate, or prodrug thereof, each Y is independently H, optionally substituted alkyl, halo, or cyano. In some embodiments of a compound disclosed herein, or a pharmaceutically acceptable salt, solvate, or prodrug thereof, each Y is independently H, halo, or cyano. In some embodiments of a compound disclosed herein, or a pharmaceutically acceptable salt, solvate, or prodrug thereof, each Y is independently H or halo. In some embodiments of a compound disclosed herein, or a pharmaceutically acceptable salt, solvate, or prodrug thereof, each Y is independently H, F, or Cl. In some embodiments of a compound disclosed herein, or a pharmaceutically acceptable salt, solvate, or prodrug thereof, each Y is H.

In some embodiments of a compound disclosed herein, or a pharmaceutically acceptable salt, solvate, or prodrug thereof, m is 0 to 4. In some embodiments of a compound disclosed herein, or a pharmaceutically acceptable salt, solvate, or prodrug thereof, m is 0 to 1, 0 to 2, 0 to 3, 0 to 4, 1 to 2, 1 to 3, 1 to 4, 2 to 3, 2 to 4, or 3 to 4. In some embodiments of a compound disclosed herein, or a pharmaceutically acceptable salt, solvate, or prodrug thereof, m is 0, 1, 2, 3, or 4. In some embodiments of a compound disclosed herein, or a pharmaceutically acceptable salt, solvate, or prodrug thereof, in is 0 or 1. In some embodiments of a compound disclosed herein, or a pharmaceutically acceptable salt, solvate, or prodrug thereof, m is 0. In some embodiments of a compound disclosed herein, or a pharmaceutically acceptable salt, solvate, or prodrug thereof, m is 1.

In some embodiments of a compound disclosed herein, or a pharmaceutically acceptable salt, solvate, or prodrug thereof, n is 0 to 4. In some embodiments of a compound disclosed herein, or a pharmaceutically acceptable salt, solvate, or prodrug thereof, n is 0 to 1, 0 to 2, 0 to 3, 0 to 4, 1 to 2, 1 to 3, 1 to 4, 2 to 3, 2 to 4, or 3 to 4. In some embodiments of a compound disclosed herein, or a pharmaceutically acceptable salt, solvate, or prodrug thereof, n is 0, 1, 2, 3, or 4. In some embodiments of a compound disclosed herein, or a pharmaceutically acceptable salt, solvate, or prodrug thereof, n is 0 or 1. In some embodiments of a compound disclosed herein, or a pharmaceutically acceptable salt, solvate, or prodrug thereof, n is 0. In some embodiments of a compound disclosed herein, or a pharmaceutically acceptable salt, solvate, or prodrug thereof, n is 1.

In some embodiments of a compound disclosed herein, or a pharmaceutically acceptable salt, solvate, or prodrug thereof, $A_1$ is OH. In some embodiments of a compound disclosed herein, or a pharmaceutically acceptable salt, solvate, or prodrug, thereof, $A_1$ is SH.

In some embodiments of a compound disclosed herein, or a pharmaceutically acceptable salt, solvate, or prodrug thereof, $A_2$ is O. In some embodiments of a compound disclosed herein, or a pharmaceutically acceptable salt, solvate, or prodrug thereof, $A_2$ is S.

In some embodiments of a compound disclosed herein, or a pharmaceutically acceptable salt, solvate, or prodrug thereof, $A_1$ is OH and $A_2$ is O.

In some embodiments of a compound disclosed herein, or a pharmaceutically acceptable salt, solvate, or prodrug thereof, $R^5$ is H, halogen, optionally substituted alkyl, hydroxyl, or alkoxyl. In some embodiments of a compound disclosed herein, or a pharmaceutically acceptable salt, solvate, or prodrug thereof, $R^5$ is H unsubstituted alkyl, or alkoxyl. In some embodiments of a compound disclosed herein, or a pharmaceutically acceptable salt, solvate, or prodrug thereof, $R^5$ is H.

In some embodiments of a compound disclosed herein, or a pharmaceutically acceptable salt, solvate, or prodrug thereof, $R^1$ and $R^2$ are independently H or optionally substituted alkyl. In some embodiments of a compound disclosed herein, or a pharmaceutically acceptable salt, solvate, or prodrug thereof, $R^1$ and $R^2$ are independently H, or unsubstituted alkyl.

In some embodiments of a compound disclosed herein, or a pharmaceutically acceptable salt, solvate, or prodrug thereof, $R^1$ is H. In some embodiments of a compound disclosed herein, or a pharmaceutically acceptable salt, solvate, or prodrug thereof. $R^1$ is optionally substituted alkyl. In some embodiments of a compound disclosed herein, or a pharmaceutically acceptable salt, solvate, or prodrug thereof, $R^1$ is unsubstituted alkyl.

In some embodiments of a compound disclosed herein, or a pharmaceutically acceptable salt, solvate, or prodrug thereof, $R^2$ is H. In some embodiments of a compound disclosed herein, or a pharmaceutically acceptable salt, solvate, or prodrug thereof, $R^2$ is optionally substituted alkyl. In some embodiments of a compound disclosed herein, or a pharmaceutically acceptable salt, solvate, or prodrug thereof, $R^2$ is unsubstituted alkyl.

In some embodiments of a compound disclosed herein, or a pharmaceutically acceptable salt, solvate, or prodrug thereof, $R^1$ and $R^2$ are H.

In some embodiments of a compound disclosed herein, or a pharmaceutically acceptable salt, solvate, or prodrug thereof, $R^1$ and $R^2$ are taken together with the carbon to which they are attached to form $=C(R^{11})_2$, $=NR^{11}$, $=O$, or $=S$. In some embodiments of a compound disclosed herein, or a pharmaceutically acceptable salt, solvate, or prodrug thereof, $R^1$ and $R^2$ are taken together with the carbon to which they are attached to form $=C(R^{11})_2$. In some embodiments of a compound disclosed herein, or a pharmaceutically acceptable salt, solvate, or prodrug thereof. $R^1$ and $R^2$ are taken together with the carbon to which they are attached to form an unsubstituted alkenyl. In some embodiments of a compound disclosed herein, or a pharmaceutically acceptable salt, solvate, or prodrug thereof, $R^1$ and $R^2$ are taken together with the carbon to which they are attached to form a $=NR^{11}$. In some embodiments of a compound disclosed herein, or a pharmaceutically acceptable salt, solvate, or prodrug thereof, $R^1$ and $R^2$ are taken together with the carbon to which they are attached to form a $=O$. In some embodiments of a compound disclosed herein, or a pharmaceutically acceptable salt, solvate, or prodrug thereof, $R^1$ and $R^2$ are taken together with the carbon to which they are attached to form a $=S$.

In some embodiments of a compound disclosed herein, or a pharmaceutically acceptable salt, solvate, or prodrug thereof, $R^1$ and $R^2$ are taken together with the carbon to which they are attached to form an optionally substituted 3- to 6-membered carbocyclyl or optionally substituted 4- to 7-membered heterocyclyl containing 1 or 2 heteroatoms selected from O, N, and S. In some embodiments of a compound disclosed herein, or a pharmaceutically acceptable salt, solvate, or prodrug thereof, $R^1$ and $R^2$ are taken together with the carbon to which they are attached to form an optionally substituted 3- to 6-membered carbocyclyl. In some embodiments of a compound disclosed herein, or a pharmaceutically acceptable salt, solvate, or prodrug thereof, $R^1$ and $R^2$ are taken together with the carbon to which they are attached to form an unsubstituted 3- to 6-membered carbocyclyl. In some embodiments of a compound disclosed herein, or a pharmaceutically acceptable salt, solvate, or prodrug thereof, $R^1$ and $R^2$ are taken together with the carbon to which they are attached to form a cyclopropyl, cyclobuta, cyclopentyl, or cyclohexyl. In some embodiments of a compound disclosed herein, or a pharmaceutically acceptable salt, solvate, or prodrug thereof, $R^1$ and $R^2$ are taken together with the carbon to which they are attached to form a cyclopropyl. In some embodiments of a compound disclosed herein, or a pharmaceutically acceptable salt, solvate, or prodrug thereof, $R^1$ and $R^2$ are taken together with the carbon to which they are attached to form an optionally substituted 4- to 7-membered heterocyclyl containing 1 or 2 heteroatoms selected from O, N, and S. In some embodiments of a compound disclosed herein, or a pharmaceutically acceptable salt, solvate, or prodrug thereof, $R^1$ and $R^2$ are taken together with the carbon to which they are attached to form an unsubstituted 4- to 7-membered heterocyclyl containing 1 or 2 heteroatoms selected from O, N, and S.

In some embodiments of a compound disclosed herein, or a pharmaceutically acceptable salt, solvate, or prodrug thereof, the compound of Formula (I) or Formula (II) has the structure of Formula (III):

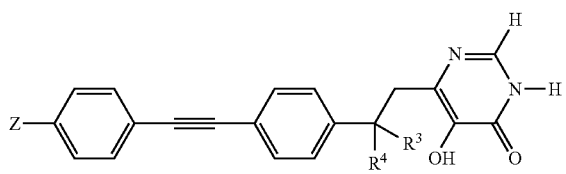

Formula (III)

wherein,
$R^3$ is optionally substituted alkyl, optionally substituted carbocyclyl, optionally substituted carbocyclylalkyl, optionally substituted aryl, optionally substituted aralkyl, optionally substituted heteroaryl, optionally substituted heteroaralkyl, optionally substituted heterocyclyl, optionally substituted heterocyclyalkyl, optionally substituted ($C_0$-$C_4$ alkylene)-$COR^{11}$, optionally substituted ($C_0$-$C_4$ alkylene)-$CO_2R^{11}$, optionally substituted ($C_0$-$C_4$ alkylene)-$CON(R^{11})_2$, optionally substituted ($C_0$-$C_4$)alkylene)-CN, optionally substituted ($C_0$-$C_4$ alkylene)-$OR^{11}$, optionally substituted ($C_0$-$C_4$ alkylene)-$N(R^{11})_2$, optionally substituted ($C_0$-$C_4$ alkylene)-$N(R^{12})$—$COR^{11}$, optionally substituted ($C_0$-$C_4$ alkylene)-$N(R^{12})$—$CO_2R^{11}$, optionally substituted ($C_0$-$C_4$ alkylene)-$N(R^{12})$—$CON(R^{11})_2$, optionally substituted ($C_0$-$C_4$ alkylene)-$N(R^{12})$—$SO_2N(R^{11})_2$, optionally substituted ($C_0$-$C_4$ alkylene)-O—$SO_2N(R^{11})_2$, optionally substituted ($C_0$-$C_4$ alkylene)-N($R^{11}$)—PO (optionally substituted $C_1$-$C_4$ alkyl)$_2$, optionally substituted ($C_0$-$C_4$ alkylene)-$SO_2R^{11}$, optionally substituted ($C_0$-$C_4$ alkylene)-O—$SO_2R^{11}$, optionally substituted ($C_0$-$C_4$ alkylene)-$N(R^{12})$—$SO_2R^{11}$, optionally substituted ($C_0$-$C_4$ alkylene)-$C(=N$—$OR^{11})(R^{11})$, or optionally substituted ($C_0$-$C_4$ alkylene)-$OP(=O)(OR^{11})_2$;

$R^4$ is H or optionally substituted alkyl;
or $R^3$ and $R^4$ are taken together with the carbon to which they are attached to form $=C(R^{11})_2$, $=NR^{11}$, $=O$, or $=S$;
or $R^3$ and $R^4$ are taken together with the carbon to which they are attached to form an optionally substituted 3- to 6-membered carbocyclyl or optionally substituted 4- to 7-membered heterocyclyl containing 1 or 2 heteroatoms selected from O, N, and S;

Z is H, halo, nitro, or -L-G;
L is a bond or optionally substituted $C_1$-$C_4$ alkylene;
G is optionally substituted alkyl, optionally substituted alkenyl, optionally substituted alkynyl, optionally, substituted carbocyclyl, optionally substituted aryl, optionally substituted heterocyclyl, optionally substituted heteroaryl, —CN, —$N(R^{13})_2$, —$OR^{13}$, —$COR^{13}$, —$CO_2R^{13}$, —$CON(R^{13})_2$, —$N(R^{14})$—$COR^{13}$, —$SO_2R^{13}$—, —$SO_2N(R^{13})_2$, —$N(R^{14})$—$SO_2R^{13}$, —$N(R^{14})$—$CON(R^{13})_2$, —$N(R^{14})$—$CO_2R^{13}$, —O—$CON(R^{13})_2$—, —$N(R^{14})$—$SO_2N(R^{13})_2$, —O—$SO_2N(R^{13})_2$, —$N(R^{14})$—$SO_2$—$OR^{13}$, or —$C(=N$—$OR^{14})(R^{13})$;

each $R^{11}$ is independently H, optionally substituted alkyl, optionally substituted alkenyl, optionally substituted alkynyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl;

or two $R^{11}$ on the same nitrogen atom are taken together with the nitrogen to which they are attached to form an optionally substituted N-heterocyclyl;

each $R^{12}$ is independently H, optionally substituted alkyl, optionally substituted carbocyclyl, optionally substituted carbocyclylalkyl, optionally substituted heterocyclyl, or optionally substituted heterocyclylalkyl;

each $R^{13}$ is H, optionally substituted alkyl, optionally substituted alkenyl, optionally substituted alkynyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl or two $R^{13}$ on the same nitrogen atom are taken together with the nitrogen to which they are attached to form an optionally substituted N-heterocyclyl; and each $R^{14}$ is independently H, optionally substituted alkyl, optionally substituted carbocyclyl, optionally substituted carbocyclylalkyl, optionally substituted heterocyclyl, or optionally substituted heterocyclylalkyl.

In some embodiments of a compound disclosed herein, or a pharmaceutically acceptable salt, solvate, or prodrug thereof, $R^3$ and $R^4$ are taken together with the carbon to which they are attached to form $=C(R^{11})_2$, $=NR^{11}$, $=O$, or $=S$. In some embodiments of a compound disclosed herein, or a pharmaceutically acceptable salt, solvate, or prodrug thereof, $R^3$ and $R^4$ are taken together with the carbon to which they are attached to form $=C(R^{11})_2$. In some embodiments of a compound disclosed herein, or a pharmaceutically acceptable salt, solvate, or prodrug thereof, $R^3$ and $R^4$ are taken together with the carbon to which they are attached to form an unsubstituted alkenyl. In some embodiments of a compound disclosed herein, or a pharmaceutically acceptable salt, solvate, or prodrug thereof, $R^3$ and $R^4$ are taken together with the carbon to which they are attached to form a $=NR^{11}$. In some embodiments of a compound disclosed herein, or a pharmaceutically acceptable salt, solvate, or prodrug thereof, $R^3$ and $R^4$ are taken together with the carbon to which they are attached to form a $=O$. In some embodiments of a compound disclosed herein, or a pharmaceutically acceptable salt, solvate, or prodrug thereof, $R^3$ and $R^4$ are taken together with the carbon to which they are attached to form a $=S$.

In some embodiments of a compound disclosed herein, or a pharmaceutically acceptable salt, solvate, or prodrug thereof, $R^3$ and $R^4$ are taken together with the carbon to which they are attached to form an optionally substituted 3- to 6-membered carbocyclyl or optionally substituted 4- to 7-membered heterocyclyl containing 1 or 2 heteroatoms selected from O, N, and S. In some embodiments of a compound disclosed herein, or a pharmaceutically acceptable salt, solvate, or prodrug thereof, $R^3$ and $R^4$ are taken together with the carbon to which they are attached to form an optionally substituted 3- to 6-membered carbocyclyl. In some embodiments of a compound disclosed herein, or a pharmaceutically acceptable salt, solvate, or prodrug thereof, $R^3$ and $R^4$ are taken together with the carbon to which they are attached to form an unsubstituted 3- to 6-membered carbocyclyl. In some embodiments of a compound disclosed herein, or a pharmaceutically acceptable salt, solvate, or prodrug thereof, $R^3$ and $R^4$ are taken together with the carbon to which they are attached to form a cyclopropyl, cyclobutyl, cyclopentyl, or cyclohexyl. In some embodiments of a compound disclosed herein, or a pharmaceutically acceptable salt, solvate, or prodrug thereof, $R^3$ and $R^4$ are taken together with the carbon to which they are attached to form a cyclopropyl. In some embodiments of a compound disclosed herein, or a pharmaceutically acceptable salt, solvate, or prodrug thereof, $R^3$ and $R^4$ are taken together with the carbon to which they are attached to form an optionally substituted 4- to 7-membered heterocyclyl containing 1 or 2 heteroatoms selected from O, N, and S. In some embodiments of a compound disclosed herein, or a pharmaceutically acceptable salt, solvate, or prodrug thereof, $R^3$ and $R^4$ are taken together with the carbon to which they are attached to form an unsubstituted 4- to 7-membered heterocyclyl containing 1 or 2 heteroatoms selected from O, N, and S.

In some embodiments of a compound disclosed herein, or a pharmaceutically acceptable salt, solvate, or prodrug thereof, $R^4$ is H. In some embodiments of a compound disclosed herein, or a pharmaceutically acceptable salt, solvate, or prodrug thereof, $R^4$ is optionally substituted alkyl. In some embodiments of a compound disclosed herein, or a pharmaceutically acceptable salt, solvate, or prodrug thereof, $R^4$ is unsubstituted alkyl.

In some embodiments of a compound disclosed herein, or a pharmaceutically acceptable salt, solvate, or prodrug thereof, the compound of Formula (I) or Formula (II) or Formula (III) has the structure of Formula (IV):

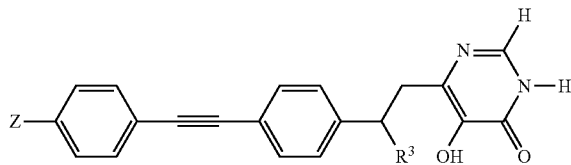

Formula (IV)

wherein, $R^3$ is optionally substituted alkyl, optionally substituted carbocyclyl, optionally substituted carbocyclyl alkyl, optionally substituted aryl, optionally substituted aralkyl, optionally substituted heteroaryl, optionally substituted heteroaralkyl, optionally substituted heterocyclyl, optionally substituted heterocyclylalkyl, optionally substituted $(C_0\text{-}C_4$ alkylene$)$-$COR^{11}$, optionally substituted $(C_0\text{-}C_4$ alkylene$)$-$CO_2R^{11}$, optionally substituted $(C_0\text{-}C_4$ alkylene$)$-$CON(R^{11})_2$, optionally substituted $(C_0\text{-}C_4$ alkylene$)$-CN, optionally substituted $(C_0\text{-}C_4$ alkylene$)$-$OR^{11}$, optionally substituted $(C_0\text{-}C_4$ alkylene$)$-$N(R^{11})_2$, optionally substituted $(C_0\text{-}C_4$ alkylene$)$-$N(R^{12})$—$COR^{11}$, optionally substituted $(C_0\text{-}C_4$ alkylene$)$-$N(R^{12})$—$CO_2R^{11}$, optionally substituted $(C_0\text{-}C_4$ alkylene$)$-$N(R^{12})$—$CON(R^{11})_2$, optionally substituted $(C_0\text{-}C_4$ alkylene$)$-$N(R^{12})$—$SO_2N(R^{11})_2$, optionally substituted $(C_0\text{-}C_4$ alkylene$)$-$O$—$SO_2N(R^{11})_2$, optionally substituted $(C_0\text{-}C_4$ alkylene$)$-$N(R^{11})$—PO (optionally substituted $C_1\text{-}C_4$ alkyl$)_2$, optionally substituted $(C_0\text{-}C_4$ alkylene$)$-$SO_2R^{11}$, optionally substituted $(C_0\text{-}C_4$ alkylene$)$-$O$—$SO_2R^{11}$ optionally substituted $(C_0\text{-}C_4$ alkylene$)$-$N(R^{12})$—$SO_2R^{11}$, optionally substituted $(C_0\text{-}C_4$ alkylene$)$-$C(=N$—$OR^{11})(R^{11})$, or optionally substituted $(C_0\text{-}C_4$ alkylene$)$-$OP(=O)(OR^{11})_2$;

Z is H, halo, nitro, or -L-G;

L is a bond or optionally substituted $C_1\text{-}C_4$ alkylene

G is optionally substituted alkyl, optionally substituted alkenyl, optionally substituted alkynyl, optionally substituted carbocyclyl, optionally substituted aryl, optionally substituted heterocyclyl, optionally substituted heteroaryl, —CN, —$N(R^{13})_2$, —$OR^{13}$, —$COR^{13}$, —$CO_2R^{13}$, —$CON(R^{13})_2$, —$N(R^{14})$—$COR^{13}$, —$SO_2R^{13}$—, —$SO_2N(R^{13})_2$, —$N(R^{14})$—$SO_2R^{13}$, —$N(R^{14})$—$CON(R^{13})_2$, —$N(R^{14})$—$CO_2R^{13}$, —O—$CON(R^{13})_2$—, —$N(R^{14})$—$SO_2N(R^{13})_2$, —O—$SO_2N(R^{13})_2$, —$N(R^{14})$—$SO_2$—$OR^{13}$, or —$C(=N$—$OR^{14})(R^{13})$;

each $R^{11}$ is independently H, optionally substituted alkyl, optionally substituted alkenyl, optionally substituted alkynyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl;

or two $R^{11}$ inn the same nitrogen atom are taken together with the nitrogen to which they are attached to form an optionally substituted N-heterocyclyl;

each $R^{12}$ is independently H, optionally substituted alkyl, optionally substituted carbocyclyl, optionally substituted carbocyclylalkyl, optionally substituted heterocyclyl, or optionally substituted heterocyclylalkyl;

each $R^{13}$ is H, optionally substituted alkyl, optionally substituted alkenyl, optionally substituted alkynyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl;

or two $R^{13}$ on the same nitrogen atom are taken together with the nitrogen to which they are attached to form an optionally substituted N-heterocyclyl; and each $R^{14}$ independently H, optionally substituted alkyl, optionally substituted carbocyclyl, optionally substituted carbocyclylalkyl, optionally substituted heterocyclyl, or optionally substituted heterocyclylalkyl.

In some embodiments of a compound disclosed herein, or a pharmaceutically acceptable salt, solvate, or prodrug thereof, the compound is of Formula (IVa):

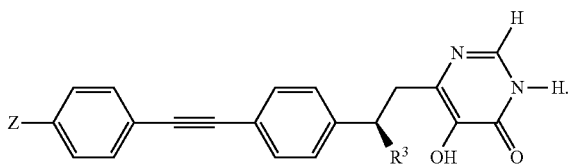

Formula (IVa)

In some embodiments of a compound disclosed herein, or a pharmaceutically acceptable salt, solvate, or prodrug thereof, the compound is of Formula (IVb):

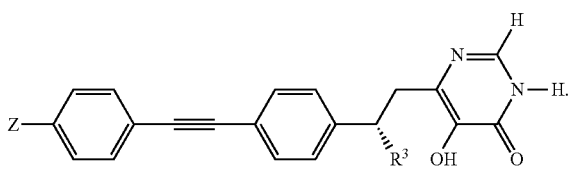

(IVb)

In some embodiments of a compound disclosed herein, or a pharmaceutically acceptable salt, solvate, or prodrug thereof, $R^3$ is optionally substituted alkyl, optionally substituted carbocyclyl, optionally substituted carbocyclylalkyl, optionally substituted aryl, optionally substituted aralkyl, optionally substituted heteroaryl, optionally substituted heteroaralkyl, optionally substituted heterocyclyl, optionally substituted heterocyclylalkyl, optionally substituted ($C_0$-$C_4$ alkylene)-$COR^{11}$, optionally substituted ($C_0$-$C_4$ alkylene)-$CO_2R^{11}$, optionally substituted ($C_0$-$C_4$ alkylene)-CON($R^{11}$)$_2$, optionally substituted ($C_0$-$C_4$ alkylene)-CN, optionally substituted ($C_0$-$C_4$ alkylene)-$OR^{11}$, optionally substituted ($C_0$-$C_4$ alkylene)-N($R^{11}$)$_2$, optionally substituted ($C_0$-$C_4$ alkylene)-N($R^{12}$)—$COR^{11}$, optionally substituted ($C_0$-$C_4$ alkylene)-N($R^{12}$)—$CO_2R^{11}$, optionally substituted ($C_0$-$C_4$ alkylene)-N($R^{12}$)—CON($R^{11}$)$_2$, optionally substituted ($C_0$-$C_4$ alkylene)-N($R^{12}$)—$SO_2N(R^{11})_2$, optionally substituted ($C_0$-$C_4$ alkylene)-O—$SO_2N(R^{11})_2$, optionally substituted ($C_0$-$C_4$ alkylene)-N($R^{11}$)—PO (optionally substituted $C_1$-$C_4$ alkyl)$_2$, optionally substituted ($C_0$-$C_4$ alkylene)-$SO_2R^{11}$, optionally substituted ($C_0$-$C_4$ alkylene)-O—$SO_2R^{11}$, optionally substituted ($C_0$-$C_4$ alkylene)-N($R^{12}$)—$SO_2R^{11}$, optionally substituted ($C_0$-$C_4$ alkylene)-C(=N—$OR^{11}$)($R^{11}$), or optionally substituted ($C_0$-$C_4$ alkylene)-OP(=O)($OR^{11}$)$_2$.

In some embodiments of a compound disclosed herein, or a pharmaceutically acceptable salt, solvate, or prodrug thereof, $R^3$ is an optionally substituted alkyl. In some embodiments of a compound disclosed herein, or a pharmaceutically acceptable salt, solvate, or prodrug thereof, $R^3$ is unsubstituted alkyl. In some embodiments of a compound disclosed herein, or a pharmaceutically acceptable salt, solvate, or prodrug thereof, $R^3$ is an optionally substituted carbocyclyl. In some embodiments of a compound disclosed herein, or a pharmaceutically acceptable salt, solvate, or prodrug thereof, $R^3$ is an optionally substituted carbocyclylalkyl. In some embodiments of a compound disclosed herein, or a pharmaceutically acceptable salt, solvate, or prodrug thereof, $R^3$ is an optionally substituted heteroaryl. In some embodiments of a compound disclosed herein, or a pharmaceutically acceptable salt, solvate, or prodrug thereof, $R^3$ is an optionally substituted heteroaralkyl. In some embodiments of a compound disclosed herein, or a pharmaceutically acceptable salt, solvate, or prodrug thereof, $R^3$ is an optionally substituted heterocyclyl. In some embodiments of a compound disclosed herein, or a pharmaceutically acceptable salt, solvate, or prodrug thereof, $R^3$ is an optionally substituted heterocycloalkyl. In some embodiments of a compound disclosed herein, or a pharmaceutically acceptable salt, solvate, or prodrug thereof, $R^3$ is optionally substituted ($C_0$-$C_4$ alkylene)-$COR^{11}$. In some embodiments of a compound disclosed herein, or a pharmaceutically acceptable salt, solvate, or prodrug thereof, $R^3$ is optionally substituted ($C_0$-$C_4$ alkylene)-$CO_2R^{11}$. In some embodiments of a compound disclosed herein, or a pharmaceutically acceptable salt, solvate, or prodrug thereof, $R^3$ is optionally substituted ($C_0$-$C_4$ alkylene)-CON($R^{11}$)$_2$. In some embodiments of a compound disclosed herein, or a pharmaceutically acceptable salt, solvate, or prodrug thereof, $R^3$ is an optionally substituted ($C_0$-$C_4$ alkylene)-CN. In some embodiments of a compound disclosed herein, or a pharmaceutically acceptable salt, solvate, or prodrug thereof, $R^3$ is an optionally substituted ($C_0$-$C_4$ alkylene)-$OR^{11}$. In some embodiments of a compound disclosed herein, or a pharmaceutically acceptable salt, solvate, or prodrug thereof, $R^3$ is an optionally substituted ($C_0$-$C_4$ alkylene)-N($R^{11}$)$_2$. In some embodiments of a compound disclosed herein, or a pharmaceutically acceptable salt, solvate, or prodrug thereof, $R^3$ is an optionally substituted ($C_0$-$C_4$ alkylene)-N($R^{12}$)—$COR^{11}$, in some embodiments of a compound disclosed herein, or a pharmaceutically acceptable salt, solvate, or prodrug thereof, $R^3$ is an optionally substituted ($C_0$-$C_4$ alkylene)-N($R^{12}$)—$CO_2R^{11}$. In some embodiments of a compound disclosed herein, or a pharmaceutically acceptable salt, solvate, or prodrug thereof, $R^3$ is an optionally substituted ($C_0$-$C_4$ alkylene)-N($R^{12}$)—CON($R^{11}$)$_2$. In some embodiments of a compound disclosed herein, or a pharmaceutically acceptable salt, solvate, or prodrug thereof, $R^3$ is an optionally substituted ($C_0$-$C_4$ alkylene)-N($R^{12}$)—$SO_2N(R^{11})_2$. In some embodiments of a compound disclosed herein, or a pharmaceutically acceptable salt, solvate, or prodrug thereof, $R^3$ is an optionally substituted ($C_0$-$C_4$ alkylene)-O—$SO_2N(R^{11})_2$. In some embodiments of a compound disclosed herein, or a pharmaceutically acceptable salt, solvate, or prodrug thereof, $R^3$ is an optionally substituted ($C_0$-$C_4$ alkylene)-N($R^{11}$)—PO (optionally substituted $C_1$-$C_4$ alkyl)$_2$. In some embodiments of a compound disclosed herein, or a pharmaceutically acceptable salt, solvate, or prodrug thereof, $R^3$ is an optionally substituted ($C_0$-$C_4$ alkylene)-SO$_2$$R^{11}$. In some embodiments of a compound disclosed herein, or a pharmaceutically acceptable salt, solvate, or prodrug thereof, $R^3$ is an optionally substituted ($C_0$-$C_4$ alkylene)-O—SO$_2$$R^{11}$. In some embodiments of a compound disclosed herein, or a pharmaceutically acceptable salt, solvate, or prodrug thereof, $R^3$ is an optionally substituted ($C_0$-$C_4$ alkylene)-N($R^{12}$)—SO$_2$$R^{11}$. In some embodiments of a compound disclosed herein, or a pharmaceutically acceptable salt, solvate, or prodrug thereof, $R^3$ is an optionally substituted ($C_0$-$C_4$ alkylene)-C(=N—O$R^{11}$)($R^{11}$). In some embodiments of a compound disclosed herein, or a pharmaceutically acceptable salt, solvate, or prodrug thereof, $R^3$ is an optionally substituted ($C_0$-$C_4$ alkylene)-OP(=O)(O$R^{11}$)$_2$.

In some embodiments of a compound disclosed herein, or a pharmaceutically acceptable salt, solvate, or prodrug thereof, $R^3$ is an optionally substituted alkyl, optionally substituted carbocyclyl, optionally substituted carbocyclylalkyl, optionally substituted aryl, optionally substituted aralkyl, optionally substituted heteroaryl, optionally substituted heteroaralkyl, optionally substituted heterocyclyl, optionally substituted heterocycloalkyl, optionally substituted ($C_0$-$C_4$ alkylene)-COR$^{11}$, optionally substituted ($C_0$-$C_4$ alkene)-CO$_2$$R^{11}$, optionally substituted ($C_0$-$C_4$ alkylene)-CON($R^{11}$)$_2$, optionally substituted ($C_0$-$C_4$ alkylene)-CN, optionally substituted ($C_0$-$C_4$ alkylene)-O$R^{11}$, optionally substituted ($C_0$-$C_4$ alkylene)-N($R^{11}$)$_2$, optionally substituted ($C_0$-$C_4$ alkylene)-N($R^{12}$)—COR$^{11}$, optionally substituted ($C_0$-$C_4$ alkylene)-N($R^{12}$)—CO$_2$$R^{11}$, optionally substituted ($C_0$-$C_4$ alkylene)-N($R^{12}$)—CON($R^{11}$)$_2$, optionally substituted ($C_0$-$C_4$ alkylene)-N($R^{11}$)—SO$_2$$R^{11}$, air optionally substituted ($C_0$-$C_4$ alkylene)-C(=N—O$R^{11}$)($R^{11}$). In some embodiments of a compound disclosed herein, or a pharmaceutically acceptable salt, solvate, or prodrug thereof, $R^3$ is an optionally substituted alkyl, optionally substituted carbocyclyl, optionally substituted carbocyclylalkyl, optionally substituted aryl, optionally substituted aralkyl, optionally substituted heteroaryl, optionally substituted heteroaralkyl, optionally substituted heterocyclyl, optionally substituted heterocycloalkyl, optionally substituted ($C_0$-$C_4$ alkylene)-COR$^{11}$, optionally substituted ($C_0$-$C_4$ alkylene)-CO$_2$$R^{11}$, optionally substituted ($C_0$-$C_4$ alkylene)-CON($R^{11}$)$_2$, optionally substituted ($C_0$-$C_4$ alkylene)-CN, optionally substituted ($C_0$-$C_4$ alkylene)-O$R^{11}$, optionally substituted ($C_0$-$C_4$ alkylene)-N($R^{11}$)$_2$, optionally substituted ($C_0$-$C_4$ alkylene)-N($R^{11}$)—COR$^{11}$, optionally substituted ($C_0$-$C_4$ alkylene)-N($R^{12}$)—CO$_2$$R^{11}$, optionally substituted ($C_0$-$C_4$ alkylene)-N($R^{12}$)—CON($R^{11}$)$_2$, or optionally substituted ($C_0$-$C_4$ alkylene)-C(=N—O$R^{11}$)($R^{11}$). In some embodiments of a compound disclosed herein, or a pharmaceutically acceptable salt, solvate, or prodrug thereof, $R^3$ is an optionally substituted alkyl, optionally substituted carbocyclyl, optionally substituted carbocyclylalkyl, optionally substituted heteroaryl, optionally substituted heteroaralkyl, optionally substituted heterocyclyl, optionally substituted heterocycloalkyl, optionally substituted ($C_0$-$C_4$ alkylene)-COR$^{11}$, optionally substituted ($C_0$-$C_4$ alkylene)-CO$_2$$R^{11}$, optionally substituted ($C_0$-$C_4$ alkylene)-CON($R^{11}$)$_2$, optionally substituted ($C_0$-$C_4$ alkylene)-CN, optionally substituted ($C_0$-$C_4$ alkylene)-O$R^{11}$, optionally substituted ($C_0$-$C_4$ alkylene)-N($R^{11}$)$_2$, optionally substituted ($C_0$-$C_4$ alkylene)-N($R^{12}$)—COR$^{11}$, optionally substituted ($C_0$-$C_4$ alkylene)-N($R^{12}$)—CO$_2$$R^{11}$, optionally substituted ($C_0$-$C_4$ alkylene)-N($R^{12}$)—CON($R^{11}$)$_2$, or optionally substituted ($C_0$-$C_4$ alkylene)-C(=N—O$R^{11}$)($R^{11}$).

In some embodiments of a compound disclosed herein, or a pharmaceutically acceptable salt, solvate, or prodrug thereof, $R^3$ is an optionally substituted alkyl, optionally substituted ($C_0$-$C_4$ alkylene)-CO$_2$$R^{11}$, optionally substituted ($C_0$-$C_4$ alkylene)-CON($R^{11}$)$_2$, optionally substituted ($C_0$-$C_4$ alkylene)-O$R^{11}$, or optionally substituted ($C_0$-$C_4$ alkylene)-N($R^{11}$)$_2$. In some embodiments of a compound disclosed herein, or a pharmaceutically acceptable salt, solvate, or prodrug thereof, $R^3$ is an optionally substituted alkyl, optionally substituted ($C_0$-$C_4$ alkylene)-CO$_2$$R^{11}$, optionally substituted ($C_0$-$C_4$ alkylene)-CON($R^{11}$)$_2$, optionally substituted ($C_0$-$C_4$ alkylene)-O$R^{11}$, or optionally substituted ($C_0$-$C_4$ alkylene)-N($R^{11}$)$_2$. In some embodiments of a compound disclosed herein, or a pharmaceutically acceptable salt, solvate, or prodrug thereof, $R^3$ is an unsubstituted alkyl, —CO$_2$$R^{11}$, —CON($R^{11}$)$_2$, optionally substituted ($C_0$-$C_4$ alkylene)-O$R^{11}$, optionally substituted ($C_0$-$C_4$ alkylene)-N($R^{11}$)$_2$, optionally substituted ($C_0$-$C_4$ alkylene)-N($R^{12}$)—SO$_2$$R^{11}$. In some embodiments of a compound disclosed herein, or a pharmaceutically acceptable salt, solvate, or prodrug thereof, $R^3$ is an unsubstituted alkyl, —CO$_2$$R^{11}$, —CON($R^{11}$)$_2$, optionally substituted ($C_0$-$C_4$ alkylene)-O$R^{11}$, or optionally substituted ($C_0$-$C_4$ alkylene)-N($R^{11}$)$_2$. In some embodiments of a compound disclosed herein, or a pharmaceutically acceptable salt, solvate, or prodrug thereof, $R^3$ is an unsubstituted alkyl, —CO$_2$Me, —CO$_2$Et, ($C_0$-$C_4$ alkylene)-OH, ($C_0$-$C_4$ alkylene)-OMe, ($C_0$-$C_4$ alkylene)-NH$_2$, ($C_0$-$C_4$ alkylene)-NHR$^{11}$, ($C_0$-$C_4$ alkylene)-N($R^{11}$)$_2$, or ($C_0$-$C_4$ alkylene)-NH—SO$_2$$R^{11}$ in some embodiments of a compound disclosed herein, or a pharmaceutically acceptable salt, solvate, or prodrug thereof, $R^3$ is an unsubstituted alkyl, —CO$_2$Me, —CO$_2$Et, ($C_0$-$C_4$ alkylene)-OH, ($C_0$-$C_4$ alkylene)-OMe, ($C_0$-$C_4$ alkylene)-NH$_2$, ($C_0$-$C_4$ alkylene)-NHR$^{11}$, or ($C_0$-$C_4$ alkylene)-N($R^{11}$)$_2$. In some embodiments of a compound disclosed herein, or a pharmaceutically acceptable salt, solvate, or prodrug thereof, $R^3$ is an unsubstituted alkyl, —CO$_2$Me, —CO$_2$Et, ($C_0$-$C_2$ alkylene)-OH, ($C_0$-$C_2$ alkylene)-OMe, ($C_0$-$C_2$ alkylene)-NH$_2$, ($C_0$-$C_2$ alkylene)-NHR$^{11}$, ($C_0$-$C_2$ alkylene)-N($R^{11}$)$_2$, or ($C_0$-$C_2$ alkylene)-NH—SO$_2$$R^{11}$. In some embodiments of a compound disclosed herein, or a pharmaceutically acceptable salt, solvate, or prodrug thereof, $R^3$ is an unsubstituted alkyl, —CO$_2$Me, —CO$_2$Et, ($C_0$-$C_2$ alkylene)-OH, ($C_0$-$C_2$ alkylene)-OMe, ($C_0$-$C_2$ alkylene)-NH, ($C_0$-$C_2$ alkylene)-NHMe, ($C_0$-$C_2$ alkylene)-NMe$_2$, or ($C_0$-$C_2$ alkylene)-NH—SO$_2$Me. In some embodiments of a compound disclosed herein, or a pharmaceutically acceptable salt, solvate, or prodrug thereof, $R^3$ is ($C_0$-$C_2$ alkylene)-NH—SO$_2$Me. In some embodiments of a compound disclosed herein, or a pharmaceutically acceptable salt, solvate, or prodrug thereof, $R^3$ is —NH—$SO_2$Me.

In some embodiments of a compound disclosed herein, or a pharmaceutically acceptable salt, solvate, or prodrug thereof, each $R^{11}$ is independently H, optionally substituted alkyl, optionally substituted carbocyclyl, optionally substituted heterocyclyl, or optionally substituted heteroarylalkyl. In some embodiments of a compound disclosed herein, or a pharmaceutically acceptable salt, solvate, or prodrug thereof, each $R^{11}$ is independently unsubstituted or substituted with halogen, —CN, —$R^b$—$OR^a$, —$R^b$—C(O)$R^a$, or —$R^b$—S(O)$_t R^a$; wherein t is 1 or 2; each $R^a$ is independently hydrogen or alkyl which is optionally substituted with halogen, hydroxy, methoxy, or trifluoromethyl; and each $R^b$ is independently a direct bond or a straight or branched alkylene. In some embodiments of a compound disclosed herein, or a pharmaceutically acceptable salt, solvate, or prodrug thereof, each $R^{11}$ is independently unsubstituted or substituted with —F, —Cl, —CN, —OH, —OMe, —$SO_2$Me, or —C(O)Me.

In some embodiments of a compound disclosed herein, or a pharmaceutically acceptable salt, solvate, or prodrug thereof, two $R^{11}$ groups are joined with the nitrogen to which they are attached join to form an optionally substituted N-heterocyclyl. In some embodiments of a compound disclosed herein, or a pharmaceutically acceptable salt, solvate, or prodrug thereof, two $R^{11}$ groups are joined with the nitrogen to which they are attached join to form an N-heterocyclyl which is optionally substituted with halogen, oxo, —CN, or —$R^b$—$OR^a$. In some embodiments of a compound disclosed herein, or a pharmaceutically acceptable salt, solvate, or prodrug thereof, two $R^{11}$ groups are joined with the nitrogen to which they are attached join to form an N-heterocyclyl which is optionally substituted with halogen, oxo, —CN, or —$R^b$—$OR^a$; wherein each $R^a$ is independently hydrogen or alkyl which is optionally substituted with halogen, hydroxy, methoxy, or trifluoromethyl, and each $R^b$ is independently a direct bond or a straight or branched alkylene. In some embodiments of a compound disclosed herein, or a pharmaceutically acceptable salt, solvate, or prodrug thereof, two $R^{11}$ groups are joined with the nitrogen to which they are attached join to form an N-heterocyclyl which is unsubstituted or substituted with —F, oxo, —CN, —OH, or —OMe. In some embodiments of a compound disclosed herein, or a pharmaceutically acceptable salt, solvate, or prodrug thereof, two $R^{11}$ groups are joined with the nitrogen to which they are attached join to form an N-heterocyclyl which is unsubstituted or substituted with —CN, —OH, or —OMe. In some embodiments of a compound disclosed herein, or a pharmaceutically acceptable salt, solvate, or prodrug thereof, two $R^{11}$ groups are joined with the nitrogen to which they are attached join to form an N-heterocyclyl which is unsubstituted or substituted with —CN, —OH, or —OMe.

In some embodiments of a compound disclosed herein, or a pharmaceutically acceptable salt, solvate, or prodrug thereof, two $R^{11}$ groups are joined with the nitrogen to which they are attached join to form a N-heterocycloalkyl which is unsubstituted or substituted. In some embodiments of a compound disclosed herein, or a pharmaceutically acceptable salt, solvate, or prodrug thereof, two $R^{11}$ groups are joined with the nitrogen to which they are attached join to form a 4- to 6-membered N-heterocycloalkyl which is unsubstituted or substituted. In some embodiments of a compound disclosed herein, or a pharmaceutically acceptable salt, solvate, or prodrug thereof, two $R^{11}$ groups are joined with the nitrogen to which they are attached join to form an unsubstituted or substituted azetidinyl, an unsubstituted or substituted pyrrolidinyl, an unsubstituted or substituted piperidinyl, an unsubstituted or substituted morpholinyl, or an unsubstituted or substituted piperazinyl. In some embodiments of a compound disclosed herein, or a pharmaceutically acceptable salt, solvate, or prodrug thereof, two $R^{11}$ groups are joined with the nitrogen to which they are attached join to form an unsubstituted or substituted azetidinyl, an unsubstituted or substituted pyrrolidinyl, or an unsubstituted or substituted piperidihyl. In some embodiments of a compound disclosed herein, or a pharmaceutically acceptable salt, solvate, or prodrug thereof, two $R^{11}$ groups are joined with the nitrogen to which they are attached join to form an unsubstituted or substituted azetidinyl. In some embodiments of a compound disclosed herein, or a pharmaceutically acceptable salt, solvate, or prodrug thereof, two $R^{11}$ groups are joined with the nitrogen to which they are attached join to form a N-heterocycloalkyl which is substituted. In some embodiments, the N-heterocycloalkyl is substituted with halogen, oxo, —CN, or —$R^b$—$OR^a$. In some embodiments, the N-heterocycloalkyl is substituted with halogen, oxo, —CN, or —$R^b$—$OR^a$; wherein each $R^a$ is independently hydrogen or alkyl which is optionally substituted with halogen, hydroxy, methoxy, or trifluoromethyl; and each $R^b$ is independently a direct bond or a straight or branched alkylene. In some embodiments, the N-heterocycloalkyl is substituted with —F, oxo, —CN, —OH, or —OMe. In some embodiments, the N-heterocycloalkyl is substituted with —F, —CN, —OH, or —OMe. In some embodiments, the N-heterocycloalkyl is substituted with —CN, —OH, or —OMe.

In some embodiments of a compound disclosed herein, or a pharmaceutically acceptable salt, solvate, or prodrug thereof, two $R^{11}$ groups are joined with the nitrogen to which they are attached join to form an unsubstituted or substituted azetidinyl. In some embodiments of a compound disclosed herein, or a pharmaceutically acceptable salt, solvate, or prodrug thereof, two $R^{11}$ groups are joined with the nitrogen to which they are attached join to form a substituted azetidinyl. In some embodiments, the azetidinyl is substituted with halogen, oxo, —CN, or —$R^b$—$OR^a$. In some embodiments, the azetidinyl is substituted with halogen, oxo, —CN, or —$R^b$—$OR^a$; wherein each $R^a$ is independently hydrogen or alkyl which is optionally substituted with halogen, hydroxy, methoxy, or trifluoromethyl; and each $R^b$ is independently a direct bond or a straight or branched alkylene. In some embodiments, the azetidinyl is substituted with —F, oxo, —CN, —OH, or —OMe. In some embodiments, the azetidinyl is substituted with —F, —CN, —OH, or —OMe. In some embodiments, the azetidinyl is substituted with —CN, —OH, or —OMe. In some embodiments, the azetidinyl is substituted with —CN. In some embodiments, the azetidinyl is substituted with —OH. In some embodiments, the azetidinyl is substituted with —OMe.

In some embodiments of a compound disclosed herein, or a pharmaceutically acceptable salt, solvate, or prodrug thereof, each $R^{12}$ is independently H, optionally substituted alkyl, optionally substituted carbocyclyl, or optionally substituted heterocyclyl. In some embodiments of a compound disclosed herein, or a pharmaceutically acceptable salt, solvate, or prodrug thereof, each $R^{12}$ is independently H or unsubstituted alkyl. In some embodiments of a compound disclosed herein, or a pharmaceutically acceptable salt, solvate, or prodrug thereof, each $R^{12}$ is independently H or unsubstituted $C_1$-$C_4$ alkyl.

In some embodiments of a compound disclosed herein, or a pharmaceutically acceptable salt, solvate, or prodrug thereof, $R^3$ is:
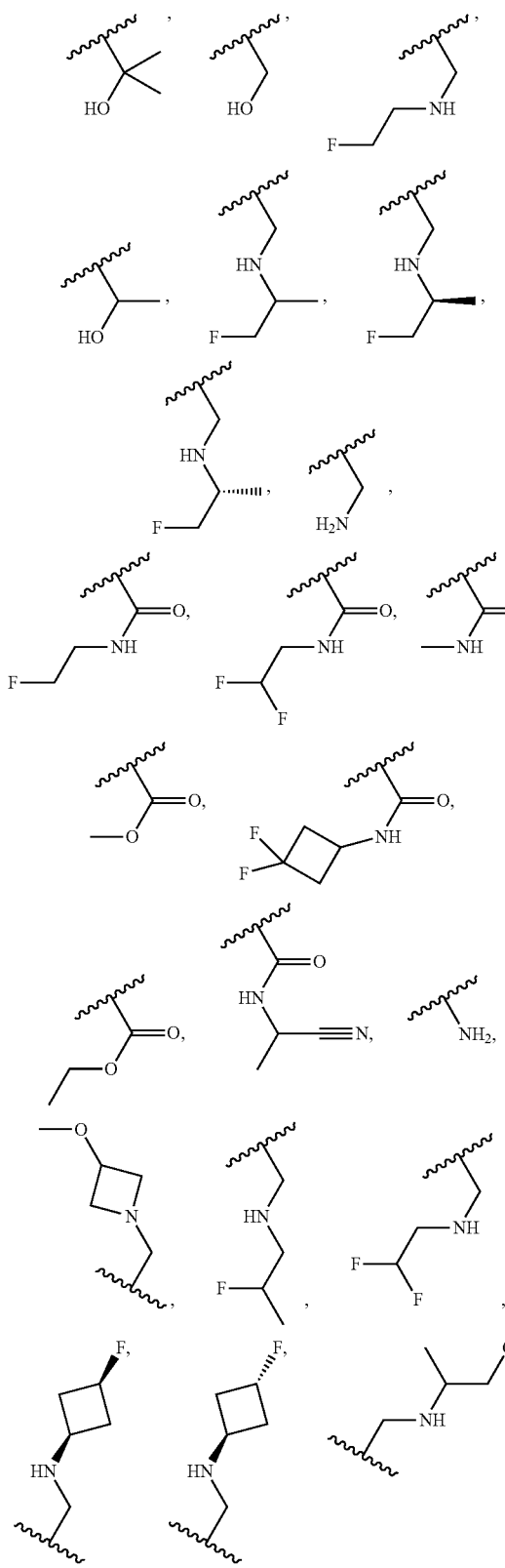
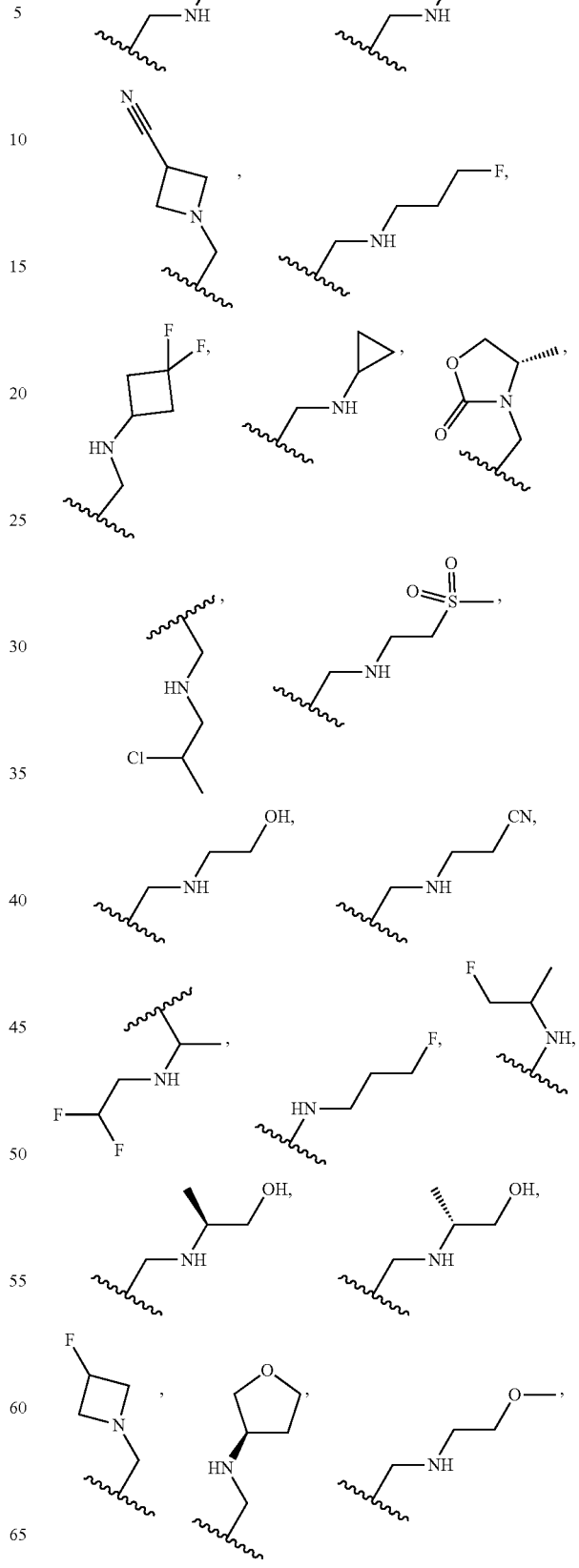

-continued

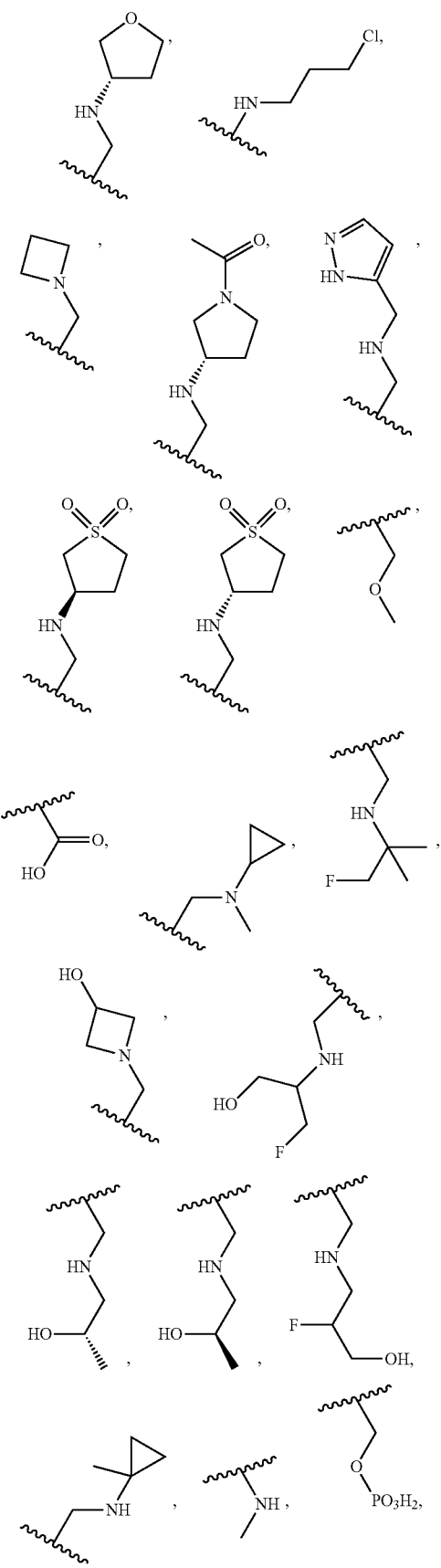

-continued

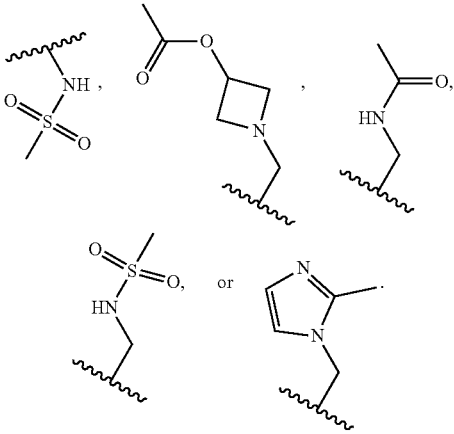

In some embodiments of a compound disclosed herein, or a pharmaceutically acceptable salt, solvate, or prodrug thereof, Z is H. In some embodiments of a compound disclosed herein, or a pharmaceutically acceptable salt, solvate, or prodrug thereof, Z is halo. In some embodiments of a compound disclosed herein, or a pharmaceutically acceptable salt, solvate, or prodrug thereof, Z is —F, —Cl, or —Br. In some embodiments of a compound disclosed herein, or a pharmaceutically acceptable salt, solvate, or prodrug thereof, Z is nitro.

In some embodiments of a compound disclosed herein, or a pharmaceutically acceptable salt, solvate, or prodrug thereof, Z is -L-G.

In some embodiments of a compound disclosed herein, or a pharmaceutically acceptable salt, solvate, or prodrug thereof, L is a bond. In some embodiments of a compound disclosed herein, or a pharmaceutically acceptable salt, solvate, or prodrug thereof, L is optionally substituted. $C_1$-$C_4$ alkylene. In some embodiments of a compound disclosed herein, or a pharmaceutically acceptable salt, solvate, or prodrug thereof, L is optionally substituted $C_1$-$C_2$ alkylene. In some embodiments of a compound disclosed herein, or a pharmaceutically acceptable salt, solvate, or prodrug thereof, L is unsubstituted $C_1$-$C_2$ alkylene. In some embodiments of a compound disclosed herein, or a pharmaceutically acceptable salt, solvate, or prodrug thereof, L is —$CH_2$—.

In some embodiments of a compound disclosed herein, or a pharmaceutically acceptable salt, solvate, or prodrug thereof, G is optionally substituted alkyl, optionally substituted alkenyl, optionally substituted alkynyl, optionally substituted carbocyclyl, optionally substituted aryl, optionally substituted heterocyclyl, optionally substituted heteroaryl, —CN, —$N(R^{13})_2$, —$OR^{13}$, —$COR^{13}$, —$CO_2R^{13}$, —$CON(R^{13})_2$, —$N(R^{14})$—$COR^{13}$, —$SO_2R^{13}$—, —$SO_2N(R^{13})_2$, —$N(R^{14})$—$SO_2R^{13}$, —$N(R^{14})$—$CON(R^{13})_2$, —$N(R^{14})$—$CO_2R^{13}$, —O—$CON(R^{13})_2$—, —$N(R^{14})$—$SO_2N(R^{13})_2$, —O—$SO_2N(R^{13})_2$, —$N(R^{14})$—$SO_2$—$OR^{13}$, or —C(=N—$OR^{14})(R^{13})$. In some embodiments of a compound disclosed herein, or a pharmaceutically acceptable salt, solvate, or prodrug thereof, G is optionally substituted alkyl, optionally substituted carbocyclyl, optionally substituted aryl, optionally substituted heterocyclyl, optionally substituted heteroaryl, —$N(R^{13})_2$, —$OR^{13}$, —CN, —$COR^{13}$, —$CO_2R^{13}$, —$CON(R^{13})_2$, —$N(R^{14})$—$COR^{13}$, —$SO_2R^{13}$—, —$SO_2N(R^{13})_2$, or —$N(R^{14})$—$SO_2R^{13}$. In some embodiments of a compound disclosed herein, or a pharmaceutically acceptable salt, solvate, or prodrug thereof, G is optionally substituted alkyl, optionally, substituted heterocyclyl, optionally substituted heteroaryl, —N($R^{13}$)$_2$, —CON($R^{13}$)$_2$, or —N($R^{14}$)—CO$R^{13}$.

In some embodiments of a compound disclosed herein, or a pharmaceutically acceptable salt, solvate, or prodrug thereof, G is optionally substituted alkyl. In some embodiments of a compound disclosed herein, or a pharmaceutically acceptable salt, solvate, or prodrug thereof, G is unsubstituted alkyl. In some embodiments of a compound disclosed herein, or a pharmaceutically acceptable salt, solvate, or prodrug thereof, G is optionally substituted carbocyclyl. In some embodiments of a compound disclosed herein, or a pharmaceutically acceptable salt, solvate, or prodrug thereof, G is optionally substituted carbocyclylalkyl. In some embodiments of a compound disclosed herein, or a pharmaceutically acceptable salt, solvate, or prodrug thereof, G is optionally substituted heterocyclyl. In some embodiments of a compound disclosed herein, or a pharmaceutically acceptable salt, solvate, or prodrug thereof, G is optionally substituted heterocyclylalkyl. In some embodiments of a compound disclosed herein, or a pharmaceutically acceptable salt, solvate, or prodrug thereof, G is optionally substituted heteroaryl. In some embodiments of a compound disclosed herein, or a pharmaceutically acceptable salt, solvate, or prodrug thereof, G is —N($R^{13}$)$_2$. In some embodiments of a compound disclosed herein, or a pharmaceutically acceptable salt, solvate, or prodrug thereof, G is —O$R^{13}$. In some embodiments of a compound disclosed herein, or a pharmaceutically acceptable salt, solvate, or prodrug thereof, is —CN. In some embodiments of a compound disclosed herein, or a pharmaceutically acceptable salt, solvate, or prodrug thereof, G is —CO$R^{13}$. In some embodiments of a compound disclosed herein, or a pharmaceutically acceptable salt, solvate, or prodrug thereof, G is —CO$_2R^{13}$. In some embodiments of a compound disclosed herein, or a pharmaceutically acceptable salt, solvate, or prodrug thereof, G is —N($R^{12}$)—CO$R^{13}$.

In some embodiments of a compound disclosed herein, or a pharmaceutically acceptable salt, solvate, or prodrug thereof, G is optionally substituted alkyl, optionally substituted heterocyclyl, optionally substituted heteroaryl, —N($R^{13}$), —O$R^{13}$, or —N($R^{12}$)—CO$R^{13}$.

In some embodiments of a compound disclosed herein, or a pharmaceutically acceptable salt, solvate, or prodrug thereof, each $R^{13}$ is independently H, optionally substituted alkyl, optionally substituted carbocyclyl, optionally substituted carbocyclylalkyl, optionally substituted aryl, optionally substituted heterocyclyl, optionally substituted heterocyclylalkyl, or optionally substituted heteroaryl. In some embodiments of a compound disclosed herein, or a pharmaceutically acceptable salt, solvate, or prodrug thereof, each $R^{13}$ is independently H, optionally substituted alkyl, optionally substituted carbocyclyl, optionally substituted carbocyclylalkyl, optionally substituted heterocyclyl, or optionally substituted heterocyclylalkyl.

In some embodiments of a compound disclosed herein, or a pharmaceutically acceptable salt, solvate, or prodrug thereof, each $R^{13}$ is independently unsubstituted or substituted with —$R^b$—O$R^a$, —$R^b$—C(O)O$R^a$, or —$R^b$—C(O)$R^a$; wherein each $R^a$ is independently hydrogen, alkyl which is optionally substituted with halogen, hydroxy, methoxy, or trifluoromethyl, or carbocyclyl which is optionally substituted with halogen, hydroxy, methoxy, or trifluoromethyl; and each $R^b$ is independently a direct bond or a straight or branched alkylene. In some embodiments of a compound disclosed herein, or a pharmaceutically acceptable salt, solvate, or prodrug thereof, each $R^{13}$ is independently unsubstituted or substituted with —OH, —OMe, —C(O)CH$_2$OH, —CH C(O)OH, —C(O)OH, —C(O)-cyclopropyl.

In some embodiments of a compound disclosed herein, or a pharmaceutically acceptable salt, solvate, or prodrug thereof, one $R^{13}$ is H. In some embodiments of a compound disclosed herein, or a pharmaceutically acceptable salt, solvate, or prodrug thereof, one $R^{13}$ is H. and the other $R^{13}$ is H, optionally substituted alkyl, optionally substituted carbocyclyl, optionally substituted carbocyclylalkyl, optionally substituted aryl, optionally substituted heterocyclyl, optionally substituted heterocyclylalkyl, or optionally substituted heteroaryl.

In some embodiments of a compound disclosed herein, or a pharmaceutically acceptable salt, solvate, or prodrug thereof, one $R^{13}$ is optionally substituted heterocyclyl. In some embodiments of a compound disclosed herein, or a pharmaceutically acceptable salt, solvate, or prodrug thereof, one $R^{13}$ is optionally substituted heterocyclyl selected from tetrahydrofuranyl, tetrahydropyranyl, pyrrolidinyl, piperidinyl, thiophenyl, sulfolanyl (1,1-dioxotetrahydrothiophenyl), 1-imino-1-oxotetrahydrothiophenyl, 1-oxotetrahydrothiophenyl, 1,1-dioxotetrahydrothiopyranyl or 1-imino-1-oxotetrahydrothiopyranyl. In some embodiments of a compound disclosed herein, or a pharmaceutically acceptable salt, solvate, or prodrug thereof, one $R^{13}$ is optionally substituted heterocyclyl selected from tetrahydrofuranyl, tetrahydropyranyl, pyrrolidinyl, or piperidinyl. In some embodiments of a compound disclosed herein, or a pharmaceutically acceptable salt, solvate, or prodrug thereof, one $R^{13}$ is optionally substituted heterocyclyl which is a bicyclic heterocycle which is fused or spirocyclic. In some embodiments of a compound disclosed herein, or a pharmaceutically acceptable salt, solvate, or prodrug thereof, one $R^{13}$ is a heterocyclyl which is optionally substituted with oxo, imino, —$R^b$—N($R^a$)$_2$, —$R^b$—O$R^a$, —$R^b$—C(O)$R^a$, —$R^b$—C(O)O$R^a$, or —$R^b$—N($R^a$)C(O)$R^a$; wherein each $R^a$ is independently hydrogen, alkyl which is optionally substituted with halogen, hydroxy, methoxy, or trifluoromethyl, or cycloalkyl which is optionally substituted with halogen, hydroxy, methoxy, or trifluoromethyl; and each $R^b$ is independently a direct bond or a straight or branched alkylene.

In some embodiments of a compound disclosed herein, or a pharmaceutically acceptable salt, solvate, or prodrug thereof, two $R^{13}$ groups are joined with the nitrogen to which they are attached join to form an optionally substituted N-heterocyclyl. In some embodiments of a compound disclosed herein, or a pharmaceutically acceptable salt, solvate, or prodrug thereof, two $R^{13}$ groups are joined with the nitrogen to which they are attached join to form an N-heterocyclyl which is unsubstituted or substituted with alkyl, optionally substituted heterocyclyl, —$R^b$—O$R^a$, —$R^b$—N($R^a$)$_2$, —$R^b$—C(O)$R^a$, —$R^b$—CN, or —$R^b$—N($R^a$)C(O)$R^a$; wherein each $R^a$ is independently hydrogen, alkyl which is optionally substituted with halogen, hydroxy, methoxy, or trifluoromethyl, or carbocyclyl which is optionally substituted with halogen, hydroxy, methoxy, or trifluoromethyl; and each $R^b$ is independently a direct bond or a straight or branched alkylene. In some embodiments of a compound disclosed herein, or a pharmaceutically acceptable salt, solvate, or prodrug thereof, two $R^{13}$ groups are joined with the nitrogen to which they are attached join to form an N-heterocyclyl Which is unsubstituted or substituted with methyl, oxetanyl, morpholinyl, —OMe, —CH$_2$OH, —NH$_2$, —CH$_2$NH$_2$, —C(O)CH$_2$OH, —CN, —CH$_2$CN, —CH$_2$NHC(O)CH$_2$OH.

In some embodiments of a compound disclosed herein, or a pharmaceutically acceptable salt, solvate, or prodrug thereof, each $R^{14}$ is independently H, optionally substituted alkyl, optionally substituted carbocyclyl, or optionally substituted heterocyclyl. In some embodiments of a compound disclosed herein, or a pharmaceutically acceptable salt, solvate, or prodrug thereof, each $R^{14}$ is independently H, unsubstituted alkyl, or unsubstituted heterocyclyl. In some embodiments of a compound disclosed herein, or a pharmaceutically acceptable salt, solvate, or prodrug thereof, each $R^{14}$ is H.

In some embodiments of a compound disclosed herein, or a pharmaceutically acceptable salt, solvate, or prodrug thereof, G is optionally substituted heterocyclyl. In some embodiments of a compound disclosed herein, or a pharmaceutically acceptable salt, solvate, or prodrug thereof, G is optionally substituted monocyclic heterocyclyl, fused bicyclic heterocyclyl, or spiro bicyclic heterocyclyl. In some embodiments of a compound disclosed herein, or a pharmaceutically acceptable salt, solvate, or prodrug thereof; G is optionally substituted 4- to 6-membered monocyclic heterocyclyl. In some embodiments of a compound disclosed herein, or a pharmaceutically acceptable salt, solvate, or prodrug thereof, G is optionally substituted heterocyclyl selected from morpholinyl, pyrrolidinyl, azetidinyl, piperidinyl, tetrahydropyranyl, and oxetanyl. In some embodiments of a compound disclosed herein, or a pharmaceutically acceptable salt, solvate, or prodrug thereof, G is optionally substituted heterocyclyl selected from morpholinyl and pyrrolidinyl. In some embodiments of a compound disclosed herein, or a pharmaceutically acceptable salt, solvate, or prodrug thereof, G is optionally substituted morpholinyl. In some embodiments of a compound disclosed herein, or a pharmaceutically acceptable salt, solvate, or prodrug thereof, G is morpholinyl. In some embodiments of a compound disclosed herein, or a pharmaceutically acceptable salt, solvate, or prodrug thereof, G is optionally substituted pyrrolidinyl. In some embodiments of a compound disclosed herein, or a pharmaceutically acceptable salt, solvate, or prodrug thereof, G is optionally substituted heterocyclyl which is a bicyclic heterocycle which is fused or spirocyclic. In some embodiments of a compound disclosed herein, or a pharmaceutically acceptable salt, solvate, or prodrug thereof, G is a heterocyclyl which is optionally substituted with alkyl, —$R^b$—CN, heterocyclyl, —$R^b$—N($R^a$)$_2$, —$R^b$—O$R^a$; —$R^b$—C(O)$R^a$, or —$R^b$—N($R^a$)C(O)$R^a$; wherein each $R^a$ is independently hydrogen or alkyl which is optionally substituted with halogen, hydroxy, methoxy, or trifluoromethyl; and each $R^b$ is independently a direct bond or a straight or branched alkylene. In some embodiments of a compound disclosed herein, or a pharmaceutically acceptable salt, solvate, or prodrug thereof, G is heterocyclyl, which is unsubstituted or substituted with alkyl, optionally substituted heterocyclyl, —$R^b$—O$R^a$, —$R^b$—N($R^a$)$_2$, —$R^b$—C(O)$R^a$, —$R^b$—CN, or —$R^b$—N($R^a$)C(O)$R^a$; wherein each $R^a$ is independently hydrogen, alkyl which is optionally substituted with halogen, hydroxy, methoxy, or trifluoromethyl, or carbocyclyl which is optionally substituted with halogen, hydroxy, methoxy, or trifluoromethyl; and each $R^b$ is independently a direct bond or a straight or branched alkylene. In some embodiments of a compound disclosed herein, or a pharmaceutically acceptable salt, solvate, or prodrug thereof, G is heterocyclyl, which is unsubstituted or substituted with methyl, oxetane, morpholine, —OMe, —$CH_2OH$, —$NH_2$, —$CH_2NH_2$, —C(O)$CH_2OH$, —CN, —$CH_2CN$, —$CH_2NHC(O)CH_2OH$.

In some embodiments, G is optionally substituted morpholinyl. In some embodiments, G is unsubstituted morpholinyl.

In some embodiments of a compound disclosed herein, or a pharmaceutically acceptable salt, solvate, or prodrug thereof, Z is:

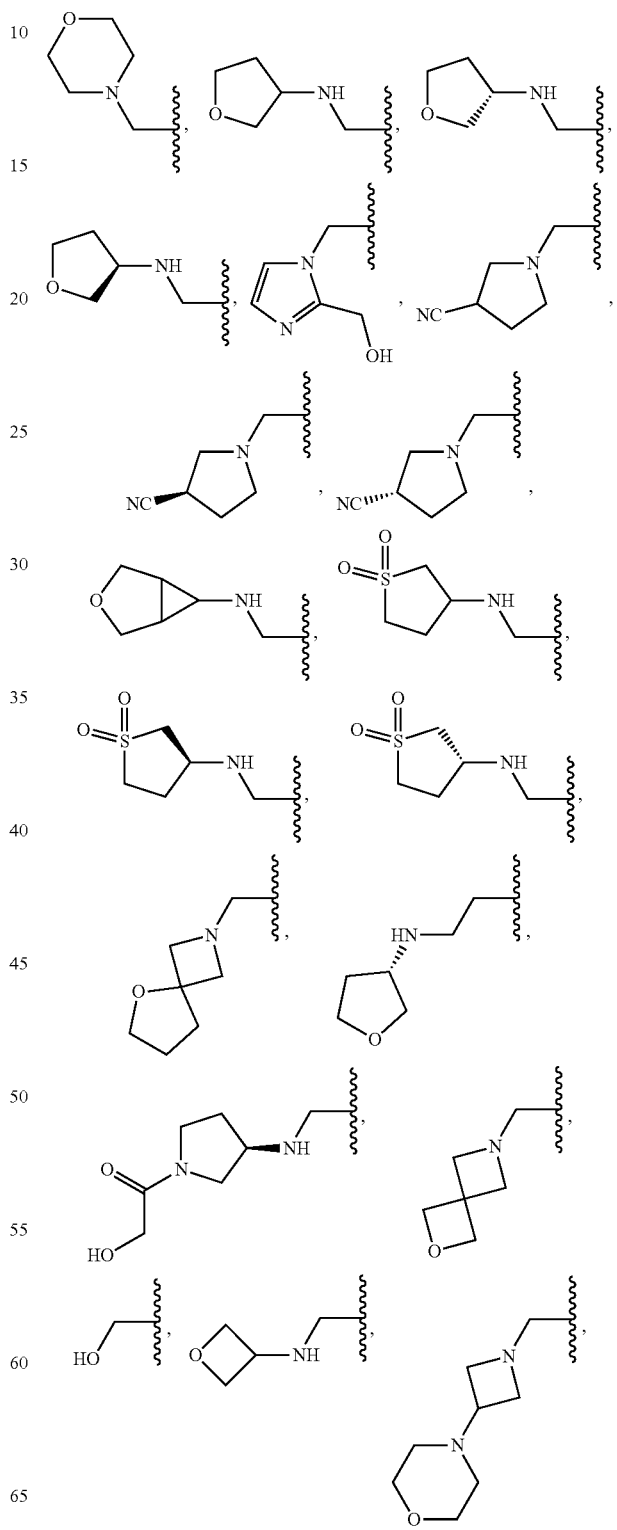

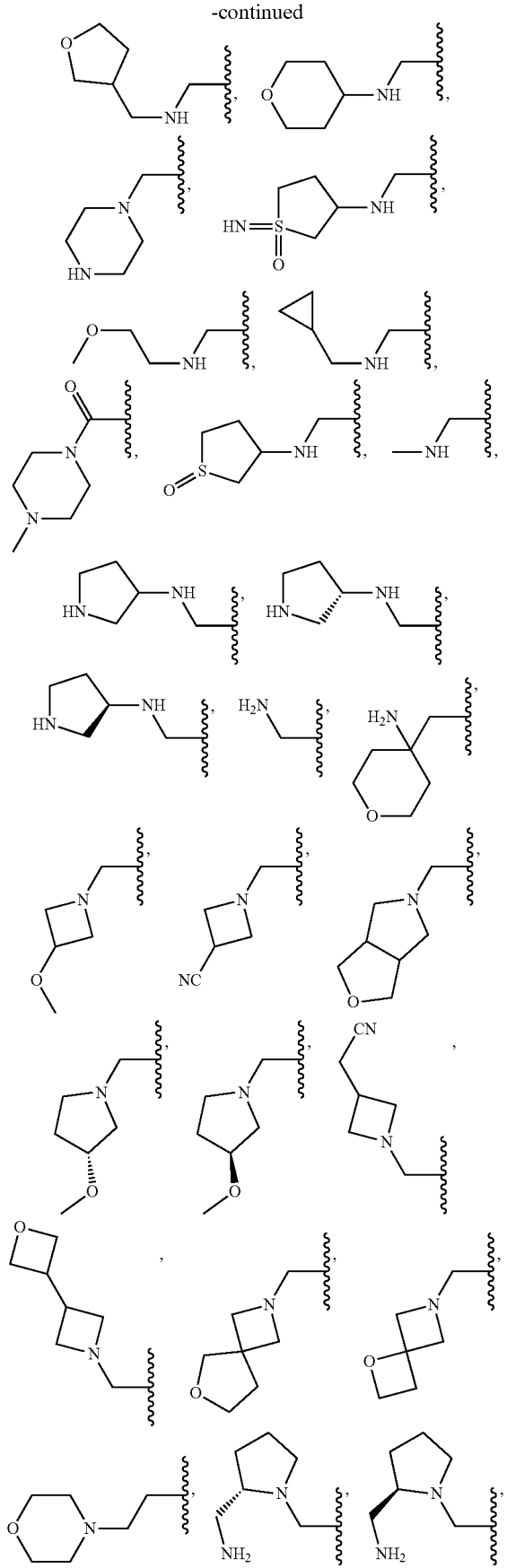
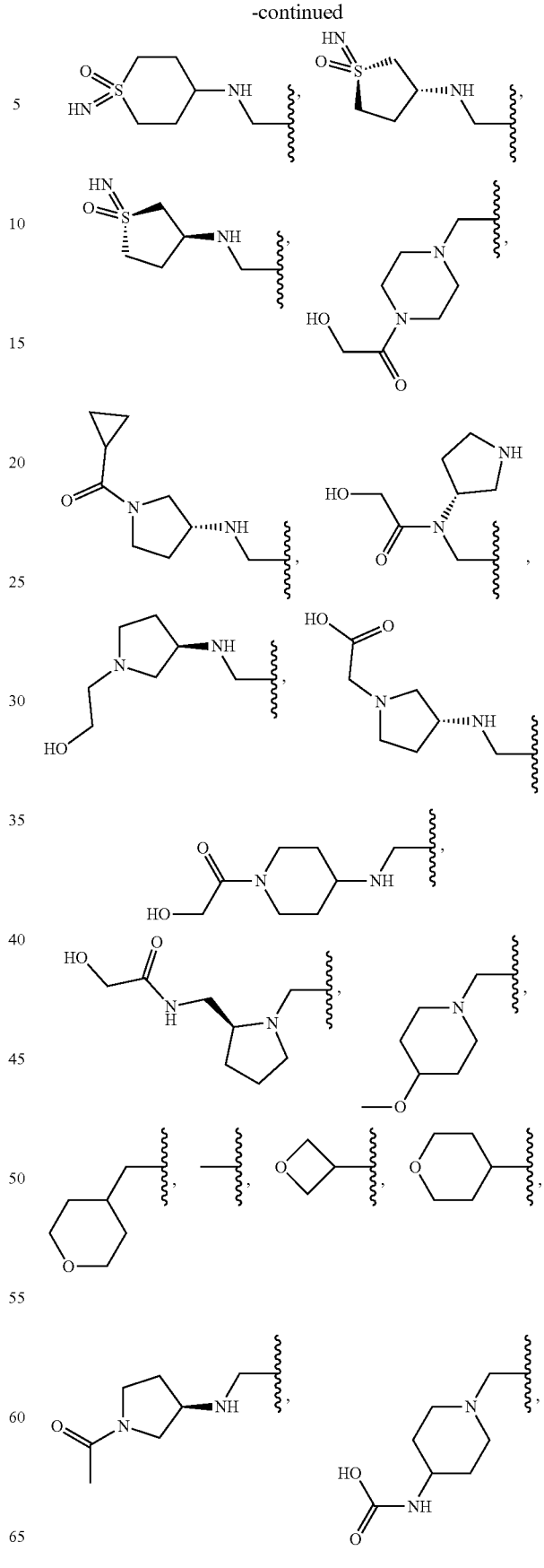

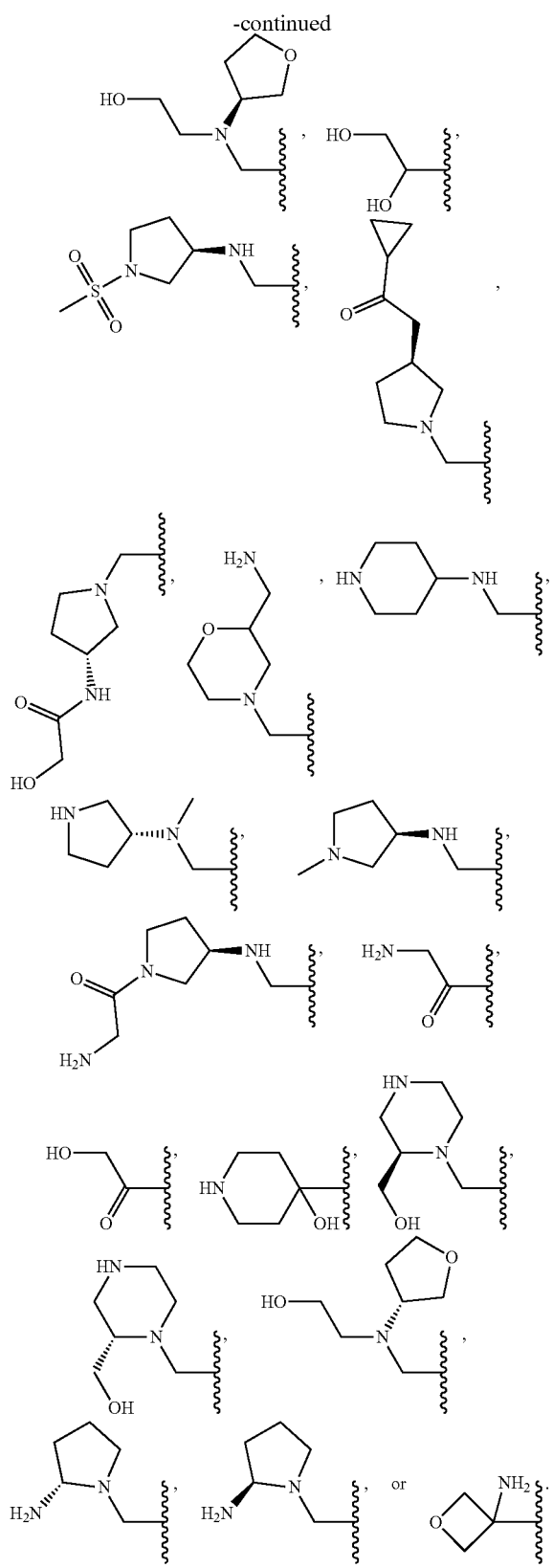

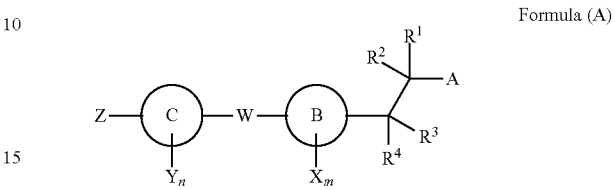

Disclosed herein are non-hydroxamic acid LpxC inhibitors comprising a basic moiety. In some embodiments, the non-hydroxamic acid LpxC inhibitors comprise a basic moiety with a pKa of less than 8. In some embodiments, the non-hydroxamic acid LpxC inhibitors comprise a basic moiety with a pKa of less than 7. In some embodiments, the non-hydroxamic acid LpxC inhibitor comprises a morpholinyl.

In some embodiments, the non-hydroxamic acid LpxC inhibitor is a compound of Formula (A), or a pharmaceutically acceptable salt, solvate, or prodrug thereof:

Formula (A)

wherein,
A is a nor-hydroxamate zinc-binding moiety:
$R^1$ and $R^2$ are each independently a group comprising 1-50 non-hydrogen atoms selected from the group consisting of C, N, O, S, P, and halogen;
or $R^1$ and $R^2$ are taken together with the carbon to which they are attached to form $=C(R^{11})_2$, $=NR^{11}$, $=O$, or $=S$;
or $R^1$ and $R^2$ are taken together with the carbon to which they are attached to form an optionally substituted 3- to 6-membered carbocyclyl or optionally substituted 4- to 7-membered heterocyclyl containing 1 or 2 heteroatoms selected from O, N, and S;
$R^3$ is optionally substituted alkyl, optionally substituted carbocyclyl, optionally substituted carbocyclylalkyl, optionally substituted aryl, optionally substituted aralkyl, optionally substituted heteroaryl, optionally substituted heteroaralkyl, optionally substituted heterocyclyl, optionally substituted heterocyclylalkyl, optionally substituted ($C_0$-$C_4$ alkylene)-$COR^{11}$, optionally substituted ($C_0$-$C_4$ alkylene)-$CO_2R^{11}$, optionally substituted ($C_0$-$C_4$ alkylene)-$CON(R^{11})_2$, optionally substituted ($C_0$-$C_4$ alkylene)-CN, optionally substituted ($C_0$-$C_4$ alkylene)-$OR^{11}$, optionally substituted ($C_0$-$C_4$ alkylene)-$N(R^{11})_2$, optionally substituted ($C_0$-$C_4$ alkylene)-$N(R^{12})$—$COR^{11}$, optionally substituted ($C_0$-$C_4$ alkylene)-$N(R^{12})$—$CO_2R^{11}$, optionally substituted ($C_0$-$C_4$ alkylene)-$N(R^{12})$—$CON(R^{11})_2$, optionally substituted ($C_0$-$C_4$ alkylene)-$N(R^{12})$—$SO_2N(R^{11})_2$, optionally substituted ($C_0$-$C_4$ alkylene)-O—$SO_2N(R^{11})_2$, optionally substituted ($C_0$-$C_4$ alkylene)-$N(R^{11})$—PO (optionally substituted $C_1$-$C_4$ alkyl)$_2$, optionally substituted ($C_0$-$C_4$ alkylene)-$SO_2R^{11}$, optionally substituted ($C_0$-$C_4$ alkylene)-O—$SO_2R^{11}$, optionally substituted ($C_0$-$C_4$ alkylene)-$N(R^{12})$—$SO_2R^{11}$, optionally substituted ($C_0$-$C_4$ alkylene)-C($=N$—$OR^{11}$)($R^{11}$), or optionally substituted ($C_0$-$C_4$ alkylene)-$OPO_2OR^{11}$,
$R^4$ is H or optionally substituted alkyl;
or $R^3$ and $R^4$ are taken together with the carbon to which they are attached to form $=C(R^{11})_2$, $=NR^{11}$, $=O$, or $=S$;
or $R^3$ and $R^4$ are taken together with the carbon to which they are attached to form an optionally substituted 3- to 6-membered carbocyclyl or optionally substituted 4- to 7-membered heterocyclyl containing 1 or 2 heteroatoms selected from O, N, and S;
Ring B is optionally substituted aryl, optionally substituted carbocyclyl, optionally substituted heteroaryl, or optionally substituted heterocyclyl;

W is a bond, —C≡C—, bicyclo[1.1.1]pentanylene, —C≡C—C≡C—, —CH═CH—, or —CH₂CH₂—;

Ring C is optionally substituted aryl, optionally substituted carbocyclyl, optionally substituted heteroaryl, or optionally substituted heterocyclyl;

each X and Y is independently H, optionally substituted alkyl, halo, fluoroalkyl, cyano, nitro, —N(R¹³)₂, or —OR¹³;

each R¹¹ is independently H, optionally substituted alkyl, optionally substituted alkenyl, optionally substituted alkynyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl;

or two R¹¹ on the same nitrogen atom are taken together with the nitrogen to which they are attached to form an optionally substituted N-heterocyclyl;

each R¹³ is H, optionally substituted alkyl, optionally substituted alkenyl, optionally substituted alkynyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl or two R¹³ on the same nitrogen atom are taken together with the nitrogen to which they are attached to form an optionally substituted N-heterocyclyl; and n is 0-4;

m is 0-4; and

Z comprises a basic group with a pKa, of less than 8.

In some embodiments, A is

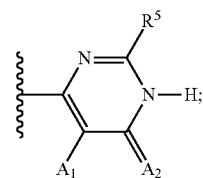

$A_1$ is OH or SH; $A_2$ is O or S; and $R^5$ is H, halogen, optionally substituted alkyl, hydroxyl, alkoxyl, cyano, amino, or nitro. In some embodiments, $R^1$ and $R^2$ are each independently U or optionally substituted alkyl. In some embodiments, Z comprises a basic group with a pKa of less than 7. In some embodiments, Z comprises a morpholinyl.

In some embodiments, the non-hydroxamic acid LpxC inhibitor has minimal toxicity. In some embodiments, the non-hydroxamic acid LpxC inhibitor has minimal cardio toxicity.

In some embodiments, the heterocyclic LpxC inhibitory compound described herein has a structure provided in Table 1.

TABLE 1

| Compound No. | Structure | Mass [M + H] |
|---|---|---|
| 1 | Racemic mixture | 474.4 |
| 2 | Racemic mixture | 446.5 |
| 3 | *Single enantiomer (1ˢᵗ eluting) | 446.5 |

TABLE 1-continued

| Compound No. | Structure | Mass [M + H] |
|---|---|---|
| 4 | (structure: morpholine-CH2-phenyl-C≡C-phenyl-CH(*)(CH2OH)-CH2-pyrimidinone with OH) *Single enantiomer (2nd eluting) | 446.5 |
| 5 | (structure: morpholine-CH2-phenyl-C≡C-phenyl-CH(CH2NH-CH2CH2F)-CH2-pyrimidinone with OH) Racemic mixture | 491.2 |
| 6 | (structure: morpholine-CH2-phenyl-C≡C-phenyl-CH(*)(CH2NH-CH2CH2F)-CH2-pyrimidinone with OH) *Single enantiomer (1st eluting) | 491.2 |
| 7 | (structure: morpholine-CH2-phenyl-C≡C-phenyl-CH(*)(NH-pyrimidinone)-CH2NH-CH2CH2F with OH) *Single enantiomer (2nd eluting) | 491.2 |
| 8 | (structure: tetrahydrofuran-NH-CH2-phenyl-C≡C-phenyl-CH(CH2OH)-CH2-pyrimidinone with OH) Racemic mixture | 446.2 |
| 9 | (structure: pyrimidinone-CH2-CH(*)(CH2OH)-phenyl-C≡C-phenyl-CH2-NH-tetrahydrofuran with OH) *Single enantiomer (1st eluting) | 446.2 |

TABLE 1-continued
| Compound No. | Structure | Mass [M + H] |
|---|---|---|
| 10 | 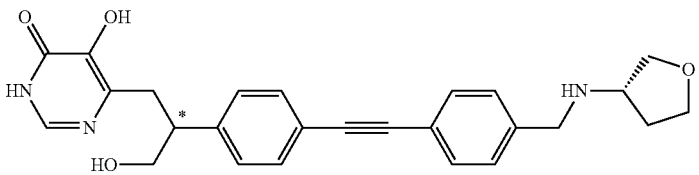 *Single enantiomer (2nd eluting) | 446.2 |
| 11 | Racemic mixture | 446.4 |
| 12 | 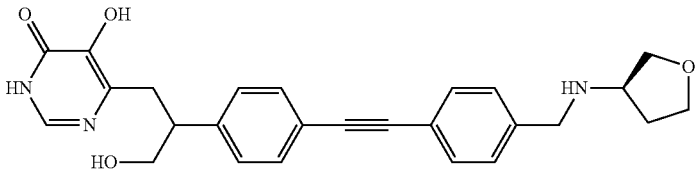 Racemic mixture | 460.5 |
| 14 | 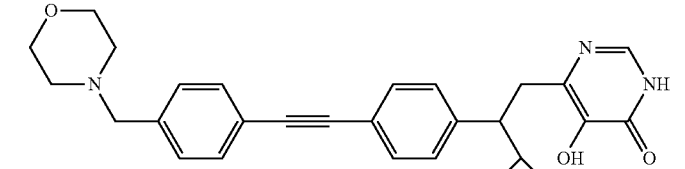 *Single enantiomer (2nd eluting) | 505.6 |
| 15 | 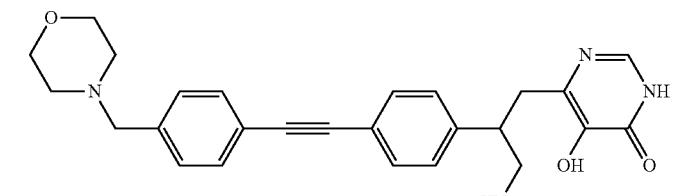 Racemic mixture | 505.6 |

TABLE 1-continued

| Compound No. | Structure | Mass [M + H] |
|---|---|---|
| 16 | *Single enantiomer (1st eluting) | 505.4 |
| 17 | *Single enantiomer (2nd eluting) | 505.6 |
| 18 | Racemic mixture | 445.4 |
| 19 | Racemic mixture | 505.6 |
| 20 | *Single enantiomer (1st eluting) | 505.6 |

TABLE 1-continued

| Compound No. | Structure | Mass [M + H] |
|---|---|---|
| 21 | *Single enantiomer (2<sup>nd</sup> eluting) | 505.6 |
| 22 | Racemic mixture | 523.4 |
| 23 | Racemic mixture | 473.5 |
| 24 | Racemic mixture | 474.5 |
| 25 | Racemic mixture | 549.4 |

TABLE 1-continued

| Compound No. | Structure | Mass [M + H] |
|---|---|---|
| 26 | Racemic mixture | 488.5 |
| 27 | Racemic mixture | 474.3 |
| 28 | Racemic mixture | 512.5 |
| 29 | Racemic mixture | 534.5 |
| 30 | Racemic mixture | 505.6 |

TABLE 1-continued

| Compound No. | Structure | Mass [M + H] |
|---|---|---|
| 31 | Racemic mixture | 460.3 |
| 32 | Racemic mixture | 460.5 |
| 33 | 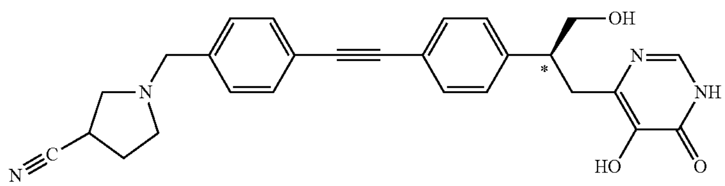 [SMILES: N#CC1CCN(Cc2ccc(C#Cc3ccc([C@@H](CO)Cc4nc[nH]c(=O)c4O)cc3)cc2)C1] | 455.2 |
| 34 | Racemic mixture | 455.4 |
| 35 | *Single enantiomer (2$^{nd}$ eluting) | 455.4 |

TABLE 1-continued
| Compound No. | Structure | Mass [M + H] |
|---|---|---|
| 36 | 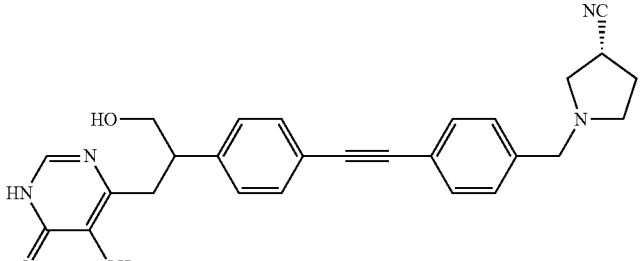 Racemic mixture | 455.5 |
| 37 | 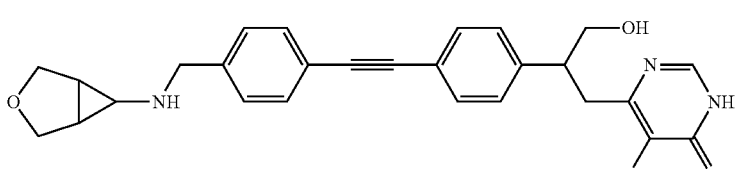 Racemic mixture | 458.3 |
| 38 | 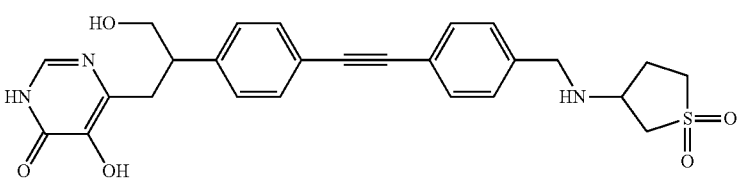 Racemic mixture | 494.2 |
| 39 | 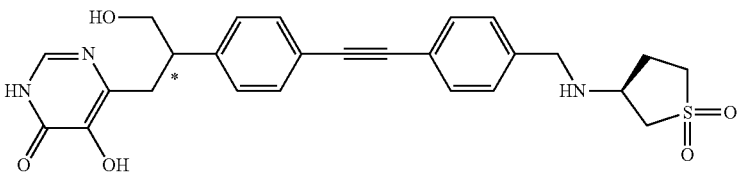 *Single enantiomer (2$^{nd}$ eluting) | 494.2 |
| 40 | 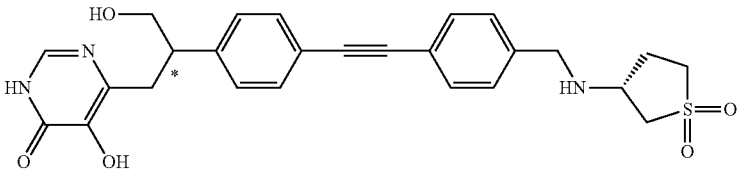 *Single enantiomer (1$^{st}$ eluting) | 494.2 |
| 41 | 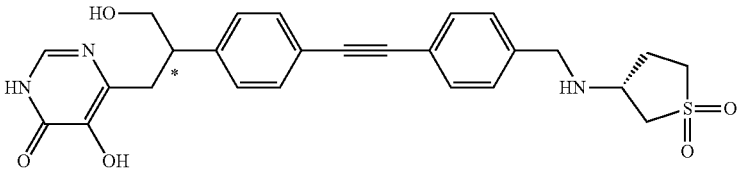 *Single enantiomer (2$^{nd}$ eluting) | 494.2 |

TABLE 1-continued
| Compound No. | Structure | Mass [M + H] |
|---|---|---|
| 42 | 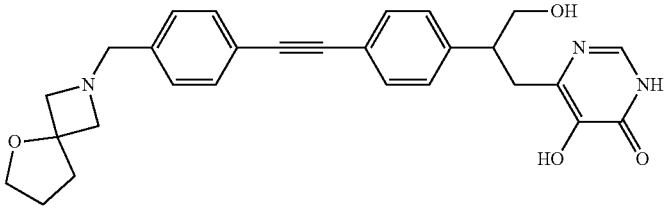<br>Racemic mixture | 472.6 |
| 43 | 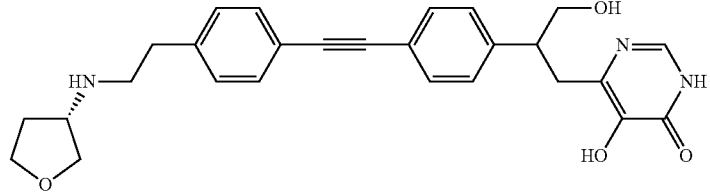<br>Racemic mixture | 160.3 |
| 44 | 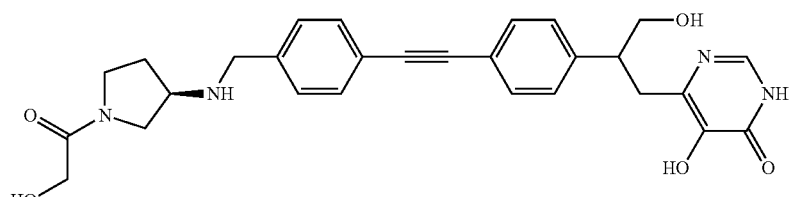<br>Racemic mixture | 503.1 |
| 45 | 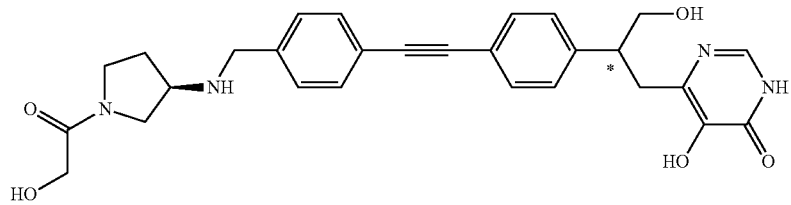<br>*Single enantiomer (1$^{st}$ eluting) | 503.1 |
| 46 | 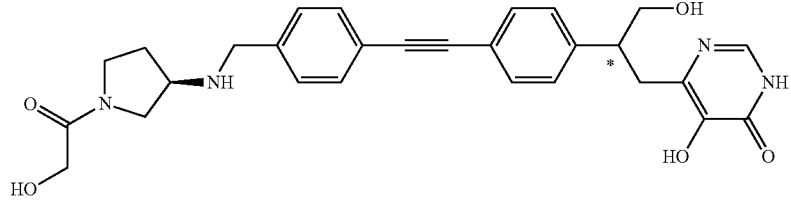<br>*Single enantiomer (2$^{nd}$ eluting) | 503.1 |
| 47 | 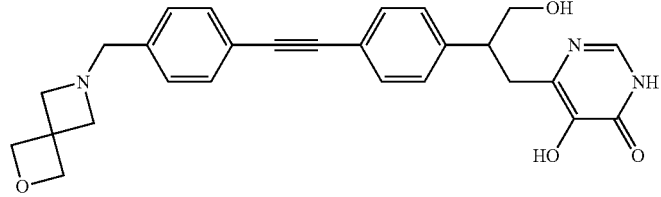<br>Racemic mixture | 458.4 |

TABLE 1-continued
| Compound No. | Structure | Mass [M + H] |
|---|---|---|
| 48 | 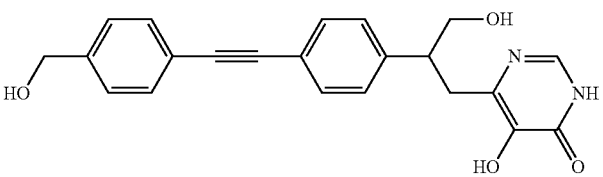 Racemic mixture | 477.5 |
| 49 | 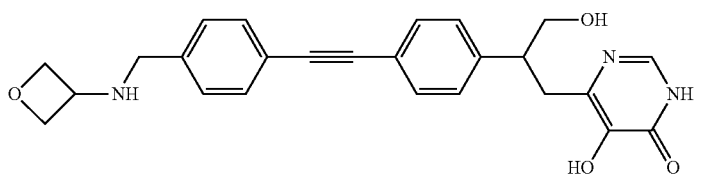 Racemic mixture | 432.4 |
| 50 | 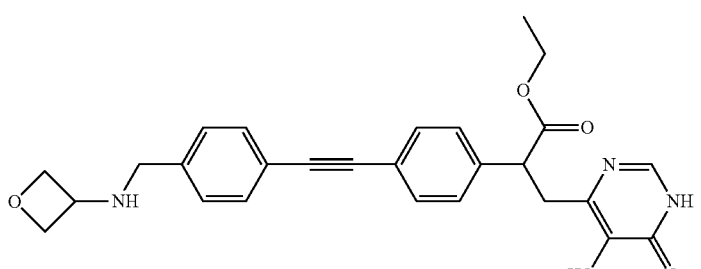 Racemic mixture | 474.3 |
| 51 | 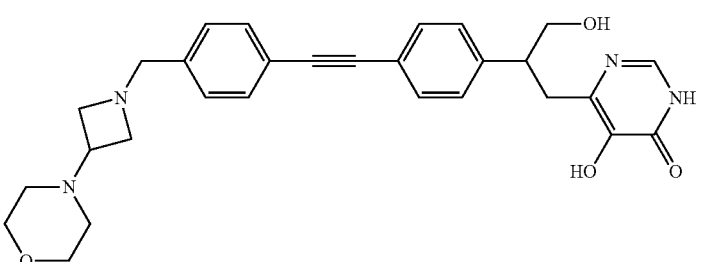 Racemic mixture | 501.5 |
| 52 | 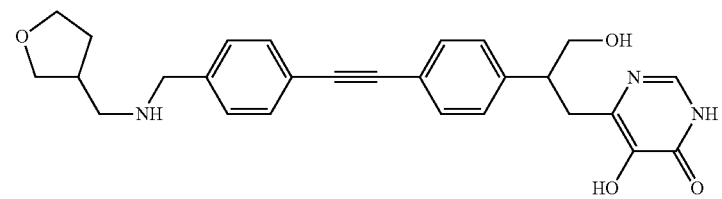 Racemic mixture | 460.6 |
| 53 | 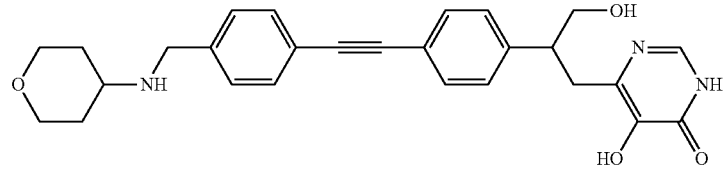 Racemic mixture | 460.3 |

TABLE 1-continued

| Compound No. | Structure | Mass [M + H] |
|---|---|---|
| 54 | Racemic mixture | 445.3 |
| 55 | *Single enantiomer (2<sup>nd</sup> eluting) | 445.3 |
| 56 | Racemic mixture | 493.2 |
| 57 | Racemic mixture | 434.2 |
| 58 | Racemic mixture | 430.5 |
| 59 | Racemic mixture | 473.6 |
| 60 | Racemic mixture | 478.3 |

TABLE 1-continued
| Compound No. | Structure | Mass [M + H] |
|---|---|---|
| 61 | 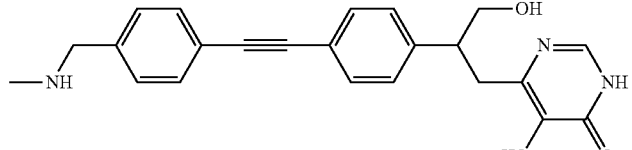<br>Racemic mixture | 390.2 |
| 62 | 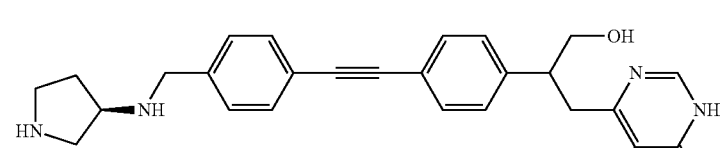<br>Racemic mixture | 445.3 |
| 63 | 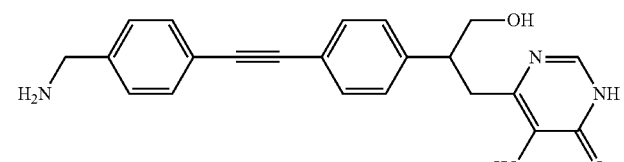<br>Racemic mixture | 376.1 |
| 64 | 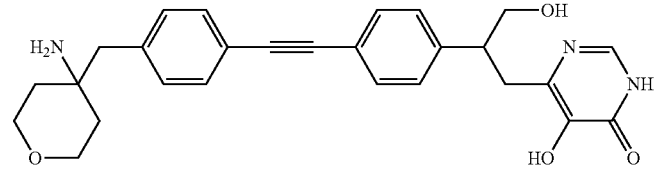<br>Racemic mixture | 460.2 |
| 65 | 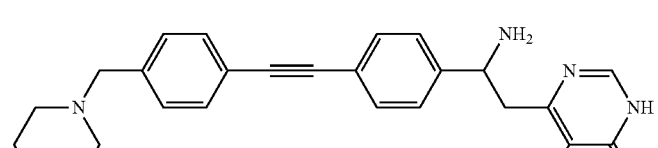<br>Racemic mixture | 431.3 |
| 66 | 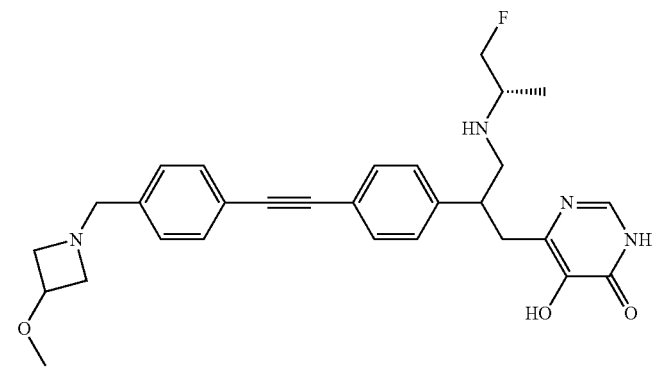<br>Racemic mixture | 505.5 |

TABLE 1-continued

| Compound No. | Structure | Mass [M + H] |
|---|---|---|
| 67 | *Single enantiomer (1st eluting) | 505.5 |
| 68 | *Single enantiomer (2nd eluting) | 505.5 |
| 69 | *Single enantiomer (1st eluting) | 505.7 |

TABLE 1-continued
| Compound No. | Structure | Mass [M + H] |
|---|---|---|
| 70 | 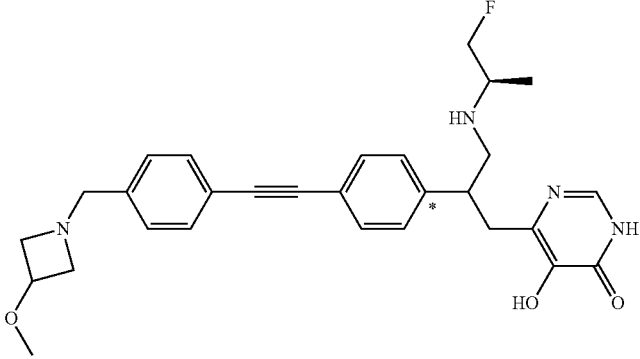 *Single enantiomer (2nd eluting) | 505.7 |
| 71 | 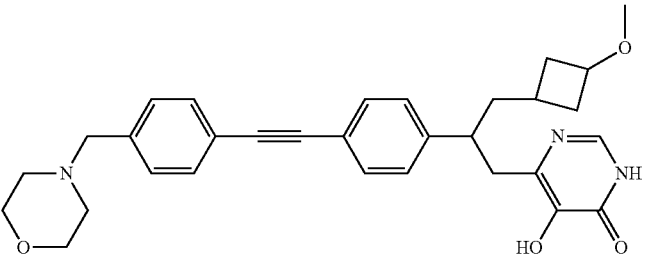 Racemic mixture | 515.2 |
| 72 | 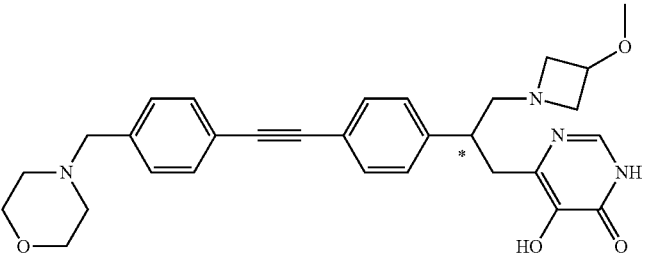 *Single enantiomer (1st eluting) | 515.2 |
| 73 | 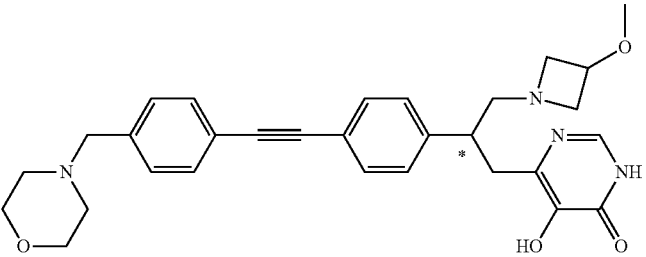 *Single enantiomer (2nd eluting) | 515.2 |

TABLE 1-continued
| Compound No. | Structure | Mass [M + H] |
|---|---|---|
| 74 | 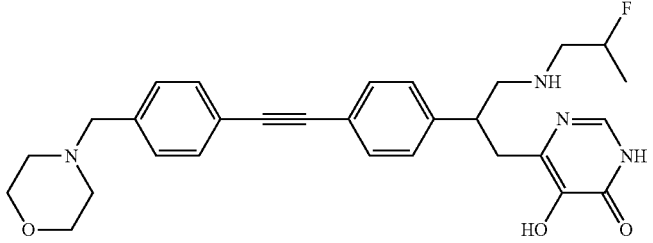Racemic mixture | 505.6 |
| 75 | *Single enantiomer (1st eluting) | 517.5 |
| 76 | *Single enantiomer (1st eluting) | 517.5 |
| 77 | *Single enantiomer (2nd eluting) | 517.5 |

TABLE 1-continued
| Compound No. | Structure | Mass [M + H] |
|---|---|---|
| 78 | 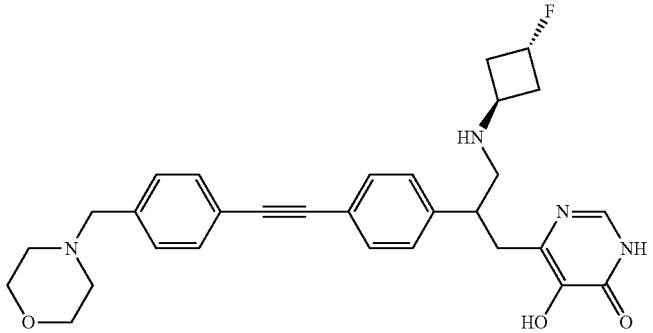<br>Racemic mixture | 517.6 |
| 79 | 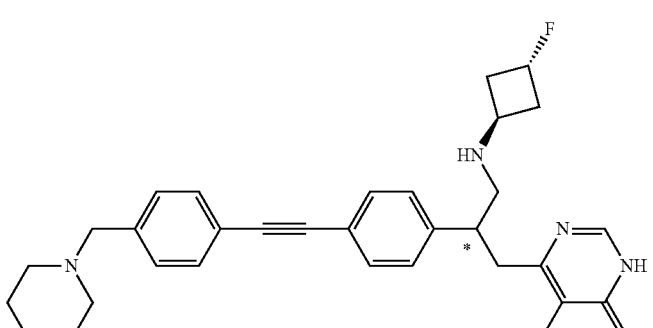<br>*Single enantiomer (1st eluting) | 517.6 |
| 80 | 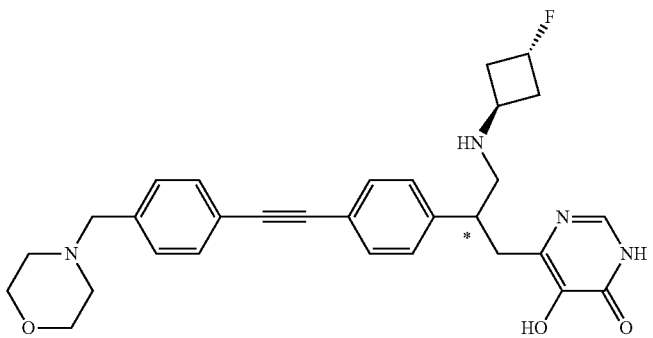<br>*Single enantiomer (2nd eluting) | 517.6 |
| 81 | 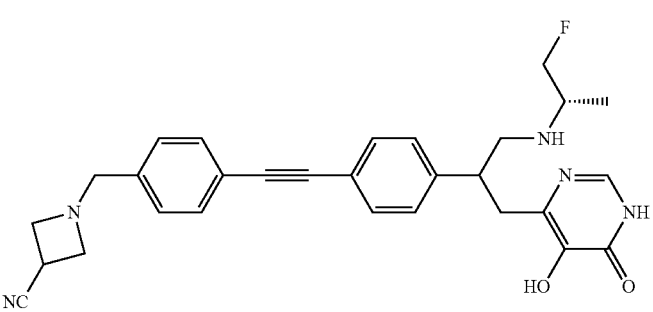<br>Racemic mixture | 500.5 |

TABLE 1-continued

| Compound No. | Structure | Mass [M + H] |
|---|---|---|
| 82 | *Single enantiomer (2<sup>nd</sup> eluting) | 500.5 |
| 83 | *Single enantiomer (2<sup>nd</sup> eluting) | 500.5 |
| 84 | Racemic mixture | 531.4 |
| 85 | *Single enantiomer (2<sup>nd</sup> eluting) | 531.4 |

TABLE 1-continued
| Compound No. | Structure | Mass [M + H] |
|---|---|---|
| 86 | 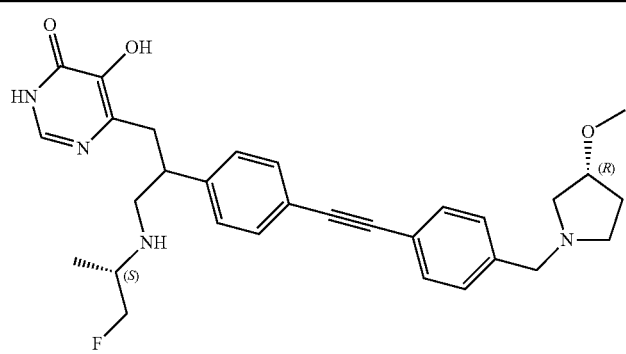<br>Racemic mixture | 519.7 |
| 87 | 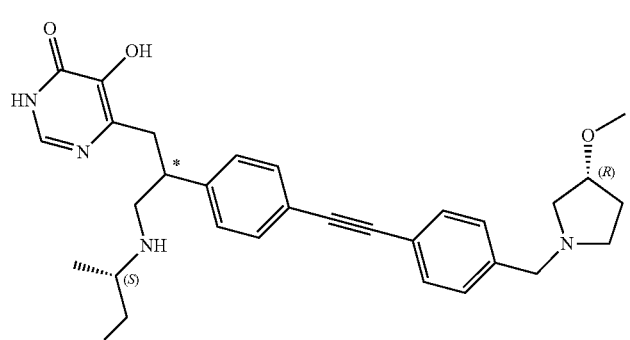<br>*Single enantiomer (1st eluting) | 519.4 |
| 88 | 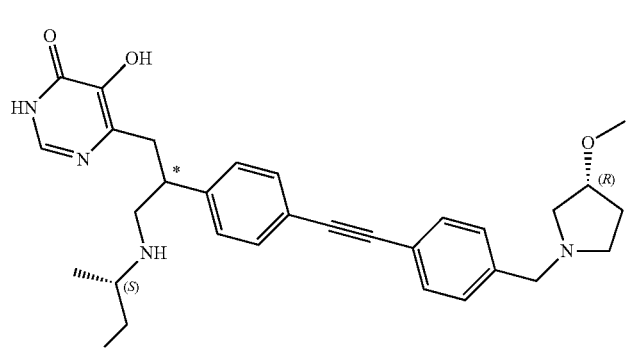<br>*Single enantiomer (2nd eluting) | 519.4 |
| 89 | 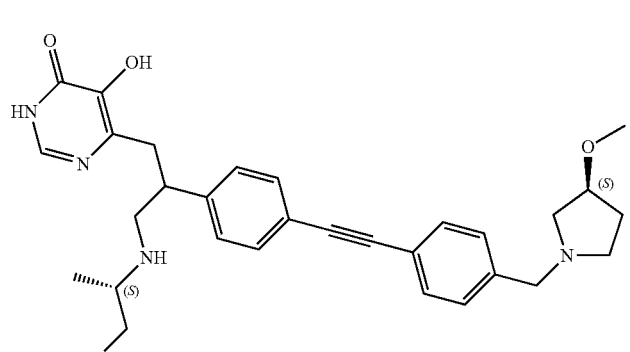<br>Racemic mixture | 519.4 |

TABLE 1-continued

| Compound No. | Structure | Mass [M + H] |
|---|---|---|
| 90 | 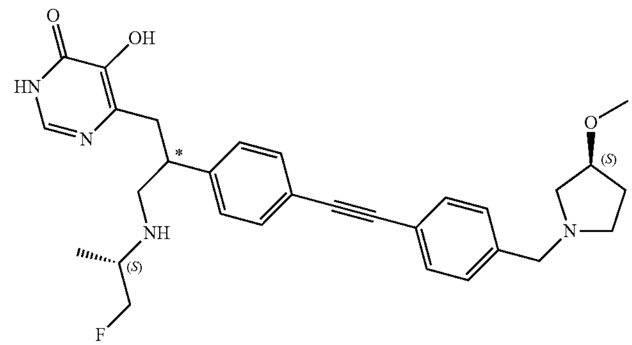 | 519.4 |
| | *Single enantiomer (2^nd eluting) | |
| 91 | 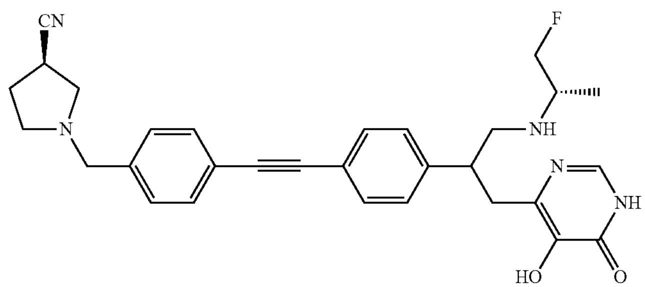 | 514.3 |
| | Racemic mixture | |
| 92 | 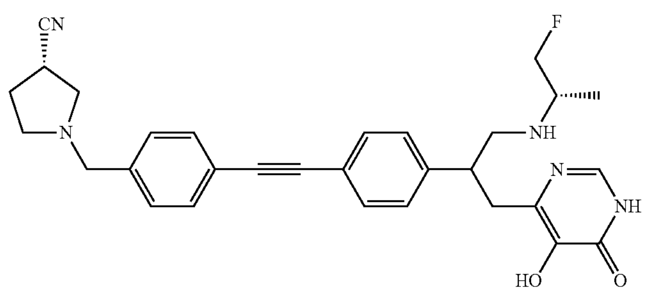 | 514.6 |
| | Racemic mixture | |
| 93 | 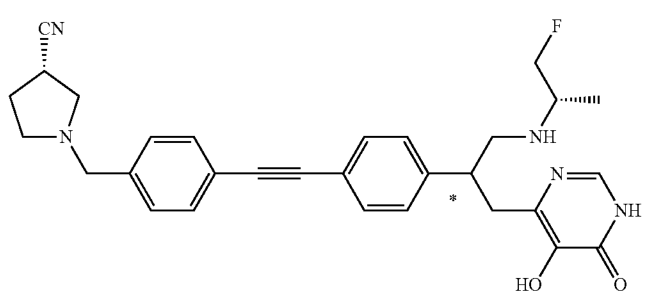 | 514.6 |
| | *Single enantiomer (2^nd eluting) | |

TABLE 1-continued

| Compound No. | Structure | Mass [M + H] |
|---|---|---|
| 94 | (structure) Racemic mixture | 491.6 |
| 95 | (structure) Racemic mixture | 514.5 |
| 96 | (structure) *Single enantiomer (2nd eluting) | 514.5 |
| 97 | (structure) Racemic mixture | 512.4 |
| 98 | (structure) *Single enantiomer (1st eluting) | 512.4 |

TABLE 1-continued

| Compound No. | Structure | Mass [M + H] |
|---|---|---|
| 99 | *Single enantiomer (2nd eluting) | 512.4 |
| 100 | *Single enantiomer (2nd eluting) | 512.4 |
| 101 | Racemic mixture | 505.5 |
| 102 | Racemic mixture | 510.4 |

TABLE 1-continued

| Compound No. | Structure | Mass [M + H] |
|---|---|---|
| 103 | *Single enantiomer (1st eluting) | 510.4 |
| 104 | *Single enantiomer (2nd eluting) | 510.4 |
| 105 | Racemic mixture | 505.6 |
| 106 | *Single enantiomer (1st eluting) | 505.6 |

TABLE 1-continued
| Compound No. | Structure | Mass [M + H] |
|---|---|---|
| 107 | 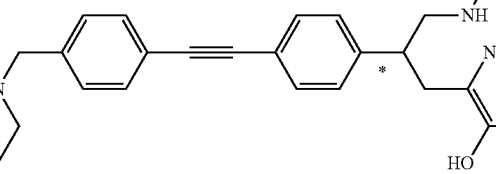<br>*Single enantiomer (2$^{nd}$ eluting) | 505.6 |
| 108 | 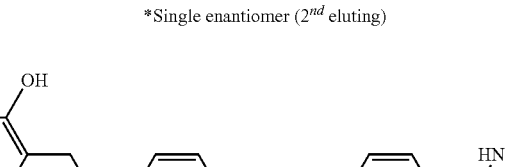<br>Racemic mixture | 505.4 |
| 109 | 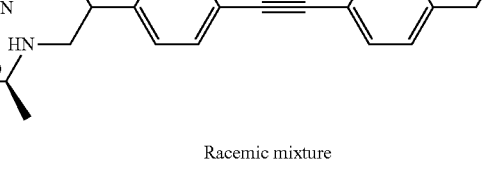<br>*Single enantiomer (1$^{st}$ eluting) | 505.4 |
| 110 | 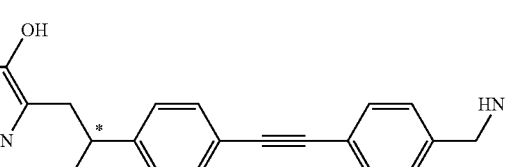<br>Racemic mixture | 505.5 |
| 111 | 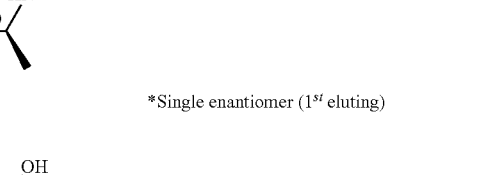<br>*Single enantiomer (2$^{nd}$ eluting) | 505.5 |

TABLE 1-continued
| Compound No. | Structure | Mass [M + H] |
|---|---|---|
| 112 | 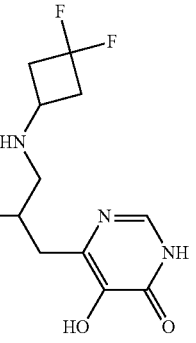 Racemic mixture | 535.6 |
| 113 | *Single enantiomer (1st eluting) | 535.6 |
| 114 | *Single enantiomer (2nd eluting) | 535.6 |
| 115 | 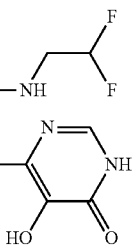 Racemic mixture | 509.3 |

TABLE 1-continued

| Compound No. | Structure | Mass [M + H] |
| --- | --- | --- |
| 116 | *Single enantiomer (1st eluting) | 509.3 |
| 117 | *Single enantiomer (2nd eluting) | 509.3 |
| 118 | Racemic mixture | 485.5 |
| 119 | *Single enantiomer (1st eluting) | 485.5 |
| 120 | *Single enantiomer (2nd eluting) | 485.5 |

TABLE 1-continued
| Compound No. | Structure | Mass [M + H] |
|---|---|---|
| 121 | 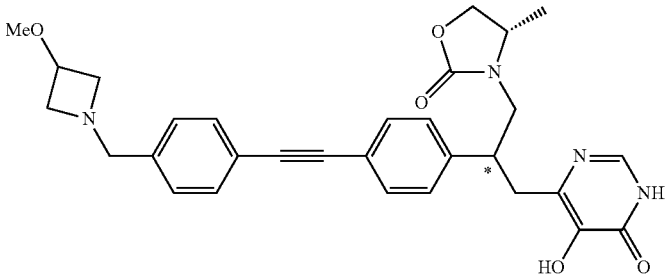 *Single enantiomer (1st eluting) | 529.3 |
| 122 | 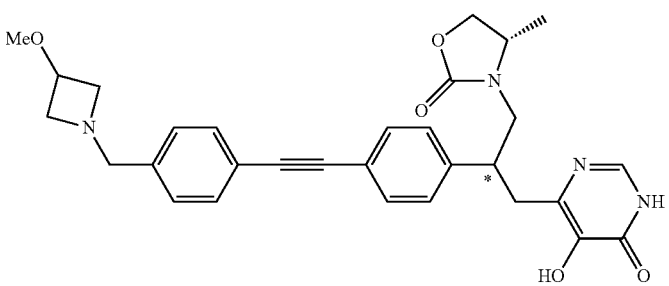 *Single enantiomer (2nd eluting) | 529.3 |
| 123 | 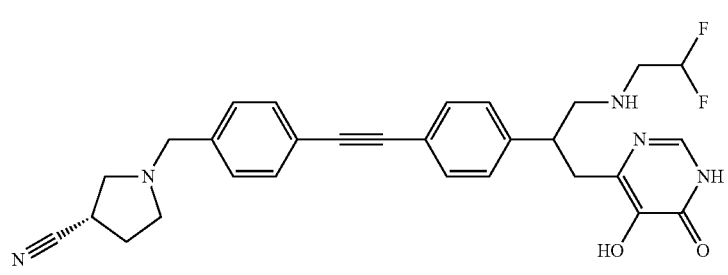 Racemic mixture | 518.6 |
| 124 | 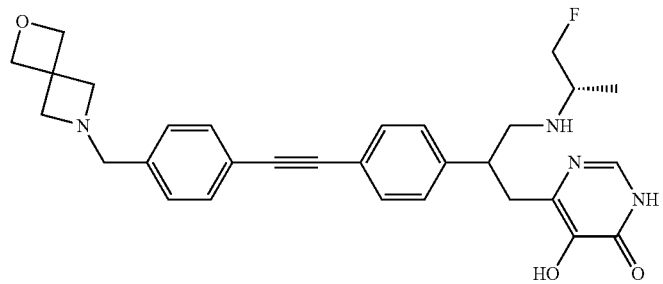 Racemic mixture | 517.7 |

TABLE 1-continued
| Compound No. | Structure | Mass [M + H] |
|---|---|---|
| 125 | 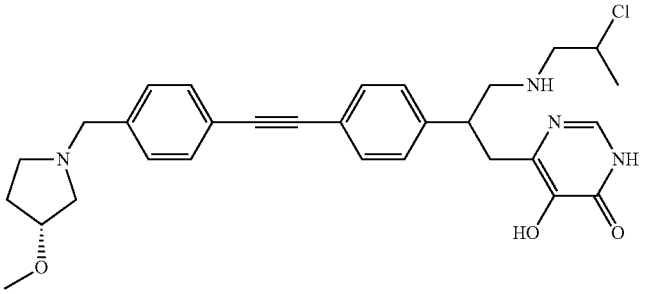<br>Racemic mixture | 536.2 |
| 126 | 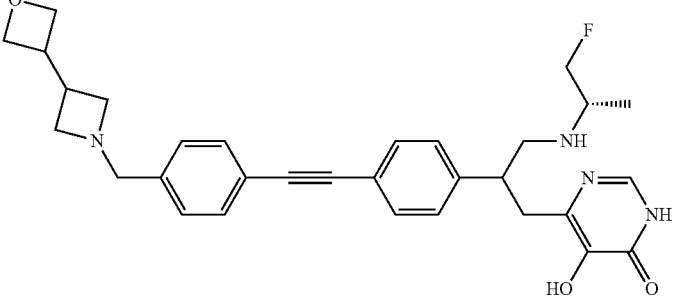<br>Racemic mixture | 531.7 |
| 127 | 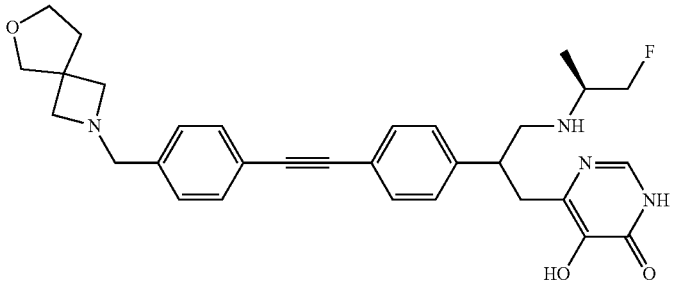<br>Racemic mixture | 531.5 |
| 128 | 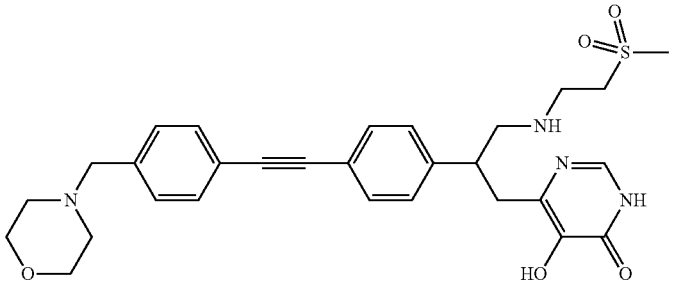<br>Racemic mixture | 551.6 |

TABLE 1-continued
| Compound No. | Structure | Mass [M + H] |
|---|---|---|
| 129 | 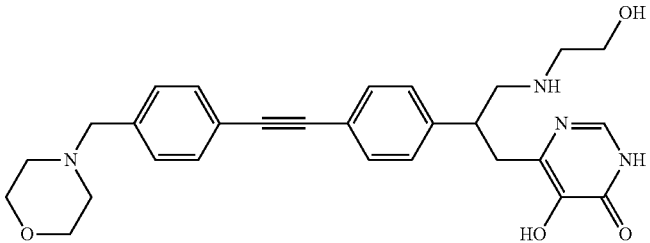<br>Racemic mixture | 489.5 |
| 130 | 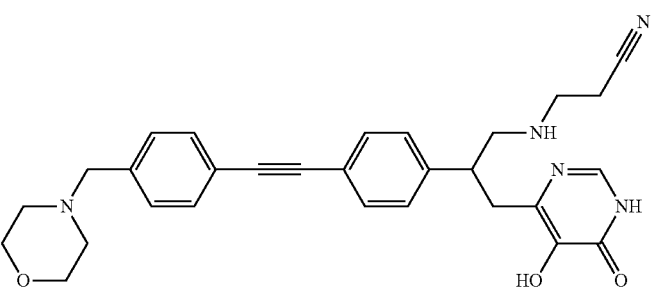<br>Racemic mixture | 498.4 |
| 131 | 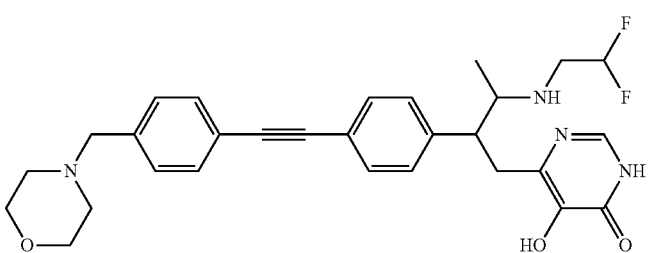<br>Racemic mixture | 523.3 |
| 132 | 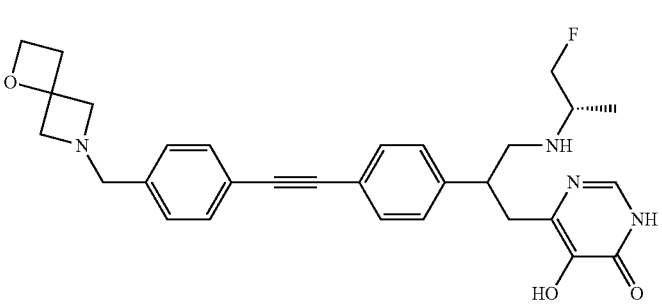<br>Racemic mixture | 517.6 |
| 133 | 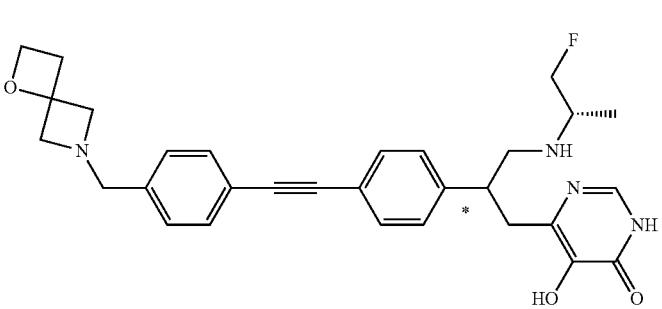<br>*Single enantiomer | 517.6 |

TABLE 1-continued
| Compound No. | Structure | Mass [M + H] |
|---|---|---|
| 134 | 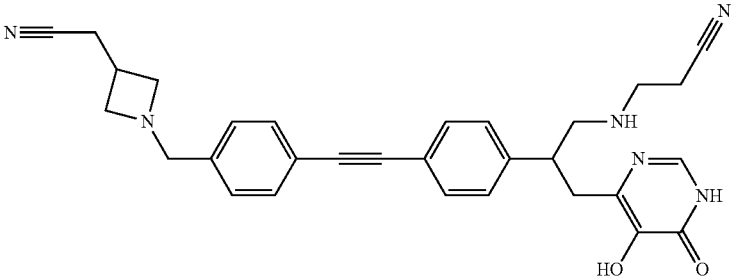 Racemic mixture | 507.4 |
| 135 | 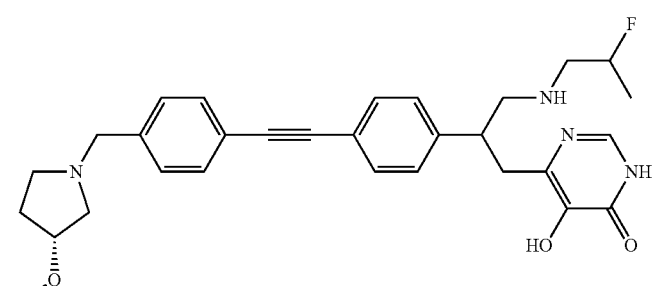 Racemic mixture | 519.7 |
| 136 | 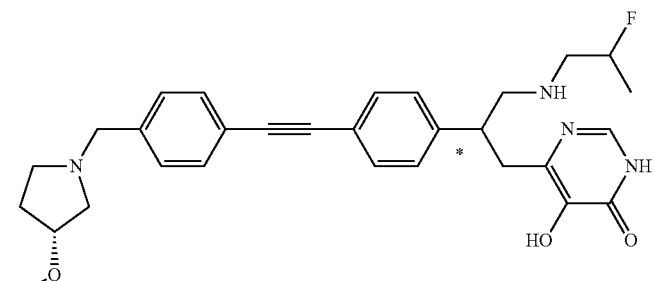 *Single enantiomer (1st eluting) | 519.7 |
| 137 | 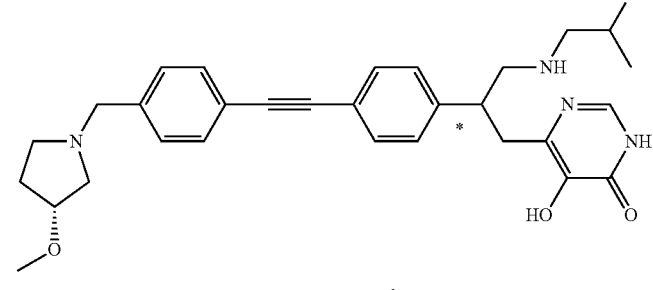 *Single enantiomer (2nd eluting) | 519.7 |

TABLE 1-continued
| Compound No. | Structure | Mass [M + H] |
|---|---|---|
| 138 | 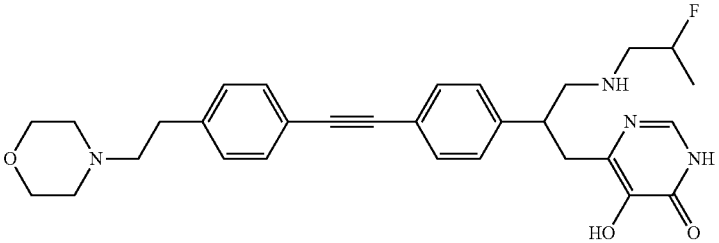<br>Racemic mixture | 519.3 |
| 139 | 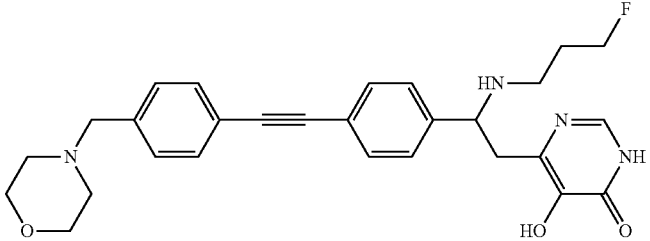<br>Racemic mixture | 491.4 |
| 140 | 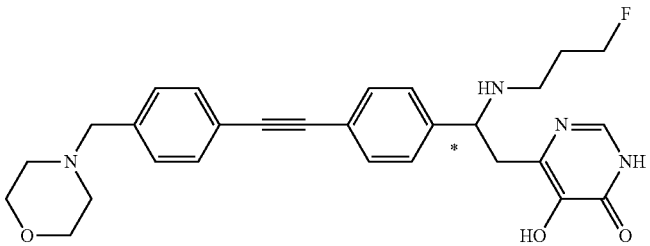<br>*Single enantiomer (2$^{nd}$ eluting) | 491.4 |
| 141 | 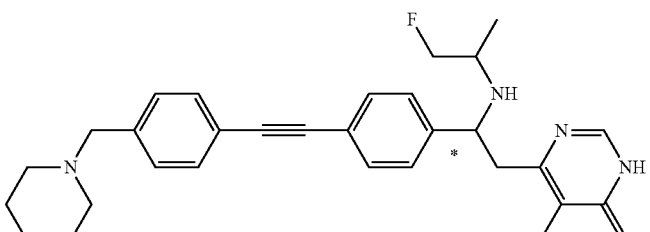<br>Racemic mixture | 491.7 |
| 142 | 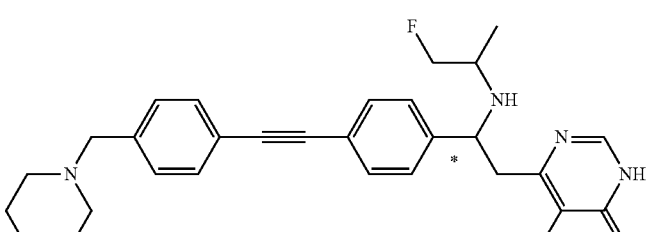<br>*Single enantiomer (2$^{nd}$ eluting) | 491.7 |

TABLE 1-continued
| Compound No. | Structure | Mass [M + H] |
|---|---|---|
| 143 | 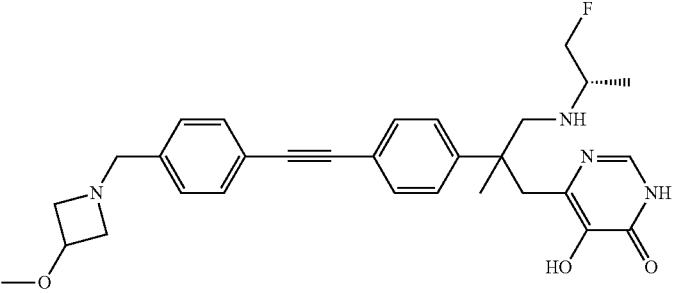 Racemic mixture | 519.6 |
| 144 | 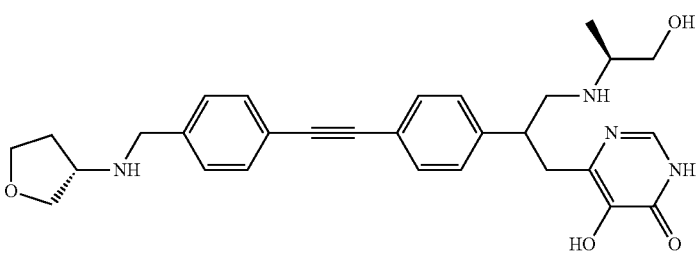 Racemic mixture | 503.6 |
| 145 | 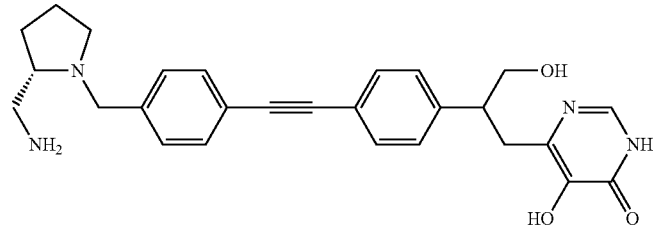 Racemic mixture | 459.3 |
| 146 | 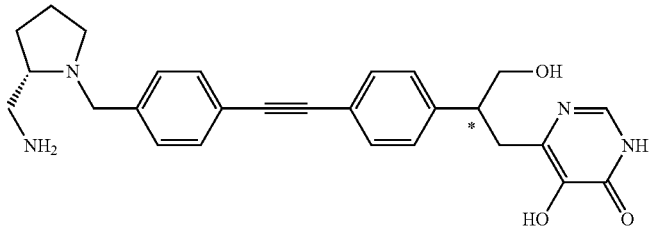 *Single enantiomer (1st eluting) | 459.3 |
| 147 | 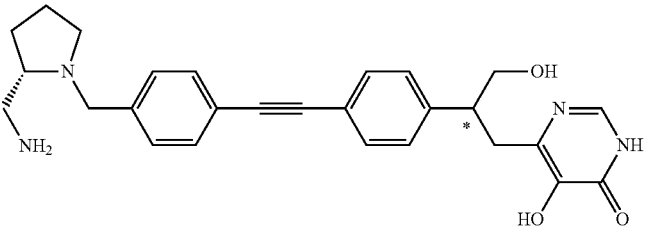 *Single enantiomer (2nd eluting) | 459.3 |

TABLE 1-continued

| Compound No. | Structure | Mass [M + H] |
|---|---|---|
| 148 | Racemic mixture | 459.3 |
| 149 | Racemic mixture | 507.2 |
| 150 | Racemic mixture | 493.2 |
| 151 | Racemic mixture | 493.2 |
| 152 | Racemic mixture | 503.2 |

TABLE 1-continued

| Compound No. | Structure | Mass [M + H] |
|---|---|---|
| 153 | 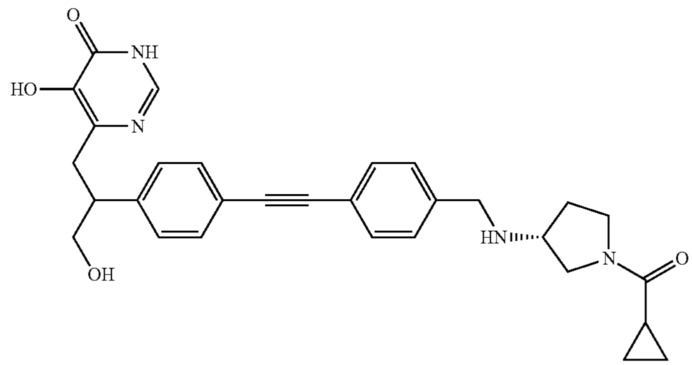 [SMILES: O=C(C1CC1)N1CC[C@@H](NCc2ccc(C#Cc3ccc(C(CO)Cc4nc[nH]c(=O)c4O)cc3)cc2)C1] | 513.3 |
| 154 | Racemic mixture | 503.2 |
| 155 | Racemic mixture | 489.2 |
| 156 | Racemic mixture | 503.2 |

TABLE 1-continued

| Compound No. | Structure | Mass [M + H] |
|---|---|---|
| 157 | *Single enantiomer (2nd eluting) | 517.4 |
| 158 | Racemic mixtures | 517.2 |
| 159 | *Single enantiomer (1st eluting) | 503.5 |
| 160 | *Single enantiomer (2nd eluting) | 503.5 |
| 161 | Racemic mixture | 515.6 |

TABLE 1-continued
| Compound No. | Structure | Mass [M + H] |
|---|---|---|
| 162 | 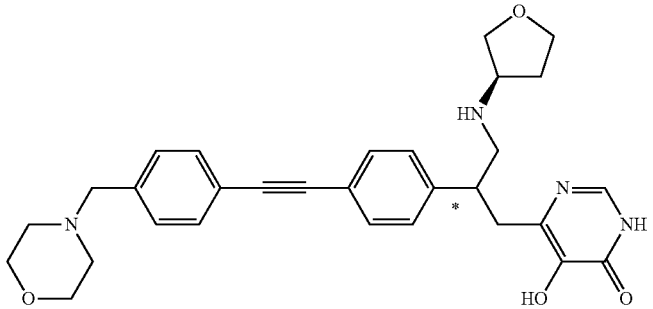 *Single enantiomer (1st eluting) | 515.6 |
| 163 | 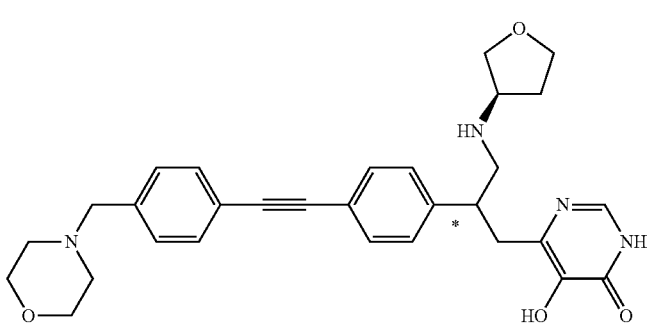 *Single enantiomer (2nd eluting) | 515.6 |
| 164 | 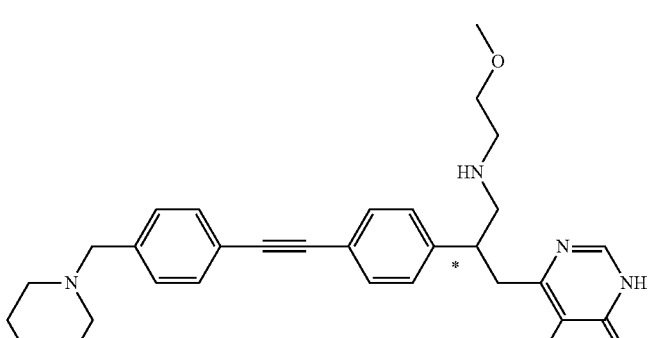 *Single enantiomer (1st eluting) | 503.3 |
| 165 | 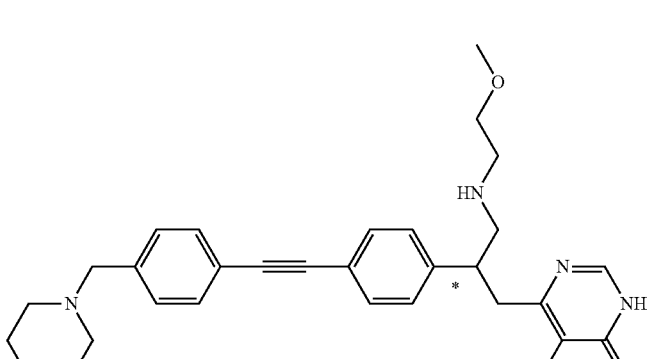 *Single enantiomer (2nd eluting) | 503.3 |

TABLE 1-continued
| Compound No. | Structure | Mass [M + H] |
|---|---|---|
| 166 | 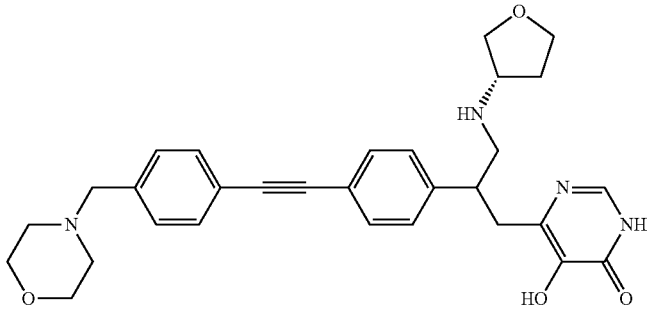<br>Racemic mixture | 515.6 |
| 167 | 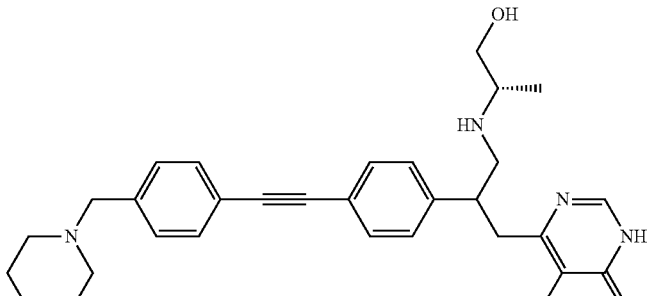<br>Racemic mixture | 503.4 |
| 168 | 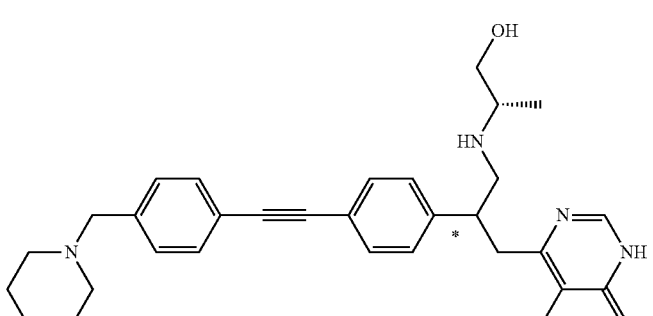<br>*Single enantiomer (1st eluting) | 503.4 |
| 169 | 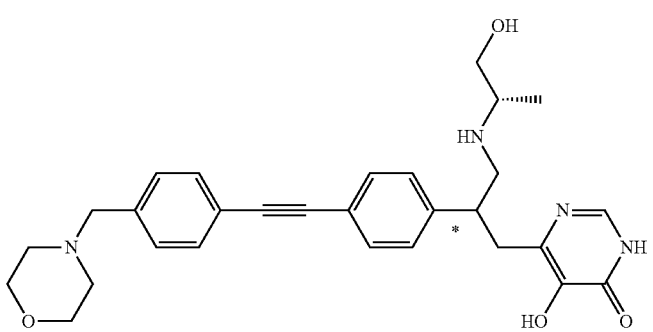<br>*Single enantiomer (2nd eluting) | 503.4 |

TABLE 1-continued

| Compound No. | Structure | Mass [M + H] |
|---|---|---|
| 170 | *Single enantiomer (1st eluting) | 503.4 |
| 171 | *Single enantiomer (2nd eluting) | 503.4 |
| 172 | Racemic mixture | 507.3 |
| 173 | Racemic mixture | 431.3 |
| 174 | Racemic mixture | 459.1 |

TABLE 1-continued

| Compound No. | Structure | Mass [M + H] |
|---|---|---|
| 175 | *Single enantiomer (1st eluting) | 515.3 |
| 176 | *Single enantiomer (2nd eluting) | 515.3 |
| 177 | Racemic mixture | 485.6 |
| 178 | *Single enantiomer (1st eluting) | 553.6 |

TABLE 1-continued

| Compound No. | Structure | Mass [M + H] |
|---|---|---|
| 179 | *Single enantiomer (2nd eluting) | 553.6 |
| 180 | *Single enantiomer (1st eluting) | 503.4 |
| 181 | *Single enantiomer (2nd eluting) | 503.4 |
| 182 | *Single enantiomer (1st eluting) | 556.7 |

TABLE 1-continued

| Compound No. | Structure | Mass [M + H] |
|---|---|---|
| 183 | *Single enantiomer (2nd eluting) | 556.7 |
| 184 | *Single enantiomer (1st eluting) | 525.6 |
| 185 | *Single enantiomer (2nd eluting) | 525.6 |
| 186 | *Single enantiomer (1st eluting) | 563.5 |

TABLE 1-continued
| Compound No. | Structure | Mass [M + H] |
|---|---|---|
| 187 | 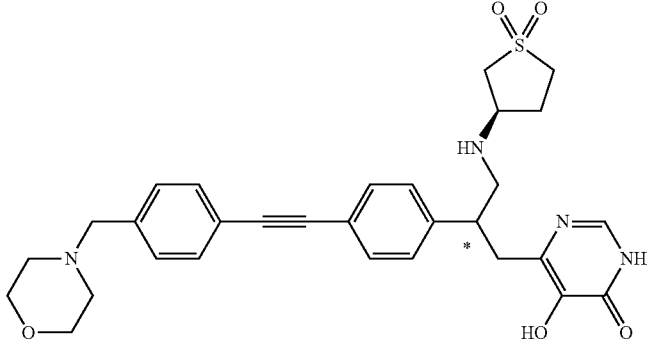<br>*Single enantiomer (2nd eluting) | 563.5 |
| 188 | 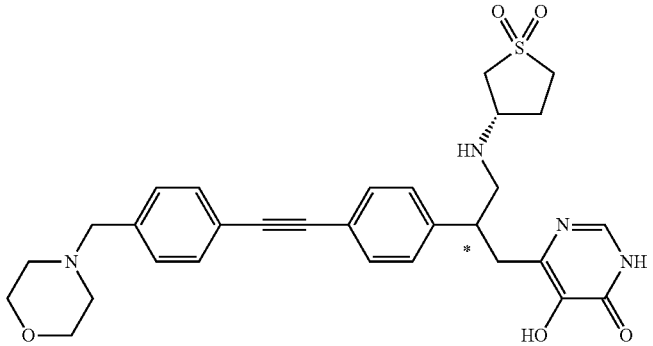<br>*Single enantiomer (1st eluting) | 563.7 |
| 189 | 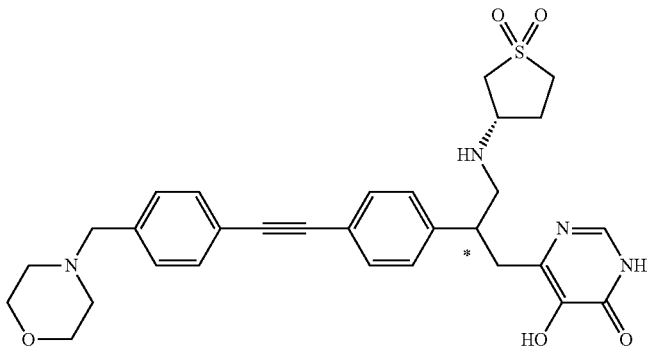<br>*Single enantiomer (2nd eluting) | 563.7 |
| 190 | 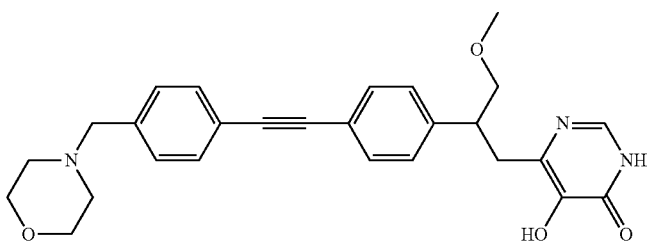<br>Racemic mixture | 460.1 |

TABLE 1-continued
| Compound No. | Structure | Mass [M + H] |
|---|---|---|
| 191 | 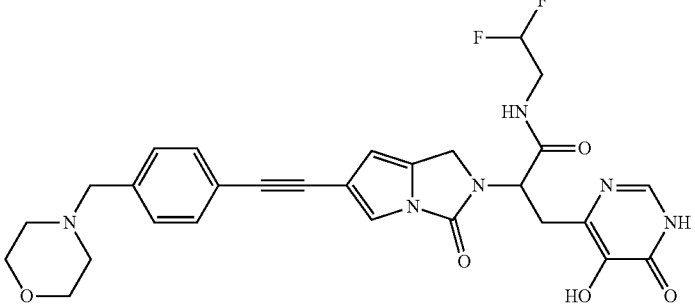  Racemic mixture | 567.2 |
| 192 | 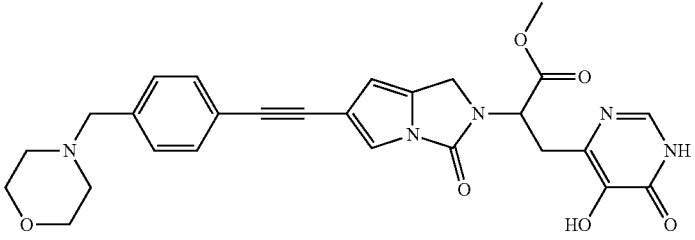  Racemic mixture | 518.3 |
| 193 | 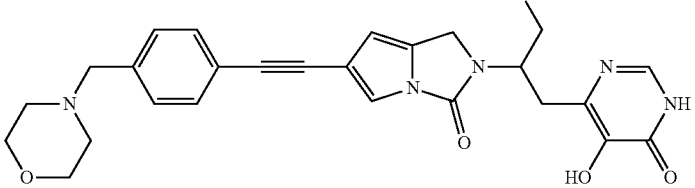  Racemic mixture | 490.4 |
| 194 | 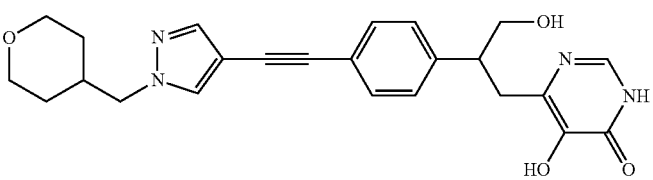  Racemic mixture | 435.3 |
| 195 | 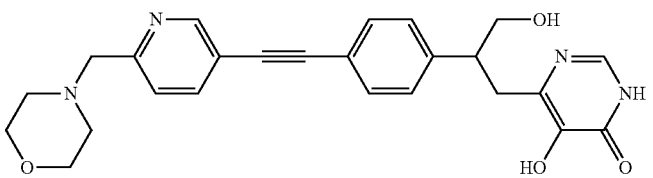  Racemic mixture | 447.5 |
| 196 | 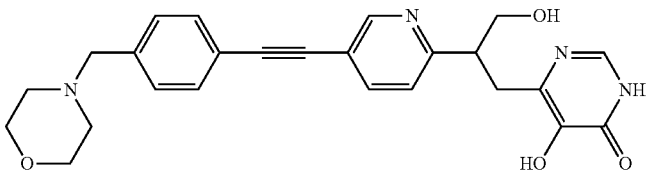  Racemic mixture | 447.4 |

US 12,325,699 B2
139                                                                                     140
TABLE 1-continued
| Compound No. | Structure | Mass [M + H] |
|---|---|---|
| 197 | 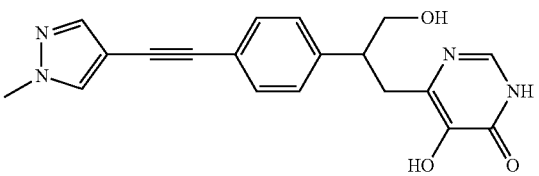<br>Racemic mixture | 351.2 |
| 198 | 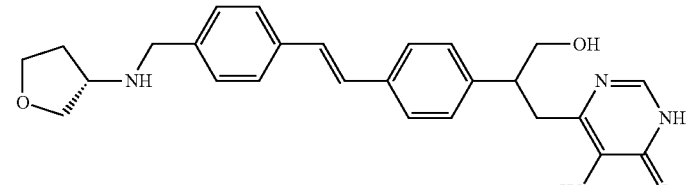<br>Racemic mixture | 448.5 |
| 199 | 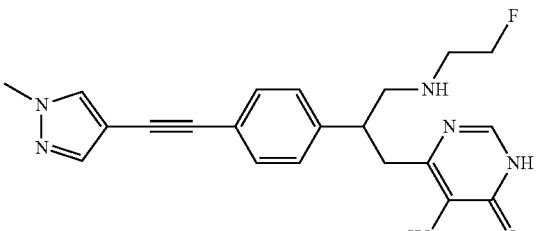<br>Racemic mixture | 396.2 |
| 200 | 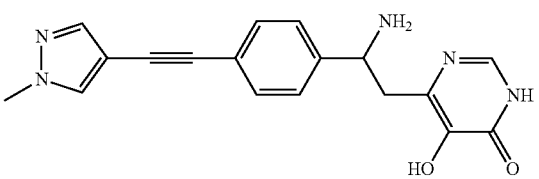<br>Racemic mixture | 336.1 |
| 201 | 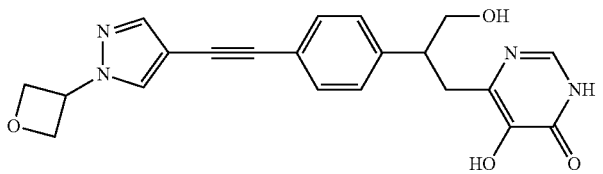<br>Racemic mixture | 393.2 |
| 202 | 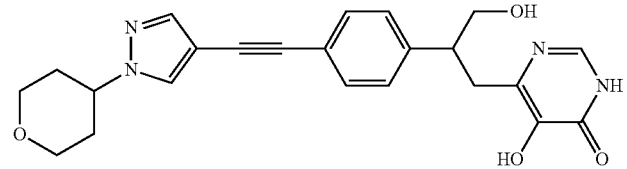<br>Racemic mixture | 421.3 |

TABLE 1-continued

| Compound No. | Structure | Mass [M + H] |
|---|---|---|
| 203 | Racemic mixture | 480.2 |
| 204 | *Single enantiomer | 452.6 |
| 205 | Racemic mixture | 466.3 |
| 206 | Racemic mixture | 480.2 |
| 207 | Racemic mixture | 431.41 |

TABLE 1-continued
| Compound No. | Structure | Mass [M + H] |
|---|---|---|
| 208 | 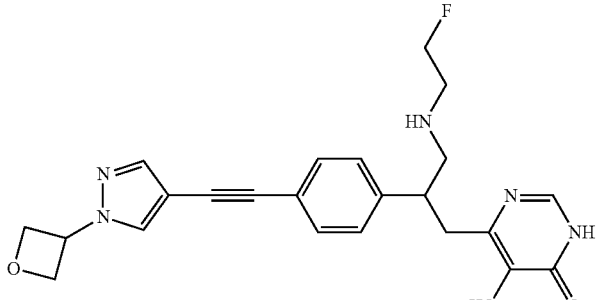 Racemic mixture | 438.3 |
| 209 | 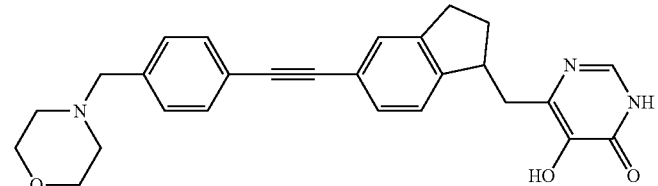 | 442.3 |
| 210 | 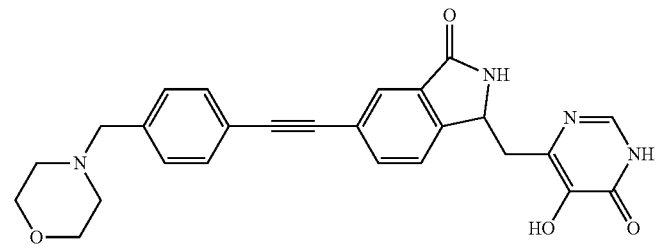 [SMILES: O=C1NC(Cc2nc[nH]c(=O)c2O)c2ccc(C#Cc3ccc(CN4CCOCC4)cc3)cc21] | 457.3 |
| 211 | 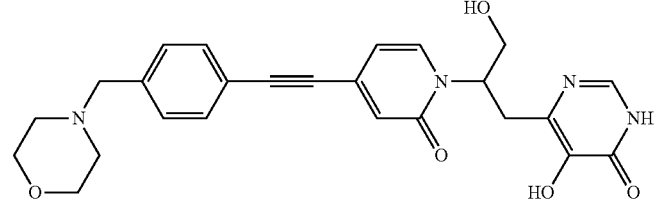 Racemic mixture | 463.3 |
| 212 | 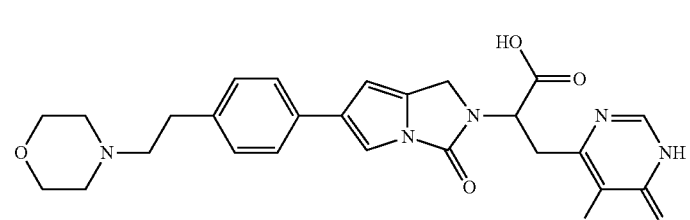 Racemic mixture | 494.2 |
| 213 | 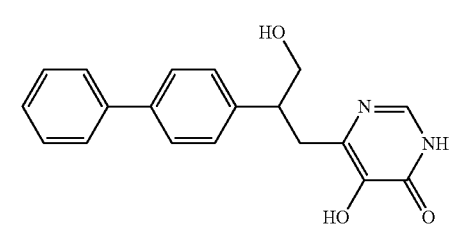 Racemic mixture | 323.4 |

TABLE 1-continued

| Compound No. | Structure | Mass [M + H] |
|---|---|---|
| 214 | Racemic mixture | 421.1 |
| 215 | *Single enantiomer (1st eluting) | 503.6 |
| 216 | *Single enantiomer (2nd eluting) | 503.6 |
| 217 | *Single enantiomer (2nd eluting) | 446.3 |
| 218 | *Single enantiomer (2nd eluting) | 510.4 |

TABLE 1-continued

| Compound No. | Structure | Mass [M + H] |
|---|---|---|
| 219 | *Single enantiomer (1st eluting) | 499.7 |
| 220 | *Single enantiomer (2nd eluting) | 499.7 |
| 221 | *Single enantiomer (1st eluting) | 519.5 |
| 222 | *Single enantiomer (2nd eluting) | 519.5 |

TABLE 1-continued
| Compound No. | Structure | Mass [M + H] |
|---|---|---|
| 223 | 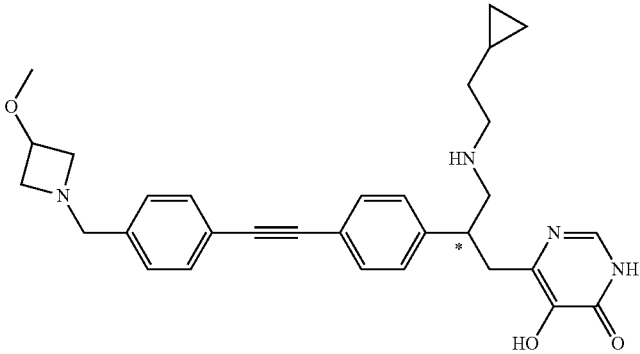<br>*Single enantiomer (1$^{st}$ eluting) | 485.5 |
| 224 | 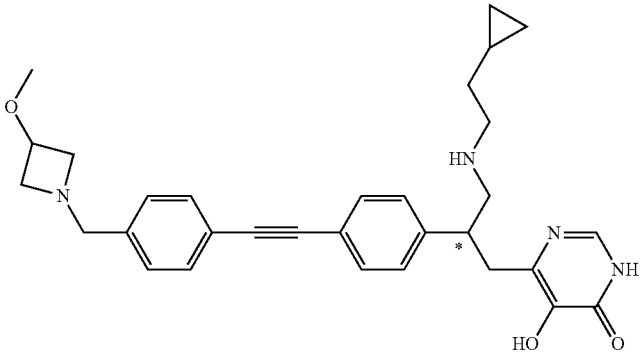<br>*Single enantiomer (2$^{nd}$ eluting) | 485.5 |
| 225 | 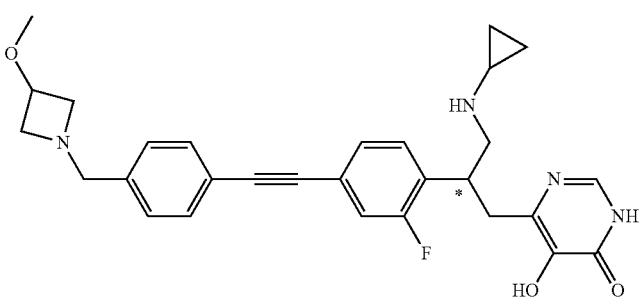<br>*Single enantiomer (1$^{st}$ eluting) | 503.4 |
| 226 | 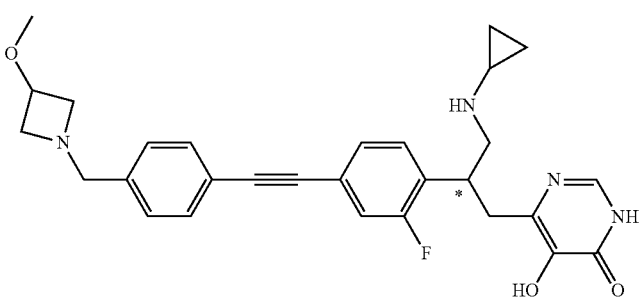<br>*Single enantiomer (2$^{nd}$ eluting) | 503.4 |

TABLE 1-continued
| Compound No. | Structure | Mass [M + H] |
|---|---|---|
| 227 | 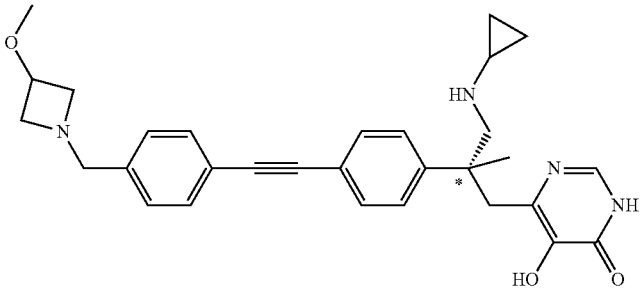 *Single enantiomer (1st eluting) | 499.6 |
| 228 | 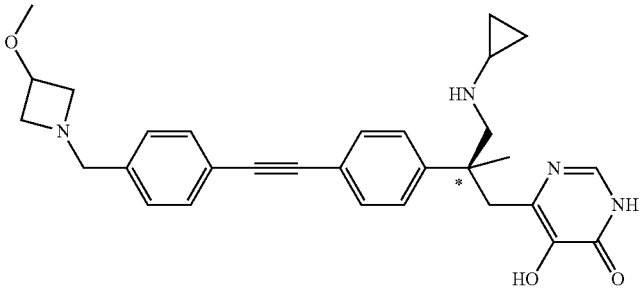 *Single enantiomer (2nd eluting) | 499.6 |
| 229 | 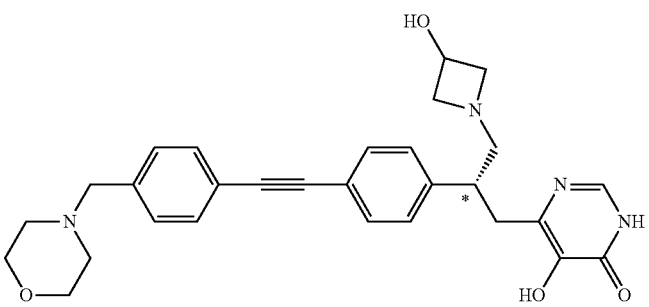 *Single enantiomer (1st eluting) | 501.5 |
| 230 | 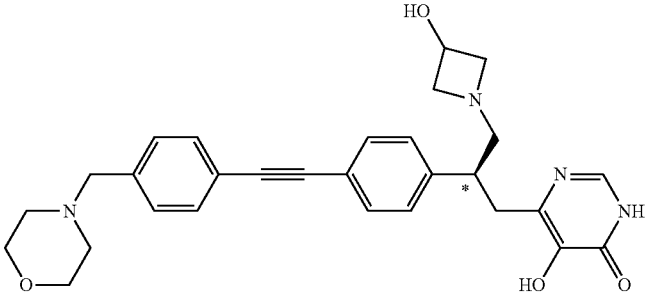 *Single enantiomer (2nd eluting) | 501.5 |

TABLE 1-continued

| Compound No. | Structure | Mass [M + H] |
|---|---|---|
| 231 | *Single enantiomer (2nd eluting) | 519.4 |
| 232 | Racemic mixture | 487.5 |
| 233 | *Single enantiomer (1st eluting) | 487.5 |
| 234 | *Single enantiomer (2nd eluting) | 487.5 |
| 235 | *Single enantiomer (1st eluting) | 519.5 |

TABLE 1-continued

| Compound No. | Structure | Mass [M + H] |
|---|---|---|
| 236 | *Single enantiomer (2nd eluting) | 519.5 |
| 237 | *Single enantiomer (2nd eluting) | 523.4 |
| 238 | *Single enantiomer (2nd eluting) | 523.2 |
| 239 | *Single enantiomer (2nd eluting) | 549.3 |

TABLE 1-continued

| Compound No. | Structure | Mass [M + H] |
|---|---|---|
| 240 | Racemic mixture | 517.3 |
| 241 | *Single enantiomer (1st eluting) | 517.3 |
| 242 | *Single enantiomer (2nd eluting) | 517.3 |
| 243 | *Single enantiomer (2nd eluting) | 490.3 |

TABLE 1-continued
| Compound No. | Structure | Mass [M + H] |
|---|---|---|
| 244 | 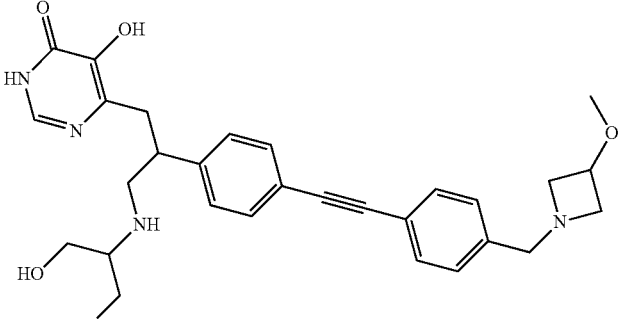 Racemic mixture | 521.6 |
| 245 | *Single enantiomer (2nd eluting) | 503.3 |
| 246 | *Single enantiomer (1st eluting) | 503.6 |
| 247 | *Single enantiomer (1st eluting) | 503.4 |

TABLE 1-continued

| Compound No. | Structure | Mass [M + H] |
|---|---|---|
| 248 | *Single enantiomer (2nd eluting) | 503.4 |
| 249 | Racemic mixture | 521.3 |
| 250 | *Single enantiomer (1st eluting) | 499.3 |
| 251 | *Single enantiomer (2nd eluting) | 499.3 |

TABLE 1-continued

| Compound No. | Structure | Mass [M + H] |
|---|---|---|
| 252 | *Single enantiomer (2nd eluting) | 466.5 |
| 253 | *Single enantiomer (1st eluting) | 523.3 |
| 254 | *Single enantiomer (2nd eluting) | 523.3 |
| 255 | Racemic mixture | 523.3 |
| 256 | Racemic mixture | 513.3 |

TABLE 1-continued

| Compound No. | Structure | Mass [M + H] |
|---|---|---|
| 257 | Racemic mixture | 503.3 |
| 258 | Racemic mixture | 475.2 |
| 259 | Racemic mixture | 459.3 |
| 260 | Racemic mixture | 459.2 |

TABLE 1-continued
| Compound No. | Structure | Mass [M + H] |
|---|---|---|
| 261 | 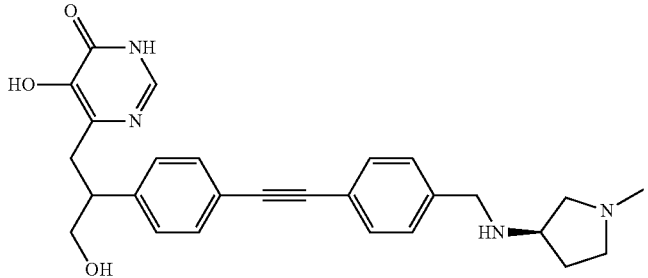<br>Racemic mixture | 459.3 |
| 262 | 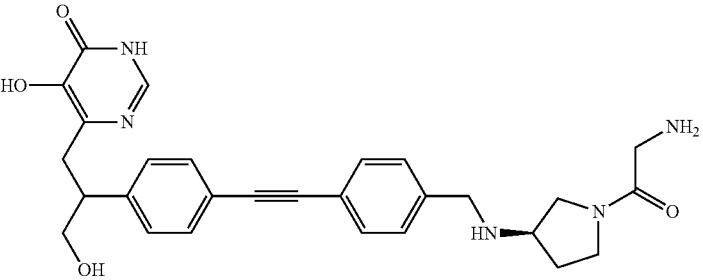<br>Racemic mixture | 502.2 |
| 263 | 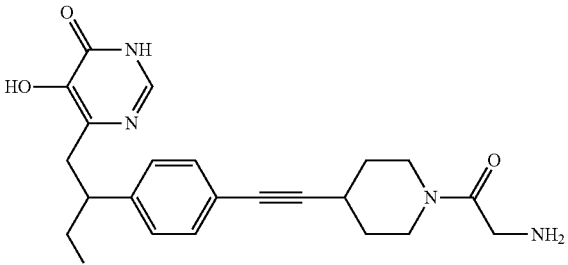<br>Racemic mixture | 411.1 |
| 264 | 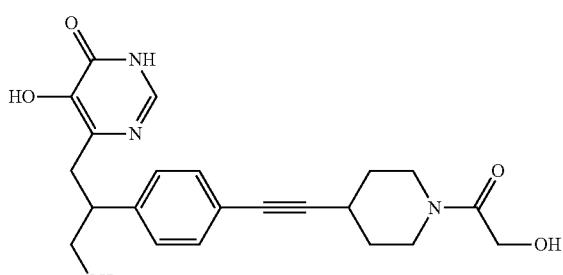<br>Racemic mixture | 412.1 |

TABLE 1-continued

| Compound No. | Structure | Mass [M + H] |
|---|---|---|
| 265 | Racemic mixture | 445.2 |
| 266 | *Single enantiomer (2nd eluting) | 446.3 |
| 267 | *Single enantiomer (2nd eluting) | 475.3 |
| 268 | *Single enantiomer (2nd eluting) | 475.3 |
| 269 | *Single enantiomer (2nd eluting) | 490.3 |

TABLE 1-continued
| Compound No. | Structure | Mass [M + H] |
|---|---|---|
| 270 | 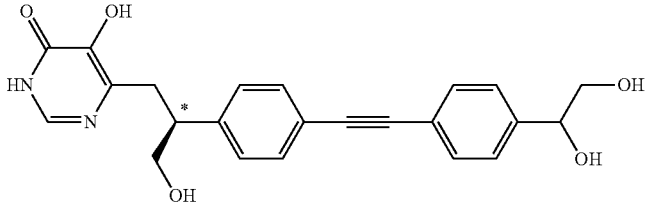 *Single enantiomer (2nd eluting) | 407.4 |
| 271 | 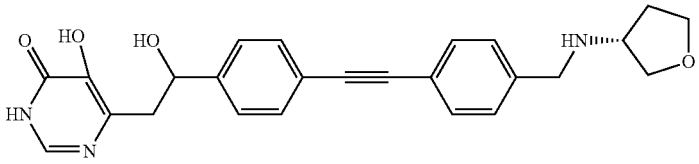 Racemic mixture | 432.3 |
| 272 | 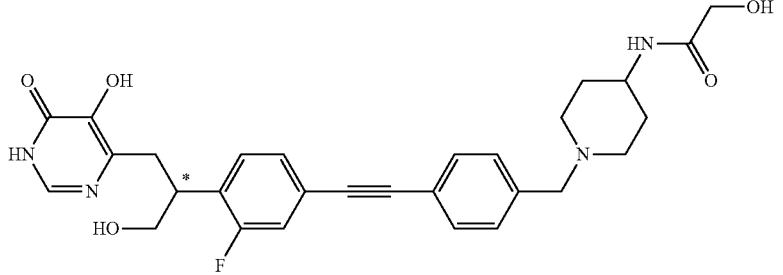 *Single enantiomer (2nd eluting) | 535.4 |
| 273 | 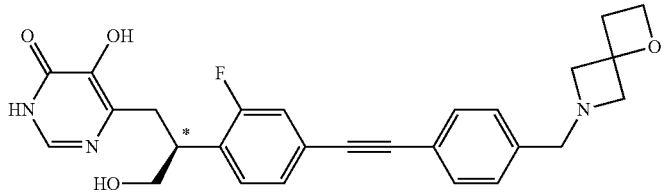 *Single enantiomer (2nd eluting) | 476.6 |
| 274 | 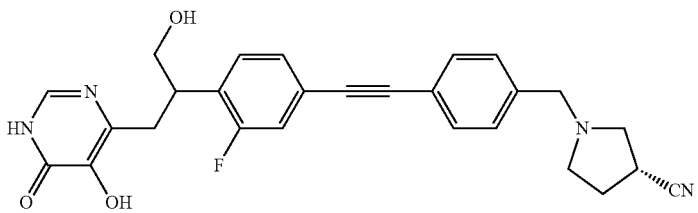 Racemic mixture | 473.3 |

TABLE 1-continued

| Compound No. | Structure | Mass [M + H] |
|---|---|---|
| 275 | *Single enantiomer (2<sup>nd</sup> eluting) | 519.4 |
| 276 | *Single enantiomer (2<sup>nd</sup> eluting) | 519.6 |
| 277 | *Single enantiomer (2<sup>nd</sup> eluting) | 519.5 |
| 278 | *Single enantiomer (2<sup>nd</sup> eluting) | 521.3 |

TABLE 1-continued

| Compound No. | Structure | Mass [M + H] |
|---|---|---|
| 279 | *Single enantiomer (2nd eluting) | 522.5 |
| 280 | *Single enantiomer (2nd eluting) | 523.6 |
| 281 | *Single enantiomer (2nd eluting) | 536.5 |
| 282 | *Single enantiomer (2nd eluting) | 527.3 |

TABLE 1-continued

| Compound No. | Structure | Mass [M + H] |
|---|---|---|
| 283 | *Single enantiomer (2nd eluting) | 527.6 |
| 284 | *Single enantiomer (2nd eluting) | 521.5 |
| 285 | *Single enantiomer (2nd eluting) | 460.3 |
| 286 | *Single enantiomer | 526.2 |
| 287 | *Single enantiomer (2nd eluting) | 459.4 |

TABLE 1-continued

| Compound No. | Structure | Mass [M + H] |
|---|---|---|
| 288 | *Single enantiomer (2nd eluting) | 459.4 |
| 289 | *Single enantiomer (1st eluting) | 509.2 |
| 290 | *Single enantiomer (1st eluting) | 509.3 |
| 291 | *Single enantiomer | 538.4 |
| 292 | Racemic mixture | 445.3 |

TABLE 1-continued

| Compound No. | Structure | Mass [M + H] |
|---|---|---|
| 293 | Racemic mixture | 418.2 |
| 294 | Racemic mixture | 518.53 |
| 295 | *Single enantiomer (2nd eluting) | 508.45 |
| 296 | *Single enantiomer (2nd eluting) | 508.54 |

TABLE 1-continued

| Compound No. | Structure | Mass [M + H] |
|---|---|---|
| 297 | *Single enantiomer (2<sup>nd</sup> eluting) | 537.54 |
| 298 | *Single enantiomer (2<sup>nd</sup> eluting) | 409.45 |
| 299 | *Single enantiomer (2<sup>nd</sup> eluting) | 508.51 |
| 300 | *Single enantiomer (2<sup>nd</sup> eluting) | 532.52 |
| 301 | *Single enantiomer (2<sup>nd</sup> eluting) | 518.60 |

TABLE 1-continued

| Compound No. | Structure | Mass [M + H] |
|---|---|---|
| 302 | *Single enantiomer (2^nd eluting) | 498.46 |
| 303 | *Single enantiomer (2^nd eluting) | 486.55 |
| 304 | *Single enantiomer (2^nd eluting) | 522.61 |
| 305 | *Single enantiomer (2^nd eluting) | 509.56 |

Compounds in Table 1 are named:

5-hydroxy-6-(3-hydroxy-3-methyl-2-(4-((4-(morpholinomethyl)phenyl)ethynyl)phenyl)butyl)pyrimidin-4(3H)-one;

5-hydroxy-6-(3-hydroxy-2-(4-((4-(morpholinomethyl)phenyl)ethynyl)phenyl)propyl)pyrimidin-4(3H)-one;

(R)-5-hydroxy-6-(3-hydroxy-2-(4-((4-(morpholinomethyl)phenyl)ethynyl)phenyl)propyl)pyrimidin one;

(S)-5-hydroxy-6-(3-hydroxy-2-(4-((4-(morpholinomethyl)phenyl)ethynyl)phenyl)propyl)pyrimidin-4(3H)-one;

6-(3-((2-fluoroethyl)amino)-2-(4-((4-(morpholinomethyl)phenyl)ethynyl)phenyl)propyl)-5-hydroxypyrimidin-4(3H)-one;

(R)-6-(3-((2-fluoroethyl)amino)-2-(4-((4-(morpholinomethyl)phenyl)ethynyl)phenyl)propyl)-5-hydroxypyrimidin-4(3H)-one;

(S)-6-(3-((2-fluoroethyl)amino)-2-(4-((4-(morpholinomethyl)phenyl)ethynyl)phenyl)propy-5-hydroxypyrimidin-4(3H)-one;

5-hydroxy-6-(3-hydroxy-2-(4-((4-((((S)-tetrahydrofuran-3-yl)amino)methyl)phenyl)ethynyl)phenyl)propyl)pyrimidin-4(3H)-one;
(R)-5-hydroxy-6-(3-hydroxy-2-(4-((4-((((S)-tetrahydrofuran-3-yl)amino)methyl)phenyl)ethynyl)phenyl)propyl)pyrimidin-4(3H)-one;
(S)-5-hydroxy-6-(3-hydroxy-2-(4-((4-((((S)-tetrahydrofuran-3-yl)amino)methyl)phenyl)ethynyl)phenyl)propyl)pyrimidine-4(3H)-one;
5-hydroxy-6-(3-hydroxy-2-(4-((4-((((R)-tetrahydrofuran-3-yl)amino)methyl)phenyl)ethynyl)phenyl)propyl)pyrimidin-4(3H)-one;
5-hydroxy-6-(3-hydroxy-2-(4-((4-(morpholinomethyl)phenyl)ethynyl)phenyl)butyl)pyrimidin-4(3H)-one;
6-((R)-3-(((S)-1-fluoropropan-2-yl)amino)-2-(4-((4-(morpholinomethyl)phenyl)ethynyl)phenyl)propyl)-5-hydroxypyrimidin-4(3H)-one;
6-(S)-3-(((S)-1-fluoropropan-2-yl)amino)-2-(4-((4-(morpholinomethyl)phenyl)ethynyl)phenyl)propyl)-5-hydroxypyrimidine-4(3H)-one;
6-(3-(((R)-1-fluoropropan-2-yl)amino)-2-(4-((4-(morpholinomethyl)phenyl)ethynyl)phenyl)propyl)-5-hydroxypyrimidin-4(3H)-one;
6-((R)-3-((R)-1-fluoropropan-2-yl)amino)-2-(4-((4-(morpholinomethyl)phenyl)ethynyl)phenyl)propyl)-5-hydroxypyrimidin-4(3H)-one;
6-((S)-3-(((R)-1-fluoropropan-2-(4-((4-(morpholinomethyl)phenyl)ethynyl)phenyl)propyl)-5-hydroxypyrimidin-4(3H)-one;
6-(3-amino-2-(4-((4-(morpholinomethyl)phenyl)ethynyl)phenyl)propyl)-5-hydroxypyrimidin-4(3H)-one;
N-(2-fluoroethyl)-3-(5-hydroxy-6-dihydropyrimidin-4-yl)-2-(4-((4-(morpholinomethyl)phenyl)ethynyl)phenyl)propanamide;
(R)—N-(2-fluoroethyl)-3-(5-hydroxy-6-oxo-1,6-dihydropyrimidin-4-yl)-2-(4-((4-(morpholinomethyl)phenyl)ethynyl)phenyl)propanamide;
(S)—N-(2-fluoroethyl)-3-(5-hydroxy-6-oxo-dihydropyrimidin-4-yl)-2-(4-((4-(morpholinomethyl)phenyl) ethynyl)phenyl)propanamide;
N-(2,2-difluoroethyl)-3-(5-hydroxy 6-dihydropyrimidin-4-yl)-2-(4-((4-(morpholinomethyl)phenyl)ethynyl)phenyl)propanamide;
3-(5-hydroxy-6-oxo-1,6-dihydropyrimidin-4-yl)-N-methyl-2-(4-((4-(morpholinomethyl)phenyl)ethynyl)phenyl)propanamide;
methyl 3-(5-hydroxy-6-oxo-1,6-dihydropyrimidin-4-yl)-2-(4-((4-(morpholinomethyl)phenyl)ethynyl)phenyl)propanoate;
N-(3,3-difluorocyclobutyl)-3-(5-hydroxy-6-oxo-1,6-dihydropyrimidin-4-yl)-2-(4-((4-(morpholinomethyl)phenyl)ethynyl)phenyl)propanamide;
ethyl 3-(5-hydroxy-6-oxo-1,6-dihydropyrimidin-4-yl)-2-(4-((4-(((tetrahydrofuran-3-yl)amino)methyl)phenyl)ethynyl)phenyl)propanoate;
methyl 3-(5-hydroxy-6-oxo-1,6-dihydropyrimidin-4-yl)-2-(4-((4-(((tetrahydrofuran-3-yl)amino)methyl)phenyl)ethynyl)phenyl)propanoate;
N-(1-cyanoethyl)-3-(5-hydroxy-6-oxo-1,6-dihydropyrimidin-4-yl)-2-(4-((4-(morpholinomethyl)phenyl)ethynyl)phenyl)propanamide;
N-(2,2-difluoroethyl)-3-(5-hydroxy-6-oxo-1,6-dihydropyrimidin-4-yl)-2-(4-((4-((2-(hydroxymethyl)-1H-imidazol-1-yl)methyl)phenyl)ethynyl)phenyl)propanamide;
N-(2-fluoroethyl)-3-(5-hydroxy-6-oxo-1,6-dihydropyrimidin-4-yl)-2-(4-((4-((((S)-tetrahydrofuran-3-yl)amino)methyl)phenyl)ethynyl)phenyl)propanamide;
5-hydroxy-6-(3-hydroxy-2-methyl-2-(4-(4-(morpholinomethyl)phenyl)ethynyl)phenyl)propyl)pyrimidin-4(3H)-one;
5-hydroxy-6-(3-hydroxy-2-methyl-2-(4-((4-((((S)-tetrahydrofuran-3-yl)amino)methyl)phenyl)ethynyl)phenyl)propyl)pyrimidin-4(3H)-one;
1-(4-((4-((S)-1-hydroxy-3-(5-hydroxy-6-oxo-1,6-dihydropyrimidin-4-yl)propan-2-yl)phenyl)ethynyl)benzyl)pyrrolidine-3-carbonitrile;
1-(4-((4-((R)-1-hydroxy-3-(5-hydroxy-6-oxo-1,6-dihydropyrimidin-4-yl)propan-2-yl)phenyl)ethynyl)benzyl)pyrrolidine-3-carbonitrile;
(3S)-1-(4-((4-(1-hydroxy-3-(5-hydroxy-6-oxo-1,6-dihydropyrimidin-4-yl)propan-2-yl)phenyl)ethynyl)benzyl)pyrrolidine-3-carbonitrile;
(3S)-1-(4-((4-(1-hydroxy-3-(5-hydroxy-6-oxo-1,6-dihydropyrimidin-4-yl)propan-2-yl)phenyl)ethynyl)benzyl)pyrrolidine-3-carbonitrile;
(S)-1-(4-((4-(S)-1-hydroxy-3-(5-hydroxy-6-oxo-1,6-dihydropyrimidin-4-yl)propan-2-yl)phenyl)ethynyl)benzyl)pyrrolidine-3-carbonitrile;
(S)-1-(4-((4-(R)-1-hydroxy-3-(5-hydroxy-6-oxo-1,6-dihydropyrimidin-4-yl)propan-2-yl)phenyl)ethynyl)benzyl)pyrrolidine-3-carbonitrile;
(3R)-1-(4-((4-(1-hydroxy-3-(5-hydroxy-6-oxo-1,6-dihydropyrimidin-4-yl)propan-2-yl)phenyl)ethynyl)benzyl)pyrrolidine-3-carbonitrile;
6-(2-(4-((4-(((3-oxabicyclo[3.1.0]hexan-6-yl)amino)methyl)phenyl)ethynyl)phenyl)-3-hydroxypropyl)-5-hydroxypyrimidin-4(3H)-one;
6-(2-(4-((4-(((1,1-dioxidotetrahydrothiophen-3-yl)amino)methyl)phenyl)ethynyl)phenyl)-3-hydroxypropyl)-5-hydroxypyrimidin-4(3H)-one;
6-(2-(4-((4-((((S)-1,1-dioxidotetrahydrothiophen-3-yl)amino)methyl)phenyl)ethynyl)phenyl)-3-hydroxypropyl)-5-hydroxypyrimidin-4(3H)-one;
6-((R)-2-(4-((4-((((S)-1,1-dioxidotetrahydrothiophen-3-yl)amino)methyl)phenyl)ethynyl)phenyl)-3-hydroxypropyl)-5-hydroxypyrimidin-4(3H)-one;
6-((S)-2-(4-((4-((((S)-1,1-dioxidotetrahydrothiophen-3-ylamino)methyl)phenyl)ethynyl)phenyl)-3-hydroxypropyl)-5-hydroxypyrimidin-4(3H)-one;
6-(2-(4-((4-((((R)-1,1-dioxidotetrahydrothiophen-3-yl)amino)methyl)phenyl)ethynyl)phenyl)-3-hydroxypropyl)-5-hydroxypyrimidin-4(3H)-one;
6-((R)-2-(4-((4-((((R)-1,1-dioxidotetrahydrothiophen-3-yl)amino)methyl)phenyl)ethynyl)phenyl)-3-hydroxypropyl)-5-hydroxypyrimidin-4(3H)-one;
6-((S)-2-(4-((4-((((R)-1,1-dioxidotetrahydrothiophen-3-yl)amino)methyl)phenyl)ethynyl)phenyl)-3-hydroxypropyl)-5-hydroxypyrimidin-4(3H)-one;
6-(2-(4-((4-((5-oxa-2-azaspiro[3.4]octan-2-yl)methyl)phenyl)ethynyl)phenyl)-3-hydroxypropyl)-5-hydroxypyrimidin-4(3H)-one;
5-hydroxy-6-(3-hydroxy-2-(4-((4-(2-(((S)-tetrahydrofuran-3-yl)amino)ethyl)phenyl)ethynyl)phenyl)propyl)pyrimidin-4(3H)-one;
5-hydroxy-6-(3-hydroxy-2-(4-((4-((((R)-1-(2-hydroxyacetyl)pyrrolidin-3-yl)amino)methyl)phenyl)ethynyl)phenyl)propyl)pyrimidin-4(3H)-one;
5-hydroxy-6-((R)-3-hydroxy-2-(4-((4-((((R)-1-(2-hydroxyacetyl)pyrrolidin-3-yl)amino)methyl)phenyl)ethynyl)phenyl)propyl)pyrimidin-4(3H)-one;
5-hydroxy-6-((S)-3-hydroxy-2-(4-((4-((((R)-1-(2-hydroxyacetyl)pyrrolidin-3-yl)amino)methyl)phenyl)ethynyl)phenyl)propyl)pyrimidin-4(3H)-one;

6-(2-(4-((4-((2-oxa-6-azaspiro[3.3]heptan-6-yl)methyl)phenyl)ethynyl)phenyl)-3-hydroxypropyl)-5-hydroxypyrimidin-4(3H)-one;

5-hydroxy-6-(3-hydroxy-2-(4-((4-(hydroxymethyl)phenyl)ethynyl)phenyl)propyl)pyrimidin-4(3H)-one;

5-hydroxy-6-(3-hydroxy-2-(4-((4-((oxetan-3-ylamino)methyl)phenyl)ethynyl)phenyl)propyl)pyrimidin-4(3H)-one;

ethyl 3-(5-hydroxy-6-oxo-1,6-dihydropyrimidin-4-yl)-2-(4-((4-((oxetan-3-ylamino)methyl)phenyl)ethynyl)phenyl)propanoate;

5-hydroxy-6-(3-hydroxy-2-(4-((4-((3-morpholinoazetidin-1-yl)methyl)phenyl)ethynyl)phenyl)propyl)pyrimidin-4(3H)-one;

5-hydroxy-6-(3-hydroxy-2-(4-((4-((((tetrahydrofuran-3-yl)methyl)amino)methyl)phenyl)ethynyl)phenyl)propyl)pyrimidin-4(3H)-one;

5-hydroxy-6-(3-hydroxy-2-(4-((4-(((tetrahydro-2H-pyran-4-yl)amino)methyl)phenyl)ethynyl)phenyl)propyl)pyrimidin-4(3H)-one;

5-hydroxy-6-(3-hydroxy-2-(4-((4-(piperazin-1-ylmethyl)phenyl)ethynyl)phenyl)propyl)pyrimidin-4(3H)-one;

(R)-5-hydroxy-6-(3-hydroxy-2-(4-((4-(piperazin-1-ylmethyl)phenyl)ethynyl)phenyl)propyl)pyrimidin-4(3H)-one;

(S)-5-hydroxy-6-(3-hydroxy-2-(4-((4-(piperazin-1-ylmethyl)phenyl)ethynyl)phenyl)propyl)pyrimidin-4(3H)-one;

5-hydroxy-6-(3-hydroxy-2-(4-((4-(((1-imino-1-oxidotetrahydro-1H-1l6-thiophen-3-yl)amino)methyl)phenyl)ethynyl)phenyl)propyl)pyrimidin-4(3H)-one;

5-hydroxy-6-(3-hydroxy-2-(4-((4-(((2-methoxyethyl)amino)methyl)phenyl)ethynyl)phenyl)propyl)pyrimidin-4(3H)-one;

6-(2-(4-((4-(((cyclopropylmethyl)amino)methyl)phenyl)ethynyl)phenyl)-3-hydroxypropyl)-5-hydroxypyrimidin-4(3H)-one;

5-hydroxy-6-(3-hydroxy-2-(4-((4-(4-methylpiperazine-1-carbonyl)phenyl)ethynyl)phenyl)propyl)pyrimidin-4(3H)-one;

5-hydroxy-6-(3-hydroxy-2-(4-((4-(((1-oxidotetrahydrothiophen-3-yl)amino)methyl)phenyl)ethynyl)phenyl)propyl)pyrimidin-4(3H)-one;

5-hydroxy-6-(3-hydroxy-2-(4-((4-((methylamino)methyl)phenyl)ethynyl)phenyl)propyl)pyrimidin-4(3H)-one;

5-hydroxy-6-(3-hydroxy-2-(4-((4-((((R)-pyrrolidin-3-yl)amino)methyl)phenyl)ethynyl)phenyl)propyl)pyrimidin-4(3H)-one;

6-(2-(4-((4-(aminomethyl)phenyl)ethynyl)phenyl)-3-hydroxypropyl)-5-hydroxypyrimidin-4(3H)-one;

6-(2-(4-((4-((4-aminotetrahydro-2H-pyran-4-yl)methyl)phenyl)ethynyl)phenyl)-3-hydroxypropyl)-5-hydroxypyrimidin-4(3H)-one;

6-(2-amino-2-(4-((4-(morpholinomethyl)phenyl)ethynyl)phenyl)ethyl)-5-hydroxypyrimidin-4(3H)-one;

6-(3-(((S)-1-fluoropropan-2-yl)amino)-2-(4-((4-((3-methoxyazetidin-1-yl)methyl)phenyl)ethynyl)phenyl)propyl)-5-hydroxypyrimidin-4(3H)-one;

6-((R)-3-(((S)-1-fluoropropan-2-yl)amino)-2-(4-((4-((3-methoxyazetidin-1-yl)methyl)phenyl)ethynyl)phenyl)propyl)-5-hydroxypyrimidin-4(3H)-one;

6-((S)-3-(((S)-1-fluoropropan-2-yl)amino)-2-(4-((4-((3-methoxyazetidin-1-yl)methyl)phenyl)ethynyl)phenyl)propyl)-5-hydroxypyrimidin-4(3H)-one;

6-(3-(((R)-1-fluoropropan-2-yl)amino)-2-(4-((4-((3-methoxyazetidin-1-yl)methyl)phenyl)ethynyl)phenyl)propyl)-5-hydroxypyrimidin-4(3H)-one;

6-((R)-3-(((R)-1-fluoropropan-2-yl)amino)-2-(4-((4-((3-methoxyazetidin-1-yl)methyl)phenyl)ethynyl)phenyl)propyl)-5-hydroxypyrimidin-4(3H)-one;

6-((S)-3-(((R)-1-fluoropropan-2-yl)amino)-2-(4-((4-((3-methoxyazetidin-1-yl)methyl)phenyl)ethynyl)phenyl)propyl)-5-hydroxypyrimidin-4(3H)-one;

5-hydroxy-6-(3-(3-methoxyazetidin-1-yl)-2-(4-((4-(morpholinomethyl)phenyl)ethynyl)phenyl)propyl)pyrimidin-4(3H)-one;

(R)-5-hydroxy-6-(3-(3-methoxyazetidin-1-yl)-2-(4-((4-(morpholinomethyl)phenyl)ethynyl)phenyl)propyl)pyrimidin-4(3H)-one;

(S)-5-hydroxy-6-(3-(3-methoxyazetidin-1-yl)-2-(4-((4-(morpholinomethyl)phenyl)ethynyl)phenyl)propyl)pyrimidin-4(3H)-one;

6-(3-((2-fluoropropyl)amino)-2-(4-((4-(morpholinomethyl)phenyl)ethynyl)phenyl)propyl)-5-hydroxypyrimidin-4(3H)-one;

6-(3-((cis-3-fluorocyclobutyl)amino)-2-(4-((4-(morpholinomethyl)phenyl)ethynyl)phenyl)propyl)-5-hydroxypyrimidin-4(3H)-one;

6-((R)-3-((cis-3-fluorocyclobutyl)amino)-2-(4-((4-(morpholinomethyl)phenyl)ethynyl)phenyl)propyl)-5-hydroxypyrimidin-4(3H)-one;

6-((S)-3-((cis-3-fluorocyclobutyl)amino)-2-(4-((4-(morpholinomethyl)phenyl)ethynyl)phenyl)propyl)-5-hydroxypyrimidin-4(3H)-one;

6-(3-((trans-3-fluorocyclobutyl)amino)-2-(4-((4-(morpholinomethyl)phenyl)ethynyl)phenyl)propyl)-5-hydroxypyrimidin-4(3H)-one;

6-((R)-3-((trans-3-fluorocyclobutyl)amino)-2-(4-((4-(morpholinomethyl)phenyl)ethynyl)phenyl)propyl)-5-hydroxypyrimidin-4(3H)-one;

6-((S)-3-((trans-3-fluorocyclobutyl)amino)-2-(4-((4-(morpholinomethyl)phenyl)ethynyl)phenyl)propyl)-5-hydroxypyrimidin-4(3H)-one;

1-(4-((4-(1-(((S)-1-fluoropropan-2-yl)amino)-3-(5-hydroxy-6-olio-1,6-dihydropyrimidin-4-yl)propan-2-yl)phenyl)ethynyl)benzyl)azetidine-3-carbonitrile;

1-(4-((4-((R)-1-(((S)-1-fluoropropan-2-yl)amino)-3-(5-hydroxy-6-oxo-1,6-dihydropyrimidin-4-yl)propan-2-yl)phenyl)ethynyl)benzyl)azetidine-3-carbonitrile;

1-(4-((4-((S)-1-(((S)-1-fluoropropan-2-yl)amino)-3-(5-hydroxy-6-oxo-1,6-dihydropyrimidin-4-yl)propan-2-yl)phenyl)ethynyl)benzyl)azetidine-3-carbonitrile;

1-(4-((4-(1-(((R)-1-fluoropropan-2-yl)amino)-3-(5-hydroxy-6-oxo-1,6-dihydropyrimidin-4-yl)propan-2-yl)phenyl)ethynyl)benzyl)azetidine-3-carbonitrile;

1-(4-((4-((R)-1-(((R)-1-fluoropropan-2-yl)amino)-3-(5-hydroxy-6-oxo-1,6-dihydropyrimidin-4-yl)propan-2-yl)phenyl)ethynyl)benzyl)azetidine-3-carbonitrile;

1-(4-((4-((S)-1-(((R)-1-fluoropropan-2-yl)amino)-3-(5-hydroxy-6-oxo-1,6-dihydropyrimidin-4-yl)propan-2-yl)phenyl)ethynyl)benzyl)azetidine-3-carbonitrile;

6-(3-(((S)-1-fluoropropan-2-yl)amino)-2-(4-((4-((tetrahydro-1H-furo[3,4-c]pyrrol-5(3H)-yl)methyl)phenyl)ethynyl)phenyl)propyl)-5-hydroxypyrimidin-4(3H)-one;

6-((2R)-3-(((S)-1-fluoropropan-2-yl)amino)-2-(4-((4-((tetrahydro-1H-furo[3,4-c]pyrrol-5 (3H)-yl)methyl)phenyl)ethynyl)phenyl)propyl)-5-hydroxypyrimidin-4(3H)-one;

6-((2S)-3-(((S)-1-fluoropropan-2-yl)amino)-2-(4-((4-((tetrahydro-1H-furo[3,4-c]pyrrol-5(3H)-yl)methyl)phenyl)ethynyl)phenyl)propyl)-5-hydroxypyrimidin-4(3H)-one;

6-(3-(((S)-1-fluoropropan-2-yl)amino)-2-(4-((4-(((R)-3-methoxypyrrolidin-1-yl)methyl)phenyl)ethynyl)phenyl)propyl)-5-hydroxypyrimidin-4(3H)-one;

6-((R)-3-(((S)-1-fluoropropan-2-yl)amino)-2-(4-((4-(((R)-3-methoxypyrrolidin-1-yl)methyl)phenyl)ethynyl)phenyl)propyl)-5-hydroxypyrimidin-4(3H)-one;

6-((S)-3-(((S)-1-fluoropropan-2-yl)amino)-2-(4-((4-(((R)-3-methoxypyrrolidin-1-yl)methyl)phenyl)ethynyl)phenyl)propyl)-5-hydroxypyrimidin-4(3H)-one;

6-(3-(((S)-1-fluoropropan-2-yl)amino)-2-(4-((4-(((S)-3-methoxypyrrolidin-1-yl)methyl)phenyl)ethynyl)phenyl)propyl)-5-hydroxypyrimidin-4(3H)-one;

6-((R)-3-(((S)-1-fluoropropan-2-yl)amino)-2-(4-((4-(((S)-3-methoxypyrrolidin-1-yl)methyl)phenyl)ethynyl)phenyl)propyl)-5-hydroxypyrimidin-4(3H)-one;

6-((S)-3-(((S)-1-fluoropropan-2-yl)amino)-2-(4-((4-(((S)-3-methoxypyrrolidin-1-yl)methyl)phenyl)ethynyl)phenyl)propyl)-5-hydroxypyrimidin-4(3H)-one;

(3R)-1-(4-((4-(1-(((S)-1-fluoropropan-2-yl)amino)-3-(5-hydroxy-6-oxo-1,6-dihydropyrimidin-4-yl)propan-2-yl)phenyl)ethynyl)benzyl)pyrrolidine-3-carbonitrile;

(3S)-1-(4-((4-(1-(((S)-1-fluoropropan-2-yl)amino)-3-(5-hydroxy-6-oxo-1,6-dihydropyrimidin-4-yl)propan-2-yl)phenyl)ethynyl)benzyl)pyrrolidine-3-carbonitrile;

(S)-1-(4-((4-((R)-1-(((S)-1-fluoropropan-2-yl)amino)-3-(5-hydroxy-6-oxo-1,6-dihydropyrimidin-4-yl)propan-2-yl)phenyl)ethynyl)benzyl)pyrrolidine-3-carbonitrile;

(S)-1-(4-((4-((S)-1-(((S)-1-fluoropropan-2-yl)amino)-3-(5-hydroxy-6-oxo-1,6-dihydropyrimidin-4-yl)propan-2-yl)phenyl)ethynyl)benzyl)pyrrolidine-3-carbonitrile;

6-(3-(((S)-1-fluoropropan-2-yl)amino)-2-(4-((4-((oxetan-3-ylamino)methyl)phenyl)ethynyl)phenyl)propyl)-5-hydroxypyrimidin-4(3H)-one;

2-(1-(4-((4-(1-(((S)-1-fluoropropan-2-yl)amino)-3-(5-hydroxy-6-oxo-1,6-dihydropyrimidin-4-yl)propan-2-yl)phenyl)ethynyl)benzyl)azetidin-3-yl)acetonitrile;

2-(1-(4-((4-((R)-1-(((S)-1-fluoropropan-2-yl)amino)-3-(5-hydroxy-6-oxo-1,6-dihydropyrimidin-4-yl)propan-2-yl)phenyl)ethynyl)benzyl)azetidin-3-yl)acetonitrile;

2-(1-(4-((4-((S)-1-(((S)-1-fluoropropan-2-yl)amino)-3-(5-hydroxy-6-coo-1,6-dihydropyrimidin-4-yl)propan-2-yl)phenyl)ethynyl)benzyl)azetidin-3-yl)acetonitrile;

3-(3-(5-hydroxy-6-oxo-1,6-dihydropyrimidin-4-yl)-2-(4-((4-(morpholinomethyl)phenyl)ethynyl)phenyl)propyl)amino)butanenitrile;

(3S)-3-((3-(5-hydroxy-6-oxo-1,6-dihydropyrimidin-4-yl)-2-(4-((4-(morpholinomethyl)phenyl)ethynyl)phenyl)propyl)amino)butanenitrile;

(S)-3-(((S)-3-(5-hydroxy-6-oxo-1,6-dihydropyrimidin-4-yl)-2-(4-((4-(morpholinomethyl)phenyl)ethynyl)phenyl)propyl)amino)butanenitrile;

(S)-3-(((R)-3-(5-hydroxy-6-oxo-1,6-dihydropyrimidin-4-yl)-2-(4-((4-(morpholinomethyl)pitenyl)ethynyl)phenyl)propyl)amino)butanenitrile;

(3R)-3-((3-(5-hydroxy-6-oxo-1,6-dihydropyrimidin-4-yl)-2-(4-((4-(morpholinomethyl)phenyl)ethynyl)phenyl)propyl)amino)butanentrile;

(R)-3-(((S)-3-(5-hydroxy-6-oxo-1,6-dihydropyrimidin-4-yl)-2-(4-((4-(morpholinomethyl)phenyl)ethynyl)phenyl)propyl)amino)butanenitrile;

(R)-3-(((R)-3-(5-hydroxy-6-oxo-1,6-dihydropyrimidin-4-yl)-2-(4-((4-(morpholinomethyl)phenyl)ethynyl)phenyl)propyl)amino) butanenitrile;

6-(3-((2-fluoropropyl)amino)-2-(4-((4-((3-methoxyazetidin-1-yl)methyl)phenyl)ethynyl)phenyl)propyl)-5-hydroxypyrimidin-4(3H)-one;

1-(3-(5-hydroxy-6-oxo-1,6-dihydropyrimidin-4-yl)-2-(4-((4-(morpholinomethyl)phenyl)ethynyl)phenyl)propyl)azetidine-3-carbonitrile;

(R)-1-(3-(5-hydroxy-6-oxo-1,6-dihydropyrimidin-4-yl)-2-(4-((4-(morpholinomethyl)phenyl)ethynyl)phenyl)propyl)azetidine-3-carbonitrile;

(S)-1-(3-(5-hydroxy-6-oxo-1,6-dihydropyrimidin-4-yl)-2-(4-((4-(morpholinomethyl)phenyl)ethynyl)phenyl)propyl)azetidine-3-carbonitrile;

6-(3-((3-fluoropropyl)amino)-2-(4-((4-(morpholinomethyl)phenyl)ethynyl)phenyl)propyl)-5-hydroxypyrimidin-4(3H)-one;

(R)-6-(3-((3-fluoropropyl)amino)-2-(4-((4-(morpholinomethyl)phenyl)ethynyl)phenyl)propyl)-5-hydroxypyrimidin-4(3H)-one;

(S)-6-(3-((3-fluoropropyl)amino)-2-(4-((4-morpholinomethyl)phenyl)ethynyl)phenyl)propyl)-5-hydroxypyrimidin-4(3H)-one;

6-(3-(((S)-1-fluoropropan-2-yl)amino)-2-(4-((4-(((R)-tetrahydrofuran-3-yl)amino)methyl)phenyl)ethynyl)phenyl)propyl)-5-hydroxypyrimidin-4(3H)-one;

6-((R)-3-(((S)-1-fluoropropan-2-yl)amino)-2-(4-((4-((((R)-tetrahydrofuran-3-yl)amino)methyl)phenyl)ethynyl)phenyl)propyl)-5-hydroxypyrimidin-4(3H)-one;

6-((S)-3-(((S)-1-fluoropropan-2-yl)amino)-2-(4-((4-((((R)-tetrahydrofuran-3-yl)amino)methyl)phenyl)ethynyl)phenyl)propyl)-5-hydroxypyrimidin-4(3H)-one;

6-(3-(((S)-1-fluoropropan-2-yl)amino)-2-(4-((4-((((S)-tetrahydrofuran-3-yl)amino)methyl)phenyl)ethynyl)phenyl)propyl)-5-hydroxypyrimidin-4(3H)-one;

6-((R)-3-(((S)-1-fluoropropan-2-yl)amino)-2-(4-((4-((((S)-tetrahydrofuran-3-yl)amino)methyl)phenyl)ethynyl)phenyl)propyl)-5-hydroxypyrimidin-4(3H)-one;

6-((S)-3-(((S)-1-fluoropropan-2-yl)amino)-2-(4-((4-((((S)-tetrahydrofuran-3-yl)amino)methyl)phenyl)ethynyl)phenyl)propyl)-5-hydroxypyrimidin-4(3H)-one;

6-(3-((3,3-difluorocyclobutyl)amino)-2-(4-((4-(morpholinomethyl)phenyl)ethynyl)phenyl)propyl)-5-hydroxypyrimidin-4(3H)-one;

(R)-6-(3-((3,3-difluorocyclobutyl)amino)-2-(4-((4-(morpholinomethyl)phenyl)ethynyl)phenyl)propyl)-5-hydroxypyrimidin-4(3H)-one;

(S)-6-(3-((3,3-difluorocyclobutyl)amino)-2-(4-((4-(morpholinomethyl)phenyl)ethynyl)phenyl)propyl)-5-hydroxypyrimidin-4(3H)-one;

6-(3-((2,2-difluoroethyl)amino)-2-(4-((4-(morpholinomethyl)phenyl)ethynyl)phenyl)propyl)-5-hydroxypyrimidin-4(3H)-one;

(R)-6-(3-((2,2-difluoroethyl)amino)-2-(4-((4-(morpholinomethyl)phenyl)ethynyl)phenyl)propyl)-5-hydroxypyrimidin-4(3H)-one;

(S)-6-(3-((2,2-difluoroethyl)amino)-2-(4-((4-(morpholinomethyl)phenyl)ethynyl)phenyl)propyl)-5-hydroxypyrimidin-4(3H)-one;

6-(3-(cyclopropylamino)-2-(4-((4-(morpholinomethyl)phenyl)ethynyl)phenyl)propyl)-5-hydroxypyrimidin-4(3H)-one;

(R)-6-(3-(cyclopropylamino)-2-(4-((4-(morpholinomethyl)phenyl)ethynyl)phenyl)propyl)-5-hydroxypyrimidin-4(3H)-one;

(S)-6-(3-(cyclopropylamino)-2-(4-((4-(morpholinomethyl)phenyl)ethynyl)phenyl)propyl)-5-hydroxypyrimidin-4(3H)-one;

(4S)-3-(3-(5-hydroxy-6-oxo-1,6-dihydropyrimidin-4-yl)-2-(4-((4-((3-methoxyazetidin-1-yl)methyl)phenyl)ethynyl)phenyl)propyl)-4-methyloxazolidin-2-one;

(S)-3-((S)-3-(5-hydroxy-6-oxo-1,6-dihydropyrimidin-4-yl)-2-(4-((4-((3-methoxyazetidin-1-yl)methyl)phenyl)ethynyl)phenyl)propyl)-4-methyloxazolidin-2-one;

(S)-3-((R)-3-(5-hydroxy-6-oxo-1,6-dihydropyrimidin-4-yl)-2-(4-((4-((3-methoxyazetidin-1-yl)methyl)phenyl)ethynyl)phenyl)propyl)-4-methyloxazolidin-2-one;

(3S)-1-(4-((4-(1-(2,2-difluoroethyl)amino)-3-(5-hydroxy-6-ono-1,6-dihydropyrimidin-4-yl)propan-2-yl)phenyl)ethynyl)benzyl)pyrrolidine-3-carbonitrile;

6-(2-(4-((4-((2-oxa-6-azaspiro[3.3]heptan-6-yl)methyl)phenyl)ethynyl)phenyl)-3-(((S)-1-fluoropropan-2-yl)amino)propyl)-5-hydroxypyrimidine-4(3H)-one;

6-(3-((2-chloropropyl)amino)-2-(4-((4-(((R)-3-methoxypyrrolidin-1-yl)methyl)phenyl)ethynyl)phenyl)propyl)-5-hydroxypyrimidin-4(3H)-one;

6-(3-(((S)-1-fluoropropan-2-yl)amino)-2-(4-((4-((3-(oxetan-3-yl)azetidin-1-yl)methyl)phenyl)ethynyl)phenyl)propyl)-5-hydroxypyrimidin-4(3H)-one;

6-(2-(4-((4-((6-oxa-2-azaspiro[3.4]octan-2-yl)methyl)phenyl)ethynyl)phenyl)-3-(((S)-1-fluoropropan-2-yl)amino)propyl)-5-hydroxypyrimidin-4(3H)-one;

5-hydroxy-6-(3-((2-(methylsulfonyl)ethyl)amino)-2-(4-((4-(morpholinomethyl)phenyl)ethynyl)phenyl)propyl)pyrimidin-4(3H)-one;

5-hydroxy-6-(3-((2-hydroxyethyl)amino)-2-(4-((4-(morpholinomethyl)phenyl)ethynyl)phenyl)propyl)pyrimidin-4(3H)-one;

3-((3-(5-hydroxy-6-oxo-1,6-dihydropyrimidin-4-yl)-2-(4-((4-(morpholinomethyl)phenyl)ethynyl)phenyl)propyl)amino)propanenitrile;

6-(3-((2,2-difluoroethyl)amino)-2-(4-((4-(morpholinomethyl)phenyl)ethynyl)phenyl)butyl)-5-hydroxypyrimidin-4(3H)-one;

6-(2-(4-((4-((1-oxa-6-azaspiro[3.3]heptan-6-yl)methyl)phenyl)ethynyl)phenyl)-3-(((S)-1-fluoropropan-2-yl)amino)propyl)-5-hydroxypyrimidin-4(3H)-one;

6-((R)-2-(4-((4-((1-oxa-6-azaspiro[3.3]heptan-6-yl)methyl)phenyl)ethynyl)phenyl)-3-(((S)-1-fluoropropan-2-yl)amino)propyl)-5-hydroxypyrimidin-4(3H)-one;

6-((S)-2-(4-((4-((1-oxo-6-azaspiro[3.3]heptan-6-yl)methyl)phenyl)ethynyl)phenyl)-3-(((S)-1-fluoropropan-2-yl)amino)propyl)-5-hydroxypyrimidin-4(3H)-one;

3-((2-(4-((4-((3-(cyanomethyl)azetidin-1-yl)ethyl)phenyl)ethynyl)phenyl)-3-(5-hydroxy-6-oxo-1,6-dihydropyrimidin-4-yl)propyl)amino)propanenitrile;

6-(3-((2-fluoropropyl)amino)-2-(4-((4-(((R)-3-methoxypyrrolidin-1-yl)methyl)phenyl)ethynyl)phenyl)propyl)-5-hydroxypyrimidin-4(3H)-one;

6-((2R)-3-((2-fluoropropyl)amino)-2-(4-((4-(((R)-3-methoxypyrrolidin-1-yl)methyl)phenyl)ethynyl)phenyl)propyl)-5-hydroxypyrimidin-4(3H)-one;

6-((2S)-3-((2-fluoropropyl)amino)-2-(4-((4-(((R)-3-methoxypyrrolidin-1-yl)methyl)phenyl)ethynyl)phenyl)propyl)-5-hydroxypyrimidin-4(3H)-one;

6-(3-((2-fluoropropyl)amino)-2-(4-((4-(2-morpholinoethyl)phenyl)ethynyl)phenyl)propyl)-5-hydroxypyrimidin-4(3H)-one;

6-(2-((3-fluoropropyl)amino-2-(4-((4-(morpholinomethyl)phenyl ethynyl)phenyl)ethyl)-5-hydroxypyrimidin-4(3H)-one;

(R)-6-(2-((3-fluoropropyl)amino)-2-(4-((4-(morpholinomethyl)phenyl)ethynyl)phenyl)ethyl)-5-hydroxypyrimidin-4(3H)-one;

(S)-6-(2-((3-fluoropropyl)amino)-2-(4-((4-(morpholinomethyl)phenyl)ethynyl)phenyl)ethyl)-5-hydroxypyrimidin-4(3H)-one;

6-(2-(((1-fluoropropan-2-yl)amino)-2-(4-((4-(morpholinomethyl)phenyl)ethynyl)phenyl)ethyl)-5-hydroxypyrimidin-4(3H)-one;

6-((2R)-2-((1-fluoropropan-2-yl)amino)-2-(4-((4-(morpholinomethyl)phenyl)ethynyl)phenyl)ethyl)-5-hydroxypyrimidin-4(3H)-one;

6-((2S)-2-((1-fluoropropan-2-yl)amino)-2-(4-((4-(morpholinomethyl)phenyl)ethynyl)phenyl)ethyl)-5-hydroxypyrimidin-4(3H)-one;

6-(3-(((S)-1-fluoropropan-2-yl)amino)-2-(4-((4-((3-methoxyazetidin-1-yl)methyl)phenyl)ethynyl)phenyl)-2-methyl propyl)-5-hydroxypyrimidin-4(3H)-one;

5-hydroxy-6-(3-(((S)-1-hydroxypropan-2-yl)amino)-2-(4-((4-((((S)-tetrahydrofuran-3-yl)amino)methyl)phenyl)ethynyl)phenyl)propyl)pyrimidin-4(3H)-one;

6-(2-(4-((4-(((S)-2-(aminomethyl)pyrrolidin-1-yl)methyl)phenyl)ethynyl)phenyl)-3-hydroxypropyl)-5-hydroxypyrimidin-4(3H)-one;

6-((R)-2-(4-((4-(((S)-2-(aminomethyl)pyrrolidin-1-yl)methyl)phenyl)ethynyl)phenyl)-3-hydroxypropyl)-5-hydroxypyrimidin-4(3H)-one;

6-((S)-2-(4-((4-(((S)-2-(aminomethyl)pyrrolidin-1-yl)methyl)phenyl)ethynyl)phenyl)-3-hydroxypropyl-5-hydroxypyrimidin-4(3H)-one;

6-(2-(4-((4-(((R)-2-(aminomethyl)pyrrolidin-1-yl)methyl)phenyl)ethynyl)phenyl)-3-hydroxypropyl)-5-hydroxypyrimidin-4(3H)-one;

5-hydroxy-6-(3-hydroxy-2-(4-((4-(((1-imino-1-oxidohexahydro-1l6-thiopyran-4-yl)amino)methyl)phenyl)ethynyl)phenyl)propyl)pyrimidin-4(3H)-one;

5-hydroxy-6-(3-hydroxy-2-(4-((4-((((1S,3R)-1-imino-1-oxidotetrahydro-1H-1l6-thiophen-3-yl)amino)methyl)phenyl)ethynyl)phenyl)propyl)pyrimidin-4(3H)-one;

5-hydroxy-6-(3-hydroxy-2-(4-((4-((((1R,3S)-1-imino-1-oxidotetrahydro-1H-1l6-thiophen-3-yl)amino)methyl)phenyl)ethynyl)phenyl)propyl)pyrimidin-4(3H)-one;

5-hydroxy-6-(3-hydroxy-2-(4-((4-((4(2-hydroxyacetyl)piperazin-1-yl)methyl)phenyl) ethynyl)phenyl)propyl)pyrimidin-4(3H)-one;

6-(2-(4-((4-((((R)-1-(cyclopropanecarbonyl)pyridimin-3-yl)amino)methyl)phenyl)ethynyl)phenyl)-3-hydroxypropyl)-5-hydroxypyrimidin-4(3H)-one;

2-hydroxy-N-(4-((4-(1-hydroxy-3-(5-hydroxy-6-oxo-1,6-dihydropyrimidin-4-yl)propan-2-yl)phenyl)ethynyl)benzyl)-N—((R)-pyrrolidin-3-yl)acetamide;

5-hydroxy-6-(3-hydroxy-2-(4-((4-(((((R)-1-(2-hydroxyethyl)pyrrolidin-3-yl)amino)methyl)phenyl)ethynyl)phenyl)propyl)pyrimidin-4(3H)-one;

2-((3R)-3-((4-((4-(1-hydroxy-3-(5-hydroxy-6-oxo-1,6-dihydropyrimidin-4-yl)propan-2-yl)phenyl)ethynyl)benzyl)amino)pyrrolidin-1-yl)acetic acid;

5-hydroxy-6-(3-hydroxy-2-(4-((4-(((1-(2-hydroxyacetyl)piperidin-4-yl)amino)methyl)phenyl)ethynyl)phenyl)propyl)pyrimidin-4(3H)-one;

(R)-5-hydroxy-6-(3-hydroxy-2-(4-((4-(((1-(2-hydroxyacetyl)piperidin-4-yl)amino)methyl)phenyl)ethynyl)phenyl)propyl)pyrimidin-4(3H)-one;

(S)-5-hydroxy-6-(3-hydroxy-2-(4-((4-(((1-(2-hydroxyacetyl)piperidin-4-yl)amino)methyl)phenyl)ethynyl)phenyl)propyl)pyrimidine-4(3H)-one;

2-hydroxy-N-(((2S)-1-(4-((4-(1-hydroxy-3-(5-hydroxy-6-oxo-1,6-dihydropyrimidin-4-yl)propan-2-yl)phenyl)ethynyl)benzyl)pyrrolidin-2 yl)methyl)acetamide;

6-(3-(3-fluoroazetidin-1-yl)-2-(4-((4-((3-methoxyazetidin-1-yl)methyl)phenyl)ethynyl)phenyl)propyl)-5-hydroxypyrimidin-4(3H)-one;

(R)-6-(3-(3-fluoroazetidin-1-yl)-2-(4-((4-((3-methoxyazetidin-1-yl)methyl)phenyl)ethynyl)phenyl)propyl)-5-hydroxypyrimidin-4(3H)-one;

(S)-6-(3-(3-fluoroazetidin-1-yl)-2-(4-((4-((3-methoxyazetidin-1-yl)methyl)phenyl)ethynyl)phenyl)propyl)-5-hydroxypyrimidin-4(3H)-one;

5-hydroxy-6-(2-(4-((4-(morpholinomethyl)phenyl)ethynyl)phenyl)-3-(((R)-tetrahydrofuran-3-yl)amino)propyl)pyrimidin-4(3H)-one;

5-hydroxy-6-((R)-2-(4-((4-(morpholinomethyl)phenyl)ethynyl)phenyl)-3-(((R)-tetrahydrofuran-3-yl)amino)propyl)pyrimidin-4(3H)-one;

5-hydroxy-6-((S)-2-(4-((4-(morpholinomethyl)phenyl)ethynyl)phenyl)-3-(((R)-tetrahydrofuran-3-yl)amino)propyl)pyrimidin-4(3H)-one;

5-hydroxy-6-(3-((2-methoxyethyl)amino)-2-(4-((4-(morpholinomethyl)phenyl)ethynyl)phenyl)propyl)pyrimidin-4(3H)-one;

(R)-5-hydroxy-6-(3-((2-methoxyethyl)amino)-2-(4-((4-(morpholinomethyl)phenyl)ethynyl)phenyl)propyl)pyrimidin-4(3H)-one;

(S)-5-hydroxy-6-(3-((2-methoxyethyl)amino)-2-(4-((4-(morpholinomethyl)phenyl)ethynyl)phenyl)propyl)pyrimidin-4(3H)-one;

5-hydroxy-6-(2-(4-((4-(morpholinomethyl)phenyl)ethynyl)phenyl)-3-(((S)-tetrahydrofuran-3-yl)amino)propyl)pyrimidin-4(3H)-one;

5-hydroxy-6-(3-(((S)-1-hydroxypropan-2-yl)amino)-2-(4-((4-(morpholinomethyl)phenyl)ethynyl)phenyl)propyl)pyrimidin-4(3H)-one;

5-hydroxy-6-((R)-3-(((S)-1-hydroxypropan-2-yl)amino)-2-(4-((4-(morpholinomethyl)phenyl)ethynyl)phenyl)propyl)pyrimidin-4(3H)-one;

5-hydroxy-6-((S)-3-(((S)-1-hydroxypropan-2-yl)amino)-2-(4-((4-(morpholinomethyl)phenyl)ethynyl)phenyl)propyl)pyrimidin-4(3H)-one;

5-hydroxy-6-(3-(((R)-1-hydroxypropan-2-yl)amino)-2-(4-((4-(morpholinomethyl)phenyl)ethynyl)phenyl)propyl)pyrimidin-4(3H)-one;

5-hydroxy-6-((R)-3-(((R)-1-hydroxypropan-2-yl)amino)-2-(4-((4-(morpholinomethyl)phenyl)ethynyl)phenyl)propyl)pyrimidin-4(3H)-one;

5-hydroxy-6-((S)-3-(((R)-1-hydroxypropan-2-yl)amino)-2-(4-((4-(morpholinomethyl)phenyl)ethynyl)phenyl)propyl)pyrimidin-4(3H)-one;

6-(2-((3-chloropropyl)amino)-2-(4-((4-(morpholinomethyl)phenyl)ethynyl)phenyl)ethyl)-5-hydroxypyrimidin-4(3H)-one;

6-(2-amino-2-(4-((4-((((R)-tetrahydrofuran-3-yl)amino)methyl)phenyl)ethynyl)phenyl)ethyl)-5-hydroxypyrimidin-4(3H)-one;

6-(2-amino-2-(4-((4-((4-methoxypiperidin-1-yl)methyl)phenyl)ethynyl)phenyl)ethyl)-5-hydroxypyrimidin-4(3H)-one;

(R)-5-hydroxy-6-(3-(3-methoxyazetidin-1-yl)-2-(4-((4-((3-methoxyazetidin-1-yl)methyl)phenyl)ethynyl)phenyl)propyl)pyrimidin-4(3H)-one;

(S)-5-hydroxy-6-(3-(3-methoxyazetidin-1-yl)-2-(4-((4-((3-methoxyazetidin-1-yl)methyl)phenyl)ethynyl)phenyl)propyl)pyrimidin-4(3H)-one;

6-(3-(azetidin-1-yl)-2-(4-((4-(morpholinomethyl)phenyl)ethynyl)phenyl)propyl)-5-hydroxypyrimidin-4(3H)-one;

6-(2-(4-((4-(((1,1-dioxidotetrahydrothiophen-3-yl)amino)methyl)phenyl)ethynyl)phenyl)-3-(((S)-1-fluoropropan-2-yl)amino)propyl)-5-hydroxypyrimidin-4(3H)-one;

6-((2R)-2-(4-((4-(((1,1-dioxidotetrahydrothiophen-3-yl)amino)methyl)phenyl)ethynyl)phenyl)-3-(((S)-1-fluoropropan-2-yl)amino)propyl)-5-hydroxypyrimidin-4(3H)-one;

6-((2S)-2-(4-((4-(((1,1-dioxidotetrahydrothiophen-3-yl)amino)methyl)phenyl)ethynyl)phenyl)-3-(((S)-1-fluoropropan-2-yl)amino)propyl)-5-hydroxypyrimidin-4(3H)-one;

6-(3-(((S)-1-acetylpyrrolidin-3-yl)amino)-2-(4-((4-(morpholinomethyl)phenyl)ethynyl)phenyl)propyl)-5-hydroxypyrimidin-4(3H)-one;

6-((R)-3-(((S)-1-acetylpyrrolidin-3-yl)amino)-2-(4-((4-(morpholinomethyl)phenyl)ethynyl)phenyl)propyl)-5-hydroxypyrimidin-4(3H)-one;

6-(S)-3-(((S)-1-acetylpyrrolidin-3-yl)amino)-2-(4-((4-(morpholinomethyl)phenyl)ethynyl)phenyl)propyl)-5-hydroxypyrimidin-4(3H)-one;

6-(3-(((1H-pyrazol-5-yl)methyl)amino)-2-(4-((4-(morpholinomethyl)phenyl)ethynyl)phenyl)propyl)-5-hydroxypyrimidin-4(3H)-one;

6-((R)-3-(((1H-pyrazol-5-yl)methyl)amino)-2-(4-((4-(morpholinomethyl)phenyl)ethynyl)phenyl)propyl)-5-hydroxypyrimidin-4(3H)-one;

6-((S)-3-(((1H-pyrazol-5-yl)methyl)amino)-2-(4-((4-(morpholinomethyl)phenyl)ethynyl)phenyl)propyl)-5-hydroxypyrimidin-4(3H)-one;

6-(3-(((R)-1,1-dioxidotetrahyrothiophen-3-yl)amino)-2-(4-((4-(morpholinomethyl)phenyl)ethynyl)phenyl)propyl)-5-hydroxypyrimidin-4(3H)-one;

6-((R)-3-(((R)-1,1-dioxidotetrahydrothiophen-3-yl)amino)-2-(4-((4-(morpholinomethyl)phenyl)ethynyl)phenyl)propyl)-5-hydroxypyrimidin-4(3H)-one;

6-((S)-3-(((R)-1,1-dioxidotetrahydrothiophen-3-yl)amino)-2-(4-((4-(morpholinomethyl)phenyl)ethynyl)phenyl)propyl)-5-hydroxypyrimidin-4(3H)-one;

6-(3-(((S)-1,1-dioxidotetrahydrothiophen-3-yl)amino)-2-(4-((4-(morpholinomethyl)phenyl)ethynyl)phenyl)propyl)-5-hydroxypyrimidin-4(3H)-one;

6-((R)-3-(((S)-1,1-dioxidotetrahydrothiophen-3-yl)amino)-2-(4-((4-(morpholinomethyl)phenyl)ethynyl)phenyl)propyl)-5-hydroxypyrimidin-4(3H)-one;

6-((S)-3-(((S)-1,1-dioxidotetrahydrothiophen-3-yl)amino)-2-(4-(4-(morpholinomethyl)phenyl)ethynyl)phenyl)propyl)-5-hydroxypyrimidin-4(3H)-one;

5-hydroxy-6-(3-methoxy-2-(4-((4-(morpholinomethyl)phenyl)ethynyl)phenyl)propyl)pyrimidin-4(3H)-one;

N-(2,2-difluoroethyl)-3-(5-hydroxy-6-oxo-1,6-dihydropyrimidin-4-yl)-2-(6-((4-(morpholinomethyl)phenyl)ethynyl)-3-oxo-1H-pyrrolo[1,2-c]imidazol-2(3H)-yl)propanamide;

methyl 3-(5-hydroxy-6-oxo-1,6-dihydropyrimidin-4-yl)-2-(6-((4-(morpholinomethyl)phenyl)ethynyl)-3-oxo-1H-pyrrolo[1,2-c]imidazol-2(3H)-yl)propanoate;

2-(1-hydroxy-3-(5-hydroxy-6-oxo-1,6-dihydropyrimidin-4-yl)propan-2-yl)-6-((4-(morpholinomethyl)phenyl)ethynyl)-1,2-dihydro-3H-pyrrolo[1,2-c]imidazol-3-one;

5-hydroxy-6-(3-hydroxy-2-(4-((1-((tetrahydro-2H-pyran-4-yl methyl)-1H-pyrazol-4-yl)ethynyl)phenyl)propyl)pyrimidin-4(3H)-one;

5-hydroxy-6-(3-hydroxy-2-(4-((6-(morpholinomethyl)pyridin-3-yl)ethynyl)phenyl)propyl)pyrimidin-4(3H)-one;

5-hydroxy-6-(3-hydroxy-2-(5-((4-(morpholinomethyl)phenyl)ethynyl)pyridin-2-yl)propyl)pyrimidin-4(3H)-one;

5-hydroxy-6-(3-hydroxy-2-(4-((1-methyl-1H-pyrazol-4-yl)ethynyl)phenyl)propyl)pyrimidin-4(3H)-one;

5-hydroxy-6-(3-hydroxy-2-(4-((E)-4-(((((S)-tetrahydrofuran-3-yl)amino)methyl)styryl)phenyl)propyl)pyrimidin-4(3H)-one;

6-(3-((2-fluoroethyl)amino)-2-(4-((1-methyl-1H-pyrazol-4-yl)ethynyl)phenyl)propyl)-5-hydroxypyrimidin-4(3H)-one;

6-(2-amino-2-(4-((1-methyl-1H-pyrazol-4-yl)ethynyl)phenyl)ethyl)-5-hydroxypyrimidin-4(3H)-one;

5-hydroxy-6-(3-hydroxy-2-(4-((1-(oxetan-3 yl)-1H-pyrazol 4-yl)ethynyl)phenyl)propyl)pyrimidin-4(3H)-one;

5-hydroxy-6-(3-hydroxy-2-(4-((1-(tetrahydro-2H-pyran-4-yl)-1H-pyrazol-4-yl)ethynyl)phenyl)propyl)pyrimidin-4(3H)-one;

2-(1-hydroxy-3-(5-hydroxy-6-oxo-1,6-dihydropyrimidin-4-yl)propan-2-yl)-6-(4-(2-morpholinoethyl)phenyl)-1,2-dihydro-3H-pyrrolo[1,2-c]imidazol-3-one;

5-hydroxy-6-((S)-3-hydroxy-2-(4-((trans-4-(morpholinomethyl)cyclohexyl)ethynyl)phenyl)propyl)pyrimidin-4(3H)-one;

5-hydroxy-6-((R)-3-hydroxy-2-(4-((trans-4-(morpholinomethyl)cyclohexyl)ethynyl)phenyl)propyl)pyrimidin-4(3H)-one;

6-(3-((2-fluoroethyl)amino)-2-(4-((1-tetrahydro-2H-pyran-4-yl)-1H-pyrazol-4-yl)ethynyl)phenyl)propyl)-5-hydroxypyrimidin-4(3H)-one;

6-(3-((2-fluoroethyl)amino)-2-(4-((1-(tetrahydro-2H-pyran-4-yl)methyl)-1H-pyrazol-4-yl)ethynyl)phenyl)propyl)-5-hydroxypyrimidin-4(3H)-one;

6-(3-((2-fluoroethyl)amino)-2-(4-(imidazo[1,5-a]pyridin-7-ylethynyl)phenyl)propyl)-5-hydroxypyrimidin-4(3H)-one;

6-(3-((2-fluoroethyl)amino)-2-(4-((1-(oxetan-3-yl)-1H-pyrazol-4-yl)ethynyl)phenyl)propyl)-5-hydroxypyrimidin-4(3H)-one;

5-hydroxy-6-((5-((4-(morpholinomethyl)phenyl)ethynyl)-2,3-dihydro-1H-inden-1-yl)methyl)pyrimidin-4(3H)-one;

3-((5-hydroxy-6-oxo-1,6-dihydropyrimidin-4-yl)methyl)-6-((4-(morpholinomethyl)phenyl)ethynyl)isoindolin-1-one;

5-hydroxy-6-(3-hydroxy-2-(4-((4-(morpholinomethyl)phenyl)ethynyl)-2-oxopyridin-1(2H)-yl)propyl)pyrimidin-4(3H)-one;

3-(5-hydroxy-6-oxo-1,6-dihydropyrimidin-4-yl)-2-(6-(4-(2-morpholinoethyl)phenyl)-3-oxo-1H-pyrrolo[1,2-c]imidazol-2(3H)-yl)propanoic acid;

6-(2-([1,1'-biphenyl]-4-yl)-3-hydroxypropyl-5-hydroxypyrimidin-4(3H)-one;

6-(2-amino-2-(4'-(2-morpholinoethyl)-[1,1-biphenyl]-4-yl)ethyl)-5-hydroxypyrimidin-4(3H)-one;

6-(3-(3-fluoroazetidin-1-yl)-2-(4-((4-(morpholinomethyl)phenyl)ethynyl)phenyl)propyl)-5-hydroxypyrimidin-4(3H)-one;

(R)-6-(3-(3-fluoroazetidin-1-yl)-2-(4-((4-(morpholinomethyl)phenyl)ethynyl)phenyl)propyl)-5-hydroxypyrimidin-4(3H)-one;

(S)-6-(3-(3-fluoroazetidin-1-yl)-2-(4-((4-(morpholinomethyl)phenyl)ethynyl)phenyl)propyl)-5-hydroxypyrimidin-4(3H)-one;

5-hydroxy-6-(3-hydroxy-2-(4-((4-((3-methoxyazetidin-1-yl)methyl)phenyl)ethynyl)phenyl)propyl)pyrimidin-4(3H)-one;

(S)-5-hydroxy-6-(3-hydroxy-2-(4-((4-(3-methoxyazetidin-1-yl)methyl)phenyl)ethynyl)phenyl)propyl)pyrimidin-4(3H)-one;

(R)-5-hydroxy-6-(3-hydroxy-2-(4-((4-((3-methoxyazetidin-1-yl)methyl)phenyl)ethynyl)phenyl)propyl)pyrimidin-4(3H)-one;

(S)-1-(3-(5-hydroxy-6-oxo-1,6-dihydropyrimidin-4-yl)-2-(4-((4-((3-methoxyazetidin-1-yl)methyl)phenyl)ethynyl)phenyl)propyl)azetidine-3-carbonitrile;

(R)-1-(3-(5-hydroxy-6-oxo-1,6-dihydropyrimidin-4-yl)-2-(4-((3-methoxyazetidin-1-yl)methyl)phenyl)ethynyl)phenyl)propyl)azetidine-3-carbonitrile;

6-(3-(cyclopropyl(methyl)amino)-2-(4-((4-((3-methoxyazetidin-1-yl)methyl)phenyl)ethynyl)phenyl)propyl)-5-hydroxypyrimidin-4(3H)-one;

(R)-6-(3-(cyclopropyl(methyl)amino)-2-(4-((4-((3-methoxy azetidin-1-yl)methyl)phenyl)ethynyl)phenyl)propyl)-5-hydroxypyrimidin-4(3H)-one;

(S)-6-(3-(cyclopropyl(methyl)amino)-2-(4-((4-((3-methoxyazetidin-1-yl)methyl)phenyl)ethynyl)phenyl)propyl)-5-hydroxypyrimidin-4(3H)-one;

6-(3-((1-fluoro-2-methylpropan-2-yl)amino)-2-(4-((4-((3-methoxyazetidin-1-yl)methyl)phenyl)ethynyl)phenyl)propyl)-5-hydroxypyrimidin-4(3H)-one;

(R)-6-(3-((1-fluoro-2-methylpropan-2-yl)amino)-2-(4-((4-((3-methoxyazetidin-1-yl)methyl)phenyl)ethynyl)phenyl)propyl)-5-hydroxypyrimidin-4(3H)-one;

(S)-6-(3-((1-fluoro-2-methylpropan-2-yl)amino)-2-(4-((4-((3-methoxyazetidin-1-yl)methyl)phenyl)ethynyl)phenyl)propyl)-5-hydroxypyrimidin-4(3H)-one;

6-(3-(cyclopropylamino)-2-(4-((4-((3-methoxyazetidin-1-yl)methyl)phenyl)ethynyl)phenyl)propyl)-5-hydroxypyrimidin-4(3H)-one;

(R)-6-(3-(cyclopropylamino)-2-(4-((4-((3-methoxyazetidin-1-yl)methyl)phenyl)ethynyl)phenyl)propyl)-5-hydroxypyrimidin-4(3H)-one;

(S)-6-(3-(cyclopropylamino)-2-(4-((4-((3-methoxyazetidin-1-yl)methyl)phenyl)ethynyl)phenyl)propyl)-5-hydroxypyrimidin-4(3H)-one;

6-(3-(cyclopropylamino)-2-(2-fluoro-4-((4-((3-methoxyazetidin-1-yl)methyl)phenyl)ethynyl)phenyl)propyl)-5-hydroxypyrimidin-4(3H)-one;

(R)-6-(3-(cyclopropylamino)-2-(2-fluoro-4-((4-((3-methoxyazetidin-1-yl)methyl)phenyl)ethynyl)phenyl)propyl)-5-hydroxypyrimidin-4(3H)-one;

(S)-6-(3-(cyclopropylamino)-2-(2-fluoro-4-((4-((3-methoxyazetidin-1-yl)methyl)phenyl)ethynyl)phenyl)propyl)-5-hydroxypyrimidin-4(3H)-one;

6-(3-(cyclopropylamino)-2-(4-((4-((3-methoxyazetidin-1-yl)methyl)phenyl)ethynyl)phenyl)-2-methylpropyl)-5-hydroxypyrimidin-4(3H)-one;

(R)-6-(3-(cyclopropylamino)-2-(4-((4-((3-methoxyazetidin-1-yl)methyl)phenyl)ethynyl)phenyl)-2-methylpropyl)-5-hydroxypyrimidin-4(3H)-one;

(S)-6-(3-(cyclopropylamino)-2-(4-((4-((3-methoxyazetidin-1-yl)methyl)phenyl)ethynyl)phenyl)-2-methylpropyl)-5-hydroxypyrimidin-4(3H)-one;

5-hydroxy-6-(3(3-hydroxyazetidin-1-yl)-2-(4-((4-(morpholinomethyl)phenyl)ethynyl)phenyl)propyl)pyrimidin-4(3H)-one;

(R)-5-hydroxy-6-(3-(3-hydroxyazetidin-1-yl)-2-(4-((4-(morpholinomethyl)phenyl)ethynyl)phenyl)propyl)pyrimidin-4(3H)-one;

(S)-5-hydroxy-6-(3-(3-hydroxyazetidin-1-yl)-2-(4-((4-(morpholinomethyl)phenyl)ethynyl)phenyl)propyl)pyrimidin-4(3H)-one;

6-(2-(2-fluoro-4-(4-(morpholinomethyl)phenyl)ethynyl)phenyl)-3-(3-hydroxyazetidin-1-yl)propyl)-5-hydroxypyrimidin-4(3H)-one;

(R)-6-(2-(2-fluoro-4-((4-(morpholinomethyl)phenyl)ethynyl)phenyl)-3-(3-hydroxyazetidin-1-yl)propyl)-5-hydroxypyrimidin-4(3H)-one;

(S)-6-(2-(2-fluoro-4-((4-(morpholinomethyl)phenyl)ethynyl)phenyl)-3-(3-hydroxyazetidin-1-yl)propyl)-5-hydroxypyrimidin-4(3H)-one;

6-(2-(4-((4-((((R)-1-acetylpyrrolidin-3-yl)amino)methyl)phenyl)ethynyl)phenyl)-3-hydroxypropyl)-5-hydroxypyrimidin-4(3H)-one;

6-((R)-2-(4-((4-((((R)-1-acetylpyrrolidin-3-yl)amino) methyl)phenyl)ethynyl)phenyl)-3-hydroxypropyl)-5-hydroxypyrimidin-4(3H)-one;

6-((S)-2-(4-((4-((((R)-1-acetylpyrrolidin-3-yl)amino) methyl)phenyl)ethynyl)phenyl)-3-hydroxypropyl)-5-hydroxypyrimidin-4(3H)-one;

(S)-1-(4-((4-((R)-1-(3-cyanoazetidin-1-yl)-3-(5-hydroxy-6-oxo-1,6-dihydropyrimidin-4-yl)propan-2-yl)phenyl)ethynyl)benzyl)pyrrolidine-3-carbonitrile;

(S)-1-(4-((4-(S)-1-(3-cyanoazetidin-1-yl)-3-(5-hydroxy-6-oxo-1,6-dihydropyrimidin-4-yl)propan-2-yl)phenyl)ethynyl)benzyl)pyrrolidine-3-carbonitrile;

6-(2-(2-fluoro-4-((4-(morpholinomethyl)phenyl)ethynyl) phenyl)-3-((3-fluoropropyl)amino)propyl)-5-hydroxypyrimidin-4(3H)-one;

(S)-6-(2-(2-fluoro-4-((4-(morpholinomethyl)phenyl)ethynyl)phenyl)-3-((3-fluoropropyl)amino)propyl)-5-hydroxypyrimidin-4(3H)-one;

(R)-6-(2-(2-fluoro-4-((4-(morpholinomethyl)phenyl)ethynyl)phenyl)-3-((3-fluoropropyl)amino)propyl)-5-hydroxypyrimidin-4(3H)-one;

6-(2-(2-fluoro-4-((4-((3-methoxyazetidin-1-yl)methyl)phenyl)ethynyl)phenyl)-3-(((S)-1-fluoropropan-2-yl)amino) propyl)-5-hydroxypyrimidin-4(3H)-one;

6-((R)-2-(2-fluoro-4-((4-((3-methoxyazetidin-1-yl methyl) phenyl)ethynyl)phenyl)-3-(((S)-1-fluoropropan-2-yl) amino)propyl)-5-hydroxypyrimidin-4(3H)-one;

6-((S)-2-(2-fluoro-4-((4-((3-methoxyazetidin-1-yl)methyl) phenyl)ethynyl)phenyl)-3-(((S)-1-fluoropropan-2-yl) amino)propyl)-5-hydroxypyrimidin-4(3H)-one;

6-(2-(2-fluoro-4-((4-((tetrahydro-1H-furo[3,4-c]pyrrol-5 (3H)-yl)methyl)phenyl)ethynyl)phenyl)-3-(((S)-1-fluoropropan-2-yl)amino)propyl)-5-hydroxypyrimidin-4(3H)-one;

6-((2R)-2-(2-fluoro-4-((4-((tetrahydro-1H-faro[3,4-c]pyrrol-5(3H)-yl)methyl)phenyl)ethynyl)phenyl)-3-(((S)-1-fluoropropan-2-yl)amino)propyl)-5-hydroxypyrimidin-4 (3H)-one;

6-((2S)-2-(2-fluoro-4-((4-((tetrahydro-1H-furo[3,4-c]pyrrol-5(3H)-yl)methyl)phenyl)ethynyl)phenyl)-3-(((S)-1-fluoropropan-2-yl)amino)propyl)-5-hydroxypyrimidin-4 (3H)-one;

2-hydroxy-N-(1-(4-((4-(1-hydroxy-3-(5-hydroxy-6-oxo-1, 6-dihydropyrimidin-4-yl)propan-2-yl)phenyl)ethynyl) benzyl)piperidin-4-yl)acetamide;

(R)-2-hydroxy-N-(1-(4-((4-(1-hydroxy-3-(5-hydroxy-6-oxo-1,6-dihydropyrimidin-4-yl)propan-2-yl)phenyl)ethynyl)benzyl)piperidin-4-yl)acetamide;

(S)-2-hydroxy-N-(1-(4-((4-(1-hydroxy-3-(5-hydroxy-6-oxo-1,6-dihydropyrimidin-4-yl)propan-2-yl)phenyl)ethynyl)benzyl)piperidin-4-yl)acetamide;

5-hydroxy-6-((S)-3-hydroxy-2-(4-((4-((2-hydroxyethyl) ((S)-tetrahydrofuran-3-yl)amino)methyl)phenyl)ethynyl) phenyl)propyl)pyrimidin-4(3H)-one;

5-hydroxy-6-((S)-3-hydroxy-2-(4-((4-(2-hydroxyethyl)(S)-tetrahydrofuran-3-yl)amino)methyl)phenyl)ethynyl)phenyl)propyl)pyrimidin-4(3H)-one;

6-(3-((1-fluoro-3-hydroxypropan-2-yl)amino)-2-(4-((4-((3-methoxyazetidin-1-yl)methyl)phenyl)ethynyl)phenyl) propyl)-5-hydroxypyrimidin-4(3H)-one;

5-hydroxy-6-((S)-3-(((S)-2-hydroxypropyl)amino)-2-(4-((4-(morpholinomethyl)phenyl)ethynyl)phenyl)propyl) pyrimidin-4(3H)-one;

5-hydroxy-6-((R)-3-(((S)-2-hydroxypropyl)amino)-2-(4-((4-(morpholinomethyl)phenyl)ethynyl)phenyl)propyl) pyrimidin-4(3H)-one;

5-hydroxy-6-((R)-3-(((R)-2-hydroxypropyl)amino)-2-(4-((4-(morpholinomethyl)phenyl)ethynyl)phenyl)propyl) pyrimidin-4(3H)-one;

5-hydroxy-6-((S)-3-(((R)-2-hydroxypropyl)amino)-2-(4-((4-(morpholinomethyl)phenyl)ethynyl)phenyl)propyl) pyrimidin-4(3H)-one;

6-(3-((2-fluoro-3-hydroxypropyl)amino)-2-(4-((4-((3-methoxyazetidin-1-yl)methyl)phenyl)ethynyl)phenyl) propyl)-5-hydroxypyrimidin-4(3H)-one;

(R)-5-hydroxy-6-(2-(4-((4-((3-methoxyazetidin-1-yl) methyl)phenyl)ethynyl)phenyl)-3-((1-methylcyclopropyl)amino)propyl)pyrimidin-4(3H)-one;

(S)-5-hydroxy-6-(2-(4-((4-((3-methoxyazetidin-1-yl) methyl)phenyl)ethynyl)phenyl)-3-((1-methylcyclopropyl)amino)propyl)pyrimidin-4(3H)-one;

6-(2-(4-((4-(1,2-dihydroxyethyl)phenyl)ethynyl)phenyl)-3-(((S)-1-fluoropropan-2-yl)amino)propyl)-5-hydroxypyrimidin-4(3H)-one;

6-((2R)-2-(4-((4-(1,2-dihydroxyethyl)phenyl)ethynyl)phenyl)-3-(((S)-1-fluoropropan-2-yl)amino)propyl)-5-hydroxypyrimidin-4(3H)-one;

6-((2S)-2-(4-((4-(1,2-dihydroxyethyl)phenyl)ethynyl)phenyl)-3-(((S)-1-fluoropropan-2-yl)amino)propyl)-5-hydroxypyrimidin-4(3H)-one;

5-hydroxy-6-((R)-3-hydroxy-2-(4-((4-((((R)-1-(methylsulfonyl)pyrrolidin-3-yl)amino)methyl)phenyl)ethynyl) phenyl)propyl)pyrimidin-4(3H)-one;

5-hydroxy-6-((S)-3-hydroxy-2-(4-((4-((((R)-1-(methylsulfonyl)pyrrolidin-3-yl)amino)methyl)phenyl)ethynyl) phenyl)propyl)pyrimidin-4(3H)-one;

5-hydroxy-6-(3-hydroxy-2-(4-((4-((((R)-1-(methylsulfonyl) pyrrolidin-3-yl)amino)methyl)phenyl)ethynyl)phenyl) propyl)pyrimidin-4(3H)-one;

N-((3R)-1-(4-((4-(1-hydroxy-3-(5-hydroxy-6-oxo-1,6-dihydropyrimidin-4-yl)propan-2-yl)phenyl)ethynyl)benzyl) pyrrolidin-3-yl)cyclopropanecarboxamide;

2-hydroxy-N-((3R)-1-(4-((4-(1-hydroxy-3-(5-hydroxy-6-ono-1,6-dihydropyrimidin-4-yl)propan-2-yl)phenyl)ethynyl)benzyl)pyrrolidin-3-yl)acetamide;

6-(2-(4-((4-((2-(aminomethyl)morpholino)methyl)phenyl) ethynyl)phenyl)-3-hydroxypropyl)-5-hydroxypyrimidin-4(3H)-one;

5-hydroxy-6-(3-hydroxy-2-(4-((4-((piperidin-4-ylamino) methyl)phenyl)ethynyl)phenyl)propyl)pyrimidin-4(3H)-one;

5-hydroxy-6-(3-hydroxy-2-(4-((4-((methyl((R)-pyrrolidin-3-yl)amino)methyl)phenyl)ethynyl)phenyl)propyl)pyrimidin-4(3H)-one;

5-hydroxy-6-(3-hydroxy-2-(4-((4-((((R)-1-methylpyrrolidin-3-yl)amino)methyl)phenyl)ethynyl)phenyl)propyl) pyrimidin-4(3H)-one;

6-(2-(4-((4-((((R)-1-glycylpyrrolidin-3-yl)amino)methyl) phenyl)ethynyl)phenyl)-3-hydroxypropyl)-5-hydroxypyrimidin-4(3H)-one;

6-(2-(4-((1-glycylpiperidin-4-yl)ethynyl)phenyl)-3-hydroxypropyl)-5-hydroxypyrimidin-4(3H)-one;

5-hydroxy-6-(3-hydroxy-2-(4-((1-(2-hydroxyacetyl)piperidin-4-yl)ethynyl)propyl)pyrimidin-4(3H)-one;

5-hydroxy-6-(2-(methylamino)-2-(4-((4-((((R)-tetrahydrofuran-3-yl)amino)methyl)phenyl)ethynyl)phenyl)ethyl) pyrimidin-4(3H)-one;

5-hydroxy-6-(3-hydroxy-2-(4-((4-(4-hydroxypiperidin-4-yl)phenyl)ethynyl)phenyl)propyl)pyrimidin-4(3H)-one;

(S)-5-hydroxy-6-(3-hydroxy-2-(4-((4-(4-hydroxypiperidin-4-yl)phenyl)ethynyl)phenyl)propyl)pyrimidin-4(3H)-one;

(R)-5-hydroxy-6-(3-hydroxy-2-(4-((4-(4-hydroxypiperidin-4-yl)phenyl)ethynyl)phenyl)propyl)pyrimidin-4(3H)-one;
5-hydroxy-6-((S)-3-hydroxy-2-(4-((4-(((R)-2-(hydroxymethyl)piperazin-1-yl)methyl)phenyl)ethynyl)phenyl)propyl)pyrimidin-4(3H)-one;
5-hydroxy-6-((S)-3-hydroxy-2-(4-((4-((S)-2-(hydroxymethyl)piperazin-1-yl)methyl)phenyl)ethynyl)phenyl)propyl)pyrimidin-4(3H)-one;
5-hydroxy-6-(3-hydroxy-2-(4-((4-(((2-hydroxyethyl)((R)-tetrahydrofuran-3-yl)amino)methyl)phenyl)ethynyl)phenyl)propyl)pyrimidin-4(3H)-one;
5-hydroxy-6-((S)-3-hydroxy-2-(4-((4-(((2-hydroxyethyl)((R)-tetrahydrofuran-3-yl)amino)methyl)phenyl)ethynyl)phenyl)propyl)pyrimidin-4(3H)-one;
5-hydroxy-6-((R)-3-hydroxy-2-(4-((4-(((2-hydroxyethyl)((R)-tetrahydrofuran-3-yl)amino)methyl)phenyl)ethynyl)phenyl)propyl)pyrimidin-4(3H)-one;
6-(2-(4-((4-(1,2-dihydroxyethyl)phenyl)ethynyl)phenyl)-3-hydroxypropyl)-5-hydroxypyrimidin-4(3H)-one;
6-((2S)-2-(4-((4-(1,2-dihydroxyethyl)phenyl)ethynyl)phenyl)-3-hydroxypropyl)-5-hydroxypyrimidin-4(3H)-one;
6-((2R)-2-(4-((4-(1,2-dihydroxyethyl)phenyl)ethynyl)phenyl)-3-hydroxypropyl)-5-hydroxypyrimidin-4(3H)-one;
6-(2-hydroxy-2-(4-((4-((((R)-tetrahydrofuran-3-yl)amino)methyl)phenyl)ethynyl)phenyl)ethyl)pyrimidine-4,5-diol;
N-(1-(4-((3-fluoro-4-(1-hydroxy-3-(5-hydroxy-6-oxo-1,6-dihydropyrimidin-4-yl)propan-2-yl)phenyl)ethynyl)benzyl)piperidin-4-yl)-2-hydroxyacetamide;
(R)—N-(1-(4-((3-fluoro-4-(1-hydroxy-3-(5-hydroxy-6-oxo-1,6-dihydropyrimidin-4-yl)propan-2-yl)phenyl)ethynyl)benzyl)piperidin-4-yl)-2-hydroxyacetamide;
(S)—N-(1-(4-((3-fluoro-4-(1-hydroxy-3-(5-hydroxy-6-oxo-1,6-dihydropyrimidin-4-yl)propan-2-yl)phenyl)ethynyl)benzyl)piperidin-4-yl)-2-hydroxyacetamide;
6-(2-(4-((4-((1-oxa-6-azaspiro[3.3]heptan-6-yl)methyl)phenyl)ethynyl-2-fluorophenyl)-3-hydroxypropyl)-5-hydroxypyrimidin-4(3H)-one;
(S)-6-(2-(4-((4-((1-oxa-6-azaspiro[3.3]heptan-6-yl)methyl)phenyl)ethynyl)-2-fluorophenyl)-3-hydroxypropyl)-5-hydroxypyrimidin-4(3H)-one;
(R)-6-(2-(4-((4-((1-oxa-6-azaspiro[3.3]heptan-6-yl)methyl)phenyl)ethynyl)-2-fluorophenyl)-3-hydroxypropyl)-5-hydroxypyrimidin-4(3H)-one;
(3R)-1-(4-((3-fluoro-4-(1-hydroxy-3-(5-hydroxy-6-oxo-1,6-dihydropyrimidin-4-yl)propan-2-yl)phenyl)ethynyl)benzyl)pyrrolidine-3-carbonitrile;
6-(2-(4-((2-fluoro-4-(morpholinomethyl)phenyl)ethynyl)phenyl)-3-(3-hydroxyazetidin-1-yl)propyl)-5-hydroxypyrimidin-4(3H)-one;
(S)-6-(2-(4-((2-fluoro-4-(morpholinomethyl)phenyl)ethynyl)phenyl)-3-(3-hydroxyazetidin-1-yl)propyl)-5-hydroxypyrimidin-4(3H)-one;
(R)-6-(2-(4-((2-fluoro-(morpholinomethyl)phenyl)ethynyl)phenyl)-3-(3-hydroxyazetidin-1-yl)propyl)-5-hydroxypyrimidin-4(3H)-one;
6-(2-(4-((3-fluoro-4-(morpholinomethyl)phenyl)ethynyl)phenyl)-3-(3-hydroxyazetidin-1-yl)propyl-5-hydroxypyrimidin-4(3H)-one;
(S)-6-(2-(4-((3-fluoro-4-(morpholinomethyl)phenyl)et ynyl)phenyl)-3-(3-hydroxyazetidin-1-yl)propyl)-5-hydroxypyrimidin-4(3H)-one;
(R)-6-(2-(4-((3-fluoro-4-(morpholinomethyl)phenyl)ethynyl)phenyl)-3-(3-hydroxyazetidin-1-yl)propyl)-5-hydroxypyrimidin-4(3H)-one;
6-(2-(3-fluoro-4-((4-(morpholinomethyl)phenyl)ethynyl)phenyl)-3-(3-hydroxyazetidin-1-yl)propyl)-5-hydroxypyrimidin-4(3H)-one;
(S)-6-(2-(3-fluoro-4-((4-(morpholinomethyl)phenyl)ethynyl)phenyl)-3-(3-hydroxyazetidin-1-yl)propyl)-5-hydroxypyrimidin-4(3H)-one;
(R)-6-(2-(3-fluoro-4-((4-(morpholinomethyl)phenyl)ethynyl)phenyl)-3-(3-hydroxyazetidin-1-yl)propyl)-5-hydroxypyrimidin-4(3H)-one;
6-(2-(2-fluoro-4-((4-(morpholinomethyl)phenyl)ethynyl)phenyl)-3-(3-fluoroazetidin-1-yl)propyl)-5-hydroxypyrimidin-4(3H)-one;
(S)-6-(2-(2-fluoro-4-((4-(morpholinomethyl)phenyl)ethynyl)phenyl)-3-(3-fluoroazetidin-1-yl)propyl)-5-hydroxypyrimidin-4(3H)-one;
(R)-6-(2-(2-fluoro-4-((4-(morpholinomethyl)phenyl)ethynyl)phenyl)-3-(3-fluoroazetidin-1-yl)propyl)-5-hydroxypyrimidin-4(3H)-one;
1-(4-((4-(1-((2,2-difluoroethyl)amino)-3-(5-hydroxy-6-oxo-1,6-dihydroxypyrimidin-4-yl)propan-2-yl)-3-fluorophenyl)ethynyl)benzyl)azetidine-3-carbonitrile;
(S)-1-(4-((4-(1-((2,2-difluoroethyl)amino)-3-(5-hydroxy-6-oxo-1,6-dihydropyrimidin-4-yl)propan-2-yl)-3-fluorophenyl)ethynyl)benzyl)azetidine-3-carbonitrile;
(R)-1-(4-((4-(1-((2,2-difluoroethyl)amino)-3-(5-hydroxy-6-oxo-1,6-dihydropyrimidin-4-yl)propan-2-yl)-3-fluorophenyl)ethynyl)benzyl)azetidine-3-carbonitrile;
6-(2-(2-fluoro-4-((4-(morpholinomethyl)phenyl)ethynyl)phenyl)-3-(((R)-1-fluoropropan-2-yl)amino)propyl)-5-hydroxypyrimidin-4(3H)-one;
6-((R)-2-(2-fluoro-4-((4-(morpholinomethyl)phenyl)ethynyl)phenyl)-3-(((R)-1-fluoropropan-2-yl)amino)propyl)-5-hydroxypyrimidin-4(3H)-one;
6-((S)-2-(2-fluoro-4-((4-(morpholinomethyl)phenyl)ethanyl)phenyl)-3-(((R)-1-fluoropropan-2-yl)amino)propyl)-5-hydroxypyrimidin-4(3H)-one;
(R)-1-(4-((4-(1-((2,2-difluoroethyl)amino)-3-(5-hydroxy-6-oxo-1,6-dihydropyrimidin-4-yl)propan-2-yl)-3-fluorophenyl)ethynyl)benzyl)pyrimidine-3-carbonitrile;
(R)-1-(4-((4-((S)-1-(2,2-difluoroethyl)amino)-3-(5-hydroxy-6-oxo-1,6-dihydropyrimidin-4-yl)propan-2 yl)-3-fluorophenyl)ethynyl)benzyl)pyrrolidine-3-carbonitrile;
(R)-1-(4-((4-((R)-1-((2,2-difluoroethyl)amino)-3-(5-hydroxy-6-oxo-1,6-dihydropyrimidin-4-yl)propan-2-yl)-3-fluorophenyl)ethynyl)benzyl)pyrrolidine-3-carbonitrile;
6-(3-((2,2-difluoroethyl)amino)-2-(2-fluoro-4-((4-((3-methoxyazetidin-1-yl)methyl)phenyl)ethynyl)phenyl)propyl)-5-hydroxypyrimidin-4(3H)-one;
(S)-6-(3-((2,2-difluoroethyl)amino)-2-(2-fluoro-4-((4-((3-methoxyazetidin-1-yl)methyl)phenyl)ethynyl)phenyl)propyl)-5-hydroxypyrimidin-4(3H)-one;
(R)-6-(3-((2,2-difluoroethyl)amino)-2-(2-fluoro-4-((4-((3-methoxyazetidin-1-yl)methyl)phenyl)ethynyl)phenyl)propyl)-5-hydroxypyrimidin-4(3H)-one;
6-(3-((2,2-difluoroethyl)amino)-2-(2-fluoro-4-((4-(morpholinomethyl)phenyl)ethynyl)phenyl)propyl)-5-hydroxypyrimidin-4(3H)-one;
(S)-6-(3-((2,2-difluoroethyl)amino)-2(2-fluoro-4-((4-(morpholinomethyl)phenyl)ethynyl)phenyl)propyl)-5-hydroxypyrimidin-4(3H)-one;
(R)-6-(3-((2,2-difluoroethyl)amino)-2-(2-fluoro-4-((4-(morpholinomethyl)phenyl)ethynyl)phenyl)propyl)-5-hydroxypyrimidin-4(3H)-one;
6-(2-(2-fluoro-4 ((4-(morpholinomethyl)phenyl)ethynyl)phenyl)-3-(((R)-2-hydroxypropyl)amino)propyl)-5-hydroxypyrimidin-4(3H)-one;

6-((S)-2-(2-fluoro-4-((4-(morpholinomethyl)phenyl)ethynyl)phenyl)-3-(((R)-2-hydroxypropyl)amino)propyl)-5-hydroxypyrimidin-4(3H)-one;

6-((R)-2-(2-fluoro-4-((4-(morpholinomethyl)phenyl)ethynyl)phenyl)-3-(((R)-2-hydroxypropyl)amino)propyl)-5-hydroxypyrimidin-4(3H)-one;

5-hydroxy-6-(3-methoxy-2-(4-((4-((((S)-tetrahydrofuran-3-yl)amino)methyl)phenyl)ethynyl)phenyl)propyl)pyrimidin-4(3H)-one;

5-hydroxy-6-((S)-3-methoxy-2-(4-((4-((((S)-tetrahydrofuran-3-yl)amino)methyl)phenyl)ethynyl)phenyl)propyl)pyrimidin-4(3H)-one;

5-hydroxy-6-((R)-3-methoxy-2-(4-((4-((((S)-tetrahydrofuran-3-yl)amino)methyl)phenyl)ethynyl)phenyl)propyl)pyrimidin-4(3H)-one;

3-(5-hydroxy-6-oxo-1,6-dihydropyrimidin-4-yl)-2-(4-((4-(morpholinomethyl)phenyl)ethynyl)phenyl)propyl dihydrogen phosphate;

(S)-3-(5-hydroxy-6-oxo-1,6-dihydropyrimidin-4-yl)-2-(4-((4-(morpholinomethyl)phenyl)ethynyl)phenyl)propyl dihydrogen phosphate;

(R)-3-(5-hydroxy-6-oxo-1,6-dihydropyrimidin-4-yl)-2-(4-((4-(morpholinomethyl)phenyl)ethynyl)phenyl)propyl dihydrogen phosphate;

5-hydroxy-6-(3-methoxy-2-(4-((4-((((S)-pyrrolidin-3-yl)amino)methyl)phenyl)ethynyl)phenyl)propyl)pyrimidin-4(3H)-one;

5-hydroxy-6-((S)-3-methoxy-2-(4-((4-((((S)-pyrrolidin-3-yl)amino)methyl)phenyl)ethynyl)phenyl)propyl)pyrimidin-4(3H)-one;

5-hydroxy-6-((R)-3-methoxy-2-(4-((4-((((S)-pyrrolidin-3-yl)amino)methyl)phenyl)ethynyl)phenyl)propyl)pyrimidin-4(3H)-one;

5-hydroxy-6-(3-methoxy-2-(4-((4-((((R)-pyrrolidin-3-yl)amino)methyl)phenyl)ethynyl)phenyl)propyl)pyrimidin-4(3H)-one;

5-hydroxy-6-((S)-3-methoxy-2-(4-((4-((((R)-pyrrolidin-3-yl)amino)methyl)phenyl)ethynyl)phenyl)propyl)pyrimidin-4(3H)-one;

5-hydroxy-6-((R)-3-methoxy-2-(4-((4-((((R)-pyrrolidin-3-yl)amino)methyl)phenyl)ethynyl)phenyl)propyl)pyrimidin-4(3H)-one;

N-(2-(5-hydroxy-6-oxo-1,6-dihydropyrimidin-4-yl)-1-(4-((4-(morpholinomethyl)phenyl)ethynyl)phenyl)ethyl)methanesulfanamide;

(R)—N-(2-(5-hydroxy-6-oxo-1,6-dihydropyrimidin-4-yl)-1-(4-((4-(morpholinomethyl)phenyl)ethynyl)phenyl)ethyl)methanesulfanamide;

(S)—N-(2-(5-hydroxy-6-oxo-1,6-dihydropyrimidin-4-yl)-1-(4-((4-(morpholinomethyl)phenyl)ethynyl)phenyl)ethyl)methanesulfanamide;

N-(2-(5-hydroxy-6-oxo-1,6-dihydropyrimidin-4-yl)-1-(4-((4-(4-hydroxypiperidin-4-yl)phenyl)ethynyl)phenyl)ethyl)methanesulfonamide;

(R)—N-(2-(5-hydroxy-6-oxo-1,6-dihydropyrimidin-4-yl)-1-(4-((4-(4-hydroxypiperidin-4-yl)phenyl)ethynyl)phenyl)ethyl)methanesulfonamide;

(S)—N-(2-(5-hydroxy-6-oxo-1,6-dihydropyrimidin-4-yl)-1-(4-((4-(4-hydroxypiperidin-4-yl)phenyl)ethynyl)phenyl)ethyl)methanesulfonamide;

N-(2-(5-hydroxy-6-oxo-1,6-dihydropyrimidin-4-yl)-1-(4-((4-(((S)-2-(hydroxymethyl)piperazin-1-yl)methyl)phenyl)ethynyl)phenyl)ethyl)methanesulfonamide;

N—(R)-2-(5-hydroxy-6-oxo-1,6-dihydropyrimidin-4-yl)-1-(4-((4-(((S)-2-(hydroxymethyl)piperazin-1-yl)methyl)phenyl)ethynyl)phenyl)ethyl)methanesulfonamide;

N—((S)-2-(5-hydroxy-6-oxo-1,6-dihydropyrimidin-4-yl)-1-(4-((4-(((S)-2-(hydroxymethyl)piperazin-1-yl) m ethyl)phenyl)ethynyl)phenyl)ethyl) methanesulfonamide;

6-(2-(4-((4-(((R)-3-aminopyrrolidin-1-yl)methyl)phenyl)ethynyl)phenyl)-3-hydroxypropyl)-5-hydroxypyrimidin-4(3H)-one;

6-(2-(4-((4-(3-aminooxetan-3 yl)phenyl)ethynyl)phenyl-3-hydroxypropyl)-5-hydroxypyrimidin-4(3H)-one;

6-(3-(((S)-1-fluoropropan-2-yl)amino)-2-(4-((4-(2-morpholinoethyl)phenyl)ethynyl)phenyl)propyl)-5-hydroxypyrimidin-4(3H)-one;

N-(1-([1,1'-biphenyl]-4-yl)-2-(5-hydroxy-6-oxo-1,6-dihydropyrimidin-4-yl)ethyl)methanesulfonamide;

(R)—N-(1-([1,1'-biphenyl]-4-yl)-2-(5-hydroxy-6-oxo-1,6-dihydropyrimidin-4-yl)ethyl)methanesulfonamide;

(S)—N-(1-([1,1'-biphenyl]-4-yl)-2-(5-hydroxy-6-oxo-1,6-dihydropyrimidin-4-yl)ethyl)methanesulfonamide;

N-(2-(5-hydroxy-6-oxo-1,6-dihydropyrimidin-4-yl)-1-(4-((4-((3-methoxyazetidin-1-yl)methyl)phenyl)ethynyl)phenyl)ethyl)methanesulfonamide;

(R)—N-(2-(5-hydroxy-6-oxo-1,6-dihydropyrimidin-4-yl)-1-(4-((4-((3-methoxyazetidin-1-yl)methyl)phenyl)ethynyl)phenyl)ethyl)methanesulfonamide;

(S)—N-(2-(5-hydroxy-6-oxo-1,6-dihydropyrimidin-4-yl)-1 (4-((4-((3-methoxyazetidin-1-yl)methyl)phenyl)ethynyl)phenyl)ethyl)methanesulfonamide;

6-(2-(2-fluoro-4-((4-(morpholinomethyl)phenyl)ethynyl)phenyl)-3-(3-methoxyazetidin-1-yl)propyl)-5-hydroxypyrimidin-4(3H)-one;

(R)-6-(2-(2-fluoro-4-((4-(morpholinomethyl)phenyl)ethynyl)phenyl)-3-(3-methoxyazetidin-1-yl)propyl)-5-hydroxypyrimidin-4(3H)-one;

(S)-6-(2-(2-fluoro-4-((4-(morpholinomethyl)phenyl)ethynyl)phenyl)-3-(3-methoxyazetidin-1-yl)propyl)-5-hydroxypyrimidin-4(3H)-one;

6-(3-((1-fluoro-2-methylpropan-2 yl)amino-2-(4-((4-(morpholinomethyl)phenyl)ethynyl)phenyl)propyl)-5-hydroxypyrimidin-4(3H)-one;

(R)-6-(3-((1-fluoro-2-methylpropan-2-yl)amino)-2-(4-((4-(morpholinomethyl)phenyl)ethynyl)phenyl)propyl)-5-hydroxypyrimidin-4(3H)-one;

(S)-6-(3-((1-fluoro-2-methylpropan-2-yl)amino)-2-(4-((4-(morpholinomethyl)phenyl)ethynyl)phenyl)propyl)-5-hydroxypyrimidin-4(3H)-one;

6-(3-(cyclopropyl(methyl)amino)-2-(4-((4-(morpholinomethyl)phenyl)ethynyl)phenyl)propyl)-5-hydroxypyrimidin-4(3H)-one;

(S)-6-(3-(cyclopropyl(methyl)amino)-2-(4-((4-(morpholinomethyl)phenyl)ethynyl)phenyl)propyl)-5-hydroxypyrimidin-4(3H)-one;

(R)-6-(3-(cyclopropyl(methyl)amino)-2-(4-((4-(morpholinomethyl)phenyl)ethynyl)phenyl)propyl)-5-hydroxypyrimidin-4(3H)-one;

1-(3-(5-hydroxy-6-oxo-1,6-dihydropyrimidin-4-yl)-2-(4-((4-(morpholinomethyl)phenyl)ethynyl)phenyl)propyl)azetidin-3-yl acetate;

(S)-1-(3-(5-hydroxy-6-oxo-1,6-dihydropyrimidin-4-yl)-2-(4-((4-(morpholinomethyl)phenyl)ethynyl)phenyl)propyl)azetidin-3-yl acetate;

(R)-1-(3-(5-hydroxy-6-oxo-1,6-dihydropyrimidin-4-yl)-2-(4-((4-(morpholinomethyl)phenyl)ethynyl)phenyl)propyl)azetidin-3-yl acetate;

N-(3-(5-hydroxy-6-oxo-1,6-dihydropyrimidin-4-yl)-2-(4-((4-(morpholinomethyl)phenyl)ethynyl)phenyl)propyl)acetamide;

(S)—N-(3-(5-hydroxy-6-oxo-1,6-dihydropyrimidin-4-yl)-2-(4-((4-(morpholinomethyl)phenyl)ethynyl)phenyl)propyl)acetamide;

(R)—N-(3-(5-hydroxy-6-oxo-1,6-dihydropyrimidin-4-yl)-2-(4-((4-(morpholinomethyl)phenyl)ethynyl)phenyl)propyl)acetamide;

N-(3-(5-hydroxy-6-oxo-1,6-dihydropyrimidin-4-yl)-2-(4-((4-(morpholinomethyl)phenyl)ethynyl)phenyl)propypmelhanesulfonamide;

(S)—N-(3-(5-hydroxy-6-oxo-1,6-dihydropyrimidin-4-yl)-2-(4-((4-(morpholinomethyl)phenyl)ethynyl)phenyl)propyl)metlianesulfonamide;

(R)—N-(3-(5-hydroxy-6-oxo-1,6-dihydropyrimidin-4-yl)-2-(4-((4-(morpholinomethyl)phenyl)ethynyl)phenyl)propyl)metlianesulfonamide;

5-hydroxy-6-(3-(2-methyl-1H-imidazol-1-yl)-2-(4-((4-(morpholinomethyl)phenyl)ethynyl)phenyl)propyl)pyricin-4(3H)-one;

(S)-5-hydroxy-6-(3-(2-methyl-1H-imidazol-1-yl)-2-(4-((4-(morpholinomethyl)phenyl)ethynyl)phenyl)propyl)pyrimidin-4(3H-one; and (R)-5-hydroxy-6-(3-(2-methyl-1H-imidazol-1-yl)-2-(4-((4-(morpholinomethyl)phenyl)ethynyl)phenyl)propyl)pyrimidin-4(3H)-one, Preparation of Compounds The compounds used in the chemical reactions described herein are made according to organic synthesis techniques known to those skilled in this art, starting from commercially available chemicals and/or from compounds described in the chemical literature, "Commercially available chemicals" are obtained from standard commercial sources including Acros Organics (Pittsburgh, PA). Aldrich Chemical (Milwaukee, WI, including Sigma. Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, PA), Crescent Chemical Co. (Hauppauge, NY), Eastman Organic Chemicals, Eastman Kodak Company (Rochester. NY), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Maybridge Chemical Co. Ltd. (Cornwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Spectrum Quality Product, Inc. (New Brunswick, NJ), TCI America (Portland, OR), Trans World Chemicals. Inc. (Rockville, MD), and Wako Chemicals USA. Inc. (Richmond, VA).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed. Academic Press, New York, 1983; H. O. House, "Modern Synthetic Reactions", 2nd Ed., W. A. Benjamin. Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed, Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley &. Sons ISBN: 3-527-29074-5; Hoffman, R. V. "Organic Chemistry, An intermediate Text" (1996) Oxford University Press, ISBN 0-19-509618-5; Larock, R. C. "Comprehensive Organic Transformations: A Guide to Functional Group Preparations" 2nd Edition (1999) Wiley-VCR, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai's "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley &. Sons, in volumes.

Alternatively, specific and analogous reactants can be identified through the indices of known chemicals and reactions prepared byte; Chemical Abstract Service of the American Chemical Society, which are available in most public and university libraries, as well as through on-line databases (contact the American Chemical Society, Washington. D.C. for more, details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the heterocyclic LpxC inhibitory compound described herein is P. H. Stahl & C. G. Wermuth "Handbook of Pharmaceutical Salts", Verlag Helvetica Chimica Acta, Zurich, 2002.

Pharmaceutical Compositions

In certain embodiments, the heterocyclic LpxC inhibitory compound as described herein is administered as a pure chemical. In other embodiments, the heterocyclic LpxC inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, PA (2005)).

Provided herein is a pharmaceutical composition comprising at least one heterocyclic LpxC inhibitory compound as described herein, or a stereoisomer, pharmaceutically acceptable salt, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject or patient) of the composition.

One embodiment provides a pharmaceutical composition comprising a compound disclosed herein, or a pharmaceutically acceptable salt, solvate, or prodrug thereof, and a pharmaceutically acceptable excipient.

In certain embodiments, the heterocyclic LpxC inhibitory compound disclosed herein is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., Remington: The Science and Practice of Pharmacy (Gennaro, 21$^{st}$ Ed. Mack Pub, Co., Easton, PA (2005)).

The dose of the composition comprising at least one heterocyclic LpxC inhibitory compound as described herein differ, depending upon the patient's condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome), or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

LpxC, Lipid A and Gram-Negative Bacteria

Metalloproteins influence a vast diversity of biological systems, biological processes, and diseases. For example, UDP-{3-O—[(R)-3-hydroxymyristoyl]}-N-acetylglucosamine deacetylase (LpxC) is an essential enzyme involved in the first committed step in lipid A biosynthesis for gram-negative bacteria. Lipid A is an essential component of the outer membrane of gram-negative bacteria. LpxC is a zinc(III)-dependent metalloenzyme, with two histidines and an aspartic acid residue bound to the zinc(II) ion. Structures of LpxC show the zinc(II) ion is bound to two water molecules, both of which have been implicated in the mechanism of the enzyme. LpxC is highly conserved across strains of gram-negative bacteria, making LpxC an attractive target to treat gram-negative infections.

In recent years, there has been an increase in resistant and multi-drug resistant strains of bacteria. Thus, there is a need for new antibiotics, especially with new mechanisms of action. There remains a need for metalloprotein modulators of LpxC useful in the field of therapeutics, diagnostics, and research.

One embodiment provides a method of inhibiting UDP-{3-O—[(R)-3-hydroxymyristoyl]}-N-acetylglucosamine deacetylase enzyme comprising contacting the enzyme with a compound disclosed herein.

One embodiment provided herein is a pharmaceutical composition comprising a compound disclosed herein, or a pharmaceutically acceptable salt, solvate, or prodrug thereof, and a pharmaceutically acceptable excipient. Another embodiment provided herein is a pharmaceutical composition comprising a compound of Formula (I) or a pharmaceutically acceptable salt, solvate, or prodrug thereof, and a pharmaceutically acceptable excipient. Another embodiment provided herein is a pharmaceutical composition comprising a compound of Formula (II) or a pharmaceutically acceptable salt, solvate, or prodrug thereof, and a pharmaceutically acceptable excipient. Another embodiment provided herein is a pharmaceutical composition comprising a compound of Formula (III) or a pharmaceutically acceptable salt, solvate, or prodrug thereof, and a pharmaceutically acceptable excipient. Another embodiment provided herein is a pharmaceutical composition comprising a compound of Formula (IV) or a pharmaceutically acceptable salt, solvate, or prodrug thereof, and a pharmaceutically acceptable excipient.

Methods of Treatment

Disclosed herein are methods of treating disease wherein the inhibition of bacterial growth is indicated. Such disease includes gram-negative bacterial infection. In some embodiments, the method of treating a gram-negative bacterial infection in a patient in need thereof comprises administering to the patient a pharmaceutical composition comprising a compound disclosed herein, or a pharmaceutically acceptable salt, solvate, or prodrug thereof, and a pharmaceutically acceptable excipient. In some embodiments, the gram-negative bacterial infection is selected from pneumonia, sepsis, cystic fibrosis, intra-abdominal infection, skin infections and urinary tract infection. In some embodiments, the gram-negative bacterial infection is a urinary tract infection (UTI), a hospital acquired/ventilator-associated pneumonia (HAP/VAP), or an intra-abdominal infection (IAI). In some embodiments, the gram-negative bacterial infection is selected from chronic urinary tract infections, complicated urinary tract infections, cystitis, pyelonephritis, urethritis, recurrent urinary tract infections, bladder infections, urethral infections, and kidney infections. In some embodiments, the compounds described herein are used for the treatment of chronic urinary tract infections. In some embodiments, the compounds described herein are used for the treatment of complicated urinary tract infections. In other embodiments, the compounds described herein are used for the treatment of complicated intra-abdominal infection. In some embodiments, the compounds described herein are used for the treatment of chronic intra-abdominal infection. In other embodiments, the compounds described herein are used for the treatment of hospital acquired pneumonia (HAP) or ventilator associated pneumonia (YAP). In some embodiments the administration is to treat an existing infection. In some embodiments the administration is provided as prophylaxis.

In some embodiments the heterocyclic LpxC inhibitory compound as described herein is used for treating conditions caused by the bacterial production of endotoxin and, in particular, by gram-negative bacteria and bacteria that use LpxC in the biosynthesis of lipopolysaccharide (LPS) or endotoxin. In some embodiments, the method of treating a condition caused by endotoxin or LPS in a patient in need thereof comprises administering to the patient a pharmaceutical composition comprising a compound disclosed herein, or a pharmaceutically acceptable salt, solvate, or prodrug thereof, and a pharmaceutically acceptable excipient. In another embodiment, the heterocyclic LpxC inhibitory compounds as described herein are useful in the treatment of conditions that are caused or exacerbated by the bacterial production of lipid A and LPS or endotoxin, such as sepsis, septic shock, systemic inflammation, localized inflammation, chronic obstructive pulmonary disease (COPD) and acute exacerbations of chronic bronchitis (AECB). In some embodiments, the method of treating a condition caused by endotoxin or LPS in a patient in need thereof comprises administering to the patient a pharmaceutical composition comprising a compound disclosed herein, or a pharmaceutically acceptable salt, solvate, or prodrug thereof, and a pharmaceutically acceptable excipient, wherein the condition caused by endotoxin or LPS is selected from sepsis, septic shock, systemic inflammation, localized inflammation, chronic obstructive pulmonary disease (COPD) and acute exacerbations of chronic bronchitis (AECB).

In other embodiments, the compounds of the disclosure can be used for the treatment of a serious or chronic respiratory tract infection or complicated urinary tract infections including serious lung and nosocomial infections such as those caused by *Enterobacter aerogenes; Enterobacter cloacae, Escherichia coli, Klebsiella pneumoniae, Klebsiella oxytoca Kuyvera ascorbata, Kuyvera cryocrescense, Staphylococcus aureus, Shigella sonnei, Proteus mirabilis, Serrano marcescens, Stenotrophomonas Pseudomonas aeruginosa, Burkholderia cepacia, Acinetobacter baumannii, Alcaligenes xylosoxidans, Flavobacterium meningosepticum, Providencia sluarlii* and *Citrobacter freundi, Haemophilus influenzae, Kluyvera* species, *Legionella* species, *Moraxella catarrhalis, Enterobacter* species, *Acinetobacter* species. *Klebsiella* species, *Burkholderia* species and *Proteus* species, and infections caused by other bacterial species such as *Neisseria* species, *Shigella* species, *Salmonella* species, *Helicobacler pylori, Vibrionaceae* and *Bordetella* species as well as the infections caused by a *Brucella* species, *Francisella tularensis* and/or *Yersinia pestis.*

In one embodiment provided herein is a method of treating a gram-negative bacterial infection in a patient in need thereof comprising administering to the patient a pharmaceutical composition comprising a compound disclosed herein, or a pharmaceutically acceptable salt, solvate, or prodrug thereof, and a pharmaceutically acceptable excipient.

One embodiment provides a method wherein the gram-negative bacterial infection is selected from pneumonia, sepsis, cystic fibrosis, intra-abdominal infection, skin infection and urinary tract infection.

One embodiment provides a method wherein the gram-negative bacterial infection is selected from chronic urinary tract infection, complicated urinary tract infection, cystitis, pyelonephritis, urethritis, recurrent urinary tract infections, bladder infections, urethral infections and kidney infections.

One embodiment provides a method wherein the gram-negative bacterial infection is chronic urinal), tract infections. One embodiment provides a method wherein the gram-negative bacterial infection is complicated urinary tract infections. One embodiment provides a method wherein the administration is to treat an existing infection. One embodiment provides a method wherein the administration is provided as prophylaxis.

One embodiment provides a method of treating a gram-negative bacterial infection in a patient in need thereof comprising administering to the patient a pharmaceutical composition comprising a compound disclosed herein, or a pharmaceutically acceptable salt, solvate, or prodrug thereof, and a pharmaceutically acceptable excipient. In one embodiment, the gram-negative bacterial infection is selected from pneumonia, sepsis, cystic fibrosis, intra-abdominal infection, skin infection and urinary tract infection. In another embodiment, the gram-negative bacterial infection is selected from chronic urinary tract infection, complicated urinary tract infection, cystitis, pyelonephritis, urethritis, recurrent urinary tract infections, bladder infections, urethral infections and kidney infections. In one embodiment, the gram-negative bacterial infection is chronic urinary tract infections. In another embodiment, the gram-negative bacterial infection is complicated urinary tract infections. In one embodiment, the administration is to treat an existing infection. In an additional embodiment, the administration is provided as prophylaxis.

In other embodiments, the compounds of the disclosure are not active against gram-positive bacteria. In some embodiments, the compounds of the disclosure are not active against *Staphylococcus aureus.*

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Colon chromatography and thin layer chromatography (TLC) were performed on silica gel unless otherwise noted. Spectra are given in ppm (δ) and coupling constants. J are reported in Hertz. For proton spectra the solvent peak was used as the reference peak.

The following abbreviations and terms have the indicated meanings throughout:

AcOH=acetic acid
$B_2pin_2$=bis(pinacolato)diboron
Boc=tert-butoxycarbonyl
DCC=dicyclohexylcarbodiimide
DIEA=N,N-diisopropylethylamine
DMAP=4-dimethylaminopyridine
EDC=1-ethyl-3-(3-dimethylaminopropyl) carbodiimide
eq=equivalent(s)
Et=ethyl
EtOAc or EA=ethyl acetate
EtOH=ethanol
g=gram
h or hr=hour
HBTU=O-(benzotriazol-1-yl)-N,N,N',N'-tetramethyluronium hexafluorophosphate
HOBt=hydroxybenzotriazole
HPLC=high pressure liquid chromatography
kg or Kg=kilogram
L or l=liter
LC/MS=LCMS=liquid chromatography-mass spectrometry
LRMS=low resolution mass spectrometry
m/z=mass-to-charge ratio
Me=methyl
MeOH=methanol
mg=milligram
min=minute
mL=milliliter
mmol=millimole
NaOAc=sodium acetate
PE=petroleum ether
Ph=phenyl
Prep=preparative
quant.=quantitative
RP-HPLC=reverse phase-high pressure liquid chromatography
rt or RT=room temperature THF=tetrahydrofuran
UV=ultraviolet Example 1: Synthesis of 6-(3-(((((S)-1-fluoropropan-2-yl)amino)-2-(4-((4-((3-methoxyazetidin-1-yl)methyl)phenyl)ethynyl)phenyl)propyl)-5-hydroxypyrimidin-4(3H)-one (Compound 68)

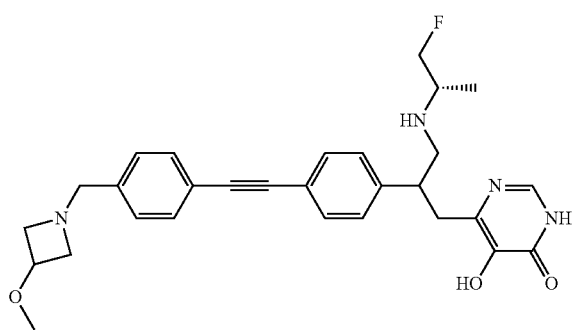 [SMILES: COC1CN(Cc2ccc(C#Cc3ccc(C(CN[C@@H](C)CF)Cc4nc[nH]c(=O)c4O)cc3)cc2)C1]

Step 1: Synthesis of 4,5-bis(benzyloxy)-6-(iodomethyl)pyrimidine

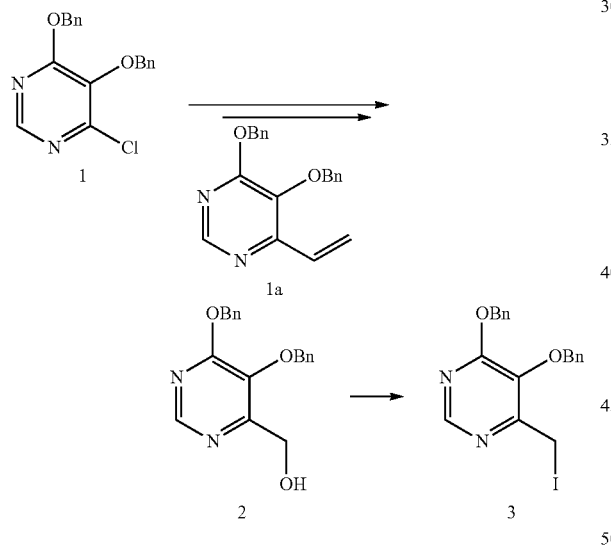

To a solution of 1 (35 g, 0.107 mmol) DMF (350 mL), tributylvinyltin (37.4 g, 0.0117 mol) was added and purged with nitrogen for 10 min. To this reaction mixture, PdCl₂(PPh₃)₄ (7.5 g, 0.010 mol) was added and heated to 100° C. for 6 h. After completion of the reaction, the reaction mixture was cooled, diluted with water and extracted with EtOAc (2*750 mL). The combined organic layers were washed with brine solution, dried over Na₂SO₄, filtered and concentrated. The crude product was purified by column chromatography to get pure 1a as colorless liquid. Yield: 23 g, 76%

A solution of 1a (23 g, 0.072 mol) in DCM: MeOH (500 mL) was cooled to −78° C. and treated with ozone for 30 min. After completion of the reaction, the reaction mixture was bubbled with oxygen for 10 min. Dimethyl sulfide (12 mL) was added and stirred the reaction mixture for 1 h. The reaction mixture was warmed to −30° C. and carefully sodium borohydride (5.34 g, 0.144 mol) was added in portions and stirred for 10 min. Solvent was removed, and the reaction mixture was dissolved in dichloromethane and washed with water (100 mL) and with brine solution, dried over Na2SO4, filtered and concentrated to get 2 as off white solid. Yield: 16 g, 69.5%. LC_MS Calculated for C19H18N2O3 is 322.36, Observed=323.2 To a 0° C. cooled solution of 2 (4 g, 0.0124 mol) in DCM (40 mL), triethylamine (2.5 g, 0.0248 mol) was added followed by methane sulfonyl chloride (2.1 g, 0.0186 mol). After completion of the reaction, the reaction mixture was washed with water and brine solution. The organic layer was dried over anhydrous Na₂SO₄, filtered and concentrated under reduced pressure to get 4.96 g crude product.

The crude product (4.96 g, 0.0124 mol) was dissolved in acetone (50 mL) and cooled to 0° C. to this NaI (3.7 g, 0.0248 mol) was added and stirred at 0° C. for 30 min. After completion of the reaction, the reaction mixture was dissolved in water extracted with DCM. The organic layer was washed with brine solution and dried over anhydrous Na₂SO₄, filtered and concentrated under reduced pressure to get 3 as pale yellow solid. Yield: 4.0 g, 74.7%. LCMS=Calculated for C19H17N2O2 is 432.26, Observed=433.1.

Step 2: Synthesis of (R)-3-(5,6-bis(benzyloxy)pyrimidin-4-yl)-2-(4-iodophenyl)propan-1-ol

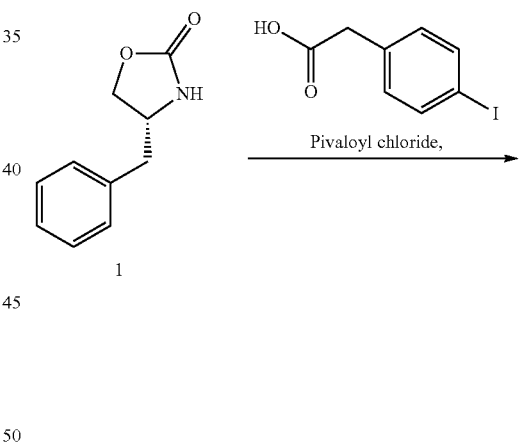

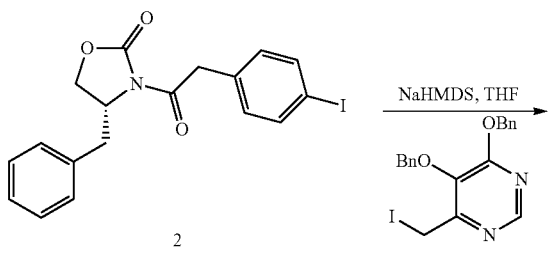

213

-continued

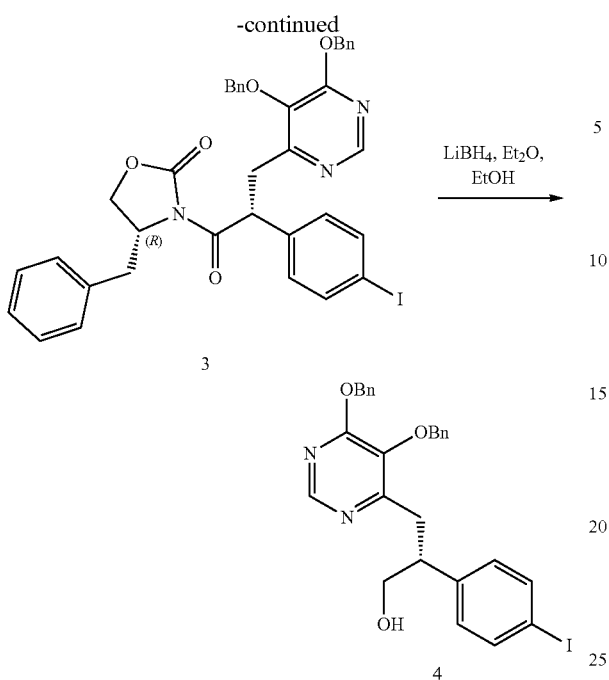

214

Step 3: Synthesis of 6-(3-((((S)-1-fluoropropan-2-yl)amino)-2-(4-((4-((3-methoxyazetidin-1-yl)methyl)phenyl)ethynyl)phenyl)propyl)-5-hydroxypyrimidin-4(3H)-one

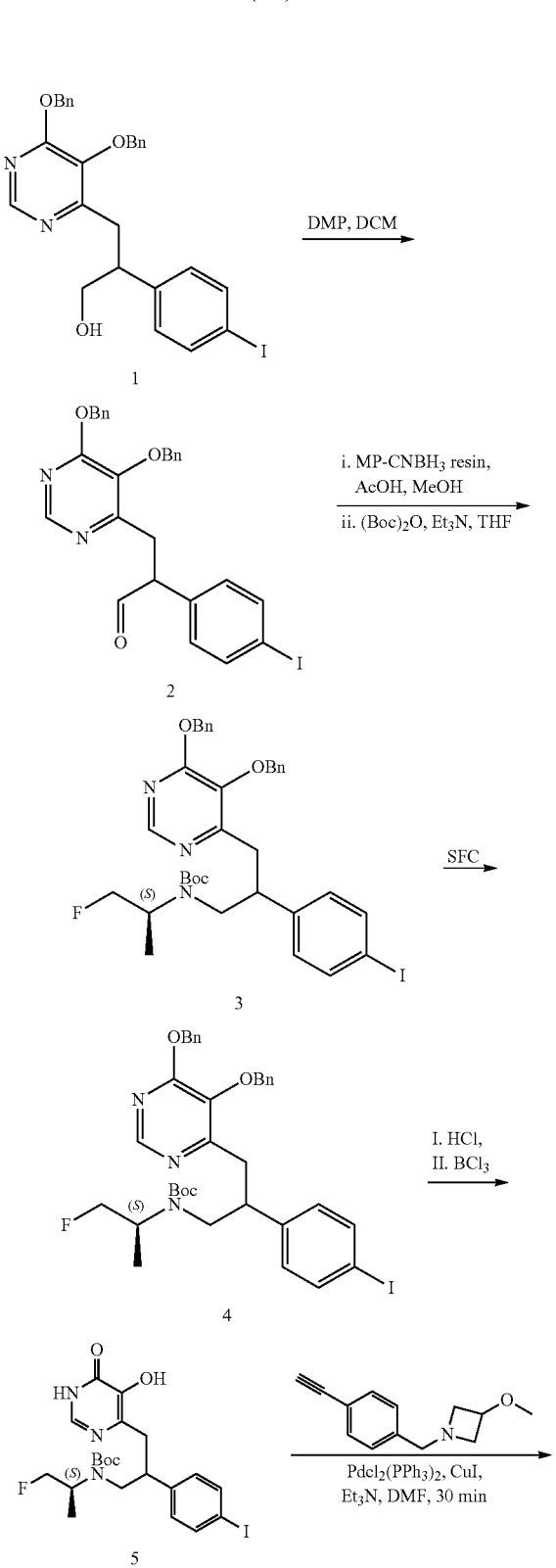

To a solution of 1 (1.7 g, 9.5 mmol) in Toluene (20 mL), 4-iodophenyl acetic acid (5 g, 19.1 mmol) and Et3N (5.34 mL, 38.3 (mmol) were added and heated the reaction mixture at 80° C. To this hot reaction mixture, solution of pivaloyl chloride (2.31 g, 19.1 mmol) in toluene (5 mL) was added and heated to 110° C. fax 2 h. After completion of the reaction, the reaction mixture was diluted with EtOAc and washed with 10% NaHCO3, water and brine solution. The organic layer was dried over Na2SO4, filtered and concentrated under reduced pressure. The crude product purified column chromatography on silica gel (230-400 mesh, 15-20% EtOAc in pet ether) to afford 2. Yield: 2.1 g, 77%. LC_MS=Calculated for C18H16INO3 is 421.23, Observed=Mass not ionized.

To a solution of 2 (2.0 g, 4.74 mmol) in THF (20 mL), was cooled −78° C. To this cooled reaction mixture, NaHMDS (1M in THF, 4.74 mL, 4.74 mmol)) was added slowly, followed by 4,5-bis(benzyloxy)-6-(iodomethyl)pyrimidine (2.05 g, 4.74 mmol) and stirred the reaction mixture for 1 h. After completion of the reaction, the reaction mixture was quenched with sat. NH4Cl. The layers were separated, organic layer was washed with brine solution and dried over Na2SO4, filtered, concentrated under reduced pressure. The crude product purified column chromatography on silica gel (230-400 mesh, 15-20% EtOAc in pet ether) to afford 3. Yield: 1.8 g, 52.3%, LC_MS=Calculated for C37H32IN3O5 is 725.58, Observed=726.1.

To a solution of 3 (1.8 g, 2.48 mmol) in a diethyl ether (10 mL) and EtOH (20 mL) was cooled 0° C., LiBH4 (2M in THF 12.4 mL, 12.4 mmol) was added and stirred for 30 min. After completion of the reaction, the reaction mixture was quenched with sat. NH4Cl solution and diluted with water. The reaction mixture was extracted with EtOAc (150 mL*2). The combined organic layers were dried over Na2SO4, filtered, concentrated under reduced pressure. The crude product was purified column chromatography on silica gel (230-400 mesh, 15-20% EtOAc in pet ether) to get 4 as off white solid. Yield: 0.9 g, 66.6%. LC_MS=Calculated for C27H25IN2O3 is 552.41, Observed=553.1.

-continued

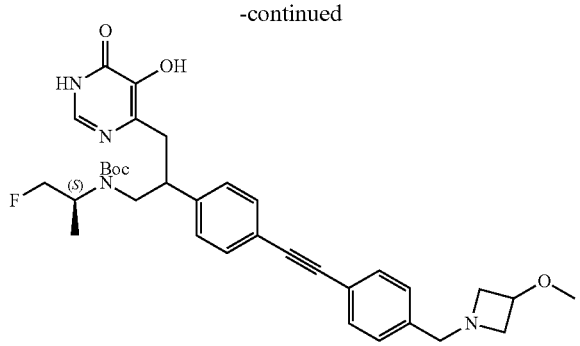

To a solution of 1 (120 g, 0.21 mol) in DCM (2.5 L), Dess-Martin periodinane (92 g, 0,434 mol) was added in portions al 0° C. for 20 min and stirred the reaction mixture for 2 h. After completion of the reaction, the reaction mixture was filtered on a Celite bed and the bed washed with DCM. The filtrate was washed with 10% NaHCO$_3$, water and brine solution. The organic layer was dried over Na$_2$SO$_4$, filtered and concentrated under reduced pressure. The crude product was passed through silica gel (230-400 mesh, 15-20% EtOAc in pet ether) to afford 2. Yield: (85 g, 66% pure), LC_MS=Calculated for C27H23IN2O3 is 550.40, Observed=551.0

To a solution of 2 (85 g, 0.154 mol) and (S)-1-fluoropropan-2-amine, hydrochloride (21 g, 0.185 mol) in MeOH (800 mL), was added AcOH (5 mL) and stirred the reaction mass for 12 h. Then MP-CNBH$_3$ resin (Loading 2.45 mmol/g, 64.1 g, 0.154 mol) was added and stirred the reaction mass for 1 h. After completion of the reaction, the resin was filtered and washed with 10 MeOH in DCM (200 mL) and the filtrate was concentrated. The obtained crude mass was dissolved in DCM and washed with 10% NaHCO$_3$ and brine solution. The organic layer was dried over Na$_2$SO$_4$, filtered, concentrated under reduced pressure to crude product.

To a solution of above crude product (65 g, 0.00116 mol) in THF (700 mL) under N$_2$, Et$_3$N (21.4 g, 0.212 mol) and Di-tert-butyl dicarbonate (46.3 g, 0.212 mol) were added and stirred at 25° C. for 12 h. Auer completion of the reaction, the reaction mixture was dissolved in water and extracted with EtOAc (2×500 mL). The combined organic layers were washed with brine, dried over Na$_2$SO$_4$, filtered and concentrated. The crude product was purified by column chromatography on silica gel (230-400 mesh, 15-50% EtOAc in Pet ether) to obtain racemic mixture 3, which was separated by chiral SFC purification to obtain 4a & 4b, Yield: (42 g, 58%), 4a: ISOMER-I: 17 g, 4b: ISOMER-II: 17 g, LC_MS=Calculated for C30H31FIN3O2 is 711.62, Observed=712.2

To a solution of 4b (17 g, 0,023 mol) in DCM (200 mL), 4 NHCl 1,4-dioxane (200 mL) was added and stirred the reaction mixture at 25° C. for 14 h. Then the reaction mixture was concentrated under reduced pressure. The crude product was dissolved in water and neutralized with 10% NaHCO$_3$ and extracted with EtOAC (500 mL×2). The combined organic layers were washed with brine solution and dried over Na2SO4, filtered and concentrated under reduced pressure.

The obtained compound was taken in DCM (100 mL), to this BCH (1M in DCM, 100 mL) was added and stirred the reaction mixture at 25° C. for 2 h. After completion of the reaction, the reaction mixture was carefully quenched with MeOH (100 mL) and stirred. After 10 min, the reaction mixture was concentrated under reduced pressure. The crude product was triturated with DCM and filtered the solid and dried to get pure 5 as a white solid. Yield: (10.5 g, 94%). LC_MS=Calculated for C16H19FIN3O2 is 431.25, Observed=432.1.

To a solution of 5 (10.5 g, 0.024 mol), 1-(4-ethynylbenzyl)-3-methoxyazetidine, (9.79 g, 0.048 mol) DMF (60 mL), Et$_3$N (33.9 mL, 0.243 mol) was added and degassed the reaction mixture under nitrogen for 10 min. Then PdCl$_2$(PPh$_3$)$_2$ (0.34 g, 0.00048 mol), CuI (0.27 g, 0.0014 mol) were added and the reaction mixture was stirred at 25° C. for 30 min. After completion of the reaction, the reaction mixture was filtered on celite bed and bed was washed with excess EtOAc. The filtrate was concentrated under reduced pressure and the crude product was purified by prep HPLC purification [YMC-ACTUS-TRIART C18 (250×30) mm, 5 μm; using ACN/water (A) and 0.1% HCOOH (B) flow rate=20 mL/min, λ=210 nm; using a stepwise gradient 8% to 20% (B) in 0-15 min and 100% at 16 min; t$_R$=14.7 min) fractions were lyophilized to get pure title compound as an off-white solid. Yield: (4.8 g, 39.3%). LC_MS=Calculated for C29H33FN4O3 is 504.61, Observed=505.3.

The compounds described herein were made according to organic synthesis analogous to those in Example 1, as well as other techniques known to those skilled in this art, starting from commercially available chemicals and/or from compounds described in the chemical literature. The LC-MS data for each compound is shown in Table 1.

II. Biological Evaluation

Example 1: In Vitro Assays to Screen Compounds and Metalloprotein Modulators Bacterial Susceptibility Testing Minimal inhibitory concentrations (MIC) were determined by the broth microdilution method in accordance with the Clinical and Laboratory Standards Institute (CLSI) guidelines. In brief, organism suspensions were adjusted to a 0.5 McFarland standard to yield a final inoculum between 3×10$^5$ and 7×10$^5$ colony-forming units (CFU)/mL. Drug dilutions and inocula were made in sterile, cation adjusted Mueller-Hinton Broth (Beckton Dickinson). An inoculum volume of 100 μL was added to wells containing 100 μL of broth with 2-fold serial dilutions of drug. All inoculated microdilution trays were incubated in ambient air at 35° C. for 18-24 h. Following incubation, the lowest concentration of the drug that prevented visible growth (OD600 nm<0.05) was recorded as the MIC. Performance of the assay was monitored by the use of laboratory quality-control strains and levofloxacin, a compound with a defined MIC spectrum, in accordance with CLSI guidelines.

Exemplary in vitro assay data against select bacteria for compounds in embodiments of the disclosure is provided in Table 2.

TABLE 2

| Compound No. | E. coli MIC | K. pneumonitie MIC |
|---|---|---|
| 1 | B | B |
| 2 | A | A |
| 3 | A | A |
| 4 | A | A |
| 5 | B | B |
| 6 | B | D |
| 7 | B | B |
| 8 | A | B |
| 9 | B | C |

TABLE 2-continued

| Compound No. | E. coli MIC | K. pneumonitie MIC |
|---|---|---|
| 10 | A | B |
| 11 | A | B |
| 12 | B | B |
| 14 | A | A |
| 15 | A | A |
| 16 | A | B |
| 11 | A | A |
| 18 | B | D |
| 19 | A | B |
| 20 | A | B |
| 21 | B | B |
| 22 | A | B |
| 23 | A | B |
| 24 | A | B |
| 25 | B | B |
| 26 | B | D |
| 27 | B | B |
| 28 | B | D |
| 29 | A | B |
| 30 | B | C |
| 31 | A | B |
| 32 | A | B |
| 33 | A | A |
| 34 | A | B |
| 35 | A | A |
| 36 | A | B |
| 37 | A | B |
| 38 | A | B |
| 39 | A | B |
| 40 | B | C |
| 41 | B | B |
| 42 | A | B |
| 43 | A | B |
| 44 | A | B |
| 45 | B | C |
| 46 | A | B |
| 47 | B | B |
| 48 | A | B |
| 49 | A | B |
| 50 | B | B |
| 51 | B | C |
| 52 | B | C |
| 53 | B | C |
| 54 | B | B |
| 55 | B | D |
| 56 | B | C |
| 57 | B | C |
| 58 | B | D |
| 59 | B | C |
| 60 | B | C |
| 61 | B | D |
| 62 | B | D |
| 63 | B | D |
| 64 | B | C |
| 65 | A | B |
| 66 | A | B |
| 67 | A | B |
| 68 | A | A |
| 69 | A | C |
| 70 | A | A |
| 71 | A | A |
| 72 | A | B |
| 73 | A | A |
| 74 | A | A |
| 75 | A | A |
| 76 | A | B |
| 77 | B | C |
| 78 | B | B |
| 79 | A | B |
| 80 | A | A |
| 81 | A | A |
| 82 | A | A |
| 83 | A | A |
| 84 | A | B |
| 85 | A | B |
| 86 | A | B |
| 87 | B | C |

TABLE 2-continued

| Compound No. | E. coli MIC | K. pneumonitie MIC |
|---|---|---|
| 89 | A | B |
| 90 | A | B |
| 91 | A | A |
| 92 | A | A |
| 93 | A | A |
| 94 | A | B |
| 95 | A | B |
| 96 | A | A |
| 97 | A | B |
| 98 | A | B |
| 99 | A | A |
| 100 | A | A |
| 101 | A | B |
| 102 | A | A |
| 103 | A | B |
| 104 | A | A |
| 105 | A | A |
| 106 | B | C |
| 107 | A | A |
| 108 | A | B |
| 109 | A | B |
| 110 | A | B |
| 111 | A | B |
| 112 | A | B |
| 113 | B | C |
| 114 | B | B |
| 115 | A | A |
| 116 | B | B |
| 117 | A | A |
| 118 | A | B |
| 110 | A | B |
| 120 | B | D |
| 121 | B | C |
| 122 | A | B |
| 123 | A | B |
| 124 | B | B |
| 175 | B | D |
| 126 | B | C |
| 127 | B | B |
| 128 | B | C |
| 129 | B | C |
| 130 | B | C |
| 131 | B | B |
| 132 | A | B |
| 133 | A | A |
| 134 | C | D |
| 135 | B | C |
| 136 | D | D |
| 137 | B | C |
| 138 | B | B |
| 139 | A | A |
| 140 | A | B |
| 141 | A | B |
| 142 | A | A |
| 143 | A | B |
| 144 | B | C |
| 145 | B | C |
| 146 | B | C |
| 147 | B | B |
| 148 | B | C |
| 149 | B | C |
| 150 | B | C |
| 151 | B | C |
| 152 | A | B |
| 153 | A | B |
| 154 | C | D |
| 155 | B | D |
| 156 | D | D |
| 157 | B | B |
| 158 | B | B |
| 159 | A | B |
| 160 | A | B |
| 162 | B | C |
| 163 | A | B |
| 164 | B | C |
| 165 | B | B |
| 166 | A | B |

TABLE 2-continued

| Compound No. | E. coli MIC | K. pneumonitie MIC |
|---|---|---|
| 167 | A | B |
| 168 | B | D |
| 169 | A | B |
| 170 | B | D |
| 171 | A | B |
| 172 | A | A |
| 173 | A | B |
| 174 | A | B |
| 175 | B | C |
| 176 | A | B |
| 177 | A | C |
| 178 | B | B |
| 179 | B | B |
| 180 | C | C |
| 181 | B | A |
| 182 | B | C |
| 183 | A | B |
| 184 | B | C |
| 185 | B | C |
| 186 | A | B |
| 187 | A | B |
| 188 | A | B |
| 189 | A | B |
| 190 | A | A |
| 191 | A | B |
| 192 | B | C |
| 193 | B | C |
| 194 | B | C |
| 195 | B | C |
| 196 | B | D |
| 197 | C | D |
| 198 | C | D |
| 199 | B | C |
| 200 | B | D |
| 201 | B | D |
| 202 | B | D |
| 203 | B | D |
| 204 | C | D |
| 205 | B | D |
| 206 | B | C |
| 207 | B | C |
| 208 | B | D |
| 209 | B | D |
| 210 | B | C |
| 211 | C | D |
| 212 | D | D |
| 214 | C | D |
| 215 | A | A |
| 216 | A | A |
| 217 | A | A |
| 218 | A | B |
| 219 | A | B |
| 220 | A | A |
| 221 | A | B |
| 222 | A | A |
| 223 | A | A |
| 224 | B | C |
| 225 | A | B |
| 226 | A | B |
| 227 | B | D |
| 228 | A | A |
| 229 | B | D |
| 230 | A | B |
| 231 | A | B |
| 232 | A | B |
| 233 | B | C |
| 234 | A | B |
| 235 | A | B |
| 236 | A | A |
| 237 | A | A |
| 238 | A | A |
| 239 | A | A |
| 240 | A | B |
| 241 | B | C |
| 242 | A | B |
| 243 | A | B |
| 244 | B | C |
| 245 | A | B |
| 246 | B | C |
| 247 | B | C |
| 248 | A | B |
| 249 | B | B |
| 250 | A | B |
| 251 | A | B |
| 252 | A | B |
| 753 | B | D |
| 254 | A | B |
| 755 | A | B |
| 256 | A | C |
| 257 | B | B |
| 258 | B | C |
| 259 | B | D |
| 260 | B | C |
| 261 | B | D |
| 262 | C | D |
| 263 | D | D |
| 264 | D | D |
| 265 | A | C |
| 266 | B | C |
| 267 | B | C |
| 268 | B | C |
| 269 | B | B |
| 270 | B | B |
| 271 | A | B |
| 273 | A | B |
| 275 | A | B |
| 276 | B | B |
| 277 | A | B |
| 278 | A | A |
| 279 | A | B |
| 280 | A | A |
| 281 | A | B |
| 282 | A | B |
| 283 | A | B |
| 285 | A | A |
| 287 | B | C |
| 288 | B | C |
| 289 | A | A |
| 292 | B | C |
| 293 | A | B |
| 294 | A | A |
| 295 | A | A |
| 296 | C | D |
| 297 | C | D |
| 298 | D | D |
| 299 | A | B |
| 300 | A | A |
| 301 | A | A |
| 302 | A | A |
| 303 | A | B |
| 304 | A | B |
| 305 | A | A |

Note:
Microbiological activity data are designated within the following ranges:
A: ≤1 μg/mL
B: >1 μg/mL to ≤8.0 μg/mL
C: >8.0 μg/mL to ≤32 μg/mL
D: >32 μg/mL LpxC Binding Assay $IC_{50}$ values against *E. coli* LpxC were determined using a Rapid Fire MS assay as previously described J. Med. Chem. 2012, 55, 1662-1670.

Table 3. Exemplary in vitro assay data against *E. coli* LpxC for compounds in embodiments of the disclosure.

TABLE 3

| Compound No. | E. coli LpxC IC$_{50}$ |
|---|---|
| 7 | A |
| 14 | B |
| 17 | A |
| 19 | D |
| 20 | A |
| 23 | B |
| 38 | A |
| 43 | B |
| 44 | B |
| 54 | B |
| 56 | B |
| 57 | B |
| 60 | B |
| 61 | C |
| 62 | D |
| 63 | D |
| 64 | B |
| 65 | A |
| 68 | B |
| 71 | B |
| 101 | B |
| 130 | A |
| 135 | D |
| 138 | B |
| 139 | A |
| 141 | A |
| 145 | D |
| 148 | B |
| 149 | D |
| 169 | A |
| 171 | A |
| 172 | A |
| 173 | B |
| 174 | B |
| 177 | B |
| 191 | A |
| 192 | B |
| 193 | A |
| 194 | B |
| 199 | B |
| 200 | D |
| 201 | B |
| 202 | B |
| 203 | D |
| 205 | D |
| 206 | D |
| 208 | C |
| 209 | B |
| 210 | B |
| 211 | B |
| 212 | D |
| 240 | A |
| 241 | B |
| 242 | B |
| 287 | B |
| 288 | B |
| 289 | A |
| 296 | B |
| 297 | B |
| 298 | D |
| 299 | A |

Note:
IC$_{50}$ data are designated within ranges the following
A: ≤10 nM
B: >10 nM to ≤50 nM
C: >50 nM to ≤100 M
D: >100 nM to 1 μM

III. Preparation of Pharmaceutical Dosage Forms

Example 1: Oral Capsule

The active ingredient is a compound of Formula (I), or a pharmaceutically acceptable salt, solvate, or prodrug thereof. A capsule for oral administration is prepared by mixing 1-1000 mg of active ingredient with starch or other suitable powder blend. The mixture is incorporated into an oral dosage unit such as a hard gelatin capsule, which is suitable for oral administration.

We claim:

1. A compound having the structure of Formula (II):

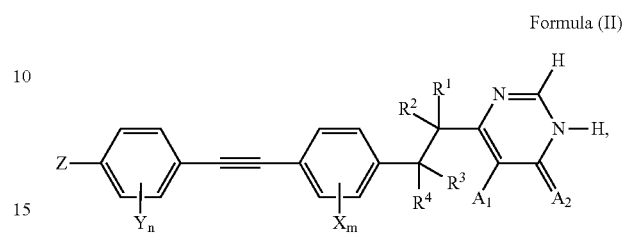

Formula (II)

or a pharmaceutically acceptable salt, or solvate thereof, wherein, n is 0-4;

m is 0-4;

$A_1$ is OH or SH;

$A_2$ is O or S;

$R^1$ and $R^2$ are each independently H or optionally substituted alkyl;

or $R^1$ and $R^2$ are taken together with the carbon to which they are attached to form =$C(R^{11})_2$, =$NR^{11}$, =O, or =S;

or $R^1$ and $R^2$ are taken together with the carbon to which they are attached to form an optionally substituted 3- to 6-membered carbocyclyl or optionally substituted 4- to 7-membered heterocyclyl containing 1 or 2 heteroatoms selected from O, N, and S;

$R^3$ is optionally substituted alkyl, optionally substituted carbocyclyl, optionally substituted carbocyclylalkyl, optionally substituted aryl, optionally substituted aralkyl, optionally substituted heteroaryl, optionally substituted heteroaralkyl, optionally substituted heterocyclyl, optionally substituted heterocyclylalkyl, optionally substituted ($C_0$-$C_4$ alkylene)-$COR^{11}$, optionally substituted ($C_0$-$C_4$ alkylene)-$CO_2R^{11}$, optionally substituted ($C_0$-$C_4$ alkylene)-$CON(R^{11})_2$, optionally substituted ($C_0$-$C_4$ alkylene)-CN, optionally substituted ($C_0$-$C_4$ alkylene)-$OR^{11}$, optionally substituted ($C_0$-$C_4$ alkylene)-$N(R^{11})_2$, optionally substituted ($C_0$-$C_4$ alkylene)-$N(R^{12})$—$COR^{11}$, optionally substituted ($C_0$-$C_4$ alkylene)-$N(R^{12})$—$CO_2R^{11}$, optionally substituted ($C_0$-$C_4$ alkylene)-$N(R^{12})$—$CON(R^{11})_2$, optionally substituted ($C_0$-$C_4$ alkylene)-$N(R^{12})$—$SO_2N(R^{11})_2$, optionally substituted ($C_0$-$C_4$ alkylene)-O—$SO_2N(R^{11})_2$, optionally substituted ($C_0$-$C_4$ alkylene)-$N(R^{11})$—PO (optionally substituted $C_1$-$C_4$ alkyl)$_2$, optionally substituted ($C_0$-$C_4$ alkylene)-$SO_2R^{11}$, optionally substituted ($C_0$-$C_4$ alkylene)-O—$SO_2R^{11}$, optionally substituted ($C_0$-$C_4$ alkylene)-$N(R^{12})$—$SO_2R^{11}$, optionally substituted ($C_0$-$C_4$ alkylene)-C(=N—$OR^{11}$)($R^{11}$), or optionally substituted ($C_0$-$C_4$ alkylene)-OP(=O)($OR^{11}$)$_2$;

$R^4$ is H or optionally substituted alkyl;

or $R^3$ and $R^4$ are taken together with the carbon to which they are attached to form =$C(R^{11})_2$, =$NR^{11}$, =O, or =S;

or $R^3$ and $R^4$ are taken together with the carbon to which they are attached to form an optionally substituted 3- to 6-membered carbocyclyl or optionally substituted 4- to 7-membered heterocyclyl containing 1 or 2 heteroatoms selected from O, N, and S;

R⁵ is H, halogen, optionally substituted alkyl, hydroxyl, alkoxyl, cyano, amino, or nitro;

each X and Y is independently H, optionally substituted alkyl, halo, fluoroalkyl, cyano, nitro, —N(R¹³)₂, or —OR¹³;

or R³ and one X are taken together with the intervening atoms to form an optionally substituted 5- to 7-membered carbocyclyl or optionally substituted 5- to 7-membered heterocyclyl containing 1 or 2 heteroatoms selected from O, N, and S;

Z is H, halo, nitro, or -L-G;

L is a bond or optionally substituted C₁-C₄ alkylene;

G is optionally substituted alkyl, optionally substituted alkenyl, optionally substituted alkynyl, optionally substituted carbocyclyl, optionally substituted aryl, optionally substituted heteroaryl, —CN, —N(R¹³)₂, —OR¹³, —COR¹³, —CO₂R¹³, —CON(R¹³)₂, —N(R¹⁴)—COR¹³, —SO₂R¹³—, —SO₂N(R¹³)₂, —N(R¹⁴)—SO₂R¹³, —N(R¹⁴)—CON(R¹³)₂, —N(R¹⁴)—CO₂R¹³, —O—CON(R¹³)₂—, —N(R¹⁴)—SO₂N(R¹³)₂, —O—SO₂N(R¹³)₂, —N(R¹⁴)—SO₂—OR¹³, or —C(=N—OR¹⁴)(R¹³);

each R¹¹ is independently H, optionally substituted alkyl, optionally substituted alkenyl, optionally substituted alkynyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl;

or two R¹¹ on the same nitrogen atom are taken together with the nitrogen to which they are attached to form an optionally substituted N-heterocyclyl;

each R¹² is independently H, optionally substituted alkyl, optionally substituted carbocyclyl, optionally substituted carbocyclylalkyl, optionally substituted heterocyclyl, or optionally substituted heterocyclylalkyl;

each R¹³ is H, optionally substituted alkyl, optionally substituted alkenyl, optionally substituted alkynyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl; and each R¹⁴ is independently H, optionally substituted alkyl, optionally substituted carbocyclyl, optionally substituted carbocyclylalkyl, optionally substituted heterocyclyl, or optionally substituted heterocyclylalkyl;

wherein each carbocyclyl is a stable non-aromatic monocyclic, fused polycyclic, or bridged polycyclic hydrocarbon ring comprising from three to ten carbon atoms;

each heterocyclyl is a stable 3- to 18-membered non-aromatic monocyclic, fused bicyclic, bridged bicyclic, or spirocyclic bicyclic ring system comprising from two to twelve carbon atoms and from one to six heteroatoms selected from nitrogen, oxygen, and sulfur which is optionally oxidized; and each heterocyclylalkyl is a —R$^c$— heterocyclyl, where R$^c$ is a C₁-C₈ alkylene.

2. The compound of claim 1, or a pharmaceutically acceptable salt or solvate thereof, wherein:
each X and Y is independently H, optionally substituted alkyl, halo, or cyano.

3. The compound of claim 1, or a pharmaceutically acceptable salt or solvate thereof, wherein:
each X and Y is independently H, F, or Cl.

4. The compound of claim 1, or a pharmaceutically acceptable salt or solvate thereof, wherein:
n is 0 or 1; and
m is 0 or 1.

5. The compound of claim 1, or a pharmaceutically acceptable salt or solvate thereof, wherein:
A₁ is OH; and
A₂ is O.

6. The compound of claim 1, or a pharmaceutically acceptable salt or solvate thereof, wherein:
R¹ is H;
R² is H;
R⁴ is H; and
R⁵ is H.

7. The compound of claim 1, or a pharmaceutically acceptable salt or solvate thereof, wherein the compound has the structure of Formula (IV):

Formula (IV)

8. The compound of claim 7, or a pharmaceutically acceptable salt or solvate thereof, wherein the compound has the structure of Formula (IVa) or Formula (IVb):

Formula (IVa)

Formula (IVb)

9. The compound of claim 1, or a pharmaceutically acceptable salt or solvate thereof, wherein:
R³ is optionally substituted alkyl, optionally substituted (C₀-C₄ alkylene)-CO₂R¹¹, optionally substituted (C₀-C₄ alkylene)-CON(R¹¹)₂, optionally substituted (C₀-C₄ alkylene)-OR¹¹, optionally substituted (C₀-C₄ alkylene)-N(R¹¹)₂, or optionally substituted (C₀-C₄ alkylene)-N(R¹²)—SO₂R¹¹.

10. The compound of claim 9, or a pharmaceutically acceptable salt or solvate thereof, wherein:
R³ is an unsubstituted alkyl, —CO₂R¹¹, —CON(R¹¹)₂, optionally substituted (C₀-C₄ alkylene)-OR¹¹, optionally substituted (C₀-C₄ alkylene)-N(R¹¹)₂, or optionally substituted (C₀-C₄ alkylene)-N(R¹²)—SO₂R¹¹.

11. The compound of claim 1, or a pharmaceutically acceptable salt or solvate thereof, wherein:

each R¹¹ is H, optionally substituted alkyl, optionally substituted carbocyclyl, optionally substituted heterocyclyl, or optionally substituted heteroarylalkyl; wherein each R¹¹ is independently unsubstituted or substituted with halogen, —CN, —R$^b$—OR$^a$, —R$^b$—C(O)R$^a$, or —R$^b$—S(O)$_t$R$^a$; wherein t is 1 or 2; each R$^a$ is independently hydrogen or alkyl which is optionally substituted with halogen, hydroxy, methoxy, or trifluoromethyl; and each R$^b$ is independently a direct bond or a straight or branched alkylene; or two R¹¹ groups are joined with the nitrogen to which they are attached join to form an optionally substituted N-heterocyclyl which is optionally substituted with halogen, oxo, —CN, or —R$^b$—OR$^a$; wherein each R$^a$ is independently hydrogen or alkyl which is optionally substituted with halogen, hydroxy, methoxy, or trifluoromethyl; and each R$^b$ is independently a direct bond or a straight or branched alkylene; and each R¹² is independently H or unsubstituted alkyl.

12. The compound of claim 11, or a pharmaceutically acceptable salt or solvate thereof, wherein:
each R¹¹ is independently unsubstituted or substituted with —F, —Cl, —CN, —OH, —OMe, —SO₂Me, or —C(O)Me; or
two R¹¹ groups are joined with the nitrogen to which they are attached join to form an N-heterocyclyl which is unsubstituted or substituted with —CN, —OH, or —OMe.

13. The compound of claim 1, or a pharmaceutically acceptable salt or solvate thereof, wherein:
Z is H or -L-G;
L is a bond or optionally substituted C₁-C₂ alkylene;
G is optionally substituted alkyl, optionally substituted carbocyclyl, optionally substituted aryl, optionally substituted heteroaryl, —N(R¹³)₂, —OR¹³, —CN, —COR¹³, —CO₂R¹³, —CON(R¹³)₂, —N(R¹⁴)—COR¹³, —SO₂R¹³, —SO₂N(R¹³)₂, or —N(R¹⁴)—SO₂R¹³; wherein G is unsubstituted or substituted with alkyl, —R$^b$—OR$^a$, —R$^b$—N(R$^a$)₂, —R$^b$—C(O)R$^a$, —R$^b$—CN, or —R$^b$—N(R$^a$)C(O)R$^a$;
each R¹³ is independently H, optionally substituted alkyl, optionally substituted carbocyclyl, optionally substituted carbocyclylalkyl, optionally substituted heterocyclyl, or optionally substituted heterocyclylalkyl; each of which is independently unsubstituted or substituted with —R$^b$—OR$^a$, —R$^b$—C(O)OR$^a$, or —R$^b$—C(O)R$^a$;
each R$^a$ is independently hydrogen, alkyl which is optionally substituted with halogen, hydroxy, methoxy, or trifluoromethyl, or carbocyclyl which is optionally substituted with halogen, hydroxy, methoxy, or trifluoromethyl;
each R$^b$ is independently a direct bond or a straight or branched alkylene; and
each R¹⁴ is independently H, unsubstituted alkyl, or unsubstituted heterocyclyl.

14. The compound of claim 1, or a pharmaceutically acceptable salt or solvate thereof, wherein:
Z is -L-G;
L is —CH₂—;
G is optionally substituted alkyl, optionally substituted heteroaryl, —N(R¹³)₂, —OR¹³, —CON(R¹³)₂, or —N(R¹⁴)—COR¹³; wherein G is unsubstituted or substituted with methyl, —OMe, —CH₂OH, —NH₂, —CH₂NH₂, —C(O)CH₂OH, —CN, —CH₂CN, —CH₂NHC(O)CH₂OH;

each R¹³ is independently H, optionally substituted alkyl, optionally substituted carbocyclyl, optionally substituted carbocyclylalkyl, optionally substituted heterocyclyl, or optionally substituted heterocyclylalkyl; wherein each R¹³ is independently unsubstituted or substituted with —OH, —OMe, —C(O)CH₂OH, —CH₂C(O)OH, —C(O)OH, —C(O)-cyclopropyl; and
each R¹⁴ is independently H, unsubstituted alkyl, or unsubstituted heterocyclyl.

15. The compound of claim 1, or a pharmaceutically acceptable salt or solvate thereof, wherein:
G is —N(R¹³)₂.

16. The compound of claim 1, or a pharmaceutically acceptable salt or solvate thereof, wherein:
n is 0;
m is 0;
R³ is

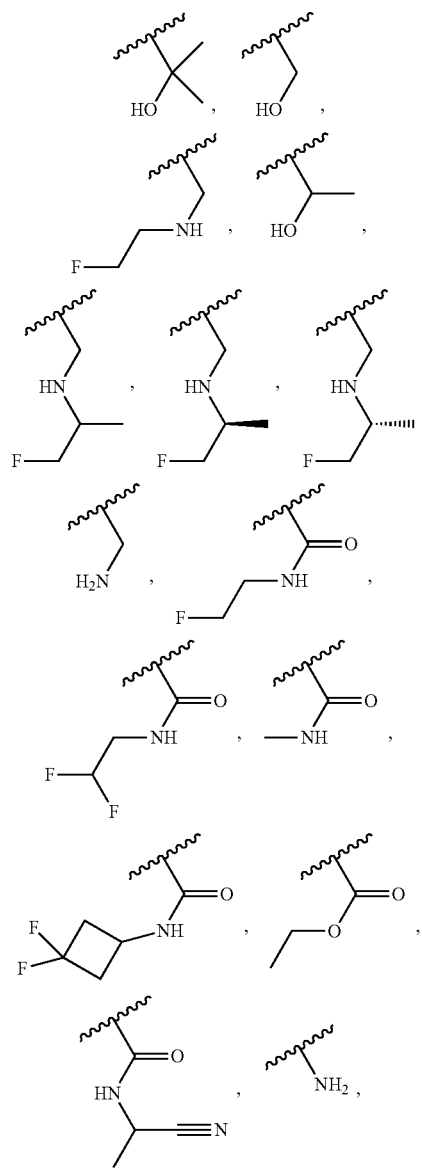

227
-continued
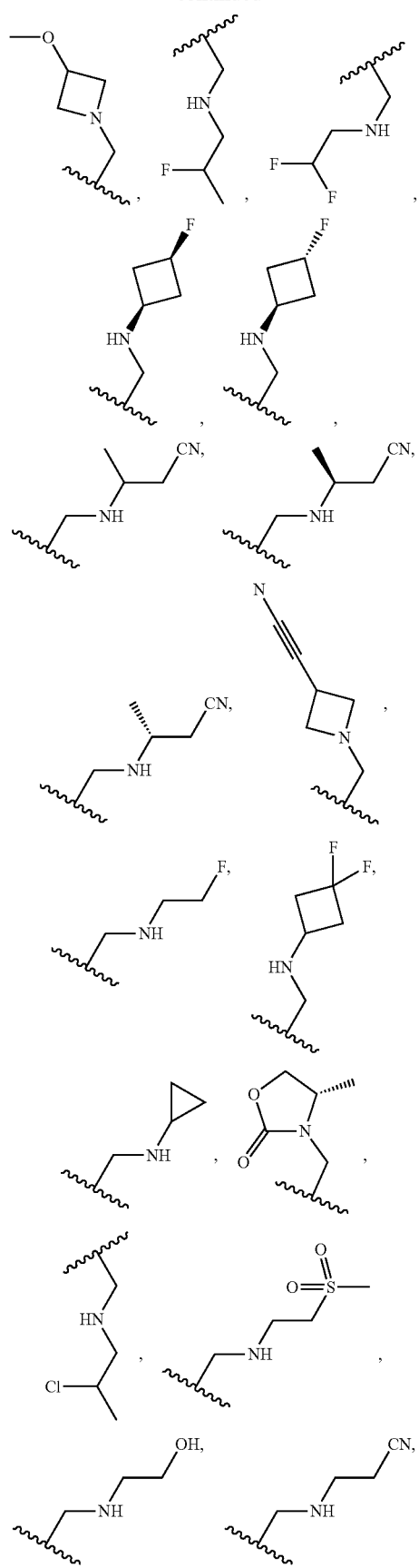
228
-continued
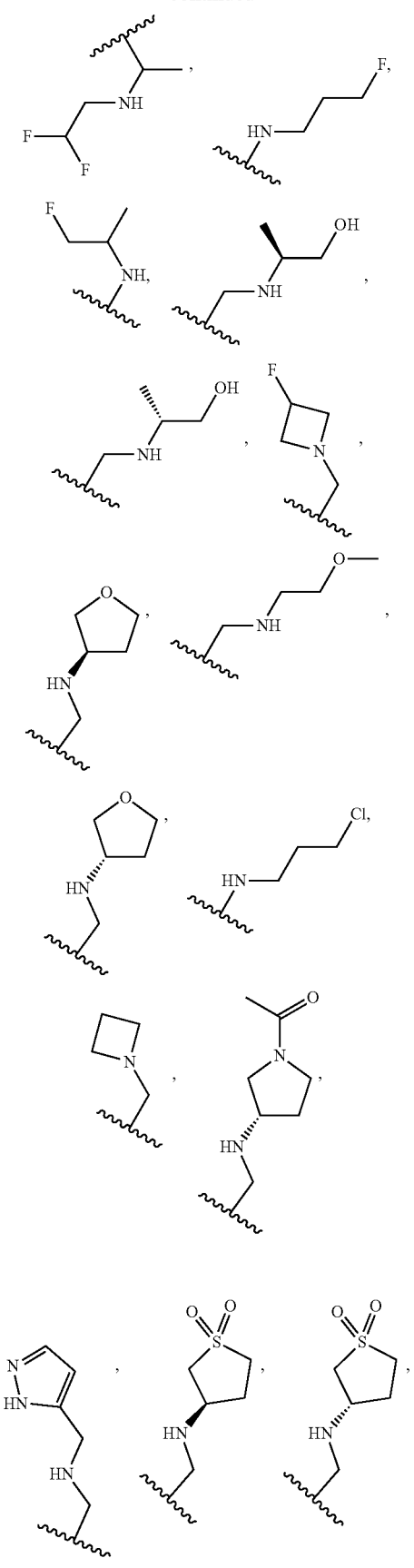

229
-continued
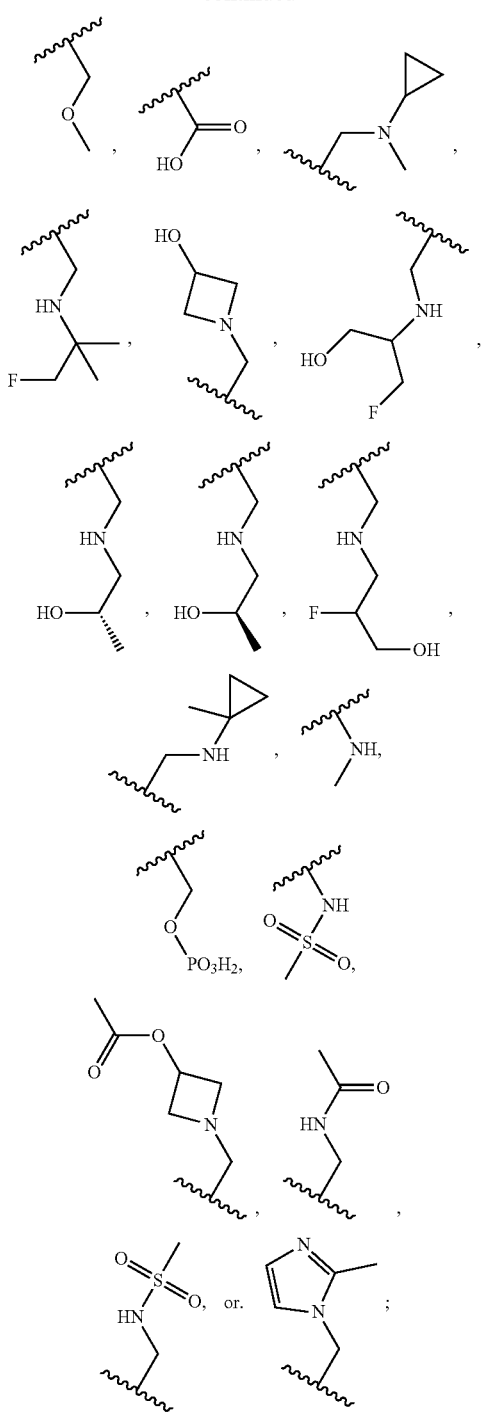
and
Z is
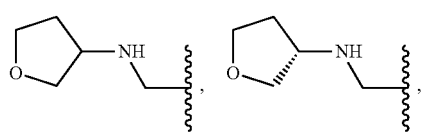
230
-continued
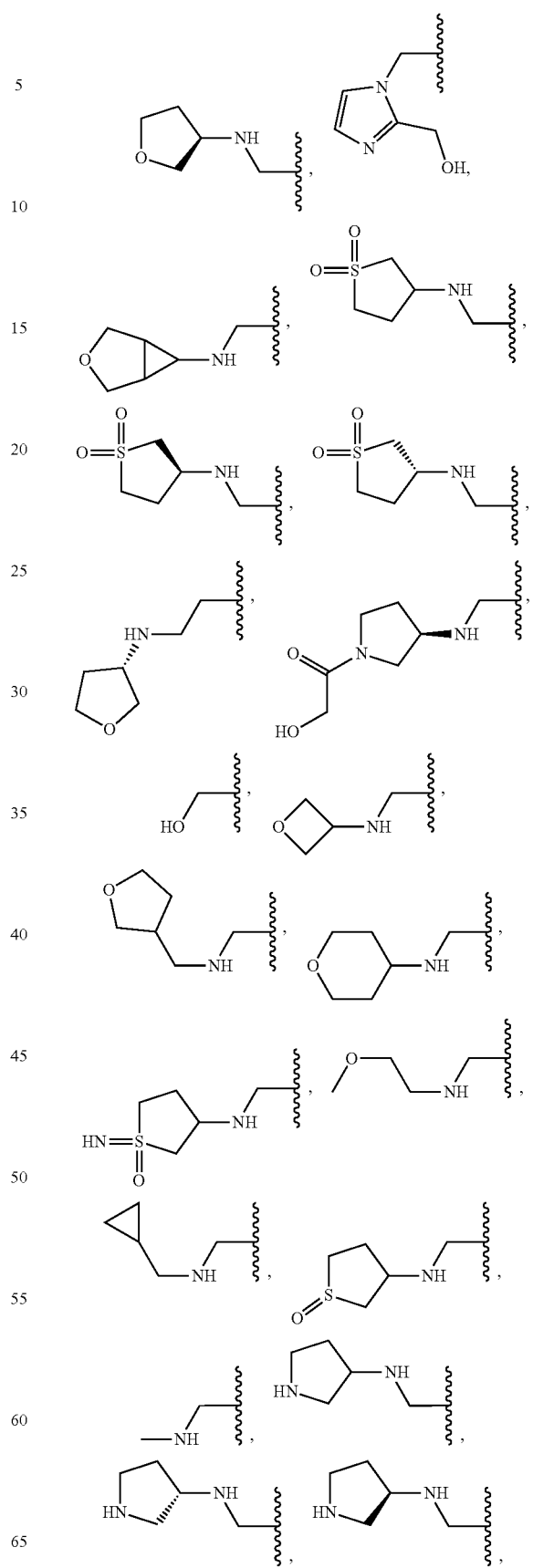

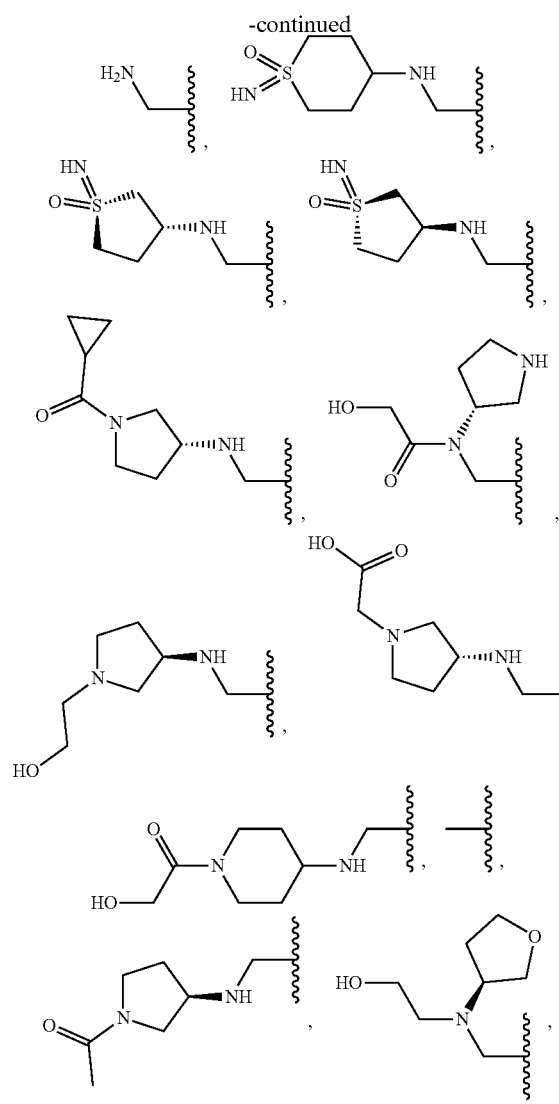
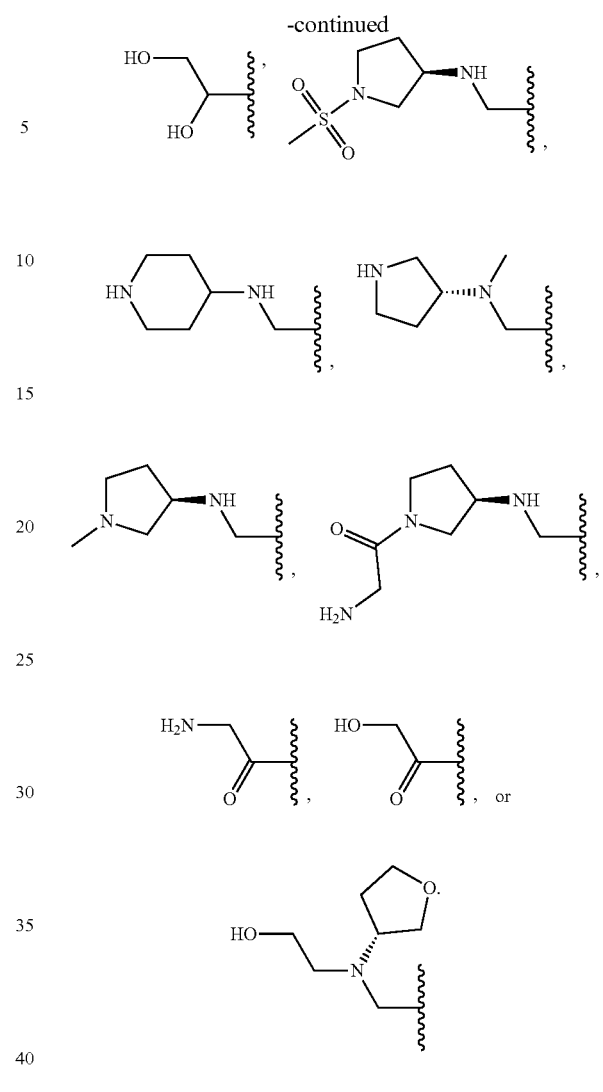
17. The compound of claim 1, selected from:
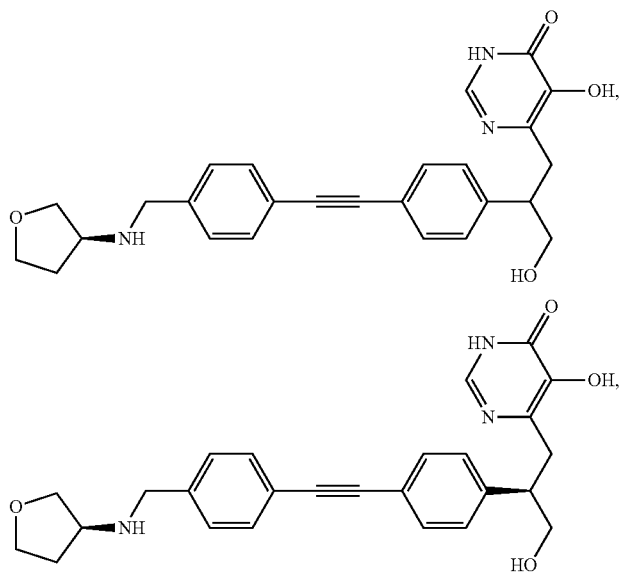

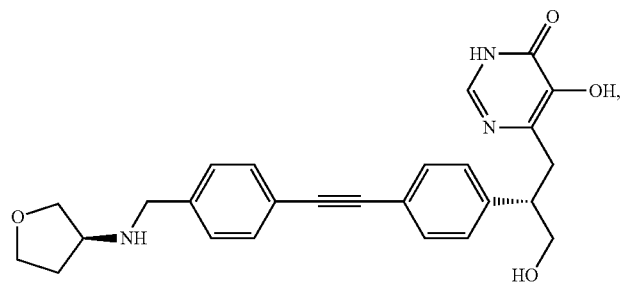
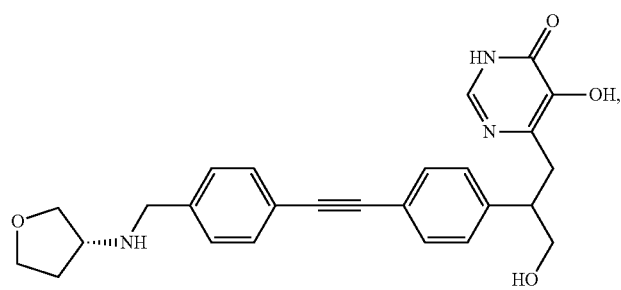
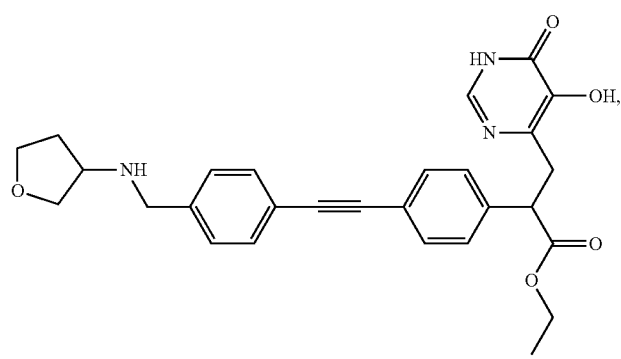
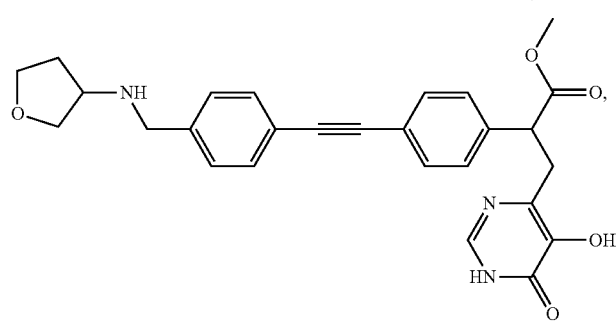
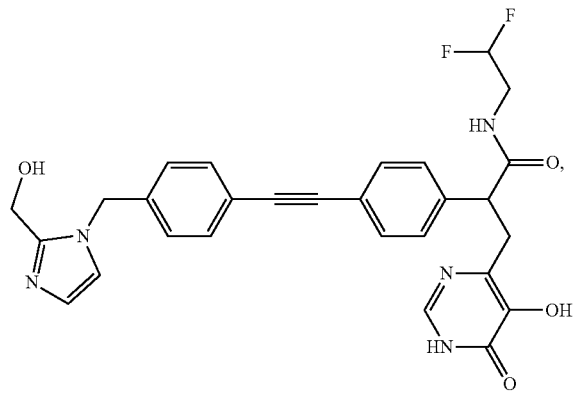

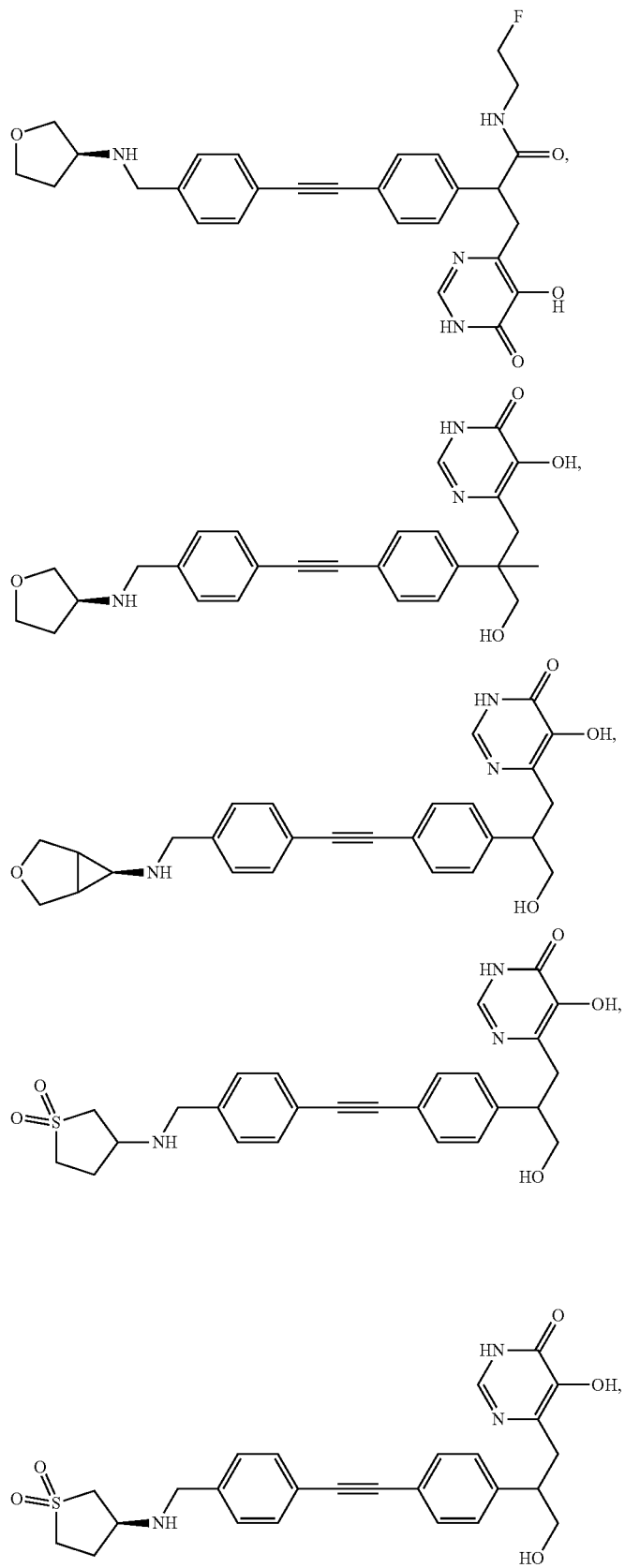

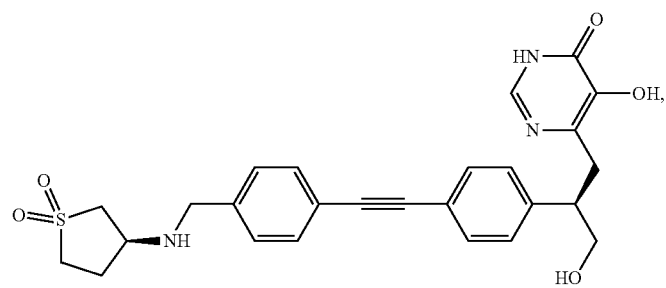
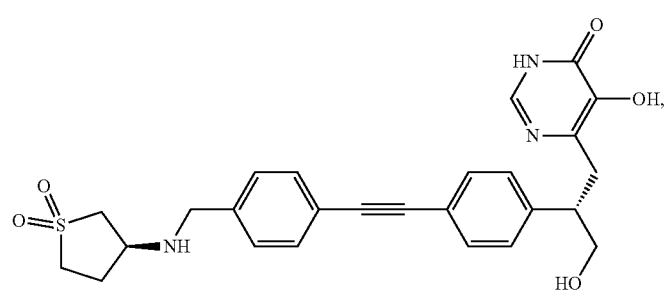
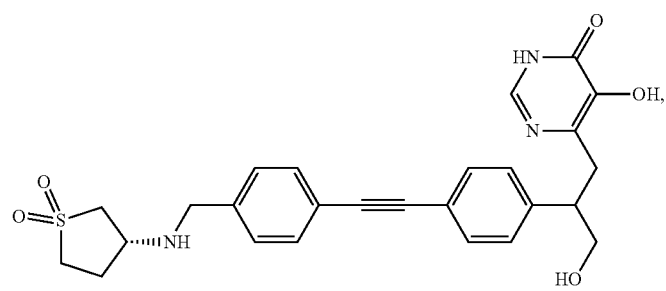
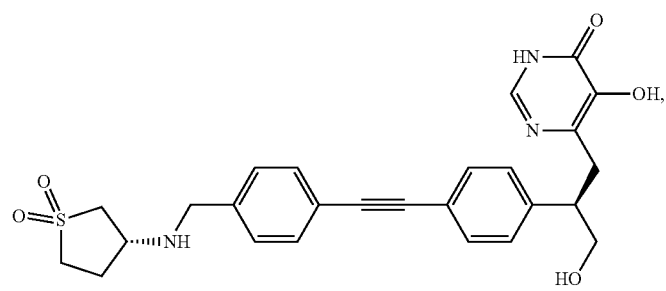
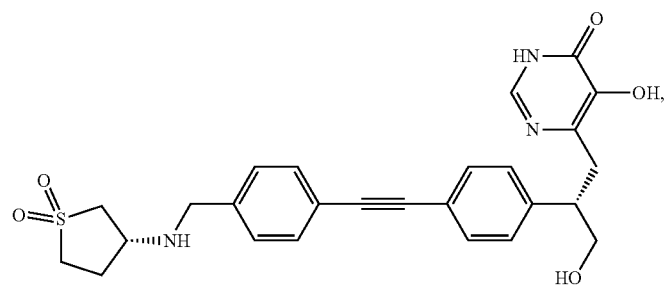

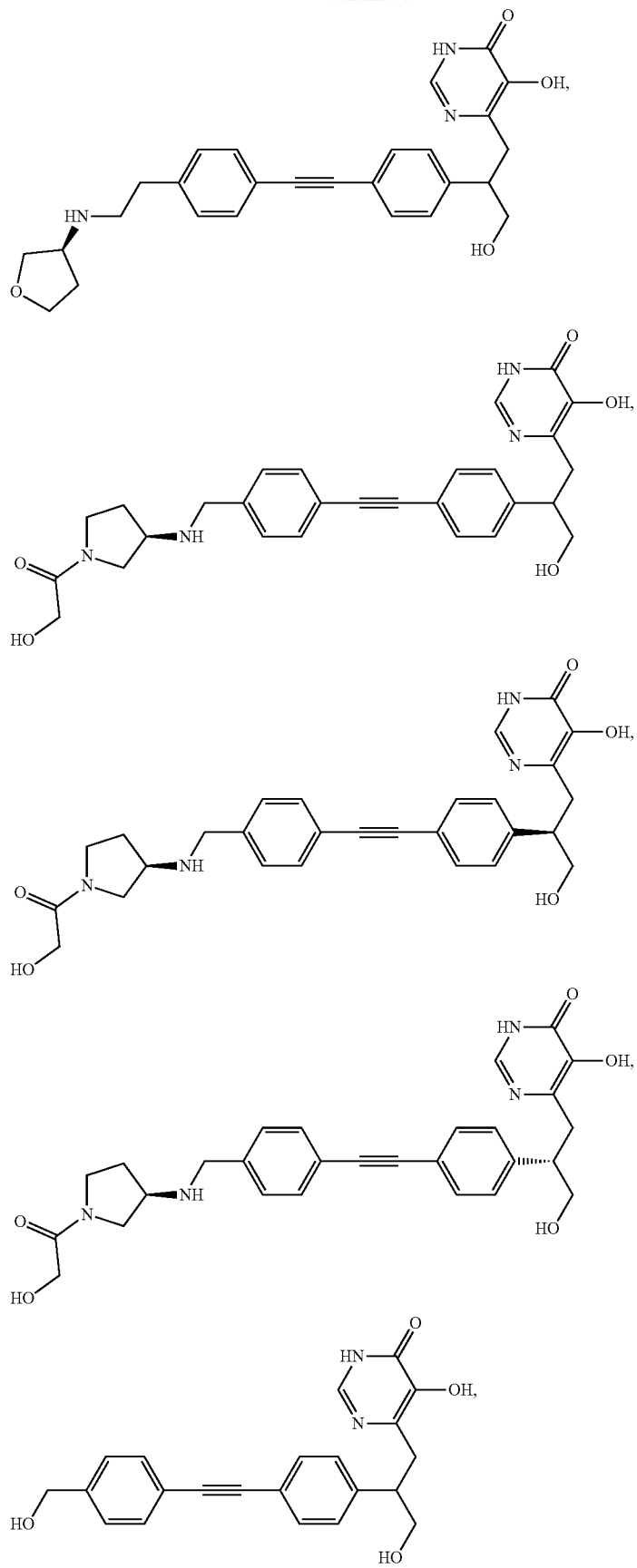

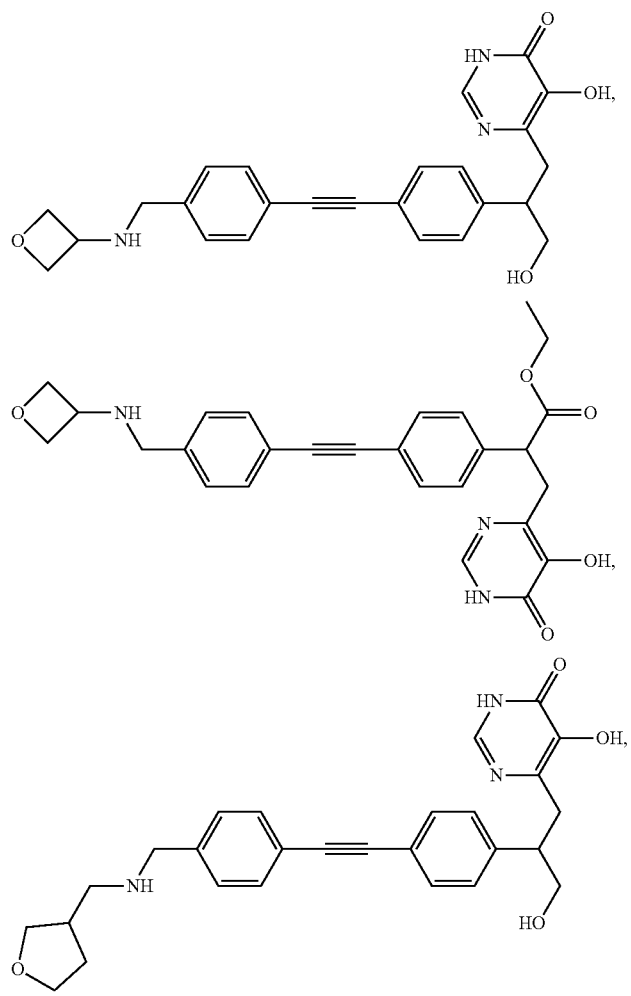
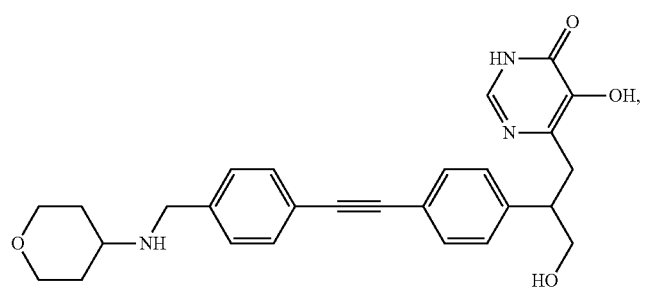
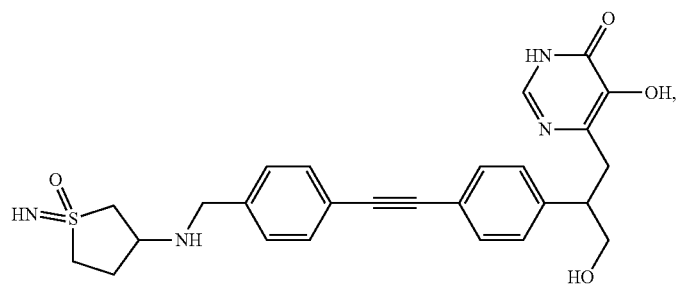

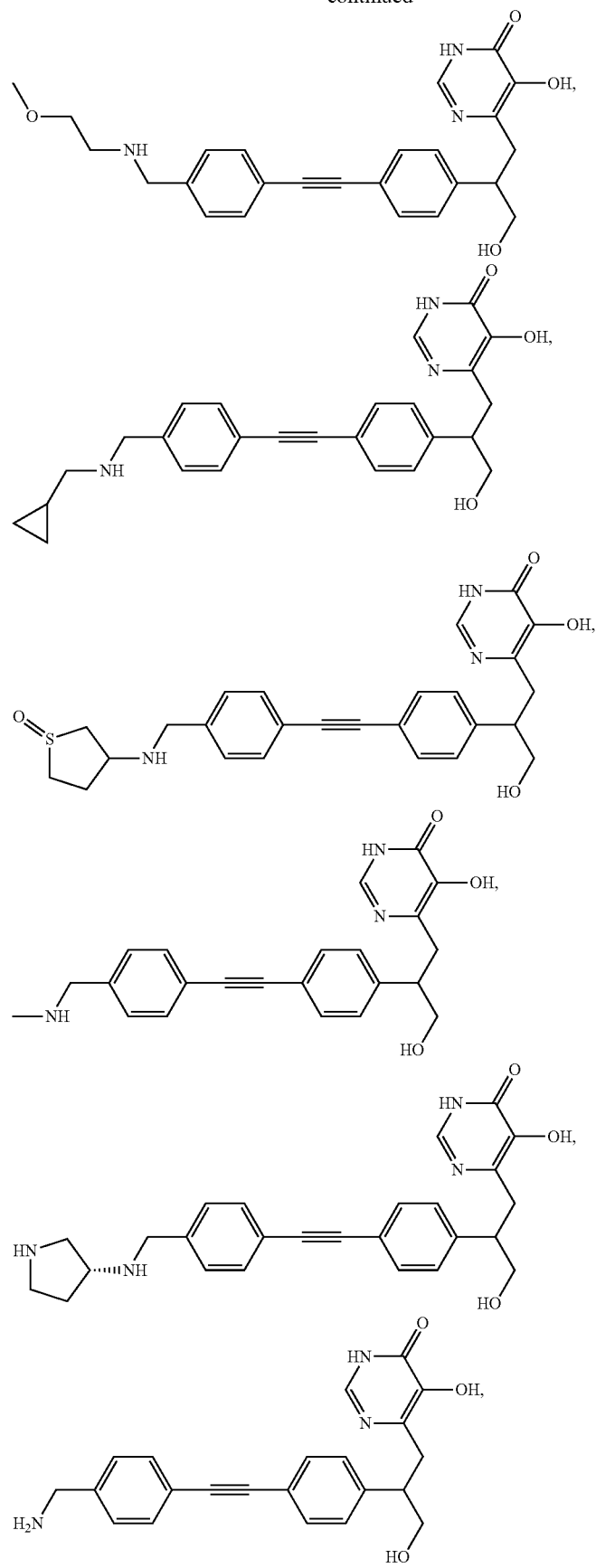

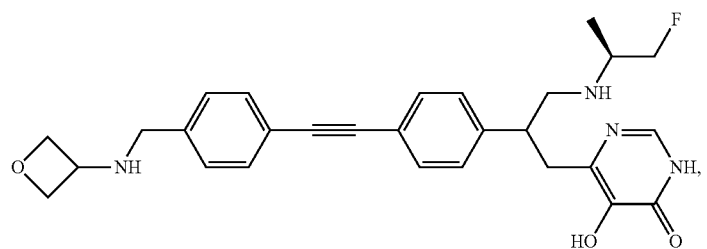
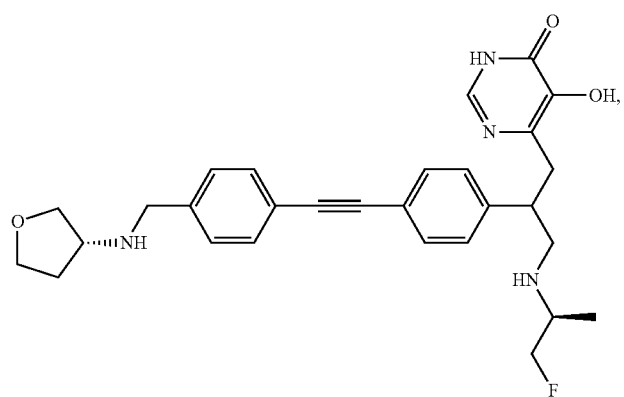
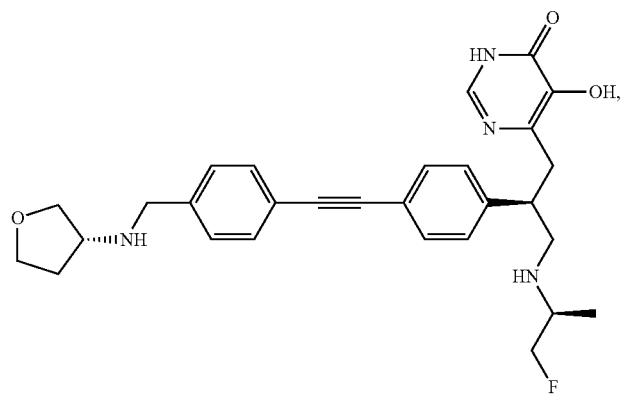
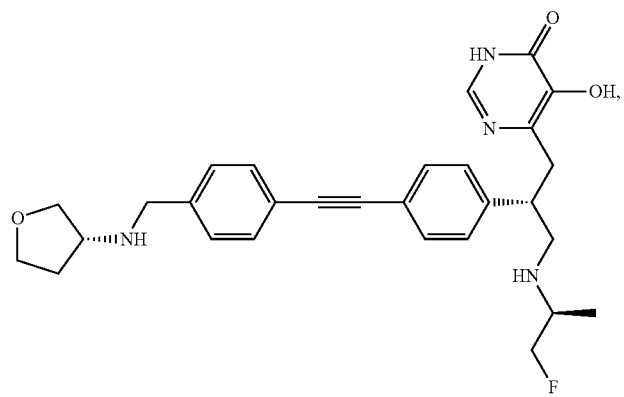

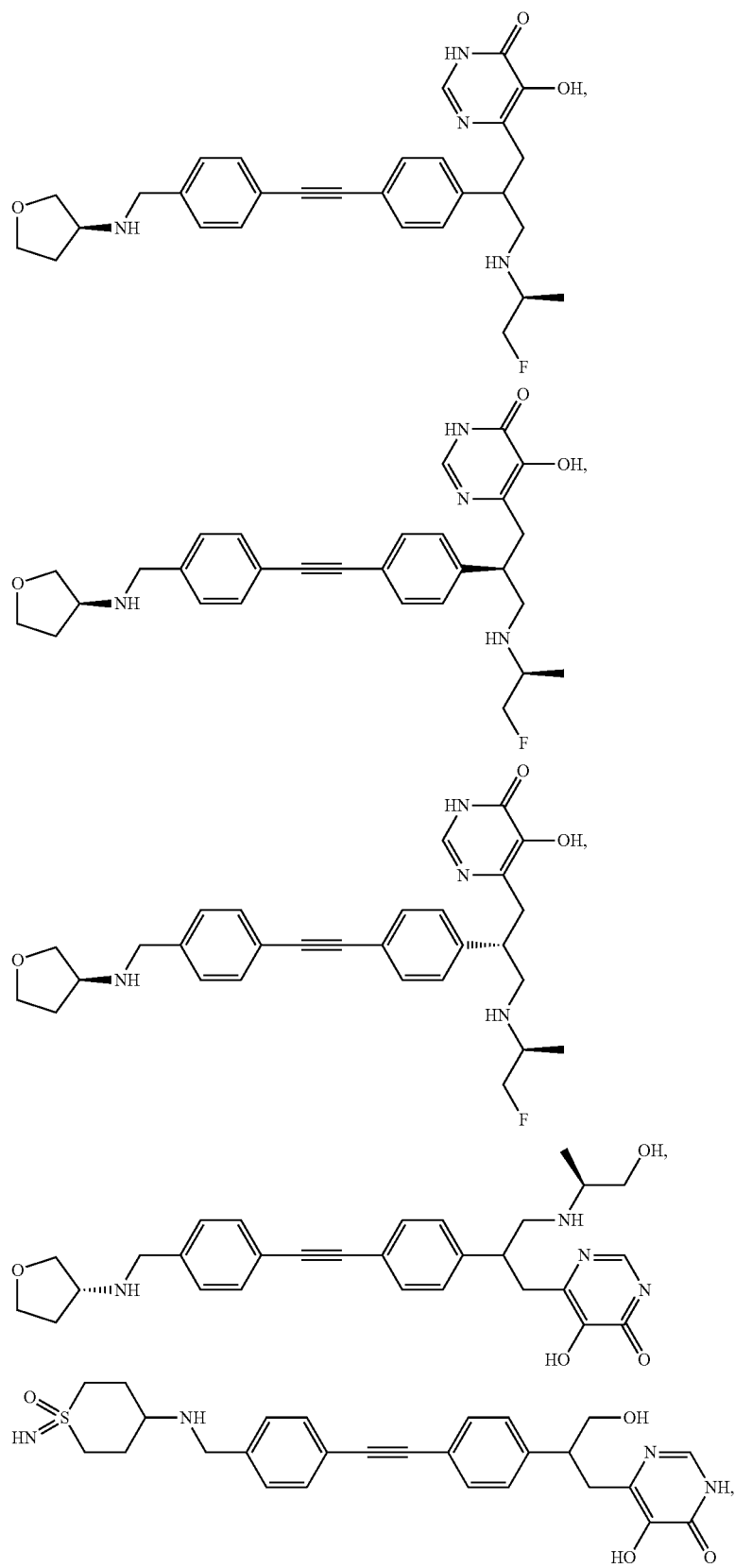

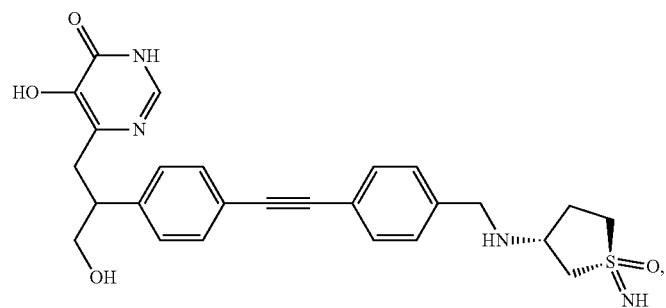
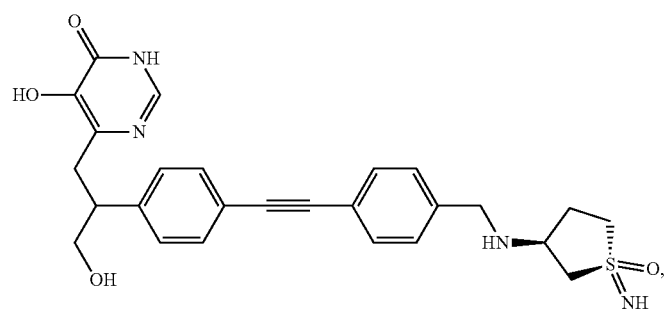
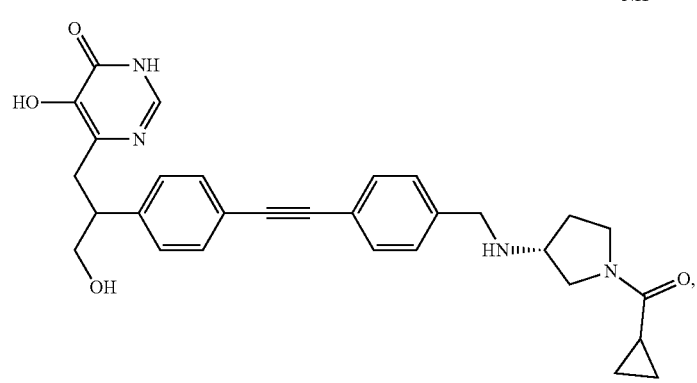
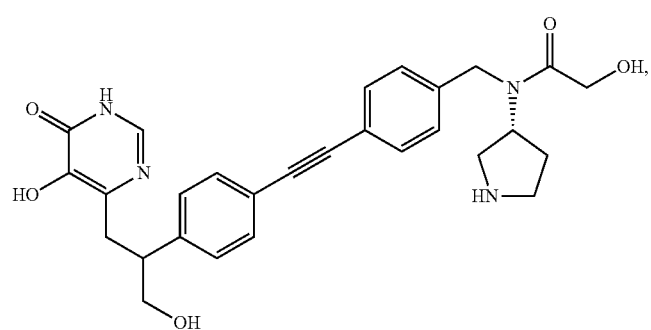
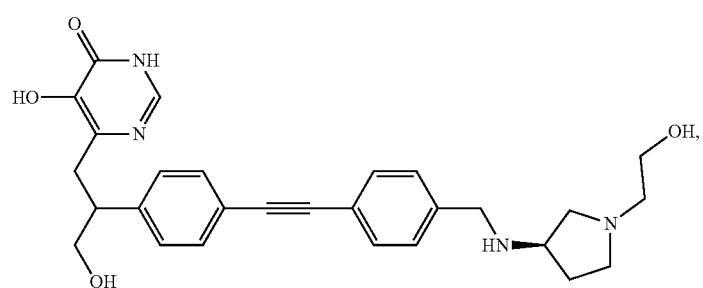

-continued
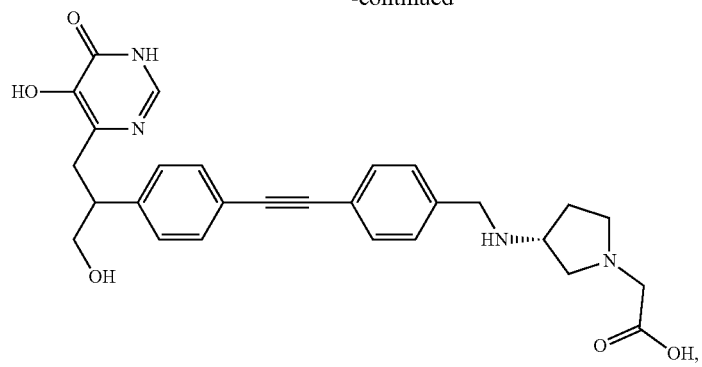
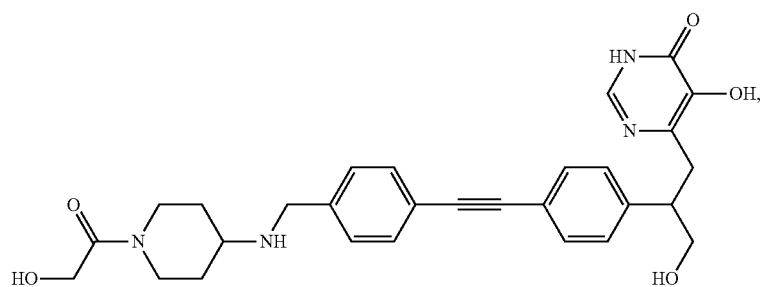
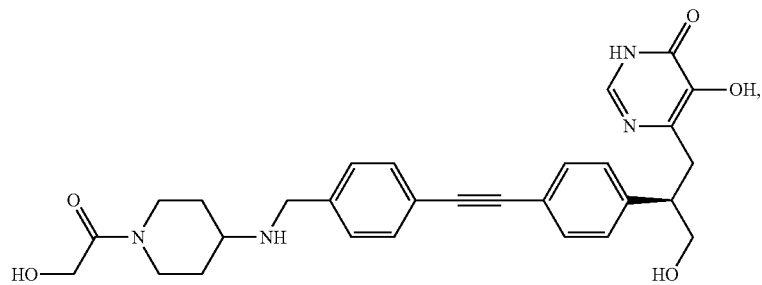
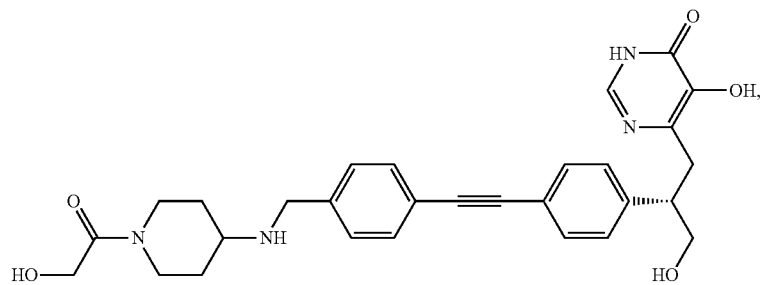
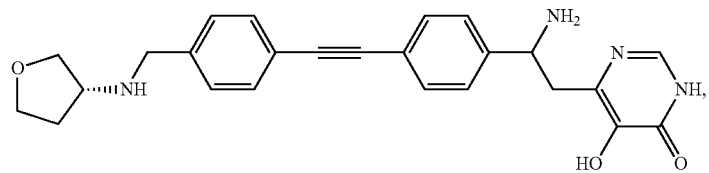

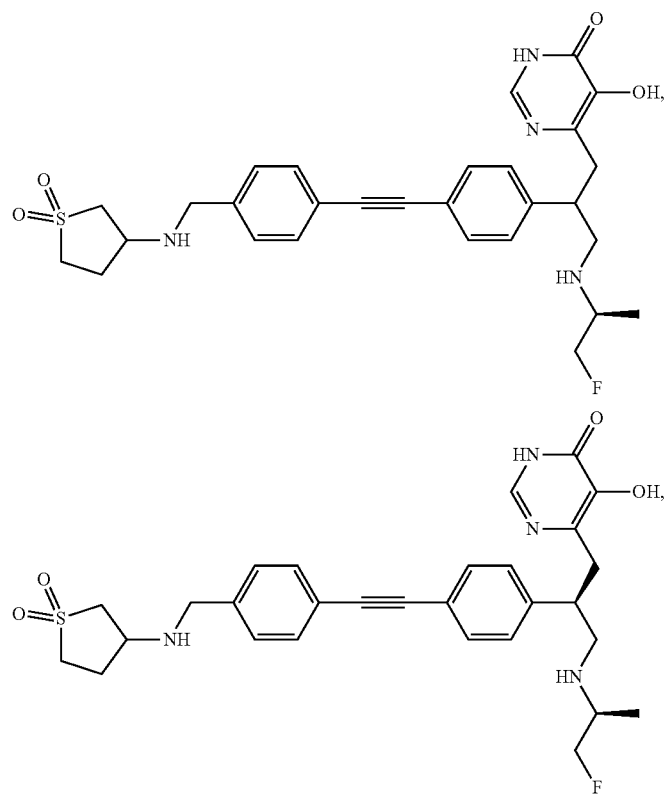
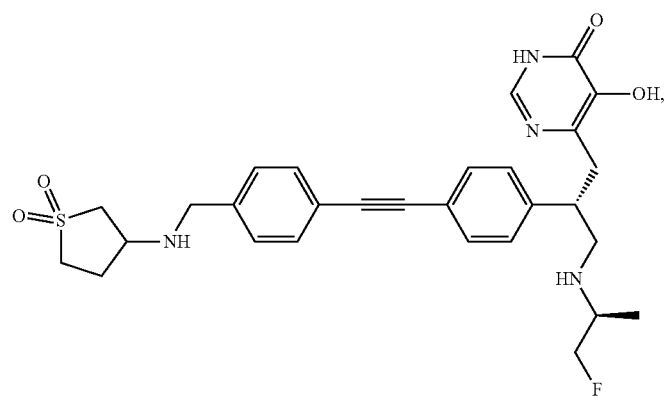
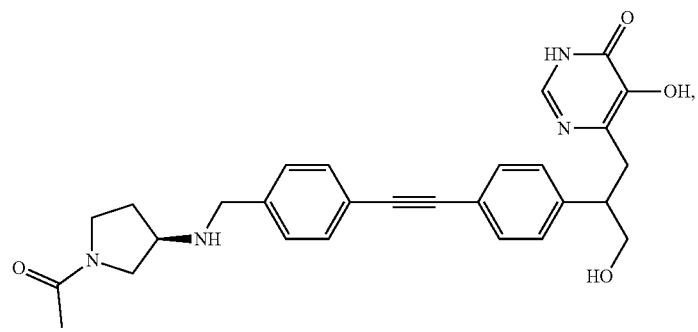

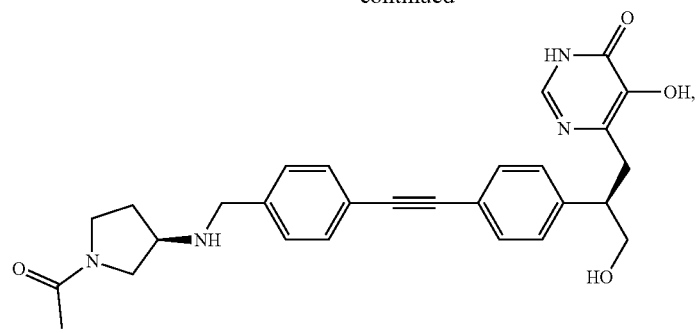
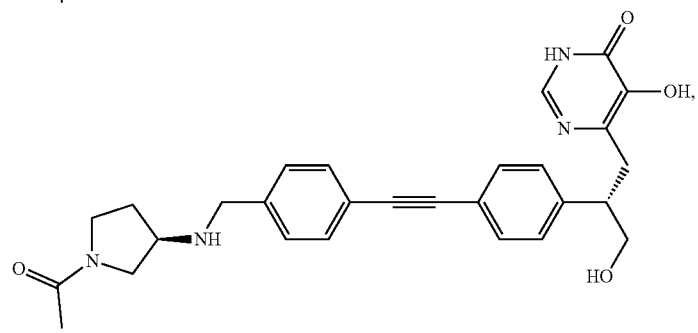
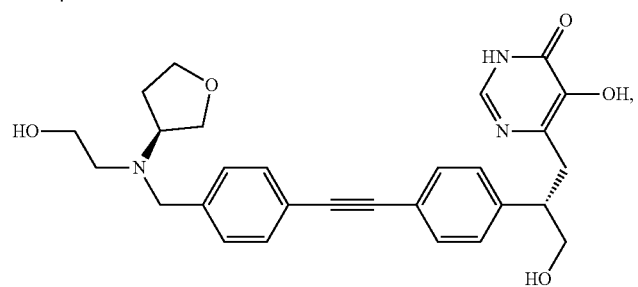
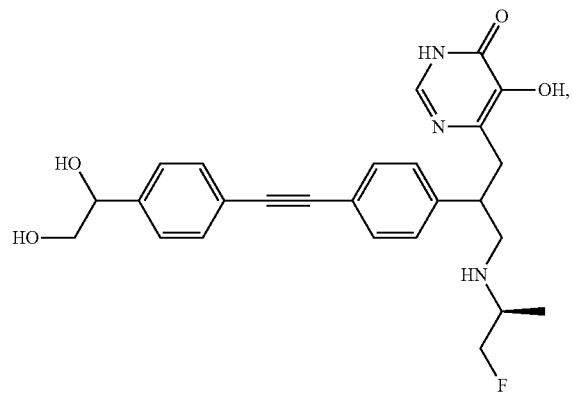
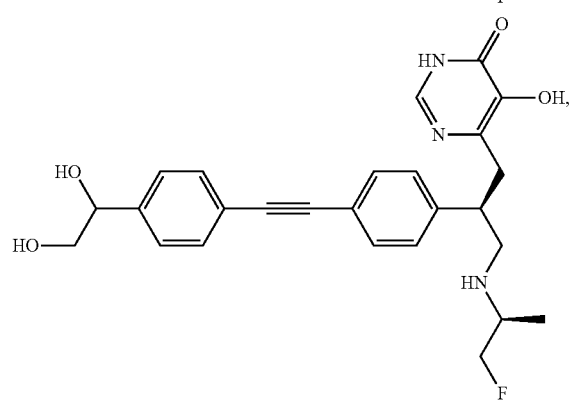

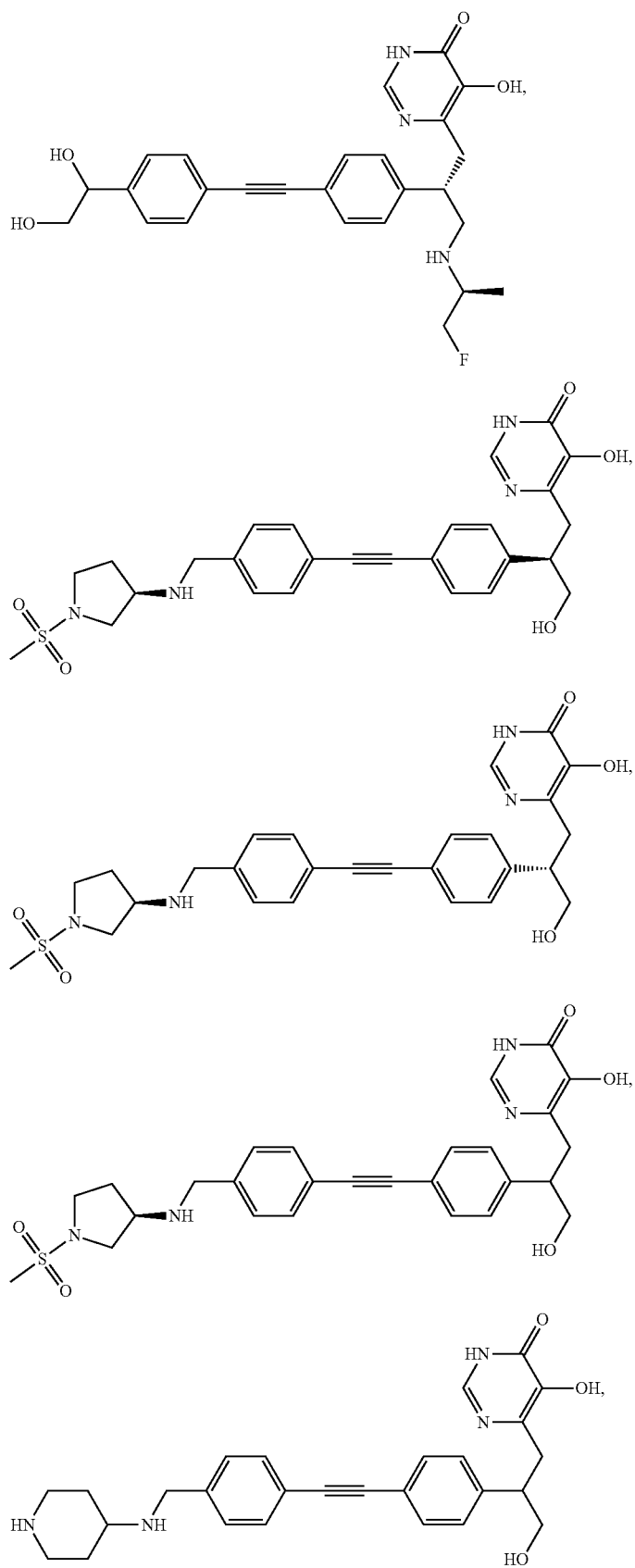

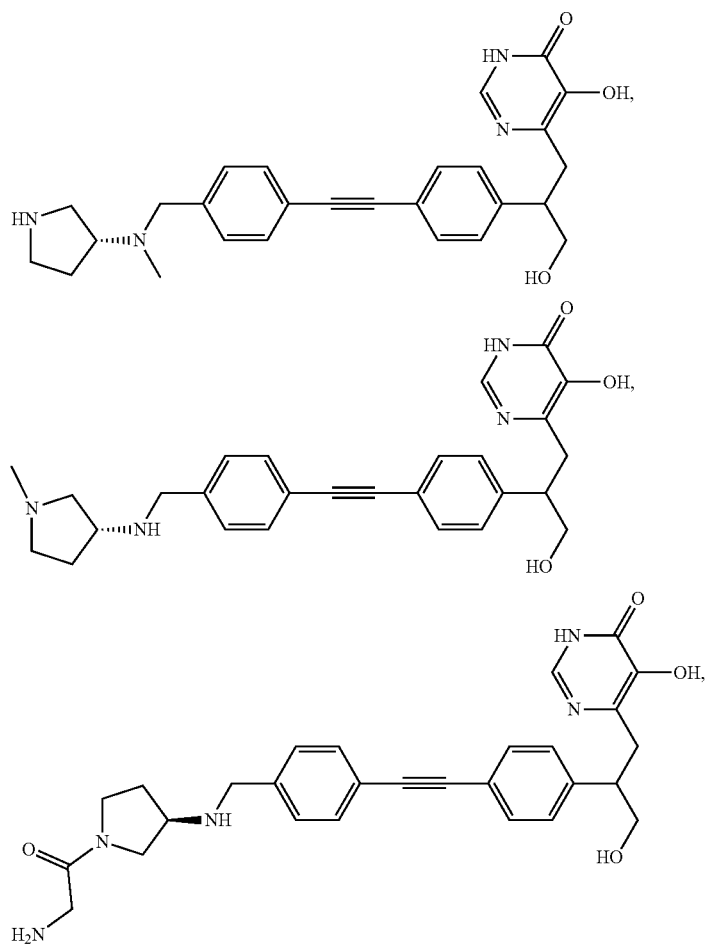
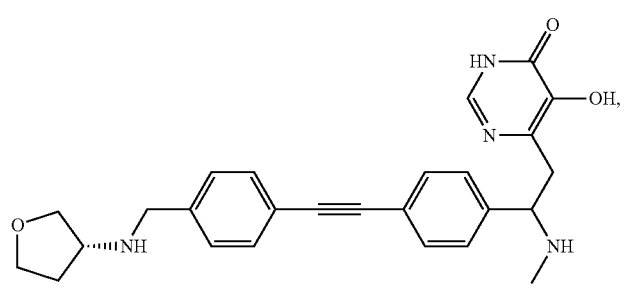
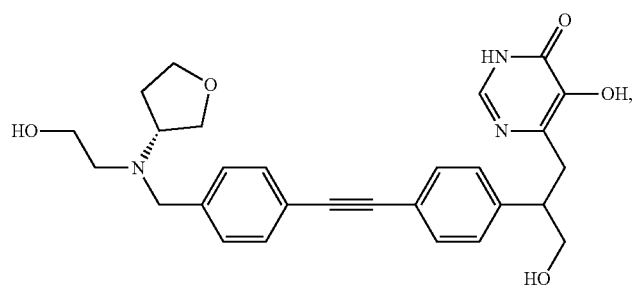

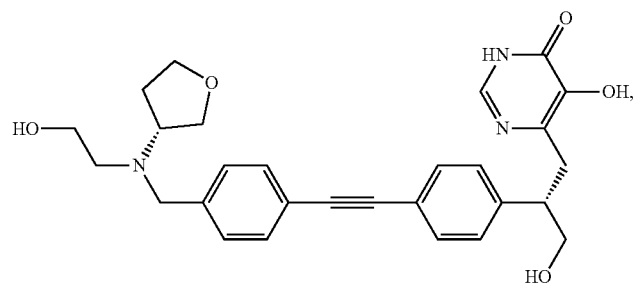
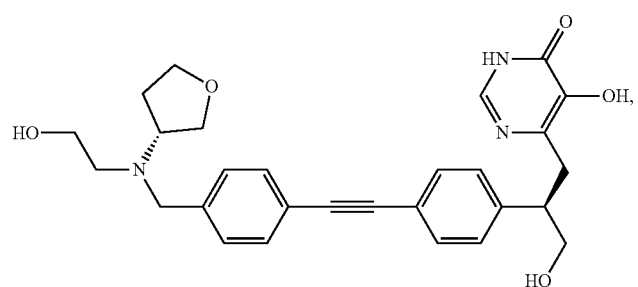
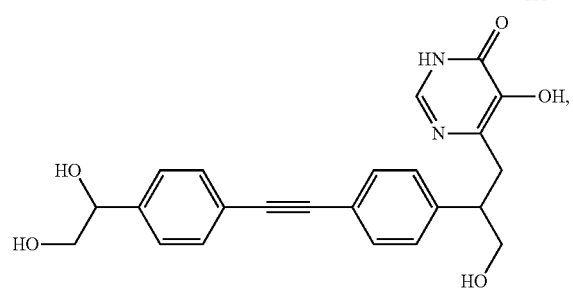
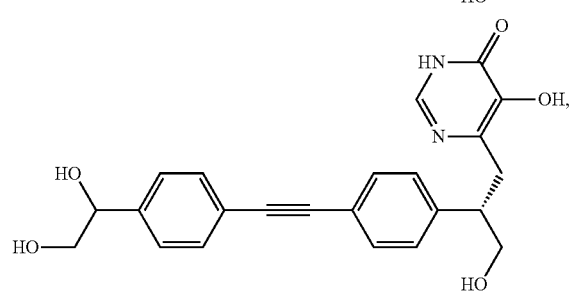
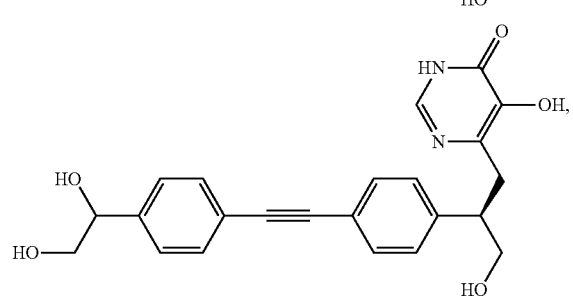
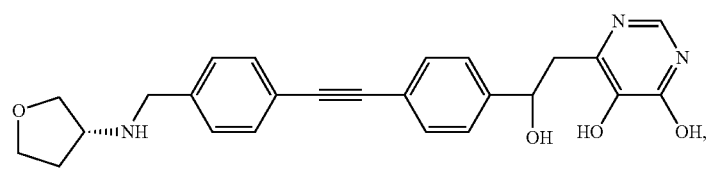

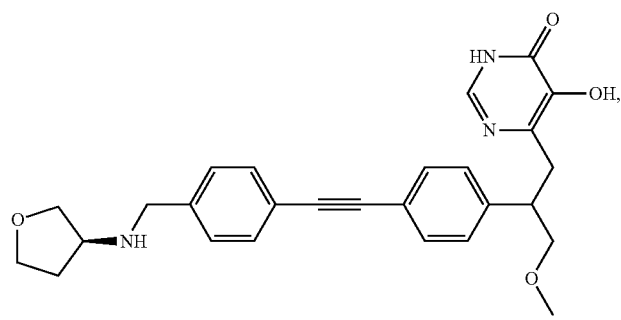
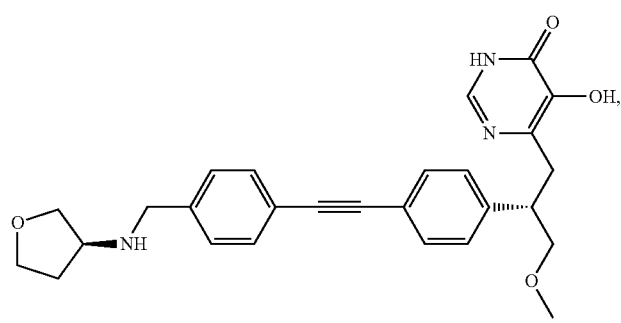
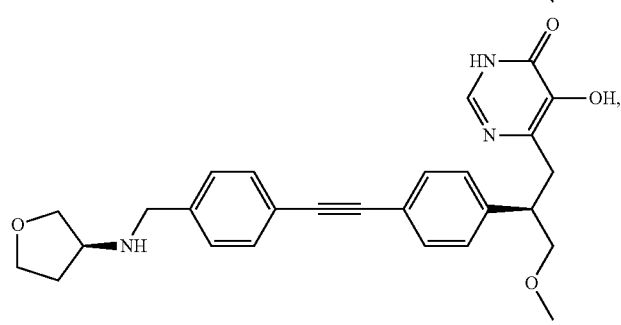
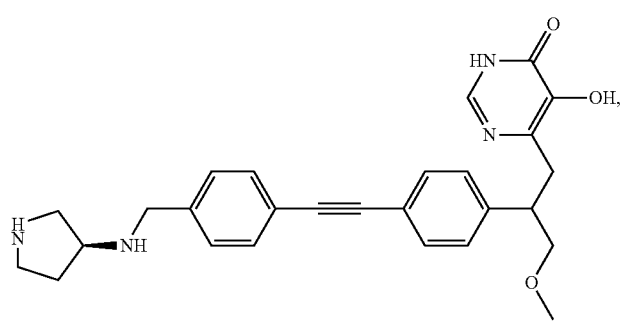
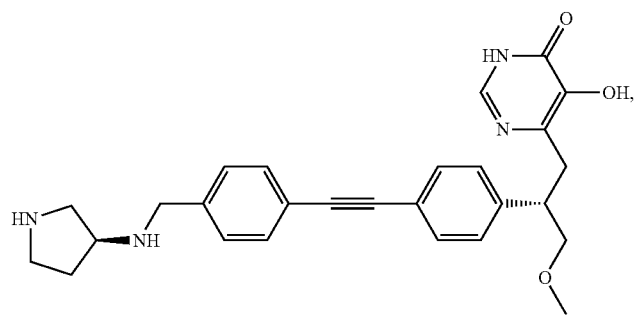

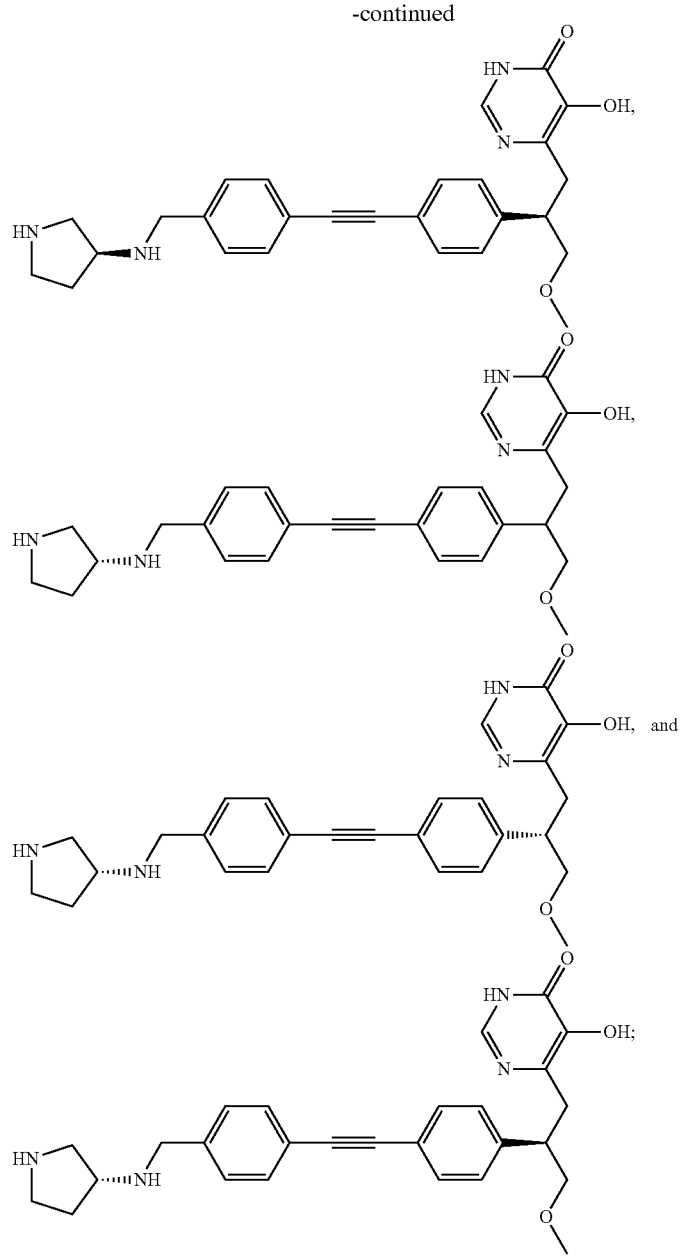
or a pharmaceutically acceptable salt, or solvate thereof.
18. A pharmaceutical composition comprising a compound of claim 1, or a pharmaceutically acceptable salt or solvate thereof, and a pharmaceutically acceptable excipient.
* * * * *